(12) United States Patent
Greenspan

(10) Patent No.: US 7,378,080 B2
(45) Date of Patent: *May 27, 2008

(54) METHODS FOR IDENTIFYING COMPOUNDS FOR MOTION SICKNESS, VERTIGO AND OTHER DISORDERS RELATED TO BALANCE AND THE PERCEPTION OF GRAVITY

(75) Inventor: Ralph J Greenspan, Coronado, CA (US)

(73) Assignee: Neurosciences Research Foundation, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/255,536

(22) Filed: Sep. 25, 2002

(65) Prior Publication Data

US 2003/0087807 A1    May 8, 2003

Related U.S. Application Data

(63) Continuation of application No. 09/669,751, filed on Sep. 26, 2000, now Pat. No. 6,551,575.

(60) Provisional application No. 60/168,579, filed on Dec. 2, 1999.

(51) Int. Cl.
    C12Q 1/68    (2006.01)
    A61K 49/00   (2006.01)
(52) U.S. Cl. ................ 424/9.2; 435/6; 435/69.1; 435/252.3; 435/320.1; 536/23.1; 514/2; 530/350
(58) Field of Classification Search ............. 424/9.2; 536/23.1; 435/6, 69.1, 252.3, 320.1; 514/2; 530/350

See application file for complete search history.

(56) References Cited

FOREIGN PATENT DOCUMENTS

WO     WO 97/30722     8/1997

OTHER PUBLICATIONS

Avraham et al., "Characterization of Unconventional *MY06*, the Human Homologue of the Gene Responsible for Deafness in Snell's Waltzer Mice," *Hum. Molec. Genet.*, 6(8):1225-1231 (1997).
Baloh et al., "Familial Vestibulopathy: A New Dominantly Inherited Syndrome," *Neurology*, 44:20-25 (1994).
Barinaga, "News of the Week: New Ion Channel May Yield Clues to Hearing," *Science*, 287:2132-2133 (2000).
Bellen, "The Fruit Fly: A Model Organism to Study the Genetics of Alcohol Abuse and Addiction?" *Cell*, 93:909-912 (1998).
Bermingham et al., "Math1: An Essential Gene for the Generation of Inner Ear Hair Cells," *Science*, 284:1837-1841 (1999).
Blake et al., "The Products of *Ribbon* and *Raw* Are Necessary for Proper Cell Shape and Cellular Localization of Nonmuscle Myosin in *Drosophila*," *Dev. Biol.*, 203:177-188 (1998).
Boonstra, "Growth Factor-Induced Signal Transduction in Adherent Mammaliam Cells is Sensitive to Gravity," *FASEB J.*, 13:S35-S42 (1999).
Brand and Perry, "Drugs Used in Motion Sickness—A Critical Review of the Methods Available for the Study of Drugs of Potential Value in Its Treatment and of the Information Which Has Been Derived by These Methods," *Pharmac. Rev.*, 18(1):895-924, (1966).
Broughton et al., "Endogenously Inhibited Protein Kinase C in Transgenic *Drosophila* Embryonic Neuroblasts Down Regulates the Outgrowth of Type I and II Processes of Cultured Mature Neurons," *J. Cell. Biochem.*, 60:584-599 (1996).
Broughton et al., "Transport of CaM Kinase Along Processes Elicited by Neuronal Contact Evokes an Inhibition of Arborization and Outgrowth in *D. melanogaster* Cultured Neurons," *J. Cell. Biochem.*, 62:484-494 (1996).
Erlenmeyer-Kimling et al., "Studies in Experimental Behavior Genetics: III. Selection and Hybridization Analyses of Individual Differences in the Sign of Geotaxis," *J. Comp. Physiol. Psychol.*, 55(5): 722-731, (1962).
Fekete, "Cell Fate Specification in the Inner Ear," *Curr. Opin. Neuro.*, 6:533-541 (1996).
Franc et al., "Croquemort, A Novel *Drosophila* Hemocyte/Macrophage Receptor that Recognizes Apoptotic Cells," *Immunity*, 4:431-443 (1996).
Fransen et al., "High Prevalence of Symptoms of Menière's Disease in Three Families with a Mutation in the *COCH* Gene," *Hum. Mol. Genet.*, 8(8):1425-1429 (1999).
Gertler et al., "Dosage-Sensitive Modifiers of *Drosophila Abl* Tyrosine Kinase Function: *Prospero*, a Regulator of Axonal Outgrowth, and *Disabled*, a Novel Tyrosine Kinase Substrate," *Genes and Develop.*, 7:441-453 (1993).
Griffith et al., "Inhibition of Calcium/Calmodulin-Dependent Protein Kinase in *Drosophila* Disrupts Behavioral Plasticity," *Neuron*, 10:501-509 (1993).

(Continued)

*Primary Examiner*—Chih-Min Kam
(74) *Attorney, Agent, or Firm*—McDermott Will & Emery LLP

(57) ABSTRACT

The present invention provides a method of identifying a compound that modulates a mammalian vestibular system. The method consists of administering a test compound to an invertebrate, and measuring a geotactic behavior of the invertebrate, where a compound that modulates the geotactic behavior of the invertebrate is characterized as a compound that modulates a mammalian vestibular system. The invention also provides a method of identifying a gene that modulates a mammalian vestibular system consisting of obtaining a first and a second strain of an invertebrate; subjecting the first and second invertebrate strains to conditions in which the first strain exhibits a geotactic behavior different than a geotactic behavior exhibited by the second strain; measuring gene expression levels in the first and second strains, and identifying one or more genes that are differentially expressed in the first strain relative to the second strain, whereby a mammalian gene having substantially the same nucleic acid sequence as the one or more differentially expressed genes modulates the mammalian vestibular system.

2 Claims, 1 Drawing Sheet

OTHER PUBLICATIONS

Guvakova and Surmacz, "The Activated Insulin-Like Growth Factor I Receptor Induces Depolarization in Breast Epithelial Cells Characterized by Actin Filament Disassembly and Tyrosine Dephosphorylation of FAK, Cas, and Paxillin," *Exp. Cell. Res.*, 251:244-255 (1999).

Helmke et al., "SRC Binding to the Cytoskeleton, Triggered by Growth Cone Attachment to Laminin, is Protein Tyrosine Phosphatase-Dependent," *J. Cell. Sci.*, 111 :2465-2475 (1998).

Hirata et al., "Asymmetric Segregation of the Homeodomain Protein Prospero During *Drosophila* Development," *Nature*, 377:627-630 (1995).

Hirsch, "Studies in Experimental Behavior Genetics: II. Individual Differences in Geotaxis as a Function of Chromosome Variations in Synthesized *Drosophila* Populations," *J. Comp. Physiol. Psychol.*, 52(3):304-308 (1959).

Horn, "Gravity" in *Comprehensive Insect Physiology Biochemistry and Pharmacology* vol. 6, pp. 557-575 Pergamon Press (1985).

Hu et al., "Midline Fasciclin: A *Drosophila* Fasciclin-I-Related Membrane Protein Localized to the CNS Midline Cells and Trachea," *J. Neurobiol.*, 35:77-93 (1998).

Imbert et al., "Cloning of the Gene for Spinocerebellar Ataxia 2 Reveals a Locus with High Sensitivity to Expanded CAG/Glutamine Repeats," *Nature Genet.*, 14: 285-291 (1996).

Ingber, "How Cells (Might) Sense Microgravity," *FASEB J.*, 13:S3-S15 (1999).

Jaffrey and Snyder, "PIN: An Associated Protein Inhibitor of Neuronal Nitric Oxide Synthase," *Science*, 274:774-777 (1996).

Kane et al., "Learning without Performance in PKC-Deficient *Drosophila*," *Neuron*, 18:307-314 (1997).

Kirszbaum et al., "Molecular Cloning and Characterization of the Novel, Human Complement-Associated Protein, SP-40,40: A Link Between the Complement and Reproductive Systems," *EMBO J.*, 8:711-718 (1989).

Krishnan and Nash, "A Genetic Study of the Anesthetic Response: Mutants of *Drosophila melanogaster* Altered in Sensitivity to Halothane," *Proc. Natl. Acad. Sci. USA*, 87:8632-8636 (1990).

Legan et al., "The Mouse Tectorins—Modular Matrix Proteins of the Inner Ear Homologous to Components of the Sperm-Egg Adhesion System," *J. Biol. Chem.*, 272(13):8791-8801 (1997).

Lewis et al., "Spaceflight Alters Microtubules and Increases Apoptosis in Human Lymphocytes (Jurkat)," *FASEB J.*, 12:1007-1018 (1998).

Litt et al., "A Gene for Episodic Ataxia/Myokymia Maps to Chromosome 12p13," *Am. J. Hum. Genet.*, 55:702-709 (1994).

Lundquist et al., "UNC-115, a Conserved Protein with Predicted LIM and Actin-Binding Domains, Mediates Axon Guidance in *C. Elegans*," *Neuron*, 21:385-392 (1998).

Luo et al., "Human Amyloid Precursor Protein Ameliorates Behavioral Deficit of Flies Deleted for *Appl* Gene," *Neuron*, 9:595-605 (1992).

Manolis et al., "A Gene for Non-Syndromic Autosomal Dominant Progressive Postlingual Sensorineural Hearing Loss Maps to Chromosome 14q12-13," *Hum. Mol. Genet.*, 5(7):1047-1050 (1996).

Manski et al., "Endolymphatic Sac Tumors—A Source of Morbid Hearing Loss in Von Hippel-Lindau Disease," *JAMA*, 277(18):1461-1466 (1997).

McClung and Hirsh, "Stereotypic Behavioral Responses to Free-Base Cocaine and the Development of Behavioral Sensitization in *Drosophila*," *Current Biology*, 8:109-112 (1998).

McMillan and McGuire, "The Homeotic Gene *Spineless-Aristapedia* Affects Geotaxis in *Drosophila melanogaster*," *Behav. Genet.*, 22(5):557-573 (1992).

Mitchell et al., "Apoptosis of Neurons in the Vestibular Nuclei of Adult Mice Results from Prolonged Change in the External Environment," *Neurosci. Lett.*, 198:153-156 (1995).

Moore et al., "Ethanol Intoxication in *Drosophila*: Genetic and Pharmacological Evidence for Regulation by the cAMP Signaling Pathway," *Cell*, 93:997-1007 (1998).

Mustapha et al., "An $\alpha$-Tectorin Gene Defect Causes a Newly Identified Autosomal Recessive Form of Sensorineural Pre-Lingual Non-Syndromic Deafness, DFNB21," *Hum. Molec. Genet.*, 8(3):409-412 (1999).

Ophoff et al., "Familial Hemiplegic Migraine and Episodic Ataxia Type-2 Are Caused by Mutations in the $Ca^{2+}$ Channel Gene CACNL1A4," *Cell*, 87:543-552 (1996).

Osborne et al., "Natural Behavior Polymorphism Due to a cGMP-Dependent Protein Kinase of *Drosophila*," *Science*, 277:834-836 (1997).

Pan et al., "Histaminergic Ligands Attenuate Barrel Rotation in Rats Following Unilateral Labyrinthectomy," *Methods Find Exp. Clin. Pharmacol.*, 20(9):771-777 (1998).

Park and Hall, "Isolation and Chronobiological Analysis of a Neuropeptide Pigment-Dispersing Factor Gene in *Drosophila melanogaster*," *J. Biol. Rhythms*, 13(3):219-228 (1998).

Pujana et al., "Spinocerebellar Ataxias in Spanish Patients: Genetic Analysis of Familial and Sporadic Cases," *Hum. Genet.*, 104:516-522 (1999).

Pulst et al., "Moderate Expansion of a Normally Biallelic Trinucleotide Repeat in Spinocerebellar Ataxia Type 2," *Nature Genet.*, 14:269-276 (1996).

Reddy and Rodrigues, "Sibling Cell Fate in the *Drosophila* Adult External Sense Organ Lineage is Specified by Prospero Function, Which is Regulated by Numb and Notch," *Development*, 126:2083-2092 (1999).

Renn et al., "A *pdf* Neuropeptide Gene Mutation and Ablation of PDF Neurons Each Cause Severe Abnormalities of Behavioral Circadian Rhythms in *Drosophila*," *Cell*, 99:791-802 (1999).

Ricker and Hirsch, "Genetic Changes Occurring Over 500 Generations in Lines of *Drosophila melanogaster* Selected Divergently for Geotaxis," *Behav. Genet.*, 18(1):13-25, (1988).

Robertson et al., "Mutations in a Novel Cochlear Gene Cause DFNA9, a Human Nonsyndromic Deafness with Vestibular Dysfunction," *Nat. Genet.*, 20:299-303 (1998).

Roof et al., "Molecular Characterization of abLIM, a Novel Actin-Binding and Double Zinc Finger Protein," *J. Cell. Biol.*, 138(3):575-588 (1997).

Russo et al., "Fe65 and the Protein Network Centered Around the Cytosolic Domain of the Alzheimer's $\beta$-Amyloid Precursor Protein," *FEBS Lett.*, 434:1-7 (1998).

Sanpei et al., "Identification of the Spinocerebellar Ataxia Type 2 Gene Using a Direct Identification of Repeat Expansion and Cloning Technique, DIRECT," *Nature Genet.*, 14:277-284 (1996).

Schivell et al., "Isoform-Specific, Calcium-Regulated Interaction of the Synaptic Vesicle Proteins SV2 and Synaptotagmin," *J. Biol. Chem.*, 271(44):27770-27775 (1996).

Schwartzkopff, "Mechanoreception" in *The Physiology of Insecta*, Academic Press (1974).

Sedbrook et al., "ARG1 (Altered Response to Gravity) Encodes a DNAJ-Like Protein That Potentially Interacts with the Cytoskeleton," *Proc. Natl. Acad. Sci. USA*, 96:1140-1145 (1999).

Stoltenberg and Hirsch, "A Gene Correlate of Geotaxis Near *Adh* (2-50.1) in *Drosophila melanogaster*," *J. Comp. Psychol.*, 110(3):252-259 (1996).

Takasu and Harris, "Reduction of Inner Ear Inflammation by Treatment with Anti-ICAM-1 Antibody," *Ann. Otol. Rhinol. Laryngol.*, 106:1070-1075 (1997).

Török et al., "The *Overgrown Hematopoietic Organs-31* Tumor Suppressor Gene of *Drosophila* Encodes an *Importin*-Like Protein Accumulating in the Nucleus at the Onset of Mitosis," *J. Cell Biol.*, 129(6):1473-1489 (1995).

Torres and Horowitz, "Cocaethylene Synthesis in *Drosophila*," *Neuroscience Letters*, 263:201-204 (1999).

Torres and Horowitz, "Drugs of Abuse and Brain Gene Expression," *Psychosomatic Medicine*, 61: 630-650 (1999).

Torres and Horowitz, "Activating Properties of Cocaine and Cocaethylene in a Behavioral Preparation of *Drosophila melanogaster*," *Synapse*, 29:148-161 (1998).

Usami et al., "Non-Syndromic Hearing Loss Associated with Enlarged Vestibular Aqueduct is Caused by *PDS* Mutations," *Hum. Genet.*, 104:188-192 (1999).

Vaessin et al., "Prospero Is Expressed in Neuronal Precursors and Encodes a Nuclear Protein That Is Involved in the Control of Axonal Outgrowth in *Drosophila*," *Cell*, 67:941-953 (1991).

Verhoeven et al., "Mutations in the Human α-Tectorin Gene Cause Autosomal Dominant Non-Syndromic Hearing Impairment," *Nature Genet.*, 19:60-62 (1998).

Walker et al., "A *Drosophila* Mechanosensory Transduction Channel," *Science*, 287:2229-2234 (2000).

Weil et al., "Human Myosin VIIA Responsible for the Usher 1B Syndrome: A Predicted Membrane-Associated Motor Protein Expressed in Developing Sensory Epithelia," *Proc Natl.Acad. Sci. USA*, 93:3232-3237 (1996).

Willnow et al., "Defective Forebrain Development in Mice Lacking GP330/Megalin," *Proc. Natl. Acad. Sci. USA*, 93:8460-8464 (1996).

Yabe et al., "Medial Vestibular Nucleus in the Guinea-Pig: Histaminergic Receptors, II. An In Vivo Study," *Exp. Brain Res.*, 93: 249-258, (1993).

Young et al., "Morphogenesis in *Drosophila* Requires Nonmuscle Myosin Heavy Chain Function," *Genes Dev.*, 7:29-41 (1993).

Zheng et al., "Neurotrophin-4/5, Brain-Derived Neurotrophic Factor, and Neurotrophin-3 Promote Survival of Cultured Vestibular Ganglion Neurons and Protect Them Against Neurotoxicity of Ototoxins," *J. Neurobiol.*, 28(3):330-340 (1995).

http://caat.jhsph.edu/programs/grants/reports/torres.html, (1999).

http://www.cannabis.net/weblife.html, (Oct. 2000).

http://www.cavalierdaily.com/.Archives/1998/February/12/hecrack.asp.

http://www.cling.gu.se/-c15pwall/spiders/spiders.html, (Oct. 2000).

http://www.nigms.nih.gov/news/releases/cocaine.html, (Jan. 1998).

http://www.stresstips.com/caffeine.html, (1998).

Burg et al., "Genetic and Molecular Identification of a *Drosophila* Histidine Decarboxylase Gene Required in Photoreceptor Transmitter Synthesis," *EMBO J.*, 12:911-919 (1993).

Byers, "Osteogenesis Imperfecta," in *Connective Tissue and Its Heritable Disorders*, Wiley-Liss, Inc., (1993), pp. 317-350.

Cashmore et al., "Cryptochromes: Blue Light Receptors for Plants and Animals," *Science*, 284:760-765 (1999).

Celniker et al., "Sequencing of *Drosophila* chromosome 3R, region 88F-88F," EMBL ID/AC AC007769, (1999).

Ceriani et al., "Light-Dependent Sequestration of Timeless by Cryptochrome," *Science*, 285:553-556 (1999).

Cummings et al., "Chaperone Suppression of Aggregation and Altered Subcellular Proteasome Localization Imply Protein Misfolding in SCA1," *Nat. Genet.*, 19:148-154 (1998).

Danik et al., "Localization of Sulfated Glycoprotein-2/Clusterin mRNA in the Rat Brain by In Situ Hybridization," *J. Comp. Neurol.*, 334:209-227 (1993).

Davis et al., "Use of the Teleost Saccule to Identify Genes Involved in Inner Ear Function," *DNA and Cell biol.*, 14(10):833-839 (1995).

Desai et al., "Receptor Tyrosine Phosphatases Are Required for Motor Axon Guidance in the *Drosophila* Embryo," *Cell*, 84:599-609 (1996).

Doe et al., "The *Prospero* Gene Specifies Cell Fates in the *Drosophila* Central Nervous System," *Cell*, 65:451-464 (1991).

Donat and Auger, "Familial Periodic Ataxia," *Arch. Neurol.*, 36:568-569 (1979).

SEQUENCE LISTING

<160> NUMBER OF SEQ ID NOS: 261

<210> SEQ ID NO 1
<211> LENGTH: 502
<212> TYPE: DNA
<213> ORGANISM: Drosophila

<400> SEQUENCE: 1

```
acaaattgaa aacccgcgac aaccgaaagc gccacaaaga gctcttttct ctcccggtcc      60
ggttgactaa aaaaaaatta aaagatacaa ctccaacgat aacagcctaa ggcccactaa     120
caacaaggct ggtgcaggag gcgggaacgg aggcgcagca gtgcgtccgt cggcgcaggg     180
cgtctacaac aacacgtttt tcatgcactc ggccacggcg ctggtgggca gcgttgtgga     240
ggtgcgcctg cggtcgggca atatctacga gggcgtattc cgcacattct cgggcaactt     300
tgacatcgca ctggagctac cggcgtgcat taagtccaag aatctgccgg aggagggcaa     360
ggtgccaaaa cacattatat tcccggccga cactgtggtg accatcatgg ccaatgactt     420
tgactcgcaa tacgccaccg taggcgcttt tcaaacggat ggcgccattt ctgacaagtg     480
caacggtgcg cgttctgact ag                                              502
```

<210> SEQ ID NO 2
<211> LENGTH: 634
<212> TYPE: DNA
<213> ORGANISM: Drosophila

<400> SEQUENCE: 2

```
attcaatcga ttgcttgtgc atttagcaaa tcaaagccac aacaaccaaa ccagaatcaa      60
tatgaagttc ttctcagtcg tcaccgtctt tgtgttcggt ctgctggctc tggccaacgc     120
tgttcccctg tcgcccgatc caggaaatgt ggtaatcaac ggggactgca aatactgcaa     180
tgtgcacggt ggaaagtagg aaagtaggaa agtaggaaag tactcgcctt aatttcgaag     240
atgggccaaa acttacctca aatccaaagc accatatttta tactctcact cttgtactaa     300
aatgaaaact agtagtaaaa aatacatcgc caattacaaa taaaataaaa aaaaaaaaaa     360
aaaaaaaact cgagactagt tccctcaatg agagtcaagt caaaaccaag tcaagtcact     420
aggccagtca gtcagtcagt cagccaacca gtcagtcaga cagtcagtcg tttggttctt     480
aatgccattg cctatgttta acatacattt tcaaacagat taacaattga gtaattaact     540
ttaagaaagt tgtttgcatt tcgctgtgta tttcaaattg aagaatggaa tagtttattg     600
taagaacaag tcgcctcaaa actaaaaaga aacc                                 634
```

<210> SEQ ID NO 3
<211> LENGTH: 1080
<212> TYPE: DNA
<213> ORGANISM: Drosophila

<400> SEQUENCE: 3

```
actgcataac caaatatttg cgtggctcca actcgactcc gtatttgcct gggctgaagg      60
accgccgctg cctgcggatg acatgtattg gtcctgcgga tgacaccgat actgacgctc    120
ttgggttgcg tggtcgggcg gtctcccgca gtgggttatc cagtccaggt tgctatataa    180
gtcgaggatg cgccaaccga cgttcattcg caagtctcct gctgcaggtg ttccgtgctc    240
agttcctgct cctggccacc ctttcagctc ctcggactaa tggctcgctt cacgtacctt    300
gtcgcccttg tgcttctggc catttgctgc cagtggggat actgcggcgc catggccatg    360
ccggatgagg agcgctatgt gcgcaaggag tacaatcggg atctcctcga ctggttcaac    420
aacgtgggcg tgggacagtt cagtcccggc caagtggcca ctctctgtcg ctatccgctg    480
atcctcgaga actccttggg cccatccgtg cccatcagga agcgcaactc ggagctaatc    540
aactccttgt tgagtctgcc caagaacatg aacgatgcgg gcaagtaaga acggaaaatg    600
ctgaaggatt aggacgaccc accactgaaa gttggaacct ggacaagaac ttattatttg    660
atgttatcgt atgatttttt ggtgcgtcga aggaaaatga aaatccgcag ataaaagccg    720
gtgtagtcat ctaatagaga gaaaagaccg tataactttt gttgctttaa acctaaatag    780
aaaaatatac aagtagccta ttgtagaaat gttgtatatt attaggctta ctgctgaaat    840
aaacgttttc tggattgttt cgacttgaaa tctggtacaa caactagtca ggattttat     900
tcttaatcac agatactaaa gctagttaaa gatattggtt atccccgtaa agggcgaacc    960
aatgaaagcc aaaggtgttc tcaaagtaga ttttgttcaa tgctacgatt ggaataaata   1020
gatgtttcta gcttagaata gcagccccat ttcgtttatt gacttcattt attatgctat   1080
```

<210> SEQ ID NO 4
<211> LENGTH: 647
<212> TYPE: DNA
<213> ORGANISM: Drosophila

<400> SEQUENCE: 4

```
gcaggtgcag gtggcaggtt gcaggttgca ggtgaagcaa tccgtgcggc aatcgcgata      60
agtgcaccaa caaatggttg gcaaatctgg agcactcgca aagtccacaa acaatgtgca    120
aaaggtcgcg cgagttgggg acttacaagt ttaataaagt catatacacg cactcccgat    180
ggccaagatg ccaatacaca taattgtaag gatgtgtgta tatgtatgaa ttgtagggc     240
cacggctcag tctgactttt ccggcagaat gaccgacgaa cgaaatgtga ccgaaataca    300
ccatcaattt ttaatatcta tttaacattt caatcagcgg aatcgcagcg ctcgccgctc    360
gattcgtatg caaatttta ttaatattta attttcatt cattgtattt ctgtgttttg      420
cctgcaattt taatgacgca tcgcggagcg ctaataaaat taaatggccc aaacaacaca    480
ggaccgatcc actcacacag atattccggc actcacacac tctcacacag gcacactcga    540
ccgaatgagt tgtgctttag cttccttttt cgtttggctt gcttgcttgt tttgtgggtt    600
ccacgcgcta cggtcttctg ctcaacgata cgcgaaaatc caatccg                  647
```

<210> SEQ ID NO 5
<211> LENGTH: 686
<212> TYPE: DNA
<213> ORGANISM: Drosophila

<400> SEQUENCE: 5

```
gaacacaagc atcctaatcg tggccctggt ggcactttc gccattaccg aggcacttcc      60
```

-continued

```
cacaacagga cccattcgcg tccgtcgcca ggtgctcgga ggttccttaa cctccaatcc      120
cgctggtggg gctgatgctc gtttggatct gaccaagggc attggcaatc ccaaccacaa      180
tgtggtgggt caggttttcg ccgccggaaa cactcaaagt ggtccagtca caactggcgg      240
aactttggcc tacaacaagt gagttctcta aactaagaga ttactagagg atatattaac      300
tctattctat tcattttga agtgctggtc atggtgcctc tttgaccaaa acacacacgc       360
ccggagtgaa ggatgttttc cagcaggagg cccatgccaa tttattcaac aatggcagac      420
acaatctgga tgccaaggtc tttgcttcgc aaaataaact ggccaatggt ttcgagttcc      480
agcggaatgg agctggtctg gattactccc acatcaacgg acatggtgct tccttgacgc      540
acagcaactt cccaggaatc ggccagcaac tcggcctgga tggacgtgct aatctctggt      600
catcgcccaa tcgtgctact accttggatc tcacgggatc ggcgagcaag tggacgagtg      660
gaccgtttgc caaccagaag ccaaac                                           686
```

<210> SEQ ID NO 6
<211> LENGTH: 619
<212> TYPE: DNA
<213> ORGANISM: Drosophila

<400> SEQUENCE: 6

```
tttctatata tttctccagc ggtgaggtca acgttgtgcg cttgggtgaa ctggagttcg       60
ataccgacac ggatgacgcg gaacccgagg actttggcgt gctcgctctg aaggcacatc      120
ctggcttcga gaacccgcaa ctctacaatg acattggcat agttcagctg gatcgcgagg      180
tcaagttcaa taggtacaag catcctgcct gcctgcccct cgacgacggc gagcagcacg      240
agtccttcat cgccatcggc tggggccaga agaagtttgc ccagaaggag tcaaagaagc      300
tgttgaaggt gcagctccag ggctataagg accgatgtgt cagcagtgtg gatgcgaatg      360
atgagttgcc caatggctac gagcccaaga gccagctgtg catcggatca agggacaaca      420
aggacacatg caacggcgac tctggcggtc cagtgctggc ctatcacaag gatctcgcct      480
gcatgtacca cgtaatgggc atcacctcag ccggcatcac ctgctccacg cccgacattc      540
caagtgccta cacgcgggtg cactacttcc tcaactggat caagggcgaa ctggccaagc      600
agacgcaagg aatgaaatg                                                   619
```

<210> SEQ ID NO 7
<211> LENGTH: 567
<212> TYPE: DNA
<213> ORGANISM: Drosophila

<400> SEQUENCE: 7

```
ggaaatcaat aaaagcagcg cacaaattaa gcacctttg cgcttttccc cctgccagtt       60
agttgcttta ctttgctttt ccaggccgca acgtgaattt aataggatta tgcggcaagg      120
atgggccgac ggggagaaag gagacttatg caaagtcctt ccactctgcg ccactgcaat      180
cctggaaacc ctttgcgccg ccacacaata tgaacctaat tgtcgtgatt ttcgcctgat      240
ggcaactttt cacactccca ttcacagaat tgtgggtcgt ggaggacctc cgcccaagtt      300
ttgttatgcc aaaaacaaac ttcggcaatt tatgataatt caacgtcagc tgggacagtt      360
cagggaagta catagagggg aaccgtcatc acggcaaact caactcgact ccgctcaagt      420
catctgaact cagctgaact gacagctggc tagcaaaggc cttggaatat gctcgcagca      480
cacattaaac ttatttctca ccccccactcg aagcgccact aatgcccggc atcgtgtaca      540
gatttactcc gaagcagacg tacagca                                          567
```

```
<210> SEQ ID NO 8
<211> LENGTH: 652
<212> TYPE: DNA
<213> ORGANISM: Drosophila

<400> SEQUENCE: 8
cgaagataaa gaaataaatt gtttaatcca atttagccca gcaaactgca agtttgcagt      60
ttatctttct ctgcttgccc tcttcggcaa cgcgaaagtg ccttttttt agttggatag      120 cagcttttcag atcaattcca aaggcgcttc ccacgcttga gtttagctgt aaaagtaata    180
agaagggaag tctgacaatt tgaatccctt tcgtacggta cttttgcgat tccaggcacc    240
aaaggtaaag ggactaagcg atcatcgaag cgggaagtcc cagaaaaata aatttactcc    300
gaactatggc ataataaatg tcaaggccaa agcaaaacaa taacagagcc atcagaagct    360
aatgctaaaa gacgtagttg tgtgtgagat aaaagatgca actaactgcc tagggctgga    420
ttattcccac cttggctatt ccttaaaagc gtgaaccttt ggaatcctac gtatccacca    480
tgtgctgcaa gtgctgcggg gaaactcaac gaaaggtctg ggtcttcggc ttgggatcgg    540
ttttcctttt gctgggaata ctaatcgtgg tcttctggcc gggtattgca gataaccttg    600
tagaggatgg ccttaccctc aagcccggga ctgatgccta tgaaagctgg ct           652

<210> SEQ ID NO 9
<211> LENGTH: 565
<212> TYPE: DNA
<213> ORGANISM: Drosophila

<400> SEQUENCE: 9
ccgtagttct cccttcgttt tcgtcccctt ttccccgcaa acaggtaaac aaaaaatcta     60
ctgtgcgaaa tgcacgaaga agtgctccgg cgaggtgctc cgcgtggcgg acaaccactt    120
ccacaaggcc tgcttccagt gctgccagtg caagaagtcc ctggccaccg gcggattctt    180
cacaaaggac aacgcctact attgcatacc ggactatcag cggctgtacg gcaccaagtg    240
cgcaaattgc cagcagtatg tggagggcga ggtggtcagc accatgggca agacctatca    300
ccagaagtgc ttcacctgct ccaagtgcaa gcagcccttc aagtcgggca gtaaggtgac    360
caacaccgga aaggaggtgc tttgcgagca atgcgtcacg ggtgctccag tgtcgcccag    420
tcgccaggcg acgggtggag gcgtctcctc gccagctcct ccggcggaga gtccgacgag    480
agccactgcc caccagcagc acggcagtgt gatctctcat aaggcgcacc tcaaggagga    540
ctacgatccc aatgactgtg ccggc                                           565

<210> SEQ ID NO 10
<211> LENGTH: 685
<212> TYPE: DNA
<213> ORGANISM: Drosophila

<400> SEQUENCE: 10
atcgtcgaga tgccgagatt gttgagcaag tgcagcgtgt ttgccctttg ggcgcctgca     60
gtgctcctct ttgttttggc ttgcgaaaag ggattagccg gagctcagac cttaatcgaa    120
actataacca ccactactcc agcgtcctct ggcggctact gtgcggctgc actttgtgag    180
ctgtacaatg gaacgcattt ggtgcatgtg ccgcataccg catgtggcaa caatggcagc    240
ttttcacccg cctgtggacc ggaacccaag ctcctggaaa tgagcgagag gcgacgtcag    300
ctcctgttgg acatgcacaa tttggccaga tcgaagatcg ccagcggaaa tctggatggc    360
```

```
tatagaagcg ccgcacatat gccgcttctg cgttgggata ccgaactgga gcaaatggcc    420
gccttgcatg ccaaacgctg ccaattcgcg cacgacaagt gccggaatac accgcgtttc    480
aagtttagtg gtcaaaatat tggttacttt tggattggaa gagagttcaa atcgcattcg    540
cgacgcatga aatccttcgt gatcaactgg ttccgcgaac atcaggatgc caatcagagc    600
ttcatcgata gatatcatcc acatccgcaa ggcaagaaaa ttggtcactt cacattactt    660
ggttcggatc gagttaatcg cgtcg                                          685

<210> SEQ ID NO 11
<211> LENGTH: 522
<212> TYPE: DNA
<213> ORGANISM: Drosophila

<400> SEQUENCE: 11
cttaagttct cctcgtcggg atcggccaag tgcgcaagca ggaagtagca caagtgttct     60
gtacaaatag gaaactttaa agcttaatcg gacttcttca actactaata tactaataga    120
cagcaaccta ccctgctccc cttccacggc gtagaaaagc ggtgggtttc cgcccctcgc    180
ctcggatgca ttgatgacat cccgcttatg tgcacggttc tttagcaacg tcttgttcag    240
ctccagccgt tcgcaggcac gatcgtagta cttggcgaag cccttctcgt cccactcatt    300
cggattcgct gcctccaggg ttctcctgta caccgtttcc cccagctcgc gctcgtctat    360
actatcaagg attgcctcga caacaaggaa ctggttattg cgcactgcca ggtgcaaaac    420
tgtataacca tcatcgttgg ttagcagaag actgttcaaa tcgattctgc gcaacagcag    480
cctaatggac tctatattta tatggtttat caccgccaga tg                       522

<210> SEQ ID NO 12
<211> LENGTH: 636
<212> TYPE: DNA
<213> ORGANISM: Drosophila

<400> SEQUENCE: 12
agactgtcga gtatgggtca agaacccatt gcatgacgct ctatgcacga tgcacataac     60
acttgtggcc ctcatgggtg cactgtgcct ggaatgtgcc tacgacttgg atgatgccgt    120
aaacaactac tacgttgttg gactcctgaa cgtcaacaat cacggagcga acacatgcca    180
acgatggagc cctagatgtc cagaacttca caagagttaa cggcgcaagg tgtggagctc    240
gcaggccact ttgaccgccg ccgaggcaac cgttaaggag aacttggagt gggctacggc    300
caagctgggc gttttccgca gctatctggc caactatcgt agtggaagcg ccatggtcaa    360
cgccttcagc gccatcagcc ttttgatggt ggccctggtc accatgctgc gtaactaagc    420
agggattagc tcctactgga gtcaggtgcg atcgagtcac gagtgctcct taggccataa    480
agtatttgta cgcaagagca cccaataaag taacaccttt ttttaaaatt tcaacagtga    540
acatcttgtg cagaacacag accaaatatt ccaaaaatgt ctctcgttgg caagaagtac    600
aagctggaca agtccgagaa cttcgatgag tacctg                              636

<210> SEQ ID NO 13
<211> LENGTH: 628
<212> TYPE: DNA
<213> ORGANISM: Drosophila

<400> SEQUENCE: 13
agcgtccatt gcgactgatc atatccaccg ttccgaaaga tttgtgataa ccacttgata     60
accaaccagc cagtctagtg tctaataaag ttgttattga atttgcccat ttacaagatc    120
```

```
cataaacaag ctgtcaagta atctttcaat catgggtttg acgcgcgtgc tggtgaagga      180
tggcggtttc ggcacccaga tgaccgtcca tgtgggtgac tctgtggatg gggatccgct      240
atggagtgcc cgcttcaatg ccaccaatcc ggcggccatt atcagcaccc acctggactt      300
tttgcagaat ggtgccgata tcattttgac caacacctac cagtccagtg tcgatggtta      360
catggagtac ctggagctgg acgaggagca gagcatcgag ctgataaaga acacggtccg      420
cctggcccac atcgccaagg aacgctatct caccgagtgc tatcaggcgc actgtcggtg      480
caggagggat acccttttgat cattgcctcc attggaccct tggggcccca cctgcacgat      540
ggctccgagt acaccggtag ctatgccgac tttgtgccgg ccaaggagat tacgactgg       600 catcgcgtga ggatcgaagc gtgcttgg                                         628
```

<210> SEQ ID NO 14
<211> LENGTH: 566
<212> TYPE: DNA
<213> ORGANISM: Drosophila

<400> SEQUENCE: 14

```
tcgtggatac aaccccacag ttaaattcaa tgtacttact attttttgatt ttagttatcc      60 tatcagcctt ttaacctggc cttaaaactt tatcagtttc acaaaagatc gttgaaaaga     120
cttacatgag tcgagccaat gatttagaca aaatctaata gaaactacac caaaaaggta     180
caagtgcgat tacatcgcta aaaggtacat acatggaatg gctaaactta accatatcca     240
taaacaatat tagagatgct tttgataaat cctataaatt tattaataaa accgcgctga     300
tcaaaactca gacgcttatt tttcacataa aggtattgat aacacaatac aacacattac     360
aaaacctaat agtaacaaac aaaagcaaac tcactgaaga acataaagtc caatgcttca     420
aagttctcag ttcatttggt aaaagactac ataataccag cgttagacac agtattataa     480
tagaagtccc aacagaacta accaaaatag cagaattcga cgaaagccag ttaagagact     540
tggacgagtc gcagccgtta gaagat                                          566
```

<210> SEQ ID NO 15
<211> LENGTH: 562
<212> TYPE: DNA
<213> ORGANISM: Drosophila

<400> SEQUENCE: 15

```
cccgcttcgt ccaccaacgg cggctgttca gcaagcaagc ggactccgtg accgcggctg      60
ccgagcagct gaacaaggac ctgctgctgg cttcgcagat cctcgaccgg aagtcaccgc     120
gcaccaaggt ggcggacagg ccccagaacg gaccccgcc cgcaacacaa tcagcggctg     180
ccatgttcca ggcgcccaaa acgccacagg gcatgaatcc ggtggccgcc gccgcgctct     240
acaactcgat gaccggaccc ttctgcctgc cgcccgatca gcagcagcag caacagaccg     300
cccagcagca acagtccgcc cagcagcagc agcagagctc gcagcagaca caacagcagc     360
tggagcagaa cgaggccctc agcctggtgg tgacaccaaa gaagaagcgc cataaggtga     420
ccgatacgcg catcacgccg cgcaccgtca gccgcattct tgcccaggat ggcgttgtgc     480
cgtccaccgg aggcccaccg tcaaccccc agcagcagca acagcagcag caacagcaac     540
agcagcagca acaacagcag ca                                              562
```

<210> SEQ ID NO 16
<211> LENGTH: 631
<212> TYPE: DNA

<210> SEQ ID NO 16
<211> LENGTH: 631
<212> TYPE: DNA
<213> ORGANISM: Drosophila

<400> SEQUENCE: 16

```
ccagacaggt aaaaaaatta atagatgatg gaatagttga accatcaatg tctgaatata      60
atagtccatt acttttggtt ccaaagaaac cacttccgaa ttccacggaa aaaagatggc     120
gattagcagt tgactatcgt caaataaata agaaactatt atcagacaaa tttccacttc     180
caagaataga agatattctt gatcaattag gaagagcaaa gtattttca tgtctcgacc      240
taatgtctgg attccaccag atagaactag aaaaaaggta tagagatata acgtcatttt     300
caacagccaa tggctcatat cgcttcacgc gattaccata cggactgaaa gtagcaccaa     360
actccttcca acgtatgatg acacttgcat tttctggtct tgaaccatcg caagcatttc     420
tatatatgga tgacttagta gtaataggtt gttcagaaaa acatatgctc aaaaatttga     480
ctaacgtatt cgagctatgt agacgacata atttgaaact catccaggg aaatgttctt      540
tctttatgaa agaagtaaca tatttgggtc acaaatgtac cgataaaggt atactcccag     600
atgacaccaa atatgaagtt atagaaaaat a                                    631
```

<210> SEQ ID NO 17
<211> LENGTH: 581
<212> TYPE: DNA
<213> ORGANISM: Drosophila

<400> SEQUENCE: 17

```
cgagcgaatc gtgagtgcgg aaaaagaaa atcttttcat cagctggaaa actgttcttc       60
ccgatcaaaa ctgggattcg ggagatttt gaagcccaaa agcagggaac tcctcactga      120
tggccacgcg aggggcgaat gtgatttggt ttcgccatgg attgcgcctc catgataatc     180
ccgctctatt ggccgccctc gccgataagg atcagggtat agcccctaatt cccgttttca    240
tattcgatgg agagagtgca ggtaccaaga atgtgggtta caatcggatg cgtttcctcc     300
tggactcgtt gcaggacatc gatgatcagc tacaggcggc aactgatgga cgtggacgcc     360
tcctggtctt cgagggcgaa ccggcttata tcttccgccg gctacatgag caagtgcgtc     420
tgcacaggat ttgcatagag caggactgcg agccaatttg gaatgagcgc gatgaaagca     480
tccgttctct atgtcgggag ctgaatatcg actttgtcga aaggtatca cacacgcttt      540
gggatccgca attggtgatt gagaccaatg gtggcattcc a                         581
```

<210> SEQ ID NO 18
<211> LENGTH: 229
<212> TYPE: DNA
<213> ORGANISM: Drosophila

<400> SEQUENCE: 18

```
attacctacg agacagtgga ttcctgccat ggatccagac ccctgattgt ggacggcacg       60
ccggcggaac ccaaggaatt ccatttgcc gctcgcctcg gccatcggaa actaacaat       120
gaaataaaat ggttctgtgg cggcaccttg ataagcaatc gcctggtgct cacagcggct     180
cactgctttt tttccgaaca cggtgaggtc aacgttgtgc gcttgggtg                 229
```

<210> SEQ ID NO 19
<211> LENGTH: 632
<212> TYPE: DNA
<213> ORGANISM: Drosophila

<400> SEQUENCE: 19

```
cgagcgaatc gtgagtgcgg aaaaagaaa atcttttcat cagctggaaa actgttcttc       60
```

```
ccgatcaaaa ctgggattcg ggagattttt gaagcccaaa agcagggaac tcctcactga      120
tggccacgcg aggggcgaat gtgatttcgt ttcgccatgg attgcgcctc catgataatc      180
ccgctctatt ggccgccctc gccgataagg atcagggtat agccctaatt cccgttttca      240
tattcgatgg agagagtgca ggtaccaaga atgtgggtta caatcggatg cgtttcctcc      300
tggactcgtt gcaggacatc gatgatcagc tacaggcggc aactgatgga cgtggacgcc      360
tcctggtctt cgagggcgaa ccggcttata tcttccgccg gctacatgag caagtgcgtc      420
tgcacaggat ttgcatagag caggactgcg agccaatttg gaatgagcgc gatgaaagca      480
tccgttctct atgtcgggag ctgaatatcg actttgtcga aaggtatca cacacgcttt       540 gggatccgca attggtgatt gagaccaatg gtggcattcc accgctgacc taccaaatgt      600
tcctgcacac ggtgcatatt attgggcttc ca                                    632

<210> SEQ ID NO 20
<211> LENGTH: 617
<212> TYPE: DNA
<213> ORGANISM: Drosophila

<400> SEQUENCE: 20
cgaatcgtga gtgcggaaaa aagaaaatct tttcatcagc tggaaaactg ttcttcccga       60
tcaaaactgg gattcgggag attttttgaag cccaaaagca gggaactcct cactgatggc     120
cacgcgaggg gcgaatgtga tttggtttcg ccatggattg cgcctccatg ataatcccgc      180
tctattggcc gccctcgccg ataaggatca gggtatagcc ctaattcccg ttttcatatt      240
cgatggagag agtgcaggta ccaagaatgt gggttacaat cggatgcgtt cctcctgga      300 ctcgttgcag gacatcgatg atcagctaca ggcggcaact gatggacgtg gacgcctcct     360
ggtcttcgag ggcgaaccgg cttatatctt ccgccggcta catgagcaag tgcgtctgca     420
caggatttgc atagagcagg actgcgagcc aatttggaat gagcgcgatg aaagcatccg     480
ttctctatgt cgggagctga atatcgactt tgtcgagaag gtatcacaca cgctttggga     540
tccgcaattg gtgattgaga ccaatggtgg cattccaccg ctgacctacc aaatgttcct     600
gcacacggtg catatta                                                    617

<210> SEQ ID NO 21
<211> LENGTH: 573
<212> TYPE: DNA
<213> ORGANISM: Drosophila

<400> SEQUENCE: 21
aaggcctgcc aggcggtgct caatggggag tacatgggca agacgcggt gccctactgc       60 gagaagtgct accagaaggg attcggggtg aagtgtgcct actgcagtcg cttcattagc     120
ggcaaggtgc tccaggcggg cgacaaccac cacttccatc cgacctgtgc ccgctgcaca     180
aagtgcggcg atcccttcgg cgacggcgag gagatgtacc tgcagggcag tgccatctgg     240
catccgcgat gcggtccggg tccctccgag tccggcataa ttttgaacgg cggcggaggc     300
acttcgtcgg tggtcggagg tgcctccaat ggcaacttca cagacactga atgcgaccgg     360
atgagctcca gtgcccttag cgagatgtac atccgctcca gaactccgag ctttaatggt     420 tcacttttatt cctctagccg caagcactac cgaacggtga gttcgggtct gatactccgg     480
gagtacggac gacccaatgc cgaggacatc tcgcgcatct acacctacag ctatctgacg     540
gatgcgccgc actatctgcg caagccgatc gat                                   573
```

<210> SEQ ID NO 22
<211> LENGTH: 614
<212> TYPE: DNA
<213> ORGANISM: Drosophila

<400> SEQUENCE: 22

| | | | | | |
|---|---|---|---|---|---|
| tgcaagccgg | gctttgttat | cgcacaaatt | ttatgtaaac | aaaagaaaac | ttcgatctgc | 60 |
| tccatgatca | ccttagcccc | tctgatcgtc | ctagtcctcg | cttgcctggg | aaacacggcc | 120 |
| agcgagaagt | tgcccaacat | tctgctgatc | ctgtccgacg | atcaggatgt | ggagctgcgc | 180 |
| ggtatgtttc | ccatggagca | tacgatcgaa | atgctgggtt | tcggtggcgc | cctgttccac | 240 |
| aacgcctaca | cgccctcgcc | catctgctgt | ccggcgagga | cgagtctgct | gacgggcatg | 300 |
| tatgcgcaca | atcacggcac | ccggaacaat | tccgtaagtg | gtggatgcta | cggaccgcac | 360 |
| tggcggcgtg | ccctggagcc | ccgggctttg | ccatacatct | tgcagcagca | cggatacaac | 420 |
| accttctttg | gcgggaagta | cttgaatcag | tactggggcg | ctggggatgt | gccaaagggt | 480 |
| tggaataact | tctacggcct | tcacgggaac | tctagatact | ataactacac | actgcgcgaa | 540 |
| aataccggca | acgtgcacta | cgagtcgacc | tacctatccg | atctgctaag | agatcgcgcc | 600 |
| gctgactttc | taag | | | | | 614 |

<210> SEQ ID NO 23
<211> LENGTH: 613
<212> TYPE: DNA
<213> ORGANISM: Drosophila

<400> SEQUENCE: 23

| | | | | | |
|---|---|---|---|---|---|
| caaaaatgat | gcagtgcagc | cgaatgacga | cgacgttgaa | gatgacgaac | cttctgctag | 60 |
| cagtggcctg | cgccgccgtg | ctgatgggat | cggcgacggc | ggacgaggag | gagggtcca | 120 |
| tgaccgtgga | cgaggtggtg | gagctgatcg | agccctttgg | cgacgcctgc | acgccaaagc | 180 |
| cgtcgaggga | gaacatcgtc | gagatggtgc | tgaacaagga | ggacgccaag | cacgagacca | 240 |
| agtgcttccg | ccactgcatg | ctggagcagt | tcgagctgat | gcccgaggat | cagttgcagt | 300 |
| ataacgagga | caagacggtc | gatatgatca | acatgatgtt | cccggatcgc | gaggacgacg | 360 |
| gcaggcgcat | cgtcaagacc | tgcaacgagg | agctaaaggc | cgagcaggac | aagtgcgagg | 420 |
| cagcccacgg | gatcgctatg | tgcatgctgc | gcagatgcg | ctcttcgggc | ttcaagattc | 480 |
| ccgagatcaa | ggaatgaggc | catggagctg | ctcgctggcc | caccattgca | tgttctccct | 540 |
| cccttttttt | tttgttagtg | attcagttcg | atttaattac | caaagctaga | gaacttggag | 600 |
| tggtttccca | aac | | | | | 613 |

<210> SEQ ID NO 24
<211> LENGTH: 631
<212> TYPE: DNA
<213> ORGANISM: Drosophila

<400> SEQUENCE: 24

| | | | | | |
|---|---|---|---|---|---|
| ccgagtggcg | tgcgaaatac | taattctagt | ccgaggttcg | cgatcgaacc | cttgaaaata | 60 |
| ggaagaatgt | ttgccccgcg | agtggctgtt | ctcctggtgg | cctgtgtgtc | cttggcctcg | 120 |
| gcaggaactc | ggcaactgtc | tgtggatgtc | cagccgccgg | cgacgctcgc | caccgagcta | 180 |
| aatgaatacc | gcctggccga | gcacatcacg | ccggttaact | acaacattac | gctgcgtccc | 240 |
| tatttgctgg | agaccgatgg | caacaagagg | ttcaccttcg | atggcgaggt | ttggatcgag | 300 |
| gtgatttcca | accagaccac | caacgacatc | tatctgcact | cgaaaaacct | cacatattcg | 360 |

```
gtcagggaat actggcaaaa gccaaccacc gaagtggcca atcctacggt catccaaatt      420
agtgccacca atacaacgaa ctatgatacg gatattgtaa agctgacggc gtcaactgct      480
ttgaccgcca atacgacata tatactgcat ttcgtgtaca ccggtctgat ggaggacgat      540
atgcacggtt tctatcgcag ctcctatgtg gacgataaca atgttaccaa gtggctggga      600
tccacccaat tccaaaccca tcacgctcgt c                                     631
```

<210> SEQ ID NO 25
<211> LENGTH: 635
<212> TYPE: DNA
<213> ORGANISM: Drosophila
<220> FEATURE:
<221> NAME/KEY: misc_feature
<222> LOCATION: (1)...(635)
<223> OTHER INFORMATION: n = A,T,C or G

<400> SEQUENCE: 25

```
tccttggcct aacataacat attttcgact attttcggct ttgtaaaaca aaatttggta       60
aaaaggttca atatgttgcg aatgttgcgt cagaaatgtc gttccctcgt agatcggagc      120
atgccgtgcc tggagtcttt ggtaaatgcc tgttctctat tcaaggtcga ttggtccaag      180
aatctgagcc aaatcaaaac cccggccgac tgcgttggct ccagtgtgct ccggcagcac      240
ctgttacgcc gcaactacag cagtcagtct tccgccgatg attgcgggcg gccaaaggat      300
tgcgatcagg tatcgacctc caagggctgt ggtcctgctc ggttcaaggg caccatttgc      360
gatgcagtca agggcggtaa gcgcaagaag aaggaagagc caagaagga aaagtccaac       420 aagccgaagc tgccagcaaa gatgaggtcc atgtggtata ccccgactg cgagtacgtg       480 ccaaagtgcg atgtgccagt gcggtacgac atccagcact accgcatatc ggacaaagag      540
gcccgccagt accaggtgac gtggaacgag tgccccggt tggtgatcaa gcccaagaag       600
gtgtgcatcc acgcaaagcg accgcgtncg aagcc                                 635
```

<210> SEQ ID NO 26
<211> LENGTH: 749
<212> TYPE: DNA
<213> ORGANISM: Drosophila

<400> SEQUENCE: 26

```
ctaaattcat acgttttcat tcgtttcgtt ttctatagtt atttgaataa aaacatcaaa       60
atttttcaaa aaaaaaaaa acagtatcaa aattttgtcc aagtccgtat tgcttctttt       120
tgttctccca ttttgtgtga accatctaga agaaagtaaa gtaaaaacgg tggccctgtg      180
aaaattgttt tgatatatga gaagagtacg ataacgaatt cagaaaaaaa cattgcgaaa      240
agaaagagga agtagtgaaa caggcgccaa acccattacc aatcgagaag ccaaaatgac      300
tgagagcatt gtgtgtcaca agtgccagga ggccatcacc aagcgtatga tcaccgccct      360
gggcaagacg tggcacccgg agcacttcct gtgccaccac tgcgatgagc agatcctgga      420
tgccaccttc aatgttcaga gcggagaacc agtgtgcaac aagtgcttcg tggagcggta      480
cacctacacc tgtgccggct gcaagaagcc gatccttgaa aaaccatct gcgccatggg       540 ggagagctgg cacgaagatt gcttttgctg cggcggtgcc tgcaaaaagc cgctcgccaa      600
tcaaacgttc tatgagcgcg acggcaagcc ctattgcaaa aaggattacg aggacctctt      660
tgctgccagg tgcgccaagt gcgagaagcc tataacggac tcagcggtgc tcgccatgaa      720
cgtgaagtgg catcgcgatt gcttccggt                                        749
```

```
<210> SEQ ID NO 27
<211> LENGTH: 375
<212> TYPE: DNA
<213> ORGANISM: Drosophila

<400> SEQUENCE: 27
aaatttgaat cgcatgctca aaatgtttcc cggcgactat cgcatattcc ccaaaacctg      60
gctaatgcca accgatgcct acgatgtagc catttatgcg aacaaacaca agcgcacttt     120
tatcctaaag ccttattcgg cgggccaagg acgtggcatc tggataacca ccgatcttcg     180
tactgtgggc aaacgggaga agctcatctg ccaaacttac atagaacggc ccctacttat     240
agatggctac aagtttgatc tgcgcgtcta cacacttgtc acctaggtgg atccactacg     300 cattttgtg tacaatgagg gttctggcac gctttgccac ccagaaattt gtgccaccaa     360
caacgggtaa tagcc                                                      375

<210> SEQ ID NO 28
<211> LENGTH: 373
<212> TYPE: DNA
<213> ORGANISM: Drosophila

<400> SEQUENCE: 28
caagttagtg ggatcctggt caaatgtttt aacaaggcca ttaaaggtca tggcggctgg      60
cggctgttga gtcaaacgtt tctggcgcgg cggtggcttt atgtttagct gcacgtgctg     120
caccttcgaa cattcaatag gttcatttaa atcacattcc actggcgcag ggagcttggt     180
atccagcacc ggcttatccg tcagtataga cacattttg tcataaacct tgctgatctc     240
atccagcaaa aagtttccct acatatcat gtgctcgtaa tttccgcagg tattactgct     300
ttgtttcgac atttcttctg ctgggctcct cttgtggttc ttctgaagaa tctctgccgg     360
cagccagtta tcc                                                        373

<210> SEQ ID NO 29
<211> LENGTH: 323
<212> TYPE: DNA
<213> ORGANISM: Drosophila

<400> SEQUENCE: 29
aaatctgaga aaaattcaat gtgtgtagat tgtccaggtc ttttatcaaa tcacaatcgt      60
tgttgcaaga aacttagcca ccgtcctcgc atcgacccac cgtaatggcc gagcttctgt     120
cccgcgagaa ggagctcttt aagataaacc aggagctgaa tctcctgacc ctcagtccag     180
ctgccgacgc catgtatccg gcaaagggt catccaaatc cacggcggtg gcggtgccgc     240
gcttcgccac cttccagaaa caaaggggc cgagcagcct gctccggaaa aagggtgctc     300
ccacggcgtg cacgaaggca gcc                                             323

<210> SEQ ID NO 30
<211> LENGTH: 509
<212> TYPE: DNA
<213> ORGANISM: Drosophila

<400> SEQUENCE: 30
tttgtcttcg caatagagtg taatagatat aaagcgatcg gaaattcaga acgataagtt      60
tgccccaccg ccgttggcca tgcaaaacga caagtatcca gcgccaatag gcttttatcc     120
accacaagga cagccgggat atccacaacc agcgtcacag ccaggatacc ctcagccagg     180
gcagccgcaa cacatcacac cggcggagac atacggacca caaccaccgc caatgccacc     240
```

```
gcgggatcca cacaccagag tggatccacc aggaggatgc tttcagcgca accaaaagaa        300
caaacctcaa tccaatgctg tgggcgcagc tggtctcatc tttatctctg gaggtatgaa        360
catagcgtgg gcgattggct tccaaggacc aatctattac caaaccacca agcacaatta        420
cattgcctgg ttcataggcg ccattattgg agctttggtt ccgatggcgc tgaccaacaa        480
ggtggccaaa aaatatattc tgcaatttt                                          509
```

<210> SEQ ID NO 31
<211> LENGTH: 465
<212> TYPE: DNA
<213> ORGANISM: Drosophila

<400> SEQUENCE: 31

```
aaccatgggg tgatgtgaga tcgtcagata gccagcttac cctgaagcag agtgagagcc        60
gggagacgat aagaccattt gggtatgagt tagctgatcc atccgagctt agctcctacg        120
acattcacct gggtcttcta gtagagaagg gtttaattga cattaactca ttggacaagc        180
cctcgaacga ggaccttaca gactatccgg actatccggg tcttttgtcc aggtcggcgg        240
atcgtagtgg aattgctgag atagtcaaag aaatgcgaaa cgaattcatg acaagctga         300 cctctaaggc taagagcttc aaagaaatcc tgattaagaa aggcttaatg gagccaaagg        360
acgaaaatcc tgctatgcag aagaatgact ctgagaataa agcaaagacc aaagacgatt        420
ctcagattcc agatcgtaaa gacaaagcgg gaaaacctct aagag                        465
```

<210> SEQ ID NO 32
<211> LENGTH: 598
<212> TYPE: DNA
<213> ORGANISM: Drosophila

<400> SEQUENCE: 32

```
aactctcgga cctttcgttt cggccagctt ctaaattttc caaattccaa attttctt         60 caaattaatt tgaccaaata gacgctcgac gggctcaaga tgtgtgacgg atgtggatcg        120
ttggagccgc gcggatgccg cagtcgggag ttacgatgcg gcatcatgta caccacttgc        180
gactgcgtga agcggaacgg tctgcaggac aagtgcccgc ggtccgcctg ccagggccga        240
ccggcctgcc tgtgcttccc cttccccacc tgcggtccgg cggcattccc gctgcgctac        300
gctaacatga tgatgggcgt gaacaataag cgtatgcgct gtgccgccac tggagcacca        360
aatggcggtg ccggatgcgg tggacgcgtt gccggcggct gctgtggatg cggtccctgc        420
tgctgagctt tatgcccact acgctgatcc gtcaacaatg atagcatgtc ctgggctttg        480
tgagcgtaga ggtaggatcc atggaccaaa tgctgttgcc aggccccaaa tccttcatga        540
ccctttgacc tccatccgca tcctgtcgcg tgtggcttat aagtatttcc tggcaagt         598
```

<210> SEQ ID NO 33
<211> LENGTH: 552
<212> TYPE: DNA
<213> ORGANISM: Drosophila

<400> SEQUENCE: 33

```
cccagtgcta gtacacaacc ttttgtaaac ctacaaaaaa aattccacca aaattcaaaa        60
ttcaaagttt ttagttttg cctttcagc acaagtgaaa aattaagtag tatgcgctta         120
tttggcagag taaccaacat tttacagata tctagatgcg ttagctacca tgctccgcta        180
taccgaccgc gcagcctact ccatgcagaa cggttgaggc aactatgcac cagtgcctcc        240
tccggatcaa agtctagccg gaggacgaat catccgtgtc gcgtccgggt gcagaggtac        300
```

```
tcccaaaagg gtagcaatgt gttctcggtc agcgataacg tggatatgct gcgcaaacgg    360
attagctttt ccggcaactc gagcaatgcg cccaagatca tgcccattgg actgattaca    420
ccggaaacgg gtgatggcaa ggatctgaag atagtcattg tgcccttgga tctgtctggc    480
atggatggca acgaactcaa ggacacgctg gaaaccatca acaagttgcg cttgtacgcc    540
aaccacatcg ag                                                        552
```

<210> SEQ ID NO 34
<211> LENGTH: 684
<212> TYPE: DNA
<213> ORGANISM: Drosophila

<400> SEQUENCE: 34

```
tcgatcacta gatccccaca taaaccacca actctatacc cacacgtgcg ccttgaagcc     60 tagggtcat tgcacttgcg aactatgtga cagtggcact acggaaacag cgccagggcc    120
gggtttacca ctgcgtctcc ggagcaccag gatccggaaa cgcaacctaa gattaagacg    180
tcgctgaaca caggatccga ggaccaacaa ccgatcccg ggcgatcaaa acccggcgc    240 catggccatt cacgagcaga tcgacaacct gaacatctgg tggtttccgc gcgacttctg    300
tcagtcgcga ttcggggagt tccagcggag cggcaccaac tcctgcacca tcatttccct    360
aatactggcc gacaaggtgg ccaaggcgga cagattctat cacagggtct ccgatctgcc    420
gctgcgggga tgggagctct tcggcaacgc cattaacgac ggaaacagcg tgtaccacaa    480
tgtgattaca actaatacgc cgcacgccag gaatctcaac ctcaacattc cggatgctat    540
cgccgccatt cggtcgcagc acaagatgaa cttccggctg gaggagtggt tttacacgca    600
catggaggcc gatcccagca atcccatgta caaccggaac gttgctgtgc agttgtcgcg    660
ggttttccag ataacactcc agat                                           684
```

<210> SEQ ID NO 35
<211> LENGTH: 675
<212> TYPE: DNA
<213> ORGANISM: Drosophila

<400> SEQUENCE: 35

```
cggggagagt tccgtccaac gcggttgtgc caaaatgatt atcttgtggc tgattctggc     60
cctaagtgcc ctgctctact ggctccacag agccaacaag gattaccaca tcctgtcctt    120
cttcaccaaa agaattcgat taaaggatgg aaccccctgtg gagatcatcg ctcccatagc    180
caagggaaaa acaatattcg gcaacaccct tgacttgtat gggcgagatc acgctggtgt    240 ttcaattac tcgcgtgagc gtgctaagga aatgggtact agctacatag aatatgtctt    300
tggaaaggcg atttacaaca ttatcgatgc ggatagcgcg gaaaatgtgc tgaatcatcc    360
gaatctcata accaaggggc tcgtctacaa cttcctacat ccattcctaa ggacgggctt    420
gctgacatcg actggcaaaa aatggcatgc tcgccgcaag atgctcactc cgacattcca    480
tttcaacata ttgaaccagt tccaggagat ctttaaaacg gagagtcaaa agttcctgct    540
acaatttgag ggtcaagatg aggtaaccat aacgttacac gatgttattc caagatttac    600
tctaaacagt atttgtgaaa ccgccatggg tgttaagctc gacgagatgg ccgagaaggg    660
ggatcgatac cggga                                                     675
```

<210> SEQ ID NO 36
<211> LENGTH: 560
<212> TYPE: DNA

<213> ORGANISM: Drosophila

<400> SEQUENCE: 36

```
cacagtttgg acacttatat taccaaaatt tctgttaaaa ttatttgata aaaaattatt        60
cagttcaatc atgttcaaag tgcgcagctt ggcgctcatg aaattgagtg aaggcgtttt       120
cggcgcacga ctaatggcca aatcgccgaa ggattcgggc aaggattctt gcaagggtgc       180
cgattccaaa aagaagaaag acaaaagaa gaaggatatg tgtggcagaa ctgttgttcc        240
cacttcacca cgttgcaaaa acaaacccgg cggctcagac aaatccaaag atgagtgcaa       300
gaaaaagtag cagagttcga ataaatcatt tcagccccctt aaacaaaatc acagcaggcc     360
tttaaacaaa cttcaagctg ctttggccta agtcaaaatt aaagttacaa agaaaaaaa       420
aaaccatgtc ccgactttg ctgcagtgcc gcagaacttt gctgatcctt cgccatcaaa       480
cggcggtgga aaatgagaaa ggactctttg gcaaactgct gggaaagtgc cagtcctttg      540
gcaaggatga aaggatctt                                                    560
```

<210> SEQ ID NO 37
<211> LENGTH: 529
<212> TYPE: DNA
<213> ORGANISM: Drosophila

<400> SEQUENCE: 37

```
aaaagtactc ggtcggcaaa acggcaagcg gcgaaaaaca gtgaaaaaaa aaggggggaaa       60
gcgaaaagac gtgctcagga actgcggtcg aagtctttgt gagtgtgtgt gggtgcagct      120
gtcgccaaac aaatgaaaag cgcctggctt gcattaaaat cgaaaagtgc attgcatccg      180
aaaagcgaat atccagtatc caatatccat tatccgaaag cagctaatta ccgacagaca      240
aggaattatt tagagatcgc cgccaaaatg tcggaggaag tagatcgcaa cgatccggag      300
ctcaagtacc tctcggtgga gcgcaaccag ttcaacgatc cggccacgca ggccgagtgg      360
acacagaagc gtctggtgtg ggtgccacac gagaaccagg gcttcgtggc cgccagtatt      420
aaacgggagc atggcgacga ggtcgaagtg gagttggccg aaaccggcaa gcgggtgatg      480
atcctacgtg acgacataca aagatgaat ccgcctaagt tcgacaaag               529
```

<210> SEQ ID NO 38
<211> LENGTH: 593
<212> TYPE: DNA
<213> ORGANISM: Drosophila

<400> SEQUENCE: 38

```
aaaatattac actatattat ggattattta caaaatgttc ctgttttgaa gtcatttcac       60
cccgaatccc cacttcgaac cgtccagagt ggtggtggtg accccgaccg tcgtccaacg      120
gctgctcaat caatcaatat tgaaggttcc cacaccgcag gcgaggcact ggaactccat      180
gggttccacc cccttcctc gccagtgtgt tggccatttt gtttgctatt tctgtttggc       240
tttttcttgt gctgaccgct aaatataacg ttggacggct aagccgcgga ggtgtggagg      300
gtcgaccggc ggtgcaataa tctgtgaggg gaaagaggg tgggatgaaa tcggatacgg       360
gccaagtagg aagttacctt gagtgcattt ctatatatct gtatcgacag tgacaatgcc      420
cgcccaagtc caagttgcag ttcattcatg gtttcagtcg gttcgttttt tcgttctctt      480
tccgagtttg gtgtaaacag gttcacaggc tcacggcaca gaaaccgcac aagttttttcc    540
cggctgctca tcctcatcct cggcctcgtt caccttccac ttttcctcag cca            593
```

<210> SEQ ID NO 39
<211> LENGTH: 598
<212> TYPE: DNA
<213> ORGANISM: Drosophila

<400> SEQUENCE: 39

```
cttattcgga aatacgcgcg gcgtagttgc acaaaaccaa caagaacaac agcgacggaa      60
aagagcaaca actaaagcaa taactacaac aacacacggc taatttcaca aatcaaaaaa     120
ctgaaacggc aaaaattata aatattata   agtgcgcatc gccttttag   agataagagt    180
aaagttttgc ttttgcactg caaacacaaa aacaacgcag agtaagaaag aaactcaaca     240
gtcggccagc tcaaacaatc aaacacaaaa tgcacagcaa caataatagc agcagactca     300
acaacaacat aagcaacaat tattatcaac aaaaacaatc gcttatacgc tatttggatc     360
gagctgctgt tggtctgaac ggtgtcgagt tcgagggcag caagctgcat gccgagcagc     420
tggacaagaa ccagcggcgt agccagcgta accagcgcaa tccgtatccg ggtatgcccg     480
gtcccggacg ccaggcggac tttccgctgc gcattcttgt gcagagcgaa atggtgggcg     540
ccatcattgg tcgacagggc agcaccatca ggacgatcac acaacagagc cgtgctcg       598
```

<210> SEQ ID NO 40
<211> LENGTH: 557
<212> TYPE: DNA
<213> ORGANISM: Drosophila

<400> SEQUENCE: 40

```
tgctctggcg cgatcgaatt tgcctggaat tcgggagtca acataatatt ttcgaaagtc      60
accagctata gcgaaaatag tcgcggattt tcaacaaaga gcaatcatag tgatggtata     120
aaagagggga aggacgaaag caaagagagc aaaccgaaaa cagttactct gcccatgcgc     180
acagctgacc cagaacctgg cataacggta agtaattgt   gtcgtacaac aagcgaaact    240
tgacagcgaa agggaaccgg aagtcgccta aaatcgcgga gcggaaagga atcagtccg      300
ccaaccgcgg gagctgaaaa tcgaaatcac aacccacaaa agcgattcca aagtgctatc     360
ttggtgctac tcccatacaa aatgttccaa gtcctgcccc gtccgtcaag atccacgttc     420
cactgcatag cggcagccgt tgtcacagtc gtcctaatgt catgggcccg accgctgggc     480
gtgctattcc tgggactact tggctactgg atctactgga cgcgctgcag cttccgcgtt     540
gtgcctacgg acgagct                                                    557
```

<210> SEQ ID NO 41
<211> LENGTH: 550
<212> TYPE: DNA
<213> ORGANISM: Drosophila

<400> SEQUENCE: 41

```
aattcgctac ctgaatttta ttctatttaa gttcacaacc atactgatac cacggaatac      60
atctttaagg tacaggatta tcaccatacc gactagaaac taacccgaac atgggcacgt     120
caaatggata atatagaaca agtgaccgag cacataaagg acactgaatt ttcacacaga     180
cacgtattat cgggatgtcg cggatccctc gtcaagtata aattaaagat gcattatttg     240
caggccatct ggtagaggaa ctggatgatc gatcgagtcg gacgaccagt catgcaatcc     300
ttgagcaaat acggaggaac tccgtgctta gccagcattc cggtgccgtg ggtatccagg     360
tgcacccagt cggagcaggg aaccagttcg taaaggatag cagccgccaa gcaggaggat     420
gcgtgtccct ctcccgtgct gcatatatcg taggatgcac gggggccac  taatttgcgg     480
```

```
aagtacctcc ataggggcat gcgccacaaa cgatcgccgg tgagagctcc ggccttttgg      540
aaattcttcc                                                             550

<210> SEQ ID NO 42
<211> LENGTH: 643
<212> TYPE: DNA
<213> ORGANISM: Drosophila

<400> SEQUENCE: 42
aaaagaatcc accaattgtt tttttattt tactgataac attcaaaaat ttggacaaat        60
gatacacttg gaatttggag agggttagtt ttcgcgccac taatagttgc gcttcatttg      120
accggtggca aagagcacgt cgaggatttt caggaactcc cggtagttga actccatgca      180
catgcccttc ttcacgccga agcacttgca gatcgcttgg aactcgcggc tgctcagcat      240
tacatgcatg tcgcgcaccg tgatgccgcg caggaattga ttctgcgtga tcgagccgca      300
ctgttcgcga tcgaagtcct tgaacagctg actcagattg gagatctcgt ccggtttgcg      360
ggccaacttc atcagggcct gcgagcagat ggttcgctcg tcgaagctca ggaagcagtc      420
gacgcagtcc agattgggca aatggagcag tggcacggcg gtcaccacct ggtcacccat      480
gttcgtgtcc agttggatga agatctcgtc gagggccttg cagaaatcgc gatagcgaat      540
gcaggacacg cgattcggtg aacggaagat gttgcacaag atgttagctt cctcttcctt      600
gatgattaca cttgagttat ccagggctcg cttgaagtcc gat                        643

<210> SEQ ID NO 43
<211> LENGTH: 627
<212> TYPE: DNA
<213> ORGANISM: Drosophila

<400> SEQUENCE: 43
attttttcat acgctctggt cgcgcttaca cattacgatt tctatctctc cgctcttctt       60
cattttactt gatttccatt tgtcgcttcc tccgcttttt tttgtatttc gctggcgaga      120
tttcttttca cgttgaattt atactatatt gcatttatat tattgcgctt atcactggcg      180 cttttgttgct ggcttcttgc ctttcgctct ttttggggct caaattaaat ttacaatttg     240
tttggccaaa tgcaaaaagt tcaaccaaat gctgatatcg ggacaaagaa aaatggctgc      300
actgcgagtg aaaaaacgag ttaaagagta ttttgaaca aaggaaccgg aaagatgcag      360
tactcttgtg actattttga aatttaagat agcaaccaaa tacgcttctg attaagttgt      420
agtttatata tgcagatatt tgtaatattt taattcttaa agcgaaagaa aggtcaacgc      480
ctgtacttac atgccctaaa gttgcgggtt tgtattttc ttctgttcaa aatgccttt       540 ccatatatat cataaataca tatacataca tacgtataca ctactgcagt tatcgctgtt      600
ttattttagt atttgtgaac ttagttt                                         627

<210> SEQ ID NO 44
<211> LENGTH: 595
<212> TYPE: DNA
<213> ORGANISM: Drosophila

<400> SEQUENCE: 44
aactaaattc atattgttgc tcacacaaaa gacacaaaaa gcattaaaca aattctggag       60
ctgcagtcaa aagtaatttt ataaaattaa catagtgcgt ttagacgaat caaatgcaac      120
cgaaaactgc aatgccgcct tctaagctaa attgccaatg gaaccgccgg cggtatctgc      180
aacaccatgg aggtgacttt tcggatgagg aggaggatcc caggctaagg ggcatcctgc      240
```

```
ggagaaccag ctgccagcgt taccgtgaac gattgcgttc gaaccgccta tcacagctcc    300
tccatggact ttccatcgtg gcgacggtaa cactgggggt tgtcctgatg ttcttccttg    360
gaatgaagtt atccacggag cagatggatt atcccgcacc acgtgaggaa ggcctttggt    420
tgggtttcct cagactgctt ggcttggagc aggaggatta tctctcagga gacttgtatg    480
tgcataataa agatactttc tgcagtcccg aggctctgaa cttggaacgg atctttcgat    540
atatgggcag ggtggttctg aatcaggagc aggcactgtc tcgcatggaa agggc         595

<210> SEQ ID NO 45
<211> LENGTH: 618
<212> TYPE: DNA
<213> ORGANISM: Drosophila

<400> SEQUENCE: 45
atgactgtgc cgtgggtgga gggaccactg tggaggggcg gttaacctgg atctgatctc     60
ggcttacgat caaacccagc ctgtggcaca gctccttaaa ggctttgtga gaaactatgt    120
cttggtagcg agttgattcc gtaaaggtga aaaatttctc aaaagccttt atgcactcga    180
tttggttttc gatttccagc tccgtatagc tgcgatttga gcacagggtg catctgggac    240
acacggatcc atcgccaccg tattcatact tctcgttcaa aagatcgttg acccggatga    300
ggaattgggc aattagaacg gtctcaggtc tgttcgccaa cttcgcctga tcgcccacag    360
ccagctggag gcactgttta ctgtggttta ctagagtatt tcggtccaaa ggctgcatct    420
gatcgtgctc tttggtggtg aaagtcatac taagaccttg cctcctggt aatacaccaa    480 ccgcgatctc ttccagaggc atttgctcgt ctcccagttg acttagggtg tcaaagatct    540
ggcgctcgag aaaaatccca ttttcaacac gattcacggc atcaccaacg acctcgggac    600
gcagcaatgt tgtagttg                                                 618

<210> SEQ ID NO 46
<211> LENGTH: 550
<212> TYPE: DNA
<213> ORGANISM: Drosophila

<400> SEQUENCE: 46
cttcgataca cttctaaatt tctctgatca aattttataa gaaacaaaaa acaaaaatta     60 acttttact ctttcggttt attctagtcg aaacttaaaa tgtgctctcc gtgcggtcct    120
tgtagtccat gcgatccctg ctgcggtccc ttcgagtgct cacccaagtg ctacaatgcc    180
gcccaattgg aggccttgcc acaatgtgct ccacgtattc caccaccctt ccccaaatgc    240
atcaccgtgc agcaaccacc acgcatgatc tgcaagaaac gcgttgtgtt cacggagaag    300
attgtgccgg agccaatggt ggttaaccga tgcaggcaga tcaccattcc aaaggtcgtt    360
gatgccacgc gggtgatcaa ggtgcccaag ctgatttggg tgtcgcagat ggtgcgagaa    420
cccagagtaa tctactaccc ctcgatgatc cccgacccct atggtgtgtg ctatcccaag    480
cgcgtctgcg aaccacgtga ggtgtgtcag tcgatcctct gccagccgaa gccccaaacc    540
atcgacattc                                                          550

<210> SEQ ID NO 47
<211> LENGTH: 560
<212> TYPE: DNA
<213> ORGANISM: Drosophila

<400> SEQUENCE: 47
```

```
cacatctaaa acaaaaaaat gcggtgcggt cagtagttaa attgcgaaat tgaaatcgaa      60
gtaagctcgt ggcgtcttac cagttttacc caaaattatc tcgttttgat ttgaagactc     120
gctgcaaaat aattttaatc aaacaaaatt aaaatgcttg ccaaaagcaa accgctgatt     180
ggcatgtctc acttgctgca aaagcaggtt ttaggctttc tgcctccgtc ttcgtttcgc     240
cactttaact ccgagggcaa tttgtactcc caggatggct gggagagtgg ctatccggcg     300
cccttgctgc cgcgcaagga cctaaagccg ttggagaaga agacagatc aaaggtatac      360 gatgcctgtt ggcaaacgac gcggcggacc gaatacaagt gccgttcgga tccagagttt     420
cagatgcacg cctttatcga ttcgcgcaaa agttgtttag aagaccctg cgccaccgag       480 atgttggcca tcgatctcac ccactataag ccctcggaca tgggcaaacg aaagtatccg     540
cgcacctggt tcgaatgtgt                                                 560

<210> SEQ ID NO 48
<211> LENGTH: 593
<212> TYPE: DNA
<213> ORGANISM: Drosophila

<400> SEQUENCE: 48
aacaacatcg ttcttccaaa attaaaaaaa aattatataa taattataaa aagtgaaaaa      60
catagtaaaa ctctcacaaa caagaaacga tgtccaacgt tattaagaag gtgattccca     120
tgctggaccg cattctaatc cagcgtttcg aggtgaagac caccaccgcg ggcggcatcc     180
tgctgcccga ggagtcggtg cccaaggaga tgcagggcgt ggtggttgcc gtcggacccg     240
gagcccgcaa tcctgctgga gctggacact tgtccgttgg cgtcaaggag ggcgatcgcg     300
tgctgttgcc caaatacggt ggaactaagg tcgatatgga cgacaagcgc gagtatgttc     360
tgttccgcga gagcgatatc cttgctaaac tggaatagat ttgcaacact ttccgaaaca     420
tcaaagccga tatacacgat atacatataa tgctccaagc aatactcatc ctcctatctc     480
gtcacttatc ttcggtggag actgtcattt tgcttccgaa ttgcgttcga aactaaatga     540
ttataatgaa atgttatatt tgggaaatgg ccaatctaca cactccacac act            593

<210> SEQ ID NO 49
<211> LENGTH: 662
<212> TYPE: DNA
<213> ORGANISM: Drosophila

<400> SEQUENCE: 49
ttcaagcttc gattttttcca cttacgccca cgtaaccagt agccaaatca gaaccggaac     60
gatcgccacg atgccggagg acgtaatggt gcccgctggg gactacaagc tggtcaagca    120
gatacgccgg aaccaggaga cacgtcgcaa gaaggacctg ccgtggtcga agaggatatt    180
cgacatagac gagcacaaat tgttcggacg cacagctctg ggttggatgc gtatcactgg    240
cttctacctg gtactatacg ccctaatcgt gtgcattgtg gccttttggt tgggcatctt    300
tatgctggcc atcattgatc gaataagcc gcgctggctc aagggtccgc cgggtctgtc      360
gatggtgccc aaccagaatc gatccgtgct ggcctacttt acgcacatca tgagtgaggt    420
caatccgatt gcggaccgca tcgacgattt cctgaacaaa ttgaacgaca atgccattga    480
cttcttcgcc gatttcaacc aggacactac gtggggctac gccaccgaaa agccgaccgt    540
cttcatcaag ctgaacaagg ttattggcta tgtgccggag acctacgaca cgccagatga    600
cttgcccaag gaggcgccag cgagccttca ggacaccgtg gcaagctgg gcaacacgcc      660 ca                                                                   662
```

<210> SEQ ID NO 50
<211> LENGTH: 489
<212> TYPE: DNA
<213> ORGANISM: Drosophila

<400> SEQUENCE: 50

| aaaagcggag gtaacggaac aggaagatcg tagtggaact cgatgcacta gcttacgagg | 60 |
| atccacgttt aaattttgct ttgaaagttt aacactctcc aaatcgacat ttcgctacac | 120 |
| ttacacaaaa atggtcaagc catccaaggc acctcgttcg atgacagcca gcggtggccg | 180 |
| cagtggtggc cgaagcggaa gtttcagctc caaggattcc gaccaggtct attgcgtgct | 240 |
| gctccacgtg gtcgaggcga taaacttcat tggacgcgat gccacagatc ggcagcagat | 300 |
| agtgatgaac gccgctctga acagtgtgga ctttgaggtg gagggcaccc agtcggagga | 360 |
| gaccattatc tttaacagca actgtatctg ggagtgtgac ctggctggga ttaagcggct | 420 |
| caaaaccgat caccgtcccg tcaaaatgac cttctatgcc tgtcgtggcg gcggagcgga | 480 |
| acgaaagaa | 489 |

<210> SEQ ID NO 51
<211> LENGTH: 604
<212> TYPE: DNA
<213> ORGANISM: Drosophila

<400> SEQUENCE: 51

| cactttagta taacaaattc tcgccaagat atgaagccgt atttagattc agattattcc | 60 |
| atcagtcgca atttgcgtca gagacataga aaaaaggag tttctaacga atactcaaat | 120 |
| tatttagatt ccgaaaataa aaaaaaaggc agaaagaaat gtcaaaatag cgcatatgat | 180 |
| gaatacggaa atattcgctc aaacggtctg gacatatgcg actgtatgaa tcaagaatgt | 240 |
| gatggttgct ggtataattg ccgaagttgt ggctctacca ggtgtggtcc ccaatgtcgc | 300 |
| tcgaatcgaa agttttttta tgaggacata acatatgacg gtaaagattt aaatattcaa | 360 |
| aataaatata taccaagata aagttaagca atcacatgt attaattaaa tatttgtaac | 420 |
| ttaatataag tattaatgaa cagccaaacg agcattaaac tatcattcag acgaaataca | 480 |
| tcacatataa caattcttaa caaagttatt gcttcagaaa aatacattat gtgctaattg | 540 |
| aaaggaaatg attccaaaat aaagtaaatt cttcagcagc tatggtgaag acttattgta | 600 |
| cttg | 604 |

<210> SEQ ID NO 52
<211> LENGTH: 536
<212> TYPE: DNA
<213> ORGANISM: Drosophila

<400> SEQUENCE: 52

| ttcctgctgc catgccataa cgaagtaacg cgaatccgct atagttgtgt atatgacatg | 60 |
| cggccattcg ctaaataacg aaagttgtag gttacgtcat tgaatttatg catactgcgt | 120 |
| gatagtcctc accaattgac agcatccaag tgcacagagt gcatacgggg tcgtagttcc | 180 |
| tcctcgcaga agtaatacac attcacatgt agcgaggtta gcttcacctc cctcttgtga | 240 |
| tggtccagcg gcctgcttcg catttccagg tacaccggcg tcgaattgtg cacgcaaatg | 300 |
| cggctgccaa acggcgtaaa gatctctttc tctgtaatgc atcaaagagg ctagaaagat | 360 |
| tcgtaaagtg tataaatgat cataacccac cgctagtcag gcgccgcact ctgcccaggt | 420 |

```
aaacccatcg cgggcccatt ttcaactcct gctcgacgtc tttgggctcg cgcgaaggtg      480
tttgaggcag cttttggagat ggagattttc tggcgccatc aaaggaggga ttatgt        536
```

<210> SEQ ID NO 53
<211> LENGTH: 683
<212> TYPE: DNA
<213> ORGANISM: Drosophila

<400> SEQUENCE: 53

```
atcactcgtt tagcatttgt tttatacatt cgaacgggaa atgttgtctg ccgcacaaaa      60
tgcagaaaaa taaaatcttt cgttgttgtt acccgagttt tggatggaaa ttaaaacaga     120
gaatcacgcg aaaacgagct gtgcggaaat tgcgccactt actggtgaag tacaatatcc     180
aaattgagaa ttgaaggctt tcggaattga gatttcagct tgagcctagt gaataattgt     240
attgacttac acactcaatc actcaaccgc acaacatggc caagaagagg ggaagaaagg     300
gcaagaaggg caagaagcca aaggtcgact gcaagttcaa gatcaccaat gagatgctca     360
agcccatgaa cgagaatgtg gacgactgtg atggctgctg tcagtgcgcc tgcgattgcg     420
actgcagtcc ggagttggct ccctgcttca tccagccgac caagccggat ccgggtccgg     480
aggcgtacga cgagttcgag gcctgcctca atggcagcgg tctgaccata cgcgtactca     540
agaacaccca aaggtggag agcgtgatgg atggcagcga gactgcgccc aatctgggcg     600
catgcgatga tccctgctat cgcgatgacc ccaatgactg cgagcccgca aaggagtcct     660
gcctgcacga tatgctccag cgc                                             683
```

<210> SEQ ID NO 54
<211> LENGTH: 647
<212> TYPE: DNA
<213> ORGANISM: Drosophila

<400> SEQUENCE: 54

```
gaagctgccg atcttgtagt ttattgagta acttgcgaag gtaaaacaaa gtgggatcca      60
ccgccactaa tcaaaattcg tgtataatgt gtagtagtaa aattaaaatc attttgcggg     120
cccagcaacc gaggcgatct cctcccgtcc tcctgcacca gtcgtcccca taggtcttgc     180
atgcatttca gcgtgaaatg gcgatggact aacgaatgtg agagcgctcc aaggaattct     240
aacgactgcg ccccgaatcc tgcggatcga tattggacac ccattgcacg ggattgatgt     300
aaatgttgga tatggtaccg cgcagcgtgt caaagccctg attgagggga accggcttgg     360
cccgcttgtc cacctgtttc atccagttct gccaggcgct ttgcggcgc tgacggcgtt     420 cctcctccag tttctgcttg ttgcactgca gtcggatcag gcgttgtttt tcctgttgct     480
gctgctcccg cttggcttgc tcccacttct gcagacggtt ctttgtgttc tcgggagaca     540
ccttccttgt aggggcggtg ctaaagctgg aaaccgatcc caaactggag ctagaggtcg     600
aggatttctt ttgcttttgc cgctgctgct gctgctgctc tccttg                   647
```

<210> SEQ ID NO 55
<211> LENGTH: 586
<212> TYPE: DNA
<213> ORGANISM: Drosophila
<220> FEATURE:
<221> NAME/KEY: misc_feature
<222> LOCATION: (1)...(586)
<223> OTHER INFORMATION: n = A,T,C or G

<400> SEQUENCE: 55

```
cgtgttttta aatgaaagaa caattatttt atttcctctt tttgattaac atctgaataa      60
```

-continued

```
ggctgctctt cgcccatgtc agtactgtga gaagtataag gttaactact taacctgaca      120
aattgtttag cagcgcttgg ctttctcctt gtagtttcga ttgaacgttt gaagatgagt      180
tcgacgttga ctgcgacgat gaatgtgacg atgattgaga cgacgactcg gacttcgact      240
ccgactgagt cttggagctc gattgatcta gtagcaaggt atttcgattg ccagcctcct      300
gtcgttgtgc ttcagactgt gatgcctgcg atgactgtga tgacgaactc tgcgagtttt      360
gtgagttact gtgcgagctt gaagaagagg ttttctgatc attttccgtc tgaattcgca      420
gttgttcctg ctccttcaat cgctgaagag cggcgctttg agatgcagaa ctttctgtgc      480
cttgtaggga actantctgc aggccantgg atccagcttg aagaccctgc tgtgagcctt      540
gagctccagt actttgtata tcttgctgta acttggtctg agaact                    586
```

<210> SEQ ID NO 56
<211> LENGTH: 541
<212> TYPE: DNA
<213> ORGANISM: Drosophila

<400> SEQUENCE: 56

```
aatcgtcggc cacgtcactg ccggaggcca agggatgcac tgccaccgaa aactgccagt       60
tgctagcgca agaggcggaa acaaagaacg ccagcaacga acaaggtgga ttgggcaaaa       20
tgtcggttag cctgccgcaa caaaactgga acgctaatca atcgtcggcc acgtcactgc      180
cggaggccaa ggagatcagc tccaaagagc aggcgatcat ctactggcgg cgtcttttcg      240
atggtatcca caagcgccag cgtggcgaaa gaaaagttgc agcaatgcag cccgaaaata      300
ccacagatgt cgtgctgacg tccaagccaa acctggcatt gcgctacaag ccctcccatg      360
agtcgcttaa aaacaagcgg atcaaggacc tggctcctga acgatgcccg agcacgtccc      420
ggggatcaac gtcctgcaaa ctggtatcgg acctcaagat ggagacgttc agcctgccgc      480
cgcagcagac gtgtgtggtg cgcgaggtgg agcctcggtt tggccagcgc cgacgcatgt      540
t                                                                     541
```

<210> SEQ ID NO 57
<211> LENGTH: 587
<212> TYPE: DNA
<213> ORGANISM: Drosophila

<400> SEQUENCE: 57

```
taaaatgaaa gccatcaccg tttgcctttt ggttctggtt tcggccacct gtctgctgac       60
cacgcgggcc aatgcaatag aattgctgga gaacgagaac ttcgactatg atttcgactt      120
tgaatcggaa ttggagcagt tgctggatga actggacaat gacactgact acatggatgt      180
ggaggcacag ggctttatta gaacatgcct taaaatcctt cgcaaggcat gaaaacggt       240 tcgaggcacc aactgtatta tcaaggaggt gacaaacatc cttagttcat gcaccagcta      300
tgtggatgct attgatgcct gtggcactgc cattcccaag gatgtggcca agattgtgga      360
ctccgttaag gagattatca aaatctgcga cgatattttg catctgcatt cgaaactttg      420
tgccacggat aagtccgtgg gctcgttcat caaaaactcg gccaaatgct tctggaaatt      480
gttcaaggca ttcatgaggc tgacccgaaa gatcaattaa accctaaaac tgattgccaa      540
attgccagcc gataccagtt cctgctttgt aaatgccacc aataaag                   587
```

<210> SEQ ID NO 58
<211> LENGTH: 581
<212> TYPE: DNA

<213> ORGANISM: Drosophila

<400> SEQUENCE: 58

```
tcgcgtctgc gccgttctac gtcggacatc ggattacgga tagctgaata cggaatacgg    60
atttccggcc tggcttcgcg aaaaggatcg taataagagc ccatcggaaa tggcaacgga   120
tgtgcaatct ttttacaaag acaaaactgt cttcctaaca ggcggcagtg gattccttgg   180
aaaagtgacc attgcgaagc tgctctgcac caccgaggtg aagcgcatct atgtgctgct   240
ccgtgccaaa cgcggccagg aaatgcggga gcgatgcgcc gcatgggata aggatccggt   300
attcggtaat ctaatgaaaa caaatcccga ggctctgaag cgcgtggtac cttgtggtgg   360
cgattgccag gagccggatc ttggcctgag caacagcgat cgtcaggttt tgatagatga   420
ggtgcagatt gttatccaca cggcggccac tgtgcgtttt gtggagccgc tgcacatcgt   480
cctggcttgt aacacccgag ccacccgact catgattcaa ctggccaagg agatgtccca   540
cttggagtcc tttgtccatg tgtccaccgg gtactcaaac t                       581
```

<210> SEQ ID NO 59
<211> LENGTH: 450
<212> TYPE: DNA
<213> ORGANISM: Drosophila

<400> SEQUENCE: 59

```
atgaaagtgc tcgtagtctt cgccctggct ctggccaccg cctccgccgg tctgctgccc    60
cagcaggtgc cgatccaccc ccgtgacctg cccgccgtga ccaatatcga gggtcgcatc   120
accaacggca agaccgccac ttctggccag ttcccctacc aggtgggact cagcttcgcc   180
agcaccagcg gcagctggtg gtgcggtggt tccatcatcg acaacacctg ggttctcact   240
gctgctcact gcacttctgg tgcctccgct gtgaccattt actacggagc caccgtgcgt   300
actagtgccc agctggtcca gaccgtttcc gccgataact tcgttcagca cgccagctac   360
aactcgattg tgttgaggaa cgacatttcc ctgatcaaga ccccaacggt tgccttcacc   420
gtccttatta acaaggttga gctgcccgtc                                     450
```

<210> SEQ ID NO 60
<211> LENGTH: 647
<212> TYPE: DNA
<213> ORGANISM: Drosophila

<400> SEQUENCE: 60

```
aatcgagcag gcaacacaca ctttaaaatt taatgtgagt tcagagcttg atttggggaa    60
aacagttcaa gctcttttaag cgtgatggac gaggaattct ctaatcagcc catcgatcca   120
agcatcgctc ggagtgacta ctcccggagt catttcgtta accagagctc catgacattg   180
agtcgcggat tggactccac ccgactgctt ttcgtaggcg aaaacttcca gcagacgcgc   240
agcgaacagg acttatttta cgactgtcaa ggtccgggtg aggactcgcc aaaggagggc   300
cgtagtgcca ccagccggtg caagttcgat gatccggctg cgatacggga tgccctggaa   360
cgggcggcca atgccacaca gatgctactc aagaattttg acaagtcagg tggttggaat   420
cagccatgtg ccgtcaccct ggagttgacc gctcggttgg tggaccccaa gaagggtcgc   480
gctggttgtc cgttgcacgg aaagcccgtc accgtccaga tgccgctgga gttcaatccg   540
cagagcggca agatggtcaa gtgtcagcaa aagaaacaac cggtcaccag gcatcggaaa   600
gagtccatct gccagtgccc gttcgcaagc agtatatgcc gttcccg                  647
```

<210> SEQ ID NO 61

<211> LENGTH: 550
<212> TYPE: DNA
<213> ORGANISM: Drosophila

<400> SEQUENCE: 61

| | | |
|---|---|---|
| ttgcactcac ttcgtgtctg agatcaaacg aaaaaatatt agaaccaaaa gttttgaaag | 60 |
| tttttttttt attatagttt caaacttaag tgcaaaatgt ttcggtcgtg tgtgcccaag | 120 |
| gcgattacct ctagtcgctg tttcgcgcgg atgtactcga aggacgtgcg ctttggctcc | 180 |
| ggagtacggg caatgatgat ccggggcgtt gatattctgg ctgatgccgt tgctgtgacc | 240 |
| atggggccca agggtcgcag tgtgatcgtg agcgaccat ggacctcgcc gaagatcacc | 300 |
| aaggacggct tcacggtcgc gcgctcgatt gccctaaagg accagcacat gaatctgggc | 360 |
| gccaagttgg tccaggatgt ggccgataat acgaatgagt cggcgggtga cggcacgacc | 420 |
| acagcaacag ttttggctcg agcgattgcc aaggaaggat tcaatcagat taccatgggg | 480 |
| gctaatcccg tggagattcg tcgaggtgtc atgttagctg ttgacgtcgt aaaggacaag | 540 |
| ctgaaggaaa | 550 |

<210> SEQ ID NO 62
<211> LENGTH: 628
<212> TYPE: DNA
<213> ORGANISM: Drosophila

<400> SEQUENCE: 62

| | | |
|---|---|---|
| cctaaattta aaaaaaaagc ctgtttatt ttggttccca gattgagctt aaccgtattt | 60 |
| aaccattaaa caatattgga cccgaatcgg ataaacactc caagcttggg gaataagacg | 120 |
| ataccgcaat gatgggcaca cgggctgcgg agccccgagg atccaggagg tccttggcag | 180 |
| gtcaaagcat tcaagagctc tctgtgtgcc aggaacccga cccgctaaac accttttttgg | 240 |
| agaaaccact taccctgtat cagtggatgc ggtggcgcaa ctgcaagacc cataagccgc | 300 |
| acctagagga aacatacccc agcattctac cgcctatatc caaatgtgac gatgccaaga | 360 |
| ctctgaagta cgttgaaaat gccatggagg ccaacaaatg taaagaatac gtcaaggaag | 420 |
| acgtgctgac cgtgtggaac tacagtcccc aaaaggaatc cttggtgtgg tatggcgtta | 480 |
| aatcgcagta cccgtctcca caggccgtcc tctatgaccg cgctttgaaa aagagcctaa | 540 |
| aggcggctag tcttgctcca aaaccgccga agaagtccaa cataaagcct aaatggcaac | 600 |
| ttcagaagaa gccccccag cctggcgc | 628 |

<210> SEQ ID NO 63
<211> LENGTH: 494
<212> TYPE: DNA
<213> ORGANISM: Drosophila

<400> SEQUENCE: 63

| | | |
|---|---|---|
| tggcgcaaga accgtcgtcc caacggatac cgcaacgaaa gtggagattg ctacggcatt | 60 |
| gacatgaacc gcaactttga ctaccactgg ggaggtgccg gctggaacat cgatgagccc | 120 |
| tgcgatcact ggttcggtgg tgaggagccc aacaccgagg tggagatcat ctcgctgcag | 180 |
| aactttgtga gctccttcga ggatggctac atccgatcgt acatggccta ccatgcctac | 240 |
| ggacagtatg tcctcctgcc ctacggacac tccaacaccg agttcccgcc caactacgag | 300 |
| cagatgaagc gcattgccgc tgcattctcc gatgctgccg ctgatgtcta tggttccacc | 360 |
| ttcacctatg gagctagtgg tctgcttaac tatgtcgttt cggagctgc caaggattgg | 420 |
| gcctatggcg taaagaaaat cccattcacc tgcaccgtgg aactgcgtga caagggcacc | 480 |

```
ttcggattct tcct                                                      494

<210> SEQ ID NO 64
<211> LENGTH: 703
<212> TYPE: DNA
<213> ORGANISM: Drosophila

<400> SEQUENCE: 64
tcacgagaac atcggatact cgacccgatt ttgtacagaa cattttcatg gaaattttc      60 taaacatatt ttaacacttc tttgtcaaac tcttctttcc ttaaaaatca aaatttaatt    120
ctactctaaa agccccatat cattagaaat tatcatagct cgcggagatg gagaagcaac    180
taacagagca catggtggaa agcatgtcca ggtgcaggga ctatgccaag gccttgaagt    240
tgaatttctg taactgcggc ctgaatgaca taagtctctg cctcaagatg ccgtacctgg    300
aggtcctttc gcttagcatg aacaagatca cttcattgaa aagcctggtg agatgcactc    360
gactgaagga gctgtacttg cgccagaacg agatagcaga ctttgatgag ctgaaatatc    420
tagtcaatgc caaatccctc acatccctct ggctgctgga caatccatgc tctattgccg    480
ctggctccaa ctatcgggca tctgtgctac gaatgctgcc gaatctaaag aagctggaca    540
acgtagatgt tgccgaagag gagctggaat ccgctttgcg atacgattac tacccggacg    600
tagggagtgc gatccttaat cctgttttgg atttaagcaa ctgcagtccc gatgacatgg    660
cataccgcga tatgatcgaa cagtgcgatc ggacgatccg tca                      703

<210> SEQ ID NO 65
<211> LENGTH: 609
<212> TYPE: DNA
<213> ORGANISM: Drosophila

<400> SEQUENCE: 65
ataaattcca ttaattgggc gcacaatgga aatctataac taacttagga tctacgtttt     60
agaatagctt ggcggccaga aggcaggcaa ggattgccaa aatggaggcg ttcagggcgg    120
agctgccgct gcggaatccg gcgacccagg tcatcagggg atccctgttg gaagccagcc    180
acgcgtagtt ggcattcacg ttgctatcca cgctatcctg cagagtgctg gcacatact     240 cagaacccctt gacagtgtcc accaactctt gcaaggcatc cttctgcttg tcgttgacgg    300
tataggcgga aatacccaca atgtcgctgt acagaggatt tacgccacca aagccggaat    360
ttagctgacc atactttttcc cagttcttct gcaggaactc aatggcgacc agcagaccca    420
cctcgccgcg ggagtagacc ggactcagca ccgtgatcct ttcctgatcc ctcaaaccct    480
ctggctcaat gctgctgtac acgaacttct ctagctgggc agtgttctgg gagcagccca    540
gggcggagat cagaagacga cgctcggcct gatcggtgga gttcagcagc ttgttgaaca    600
caaagtcaa                                                            609

<210> SEQ ID NO 66
<211> LENGTH: 638
<212> TYPE: DNA
<213> ORGANISM: Drosophila

<400> SEQUENCE: 66
tgagcacagt gtggaaatga ttcggctact caagacgctt ctttattgcc tgctcctcat     60
ctcccctgct gatgtgctgg gccggcttaa tgccagaaag tcggcgaacg aggcgagtct    120
ctatagcgat acagacaatg tgattatgtt ggacatcgaa tcgctgaggc cagctctaaa    180
```

```
cttgaagaac agcaagctgg ttcagttcct caacagcttc tgcggtgact gtcatcgctt    240
cgcaccggtc ttcaagaccc tttcccgcga cctctacaag tggcgaagaa ttctccggat    300
ctatgccgta gattgtgccc aggagagaaa tgctcaactc tgcagggaat tcaatatccg    360
ccagacgcca tcattgcgat tctttggtcc cgacatgagg aagaacgatg atgttcttgg    420
agcggtaatc ccaggccaag atcccgagtt cattagctca acactggccg aattggtatc    480
ccaaaatgac tatggacccg ccagccaaa ctttcgtccc ctaaaagcaa cagactatga    540
aattttccaa gatcaagatg gggaaactcc gatacaattt gtggctcttg tccttcagcc    600
aaaaaattca aagatcggca gggacacgct gctagaac                            638

<210> SEQ ID NO 67
<211> LENGTH: 597
<212> TYPE: DNA
<213> ORGANISM: Drosophila

<400> SEQUENCE: 67
caaacctgct gaattcctga attacacaaa tataaattaa aaatatatat attttttgag     60
ataggaatcg agaaattgaa atagtaccaa caaaatggag gagctggata taacaagcgt    120
gggtcaattc cagaccctgg tgcgctacaa caacccggtg ctggtggtga agcacccgga    180
caagaaaggg ggtgctccgc tcacagagat agagatgaaa aggccccaaa cggcgggcgc    240
tttgctagat accaaaaggg aaactgagga aattctaaat tctatattgc caccgcgctg    300
ctgggaggag gatggccagt tgtggcagca gtctgtgtcc agtactccag caacacgcca    360
ggatgtgatc aatttgcagg agatgcttga tactaggctg cagcagaccc aagctcgtga    420
gacaggtatt tgtcccgtgc gccgcgagct gtactcacaa tgttttgacg agatcattcg    480
ccaggtcacc attaactgtt cagagcgtgg cctgctactg cttcgcatcc gcgatgagat    540
cgccatgtca atggaggcct atgaaacatt gtactgcagt tccgtagcct ttgcatg       597

<210> SEQ ID NO 68
<211> LENGTH: 680
<212> TYPE: DNA
<213> ORGANISM: Drosophila

<400> SEQUENCE: 68 ggaatttttag tcatatctaa aatttcggca acataagacc ttccaatttt tgtttgtaaa    60
taagaacgtt ttttaaattt aacttcggtt tttgttctgt tgggtagtta gtttccgcac    120
tcgaaacacc gacaaaaacc atgtttcgca atctttcgat gctgaggaat cagctggcgc    180
tgcaccgtgt ccgtgtggcc cgctcgacct tgcactccaa aatgtctact ggtcttactt    240
gcctcaccat tgaccgtccg cggaacatcg atggcgtgac cgtgatagat atcaatataa    300
atgagatggc caagactgac gtagagttta atcgcaattt cgtcaattcg ctgacattga    360
tggaccatac tccattcaaa gaggtgacca acatagtgga cgcggatgca gttgagtcgc    420
caccagcaga gaatccgatt tctggagata ccgtggagat cctgcctact ggcgcaccta    480
gttccgtcgt aggcgtcgac ggcaacccca ttgtccccat cgagattgat ggctggaacc    540
aggacgagga ggatcccacc gtgcaaaaga acgtccagga cgtggacatt ggtaacgatg    600
acgagtacaa ggccgagatg gagctgcggg tgccggaggt catggaaggt cgaaccgagt    660
acaagggcat caaggtgacg                                                680

<210> SEQ ID NO 69
<211> LENGTH: 495
```

```
<212> TYPE: DNA
<213> ORGANISM: Drosophila

<400> SEQUENCE: 69
aaaaattgaa ggcaaacgtt gaagcaaact tcgctaaaaa aaattcgaaa aggcaaaaaa      60
aattcctttg tctagacagg gttgtgaata aagagaaaaa aaatcaaaaa tgtcaattat     120
accactgctg cacttggccc gggagttgga tcatgactac cgcaccgact gggggcattt     180
gctggaggat gacttcggtt ttggcgtcca tgcccacgat ctgttccatc cgcgtcgcct     240
gctactgccc aacaccctgg gactgggtcg tcgtcgctat tcgccgtacg agaggagcca     300
tggccaccac aatcaaatgt cacgtcgcgc gtcgggaggt ccaaacgctc tgctgcccgc     360
cgtgggcaaa gatggcttcc aggtgtgcat ggatgtgtcg cagttcaagc ccaacgagct     420
gaccgtcaag gtggtggaca acaccgtggt ggtagagggc aagcacgagg agcgcgagga     480
cggccatgga atgat                                                      495

<210> SEQ ID NO 70
<211> LENGTH: 434
<212> TYPE: DNA
<213> ORGANISM: Drosophila

<400> SEQUENCE: 70
ttagccagaa tgtaacggcg cctttcccgc tccaattgga atccgcgtgt aattttgtgt      60
ctcgtgttaa ttgtattatt tcccccgctt ttcggatttc cgcataaaaa gcgatgagtc     120
tacaggacga gagttttccg acggacgagc tgtttgacca gctgaacaat ttgagtagca     180
gtggcgccag gaatacctgg ttcgcggagc accataagcc cgcagtcttc gagcgggata     240
cagcgccatt tttggagatc tgctacgcgg atccagactt tgatgcggat ggggatgtgg     300
ccaacaagag cgccaagaca tgcgtaagcg atcccgtggg tcgtgatcag gaggatgagg     360
acgactatga tgaggatgtc gatggcgatg atcataaact gggttgcgag aaggctccat     420
tgggcagcgg gcgc                                                      434

<210> SEQ ID NO 71
<211> LENGTH: 525
<212> TYPE: DNA
<213> ORGANISM: Drosophila

<400> SEQUENCE: 71
tggtggtgcg tgtcctcgag ggtcacgagc ccgtggagtt taagcgtctc tttgccaact      60
ggttaaatgt ttggcaggag aacaccaggg gacataagcc agtgtccaca aagtttggaa     120
agctagatgc ccattcccta tgcgaacgcc ctaaaatggc tgcagataca cagctcgttg     180
atgatggcag gggtgaaaga gtaatctatc gtgtcttcgg agatcaggtg caagaggtgc     240
ccatctcaaa aacggttgtg ttcaccacca atgccagttt cgtggtcaag tacagcgtgc     300
agtgcgccac cgttgttccc gcagatttgg cctccgttgg cattaaaaca atcatctacc     360
agtggaatgg ttcggaggcc tctgtagagt ccatttcccg gcggacaag ttcgccaagg     420
ccagttttga tgggctcaag gagcctgtaa tgtttgtaca gctctatgag ttcgatgaac     480
caccgcactt ccttcagatc ttcgagggaa aacttattat catgc                     525

<210> SEQ ID NO 72
<211> LENGTH: 631
<212> TYPE: DNA
<213> ORGANISM: Drosophila
```

<400> SEQUENCE: 72

```
aaacagaacc acttaaaaat ctagttagga tttccactta tatagttagc acacatagtt      60
gcatatttcg ttacgcgata aaaaatgttt cgtttaaaat tatttcgcag tcctggagac     120
gtattaagca ctttaattag cggagctgca acgattgct gcaggaagac gtcacattgt     180
ttggagttgg atcgcgctcc cgctgtcgct gcctgctgga tctgtatgcg gatgatcagt     240
caatatcagt tcaggaccac gaaaccagcc tactatccag atcgcagcg ggaggcgaag      300
cgaacgtcag cgggagccac gcctcaacag gtgtcatctc cggctgttaa gtacccgcaa     360
agccgaggca tgcccaagga ctactactac aaagtgttag cgtcaacag gcacgccacc      420
atccagcaaa tcagatcggc tttctatgcg ctggccaagc gctatcatcc cgactcgacg     480
cactcggaac aaaagctgaa gcacttccag gagctgtcca acgcctacaa catcctaacc     540
gacgagacga agcgcttgga gtacgatcag ctgggcggga ttaaggatga gcgcgctttt     600
cttgaacagg cgggcaatcc cctaaatgtg g                                    631
```

<210> SEQ ID NO 73
<211> LENGTH: 698
<212> TYPE: DNA
<213> ORGANISM: Drosophila

<400> SEQUENCE: 73

```
ctaaaagtca caatcaagca tgcgtttcct ggtagtctta gcctgcctgg tggccgtttg      60
tgccgccggc actctgccca acgaggtgga gcagcgtctg ttggagctgg cggatcagaa     120
tggtgacatc gatctggtcg cggagcccca ggagggagtt gaagttgccc cccagtttat     180
tgtgtcctgg caggcgcgtc gcttcatccg caagctccag aagcagatgg agtgcggatg     240
gccccagtat ggcattcccg tgctggctcc tcttcgcatc aacgaattcg acctagacta     300
caaaaagggc attttcgaga ccttgaacca tgtgttccgc ctgaagatcg ccggtctgaa     360
tgacttcaat atccagaagt tcaagctgaa cgtgatcacc agcaagatta ccttcgattt     420
tctgttcaag aacatcgata ccaccgtcca gaagtacgac actgatacgc tgatcgatgc     480
cctgcgccag ttgggtctgt ccgtggagta cgagggatcc ggagagctgt tgttcgattt     540
ggtcaacctg cgtattgctg gcactctgaa gtacaagctt cccatgctgt ggggttccgc     600
caagatcacc tcgctgaaga ccaccatctc gttggagtct gtgacttcgg acatcactgg     660
attcatgggc aacggcaaga tcaaccgggc catcaaca                             698
```

<210> SEQ ID NO 74
<211> LENGTH: 591
<212> TYPE: DNA
<213> ORGANISM: Drosophila

<400> SEQUENCE: 74

```
atagaaatgc gcaacttcgt gatcatattt agcctatctc tggcatttgg catcgcctcc      60
gccaccgatt attgcaaaaa gagctgcgga agcaccaaga atctgggatg cgacaataat     120
ggagcctggg cctcaagctg tcccagtgac gccaccctgt tgaccctctc cagcgctgag     180
aaggatgcac tggtggccag gacgaacgag tatcgcaacc acatcgccgg cggactgaat     240
gccaatctga gtgccgcctg tcgaatggcc acgatcaagt ggaacgatga actggcttac     300
ttggccagtt tgaacgtgaa aagttgtcaa atgaaacacg acggctgcca caatacggat     360
gctttcgact ggtctggcca gaatctggcc tggatgggct actacaatcc gctaaatgtt     420
acacactatc tagaatgggg cgtcgatatg tggtacgatg aggcggtgta caccaaacag     480
```

```
gcctacatcg atgcctatcc gtcgaactac aatggtccgg ccattggaca tttcacggtg    540
ctcgttgccg atcggaatac ggaagtgggt tgtgccgcgg ccacgtactc c             591
```

<210> SEQ ID NO 75
<211> LENGTH: 643
<212> TYPE: DNA
<213> ORGANISM: Drosophila

<400> SEQUENCE: 75

```
agcgttcgcc tgtacagacc aaaatttcgt gtctctcaac ctgccacagc accggttcca    60
atccaaaacc tccgtttagt tatgtttctg gccaaaagtt catcaatact tcgcccgcag    120
cttcttaatg aggtgaaggg actagtgaag tcacaatttc tggctctgtc acaggtcgac    180
cgacgctttg cccactcgga cgataggtgc gccaataaga aatccaggaa gtgcgagcag    240
agcccaccca agggtgtagg tttgccccccc cgggatcgaa gacattctca tacgcgatggc    300 gtcagtgata agtgcgcgaa gaacaaaaaa gataagcggg agtgcaagaa gtttgagtcc    360
gagaatgcca aaaagccgga atgcaaaccg cccgttgtcc gtgctccaaa atactacaag    420
cagctaaaac cgtgcaagac cgacaaggag ctctccgagc tgcatcccaa gtatctgggt    480 gtatggggc gttgcgacat accctacaag ccagagcccg attgcaccga tccctgtgat    540
ttggccgtac gtttggatga caagtactac aaacccagca atcgctgga ccgcgaattc    600 gaccagtact gggtggagtg cttcttcgga agcagaaacg ctg                     643
```

<210> SEQ ID NO 76
<211> LENGTH: 606
<212> TYPE: DNA
<213> ORGANISM: Drosophila

<400> SEQUENCE: 76

```
agcggattca gttcgttaca cgccgcctct ttggaagcag gctacatttt ggcattccaa    60
tactaaaact tacacaattc cctaattctt ttaataaaat ttctaaaact gtaaaaaaaa    120
aaaaaatatc ttccgagaat ggttaacatc acggtggca ctcggatgat ggtgaaccgt     180
tgcatcgagc tcctccgtgc gcggatcgaa tgcgcctcaa cgcgtcacat tgccaggcgt    240
tcccagcggc ccagagtggg cagccaatac ctgccagacg atcagatact cagggagcgg    300
gagaaagcgg atgtgtacaa gaagaacaag cgacgctcca tgtgggagca ggacgagggc    360
cacggacgca tctcggtcgg ggacgatcag gaacgcttcg ataacgagca gtaccatccg    420
cgcgaactgg agaagcgcaa gtacgagtgc acctggttta atttcccgga cagtgtggcg    480
accaaacgaa atcgtagacg ggactttctg gagtcgatgg aaactgaggc tcctcgacgc    540
cgccgagccc aggaagaaag accgagtacg gcaaagccat gtgacgacga ggcccgtgcc    600
tttatc                                                              606
```

<210> SEQ ID NO 77
<211> LENGTH: 592
<212> TYPE: DNA
<213> ORGANISM: Drosophila

<400> SEQUENCE: 77

```
acattataaa atgtatattt attaattatg attatcatta ttcattacta ttataatgaa    60
ttaagtaccg aaaattttgt atatttccat agaaaacctt tttccctaga tatcaccgaa    120
tgctgccttg actggcaagt ccacagaaaa cgaatgtatg acttttctat gaattaggat    180
```

```
agcaaaaagc aagtaaatgc agtaaaacac gatagaaaat atgcccacgg agcgcctggc        240
gaaaaatccc agcgtcgtgg accatagaag agtggaaaac acacccaggt ttagaaaaat        300
gaatgcattt aagccgtaat tgcccgtttg gttagcttcc gagaccggga ggccaaatag        360
attcttgaca tgcatcacag tgctggcgga catgacaacg gtgaagaagg gtcctccaat        420
ggctgaggcg taggccatcc tgggatatcc gtgcaatgcc atcgcacgt tggcaattag         480 tggacccaga cttcccgtac aagccttcac cgttgcgccc ataaagtcgt cctccacctt        540
caggatgtgg ccaataactt ccaggacctt gtctatttcc gtcgcgcaaa tg               592
```

<210> SEQ ID NO 78
<211> LENGTH: 588
<212> TYPE: DNA
<213> ORGANISM: Drosophila
<220> FEATURE:
<221> NAME/KEY: misc_feature
<222> LOCATION: (1)...(588)
<223> OTHER INFORMATION: n = A,T,C or G

<400> SEQUENCE: 78

```
aaataaattt aaaaatcata gttcggttta tttctagtct gaattttacg cacggtagaa         60
aagttacttt aactggatcg gtttggaata tttaggtcaa cggaacaaga tactgagcgc        120
tgggattagg attcaaacag cactatggaa ttaagcccta ctgcccccgc agtttggctt        180
ccgtggattt ccttcgaact tcttcagctc acgaatcagg tcacaggatc ttggaacatc        240
tatgcagttg cattcaacgc cccgaggctt gcgaagacga gagcggctgc actcggagaa        300
ggaaggatan ggggccttga cttttgacgca ntcggtctta cttctaacga cgtggcaaga     360
gacgctgtct acggcttac agccgggcat cttgattcta gggcagggtc ctccctccgt        420
ggggcattcg acattcgtgg gacactcggc ggatgtcacg aacttcttgc gcttgcgcct        480
tgggatcggc ggacgaattc ngcctcgta ncagcagatc ttcttgggct ttatctttat        540
gggcggacac tccacccagg tgacctgtta cttgcgcgtg gccttgtc                    588
```

<210> SEQ ID NO 79
<211> LENGTH: 669
<212> TYPE: DNA
<213> ORGANISM: Drosophila

<400> SEQUENCE: 79

```
ccccactgtt ctaaatttcc cattcggcta acatcatttt tctgattttt ttttggcgt         60 aaaattaaca cgttattaga gggaccctgt gattgcgcgg acatctaatc cataatcctt        120
tgaagatgtg cgacaagccc gcctgccccc cgcctccgcg atgctgtcct ccgccaccgc        180
ctccctgtcg cccgccgccc accttgtggc agaaattgaa ctgcgttccg tgcaaccgtt        240
ttgtgttctt catgatcggg gcgggcatcg gattattctg ggaccatatg aagaaggagg        300
cccagaaggc ggccgaggag gccgcgaaat cgcccaagga aaggagaag gaggccaagg        360 agcgcgagaa gaagcagaag gaaaagaga aggccgaaaa ggagaaggcg gagaaggaga        420
agaaggagag ggagaagaag gagaaggaaa agaaggagaa ggaaaagaag gagaaggagg       480
ccaagggcaa agagaagggc aaggagggca agtaacgact atagacccc aaacggacat        540 gtcaaggagc aggatgtttt ccccaaaat tctcatcgaa tccatatcgt ttctaaactt        600
caaaattttc aagtgcatta tatggcatac ctaacgataa ctattggtca gtccattgcc        660
gcgttgatg                                                               669
```

<210> SEQ ID NO 80
<211> LENGTH: 412
<212> TYPE: DNA
<213> ORGANISM: Drosophila

<400> SEQUENCE: 80

| | | | | |
|---|---|---|---|---|
| ttaacacctt tgaaaatagt ttgtgtctta cgttttccgg tacctatttt ggtggttcta | 60 |
| agatcctatt tctgtaaata ggccaaattc cacttagctg ccctttttaga aggaaattag | 120 |
| gataccctga acgcttttcc ccaagacaaa ataaaatcga agatcatgtg ctgcggaccc | 180 |
| tgtggacctc gctgctgcga tccgtgcggc ggatgctaca actgctgcgt ggaactctgc | 240 |
| tgtgtaccct gcaccccagc ctacatccag tgctcattta tgccctgcgg accaagaggc | 300 |
| tgttgctgaa gtggggatgt gccaggtgcc gaaacacgtt caaccatatt gtacctgaaa | 360 |
| cactcgtaga tacccaacat gtcccaataa acgaattttta taaatgttaa aa | 412 |

<210> SEQ ID NO 81
<211> LENGTH: 523
<212> TYPE: DNA
<213> ORGANISM: Drosophila

<400> SEQUENCE: 81

| | |
|---|---|
| cgtacgggtc acagatcagc tggcaataga aatacgaaac aaaattctca gtgttaacaa | 60 |
| aaaaatttg tgaaaaaata cgcgcgtgac caaatttttag agttacgtgg ctcggaggtg | 120 |
| accaacaaac gtattaatat tatagaaaca ttgcgagtta tacaaaattt cctattcgtg | 180 |
| tgttcattgt aattctcaat ttgatattga tattgaagaa tgccttcgta caagaacatg | 240 |
| tctttggtgc gcgctggcct gcgtatggtg cgccaaaatc gttctggaca atctgtgata | 300 |
| ccgtcatatc gccgctatgc gacatcctgc aagagtccca agggtgttgt ggttggtgtt | 360 |
| tataccaagg atggcgataa gccatcgaaa accaccgcaa atgcagtgac cttggatgat | 420 |
| gctctgggtg gcaagctgtt gaccctgatc cgtgaacgtg aatggacgg cactcccgga | 480 |
| aagggtctgc tcttcagtgg cttcgagggt gaataccagg cgg | 523 |

<210> SEQ ID NO 82
<211> LENGTH: 638
<212> TYPE: DNA
<213> ORGANISM: Drosophila

<400> SEQUENCE: 82

| | |
|---|---|
| caaagcaaac cggcaaaata atctacgact ttccatggcc aaaaagtacc gaattatagc | 60 |
| ggaacttgga ggaaccatgg ccaagcgctt ttcttgccaa tgaaagactt cgcgcggtgc | 120 |
| aagaaaccgc gactggatgt tagcgttacc cgcggatcag cgcgacccag tccaccgagg | 180 |
| aacaatttcg atgggattct ctgggacgac gatgacgatg tcatcctgat ggccacccag | 240 |
| ctggcggaag cggaaatcga ggcggaggag cggaaaaaga agggcggaac agaagtggac | 300 |
| atcggcaaca gcgaggtcac cttcagcgaa tttgcaccca cttttcaggg ctcaaccagc | 360 |
| acacagcaaa tgtttccgcc gccaccgacg ccacaaaaga agcctacttc cctggatatg | 420 |
| gatgcgattt tcgcggatga tgatgatttc gattttctgg ccgttaccct catggacagt | 480 |
| gagccacaaa agatgccgga gccgaagacc agcacaagta ggataactac cagcagcata | 540 |
| agtgttcagc agaaaaccac gaccacgacg accatcaatg ccacgcaatc ccgccagcag | 600 |
| gagcatcaac taaagtttct catggataag attgaagc | 638 |

<210> SEQ ID NO 83

<211> LENGTH: 631
<212> TYPE: DNA
<213> ORGANISM: Drosophila

<400> SEQUENCE: 83

```
attttagcaa cgaaagccga caacacattt cgttcggtcc ttttttaaat atacatttta    60
cgttcgcaca tgaaacattt ttgaaacatt ttctcttttt tttttttttt tgggcacctt   120
gcaaaacttt tgaacgtggc tggtcaaaat tattagagac agttcgagag accaacattc   180
atacacttcg agagttgccg taaattgtaa aaacacacaa cagtcgtcaa aattgggcag   240
ataatagctc gcgtatatag tgcggtaaac ataataatac tatatactat gcgtggacaa   300
ctgttgctga agggacccgc attggcgagg agcttgagcc ggtgccgcgt aagtgccgtg   360
ccccaaattg gatctgttcg tcatgtgacc gccggctgtg cagctggtga taccgtcaag   420
ggcggcaaag gaatcgtctt gggcctctac gaaaaggagt cgggcaaggg acctcgatta   480
acgcctgctg gcgaaaagtt tgacgatcgt gtgcagggca agctatcgga attggtttgc   540
gaaaccaaat taactggacg attgggtcgc ggcaaggtct tcaacaatgt ggacagcgag   600
ttcagatcca tttgcgtggt gggcgttggt c                                  631
```

<210> SEQ ID NO 84
<211> LENGTH: 614
<212> TYPE: DNA
<213> ORGANISM: Drosophila

<400> SEQUENCE: 84

```
aagtgaaaca cgcacacact cggagaactt ttgaaacaca cataccaaaa caaaattatc    60
gtattggtct tccaatggac gaatttagag tacccaaaaa ggttaaccgt aacgttttca   120
aggccattag cattcttcaa tcttcccgaa ccgattttgt ctgcgctaat gcaatcgtcg   180
accaggtaaa gttccaaatg cggaaccgca ttccggtcga gcatatagat gaggccataa   240
aacagtcgct ggccaacttg accatgctgg gcatagtgcg gcgtctggga tcgtctaagt   300
attcgcttag caccatagtg tatggccggt tgggaatgcc caatcccatt gcacatccgc   360
cgggcaatcc tggtagacca catcggcgag ctgcgcagaa tgcgcgtcaa aagcgacctg   420
tcgggcgctt ggatccttgg aaatcggtca gcaagatctt gagtgaggac tctctgtctg   480
gaactgagat gaccaagatg cgcaagcgga tgcgcaccaa cacaaagcgc gttgtcaaga   540
agaaacgaat ccccaaccgt cgactatctc gagccaggaa gtataaagaa acagaaatgg   600
ccaccaccag tatc                                                     614
```

<210> SEQ ID NO 85
<211> LENGTH: 564
<212> TYPE: DNA
<213> ORGANISM: Drosophila

<400> SEQUENCE: 85

```
cggaactgaa acataggact agctcagtct tattttatt cgtttcgagg ttgaacacgt     60
acacactttt agctagtctg ggtgaaaaaa tttcatgaat tattttgaag cggcacagaa   120
aatcgaagag aaagttttca atactagtag taatattatt cagcattcat caaagtttta   180
agttaaactt caagcaaaat gtttcggttt tctcgcaatg ccataacccg ggcgtgtagt   240
ctctccattc gtcggccgga ggtgatccgt catcgcaggt acgcctcgca ggcgatcaac   300
cagatgctgc agctgcagca gatggagatc tgcgcggatc ctccgtcgcg tggcttggtc   360
gttggagtct acgccgacga ggaggacaag aacgacgctg gcatcctgac gccaaccggc   420
```

```
tggaagtaca atgtgcagaa gacgcacggt cggttgctag aagtgctgcg aatgtccgga    480
cccatgccca aaggggaga gacccgcctc ctgttcgccg tggagccgga gcgcgtgccc    540
tactattcgg cggtggcagt tatc                                          564

<210> SEQ ID NO 86
<211> LENGTH: 683
<212> TYPE: DNA
<213> ORGANISM: Drosophila

<400> SEQUENCE: 86
ctgtacgata cgtacatctt tgtcagcacc gatcgcctga gccacagcat cctgctggag     60
ctgctgggtt acctgactaa tgagcagcag tatgctcctt ggtccactgc caacactatt    120
ctgaccgtct acgatcgtta cttgcgtggc gatgattctt actacaactt ccaagatttc    180
gtgaagcgcc tgatcgatcc catcttcgat aaaatcggtg taaacgagat tcccggcgag    240
cattatctga caactatctc gcgcatcgtg ctggtcagct tggcctgcca ggtgggatcc    300
gatgattgct ataaccagtc ggccaataaa ttatccgagt acctatacaa tggcacagcc    360
attgaggcca ctctaaagac tcaagcctac tgtgctggtc tccgatcgac taccaatgaa    420
atctatagca gagtgcagtc cgatttgctc agttcctcag attccaccga tcgcagcctg    480
ttcatctcct cgttgggctg ctctggaagt acgagccagc tgcttgattt cttgagacta    540
tccctggaca ccaacaatag cttgagctac tcggagcgca cttcccttct aaactcggcc    600
tattcccgca gtgaaatcgg tcttaccgct agtttggaat cctggagag caactgggag    660 gcatatgcca acctttcaga ctc                                           683

<210> SEQ ID NO 87
<211> LENGTH: 617
<212> TYPE: DNA
<213> ORGANISM: Drosophila

<400> SEQUENCE: 87
aagaaaagca atccataaat ataacgtcat gaaactgtta atatggttgt gcctcctcgg     60
cttcctggcc agtgcctatg gcatttttcct ggacaagatt accggtcgag gggattcatc    120
tggaaacggc ctactagacg atatctttgg actcgaagac tcggataaca gcagccacaa    180
caaaacctcc caacatgcat tgccagcgtc gggaattttt actccggtta aagtagctgt    240
tgacgttatt caaatatat gggatgaatt ttctaaggga gttttaggcc ttatgggcag    300
ttttggtacc ggtgatgatg gaggcgaatc accgccgtct gggaatacag cgcctgtcac    360
aacagagtct agtttgccat cgcaagaaac cacaacgact agaacaacgc cgtttacaac    420
aacggaatcc agaacggaat cggtcttgga acaaccaca acagattcat ccacgagtac    480
tttgccgcca taaggagaaa ttctgtcgcc taaccttcgc atcggatatt gcttgtcatt    540
gtttgtttcc cagctgctttt ctgtctggtg tatttaaaca acgagaatgt aaatataagt    600
accagccacg cttaaaa                                                  617

<210> SEQ ID NO 88
<211> LENGTH: 448
<212> TYPE: DNA
<213> ORGANISM: Drosophila

<400> SEQUENCE: 88
ctcagtcggt tcagatcggt tcgttttaca attttttccccg ctacagactt cgtaaacaaa    60
```

```
ttgtatgaaa atctgaattt gaaaatcaat ttttggctat ccacactcga gctacacaac      120
ctctcgtcaa aacttttaag tttacatcgc gacaaacgga acaacaggga atcatgagat      180
ccagcaaagt tcgtgggggc aacgccagtc gattggctga cgcggaggga cagtggggaa      240
agggatgcct gggttcccag cactcaatta tcaagaatca cgggcgtggc ctttcatccc      300
aaactcccac gcaatttggt ggattctcgc cgtcgggaca gcagtatcct gccgtgtact      360
cgcagccagg attccgggcc gatggtaagc tgaaggtcac gcccaactcg ctgctccagc      420
agcagcaaca gcagcaacag cagcaaca                                         448
```

```
<210> SEQ ID NO 89
<211> LENGTH: 634
<212> TYPE: DNA
<213> ORGANISM: Drosophila

<400> SEQUENCE: 89
tttcgtagag ttaagaactc atcaaaaaaa atttaacgta aaaaaattgc ttattgcact       60
agaccccatt tcgactattt gttatttcca atttattgga aacaaaattt tacgaacgat      120
aaattcatag tttttttttt ctctcgattt tggaacaaca ttttttttgaa gggtacttta    180 cgtgtgcaga agtactggga caatgttcgg aaaaactcgt cagttgctat tcagcgtttg      240
cattcggtcc ccggtgtgcc gacgatatgt cccgaagttc atcaagcgtt catacgcctc      300
gcaggcggtt aaccagatgc tgctgctcca gcagatggac atctgtgcgg atcagccgtc      360
gcgagccttg gtcataggcg tctatgcgga tgaggaggac aagaacgatg ccggcattct      420
gacccccgcc ggctggcgtt ataatcttca aaagacaaat ggtcgtctga tagaggtgct      480
ccggatgtcg ggacccatgc ccaagagagg cgaggcccgt cttctcttcg ccgttgagcc      540
ggagcgtatt ccctattatt ctgtggtggc ggtcgttggt ctgggtaagg agtgcttggg      600
ctataatccc tatgaggtcc tggacgaaca gaag                                  634
```

```
<210> SEQ ID NO 90
<211> LENGTH: 474
<212> TYPE: DNA
<213> ORGANISM: Drosophila

<400> SEQUENCE: 90
ttctccaggg cacagacgac caggttcgag acaaaaatgc aaagtggccc actctaggag       60
tcgcgatgct atcaaaaatt ctacgtaaat atggtacaca gaacatattc ggcaatcacc      120
atccgcataa cacccatacg cgcaatccga gctgcccttg gaagtcggag tgcggatgcg      180
ggcacggatg cgtttgtggc gacgtccccg gcgattcgca ggtgatctgc gcggaatac      240 acgactggga tcggcgcagt gcggcacacc acgagcgccg taagatcatt ccgaaactgg      300
tgtatttgca caatccgtgg aagtacctgg tgaccaagtt caatctgtgg aagcttaagt      360
ggctctggga tcgggagttt agcgagcctg acttcttgga gggcgccaag caggcgggca      420
tcgtgatgac ggacatcatc cgtcagcaga gggccgataa gattagcgag tata            474
```

```
<210> SEQ ID NO 91
<211> LENGTH: 348
<212> TYPE: DNA
<213> ORGANISM: Drosophila

<400> SEQUENCE: 91
cgcttttaag gcacaatatt ttgggaattg aacaaaaaat ctttaatgaa atgtttcaag       60
atttcccttg agattgtcga cataacatct ggatatatat ttatatacaa tattttaatg      120
```

```
tttgtcaggg ctgacttgtg ataatgattt tgagtaagaa accaagcaat tccgttcatt    180
atatatttat atatttattg tgaaaaaagg agtgcgtcat atatttatac cagttctgtt    240
ttggatatat gtatagggtt agataagtgt attctattca acggttttgg tttaattact    300
atgcatcctt cacatgagta ataactatca gaccattcgg ttacgggg               348
```

```
<210> SEQ ID NO 92
<211> LENGTH: 600
<212> TYPE: DNA
<213> ORGANISM: Drosophila

<400> SEQUENCE: 92
ctgcgaaggc tgcgttggct aaagctccaa tagaatctga ggagatgccg gaagacgagg     60
acaaggagga acttcattcc gtggaatcgg gcggagagga ttccgaagat gactttgaag    120
atataaaggc catccttaac gaaaagcccc aagcgttgt cgtcgaagag gaaatcgaag    180
aggatctcga ttcggaaggc agctttgatg agcccttgcc caggctggga gtgtccataa    240
agagtgagtt tatccgcgga tttgaaagtt tgccaagcat atcggatata tcactcgatc    300
cggagccgga accagaacct gaaccggagt taagcgctca ggacaaatcc gacaccaagg    360
cggacacaga tgatggtgta tttcacaagg atggcacaga tgccggcgag ggcgagtcgg    420
ggagctcttc gggttccgat aaggatgcta gcactgctat aaatgcggcg gctgagtcgg    480
aagaagacga cgattccatt ttgatggatg atctggcgga tgagcaagag ccgacagaaa    540
aacgggtcgt cattggggag gaagtggaca ccatggccat gttaaccgag gccgtcgatg    600
```

```
<210> SEQ ID NO 93
<211> LENGTH: 533
<212> TYPE: DNA
<213> ORGANISM: Drosophila

<400> SEQUENCE: 93
aaactctaga gccctaaaac gatgcctaaa agtagttatt taccaaaaaa catgcaaatt     60
ggttctgctc gctaggtatt aatcatttag ttcatatgta tacatataat ttgccgtttg    120
caccgttttt ccgtcttcct accatccatc tgtatataat gcttatttga tctgtgtata    180
tatagaattt ctacttatgt tccataatat tcgttgtgtc agattttac tataagttac    240 gttttggatt tccttctcaa accttttgtt tttgttttct ttgttcttac gcctcccaat    300
cttcgttcag taaaagttgc aacttggaga gattttggaa tagttcagat tataagtgag    360
tagatataag tgtgtgtgta tataactgct tgaagaagat tctattgagt tgagatccat    420
catcatcatc gtcatcgtca tcattatcat cgtgatcatc tgccatttaa agaactactc    480
cgctagtaag ccgatttcta gactagattt tggttgttta taattctcat ttg          533
```

```
<210> SEQ ID NO 94
<211> LENGTH: 647
<212> TYPE: DNA
<213> ORGANISM: Drosophila

<400> SEQUENCE: 94
ctctattgat agttcaggtc gatcgcttca ggctcaagtt atctataaat tgcttacttt     60
tatgtgaatt ctcgtgacgt agcccgtgcg cttttttaaa attatttgtg caagaaaaat    120
tttagactcg tggacgaccc tatatcgatt gctaaccggc caggatggag aagtacgagt    180
gcaagccaga gccggtggag aagaaggaga agccggtgga agagctaatg aactgggatg    240
```

-continued

| | |
|---|---|
| cctactacaa gaaccgcgga ttggtcagca cccgattggg cagctgcaaa gcggactaca | 300 |
| tgcactgctc cacgtaccag gagaagggta atgcccagga gaaggacaag aagggtaagg | 360 |
| gcgcgtgctg ttgctcctcc tgtccggttc gaaaccggga agaggtatac cagcccaggt | 420 |
| gcccggctcc cggccagaag ggcaagccca acagggacta catgcgctgc tttgccgcca | 480 |
| aactgatcgt tcagaagctc aacatgcccg gtagggactt cgaatgccag gataagctgc | 540 |
| agattaaggc aaacgtgtgc cgcgggtgca agatctgcct tggttccagc agcatcaatg | 600 |
| tcaactgtct tccactgaat ccggacaaga cattccagat ggaagcc | 647 |

<210> SEQ ID NO 95
<211> LENGTH: 532
<212> TYPE: DNA
<213> ORGANISM: Drosophila

<400> SEQUENCE: 95

| | |
|---|---|
| ttttttttca ttgaaatagt ttattaaaaa actaaactat atcttctttg atgtatttat | 60 |
| acagaaaaat tattcatata ccgatcatgt ttaaaaatta atcatacaat ccaagatgtg | 120 |
| tatataat acaaattttc aactttatgc gaaattacaa taaataaaaa taagggatat | 180 |
| aagaaatgaa atctttcgcg atatatgctc acctcatgca agtttaaggg tatgtatata | 240 |
| ataattatgt tagtgagttg cgtgtggatg ggtgtttgta tatagttttt tttaggtaca | 300 |
| ttggatgcgt cgttaggtat tttaagtggg ctgtagcggg tacaaaaagt tagaaactaa | 360 |
| ctaatttaaa agcgaatttt cggatagaaa tagtagattg tgtagatgtg tagagtagag | 420 |
| gtgtaaatat aaattcaaaa caatttcaaa attttaacac ttcgtttaaa gttaatcctt | 480 |
| ttttggttt tttttttaag tttcaacaca cattactttg ttacaatgtt ag | 532 |

<210> SEQ ID NO 96
<211> LENGTH: 724
<212> TYPE: DNA
<213> ORGANISM: Drosophila

<400> SEQUENCE: 96

| | |
|---|---|
| agatcaaaca gaccaaattt ctcgttaaaa aaaaaaaaac tactaaaaaa aattgttttg | 60 |
| gccaattagt tttgtagatt tcgttatcaa gatgatgcta tcaacctatc agcacgacta | 120 |
| tgtcccgccc agtgccaaac ggtacgagtt tctaacgcgg cccaggggcg ccgaggctca | 180 |
| cagtggtccg caggtcaagg agtgcgaatg cgtcgacgag tccaagatca tgatgccgcc | 240 |
| gaacgcgtct aaggactgtg gcggcgtcga gtggacgggc atagcgccaa tgggaaagct | 300 |
| ggtggatccg cgtatcatac ccacccagct gactcaggac caggtggaca agatggcctt | 360 |
| ctccgcggaa acagattgct ttaagctgca acccaaccgc tttctcaaga tcttacgtac | 420 |
| agtctacccg gatctgtatg aacgcctgaa ggtcatgccc aaggaggagc tgagccgcag | 480 |
| gctggagacc aaccgtatga acaccaccta tcagatcgat tactgtaaca tgaacgagta | 540 |
| cccggagggt atttatgaga gcctaaagac ggaggacgag tccaagaacg ccaacaagct | 600 |
| gatgagcgaa cgtggaccct gcaacgagtt ccgctcgaac gtgatgaacg aactggagcg | 660 |
| ggaggcgtcc gctggctacg agatgtctag cgacgagtgc caaagaact acaagccatt | 720 |
| caag | 724 |

<210> SEQ ID NO 97
<211> LENGTH: 611
<212> TYPE: DNA
<213> ORGANISM: Drosophila

<400> SEQUENCE: 97

| tgtagaccca | gaaatcgata | gtgtatactt | tagaccttta | cagcttgcca | cttctcctcc | 60 |
| agttggacca | agatcagaat | ggagaggcga | agacccgaa | agtcctcgcg | taaatacgtg | 120 |
| tgctccaaat | caaactcttc | agttggagga | ggagtagagg | aagacagtgg | ctcatcattg | 180 |
| cctgccaccg | ccaaagcgtt | actcctccag | ccggacggta | ataaagcacc | aaccatgaca | 240 |
| tcccttctgg | gcgaacgact | cagaagagtt | tctcgcatcg | caagagctcc | gcacagccta | 300 |
| caagttaccg | aaaatccaga | agaaggtgga | gcaccaatcg | taccactaag | agaatccggc | 360 |
| gcatcggaag | tgtcagaagt | aaatccgggg | gttatggtca | ttccggagtc | ggccagtccc | 420 |
| cggggatcgg | cggtgcatgg | acaacacgct | agcttggtct | tcagtgctga | agccagggat | 480 |
| tcggacagta | cgcggatatc | ggaggaaatg | gtggaagtgt | tccaaacctc | ttcggcgaga | 540 |
| accacatcca | atgagcccgc | aggggggcaat | ctgcgctttg | aaaccactcc | cgtggctgta | 600 |
| agcgaaagta | t | | | | | 611 |

<210> SEQ ID NO 98
<211> LENGTH: 603
<212> TYPE: DNA
<213> ORGANISM: Drosophila

<400> SEQUENCE: 98

| tgaattccgg | aacgacaccg | tgacgctcag | aaacgcggcg | caaacccag | agtggatttg | 60 |
| caggtttatg | ttgcagttta | cggctgaccg | gactcgtata | tgacgaaatt | cgcgcagcgc | 120 |
| agcaaaaaga | cgtgcgaaat | acgcgggaca | atggatgtgt | gtgtgtgtgt | gtgtgtgtct | 180 |
| atgtggaagg | aaatttgtga | gacctgcgac | cgggaggcga | aggagaagca | gttcagcacc | 240 |
| tcggaatcgg | aacgccacac | gaaccgcggc | ctgaatcgct | atcgggatgt | gaatccgtac | 300 |
| gatcattccc | gcattgtttt | gaagcgcggc | agcgtagact | acatcaatgc | gaacctggtt | 360 |
| cagctggagc | gcgccgagcg | ccagtacatc | ctgacccaag | gaccgctggt | ggacacagtg | 420 |
| ggccacttct | ggctgatggt | atgggagcag | aagtccagag | cagttctcat | gctcaacaag | 480 |
| ctgatggaga | agaaacagat | caagtgccac | ctctactggc | ccaacgagat | gggagccgac | 540 |
| aaggccctga | aactgcccca | cgttaaactc | accgtggagc | tcgtccgtct | cgagacctac | 600 |
| cag | | | | | | 603 |

<210> SEQ ID NO 99
<211> LENGTH: 613
<212> TYPE: DNA
<213> ORGANISM: Drosophila
<220> FEATURE:
<221> NAME/KEY: misc_feature
<222> LOCATION: (1)...(613)
<223> OTHER INFORMATION: n = A,T,C or G

<400> SEQUENCE: 99

| ccagccactt | cggacagact | gatttccaca | tcaccgagtt | attataaata | aatcagaaag | 60 |
| acatctaaaa | tgggtttcga | accctctgag | gataaggcaa | ggcctggagg | tcttggcgtg | 120 |
| cgacactggc | aggcggttct | tctgttcgtg | ggcatgatga | tcaactactt | ccagcgggtg | 180 |
| aacatctcgg | ctgccattgt | gcccatgacg | cagtccaccg | cgggggctcc | gttctacacc | 240 |
| tgggatacgt | cggacaagtc | cctgatcctc | agcagctttt | tctggggcta | tgtggtctcc | 300 |
| caggtgccgg | caggactgct | tgccaagcga | tttggagcca | agttagtgct | gggcctggcg | 360 |

| | |
|---|---:|
| actgcaatcg gaggtatttt gtgcttcttc catcccattg cagccaaaag cgggtggcag | 420 |
| agtatctgcg ttctgcgcgt tcttaccggt ctggtccagg gcacggttta tccgtgtgtc | 480 |
| cacacgctgc tggctaagtg ggtgccacgc actgagcggn gactgctaac cactggcgtt | 540 |
| tattcgggag cacagttcgg aacggctgtc atcctggtca ccagtggctt catcttcgaa | 600 |
| tccagcatgg gtt | 613 |

<210> SEQ ID NO 100
<211> LENGTH: 360
<212> TYPE: DNA
<213> ORGANISM: Drosophila

<400> SEQUENCE: 100

| | |
|---|---:|
| cgctgggaaa aagattcgcg aaagaagcg aaaaagcga agccaaggg aaaactatga | 60 |
| taaaactatc ctttccatgg ggaggagtcg tcgaaaatct tccagaagta aaggcgacc | 120 |
| aagaagaaca tggtggaatt ggatcaggag cagaacttgg agcccatttc actgtctcgc | 180 |
| aactatctaa aactggaact caactggcac agatggaaaa tagtatggat atcaaaattg | 240 |
| aaaattttga tatttcggca caaggaaagc tgttattcga taaagcgagt ctgacaattg | 300 |
| tttacggaag aagatacggt ttggtcggac ccaatggaat gggaaagact actctattga | 360 |

<210> SEQ ID NO 101
<211> LENGTH: 917
<212> TYPE: DNA
<213> ORGANISM: Drosophila

<400> SEQUENCE: 101

| | |
|---|---:|
| gaaattcgcc tgcgctacgg ttctgctctt ggccaccatt cttggggccc aggctgtgga | 60 |
| ctggaattcg gtcaagaacc tgaacatcga accccgatg cccaaggtcc atggcgagac | 120 |
| cctgcccagc ggtaggatta ctggaggaca gattgccgag cccaaccagt tcccctacca | 180 |
| ggtgggacta ctgctgtaca tcactggagg agctgcctgg tgcggaggca ccatcatcag | 240 |
| tgaccgctgg atcatcaccg ccgcccattg cacggacagc ctgaccaccg gagtggatgt | 300 |
| ctacctgggc gcccacgatc gcaccaacgc caaggaggag ggacagcaga tcatcttcgt | 360 |
| ggagacaaag aatgtgatcg tgcacgagga ttggatcgcc gagaccatca ccaacgacat | 420 |
| ttccctgatc aagttgccag tgcccattga gttcaacaag tacatccagc ccgctaagct | 480 |
| gcccgtgaaa tccgacagct acagcaccta cggcggagag aatgccattg cctccggatg | 540 |
| gggcaagatc agcgactctg ctaccggagc gaccgacatt ttgcagtacg ctacggttcc | 600 |
| catcatgaac aacagcggct gctctccctg gtacttcggt ctggttgccg ccagcaacat | 660 |
| ttgcatcaag accaccggcg gaatttccac ctgcaacggc gactccggcg gtcctttggt | 720 |
| cctggatgac ggcagcaaca ccctgattgg agccacctcc ttcggcattg ctctcggctg | 780 |
| cgaggtggga tgggcccggtg tcttcacccg tatcacctac tacctggact ggatcgaaga | 840 |
| gaagagtggt gtggtcaaca acggcgacta agcgttgatt ttgatcttaa aataaacgtt | 900 |
| tattttggg ttacaag | 917 |

<210> SEQ ID NO 102
<211> LENGTH: 619
<212> TYPE: DNA
<213> ORGANISM: Drosophila

<400> SEQUENCE: 102

| | |
|---|---:|
| acaattgttt tgcagctcta tcggctacgt gcctcgcata cgtgtatttt tcatatttt | 60 |

```
tgggtttcgt ttaaaccatt tgacttaata aatactagaa taaagaaaaa aaatcacact      120
acatggctac gaaaaaaaag tatagatagt ggtaaaagta ggagtactaa aaaggtgaaa      180
agcacaaaca gttgcgttga atagttggtt aaaaggatat atagtatata cgtatacatt      240 atatagggc accactcgct aaagaccaac aaacaaaaag gtattaatca aatataaaag       300
taacgagtta aaaaacgaaa gaaaaattaa ttgactctct ggctggcttg tgcgttgggt      360
tcttattcgg tgttttagat ttataaattc gtcatcaagt tttcggtttg ggatattcat      420
cggtattcat catctatata cagggctgga ttccggtttc gggttcgggg ttgcgtgtgt      480
gtaatcgggg tcctagattt ctggattcta ggccaccgtg gcgtactgac gcttctccaa      540
cgagacattg aatccattct caagctttag gatgatgtca gcctgcagct tgaaatctgc      600
ctccgtgtcc gtggagtgg                                                  619

<210> SEQ ID NO 103
<211> LENGTH: 650
<212> TYPE: DNA
<213> ORGANISM: Drosophila

<400> SEQUENCE: 103
agacaatcgg tttgaaaaaa agaaaagcca aaaaattatt tcgtttaaca gtgtctatac       60
agcttcctcg ttcatacgcg ttcctctaaa aataaaaagg ttaagagaat ggcattttgc      120
ggccacgtta cttcctctgg acaaatagtc ctgcgggatg agatcttcag cagcaggact      180
tgcattgcgc gctccccgtc atccggaggc tcactaaact ccatgtcttc gccgagctcg      240
ctcgcccaga acaccacacg cacatacttc ttcaaggacg acggtggaaa tccttcgccc      300
caatctacga caactggtc gctcggcgga ctcaagcgat cggagatcca gagcaacttg      360
gtgccctcgc tgtgtctcag ctcgcaggaa agctccctca actatctcag ccactgcaag      420
ggaattaagg tggaccgcca accagaggcc gcctatcaga actggtactc agccaagcag      480
cagcaattac tagagaagca gcggcgaatc aaggaggagc aggagttcaa gcagcagcgg      540
acggaggagc gcaagcagct ggccaggatg tgctacgagc agtggctaaa ggacaaggcc      600
cgccaggcgg caaacttgca gctggagagc cacatccaag acgcggccat                650

<210> SEQ ID NO 104
<211> LENGTH: 657
<212> TYPE: DNA
<213> ORGANISM: Drosophila

<400> SEQUENCE: 104
gattatgttc agaaccttcc gcccggagtc atcgaagtgg gtggtctcca catcaagaac       60
cagaccagcc ctttgcccac gtatatacaa gaattcacgg agaagttctt cgacggcatt      120
gtgtacatca atatgcccta tattgagtat atgaatgacc agggattgaa ggctatgtat      180
acgatgattc acggaaatcc caatgttgcc ttcatttgga atgtggagca actagagcag      240
ttgccggcca agaaaccaaa tctgttgacg cttcatgtga atcaatcact acagcaagac      300
atcttggcta tgcagtacgt caaggggttc ctgaatcatg gagatagttt cagtcttcag      360
gaggcaattc actatggagt gcccgtcgtc gtgcttcccc ttaaactaga ggaatttaat      420
aatgcccaac gtgtaatgga acgcaacttg ggtgtgatgc ttcaggtcaa ggaatttaac      480
caaagctccc tgtcggatgc ccttacgcga atcctggatg aggagcgttt cataagtgct      540
ctccaccagg cccagttgaa gttccggacc cgtccgcaat ccgccctgga attggctgta      600
```

```
tggcatgcgg aacaacttat cgccgaacca cgactattta acatttttgc acaaact      657
```

<210> SEQ ID NO 105
<211> LENGTH: 556
<212> TYPE: DNA
<213> ORGANISM: Drosophila

<400> SEQUENCE: 105

```
cctgtacaac atgtgctccg ggttggtgta caacggcttc ctaagcacct accaaacgca       60
tccagccgac ctttgtcacc gccttccaga gtccatcagc atggaggcgg gtgccctgac      120
gcagacacta gcactggggt gccaggcgtg cttcaaggcc aatgtcacgc ccaccagcaa      180
cgtcctcatc ctgggagcct gcccaacggc tgtggcggcc ggcatatgcg caaaggccat      240
cggggccaag cgtgtggcca ttgccggatg tatggctccg gctctggatg tggtcgcccg      300
ggacttcggc ttccaagcag tcgagttcga tagcaacgca ctgttcggag aggtccttga      360
agccatctac agcaagttcc gggattggcc ggactgcgta atcaactgct ccatctctgc      420
aatgacgatg aatctggcgg tcatggctct gcagccatgt ggggtgtgtg tgctggccga      480
gtgcgattca gagtgtgcca gcttcaatgc tctggacgta ctgatgaaga acatccgcct      540
agtgcccagt tttcgt                                                     556
```

<210> SEQ ID NO 106
<211> LENGTH: 629
<212> TYPE: DNA
<213> ORGANISM: Drosophila

<400> SEQUENCE: 106

```
aagcaataac atgcagtctt ttacaattct aacccttttc accatcgttt tgatggtcca       60
aaattcaaga gctggaactc tcagcattgg gtccctgatg ggagatgtgt cccaagtggc      120
tgttgctggg gagaaggtca tccatcaact ggaaaacgct gtggccagct tcaatcgga       180
ttttgtccag ccaaccactt tgaacattct aagcgacatg ggaaacgcct ggggtgatct      240
ggctaacgcc cttactagtt taagagtgga taacgattat atgcaacccg aggccaccaa      300
tctcttgggc aatgttctgg gtggagtggg cactggtctt ggagatttgg ctaatgccat      360
taccagtctt agtgttcaga tgacgaacgc acctcaggct cgcagtcttt cgtccaatgg      420
tgcttctatt atagccaaag gaggagccgt gagtgcgaag actattgccg ctgctgcaga      480
tgcagctgcc ccttatataa agcagctaaa tgctggccta ggcgatctgg ctaatgccct      540
caccaacctc tgaagaactt tggagcagtt caattaacaa ataaatattc aatcgcgcaa      600
agagcttaaa aaaaaaaaa aaaaactcg                                        629
```

<210> SEQ ID NO 107
<211> LENGTH: 639
<212> TYPE: DNA
<213> ORGANISM: Drosophila

<400> SEQUENCE: 107

```
tccatccgta attcagaaat aagaaaacga tgtctcgtcg ttcgaccgtt ttatcaactg       60
gtaaggagag ctccaaggag gaaaagaatc gaatgtccca attggacgtt attatcggtc      120
aactgaagac gatggcggtt ggaaccggga gggccggaaa tctatccgag gccaccatca      180
catatatatg ccaggcgagc cgagagctgt ttctatccca gccgatgctc ctcgaactga      240
gtgctccggt aaagatctgc ggggatctgc acggtcagtt caaggatcta ttgaggatat      300
tccagcagtg cggtgtgcca ccgctttcaa actacctatt ccttggggat tacgtggatc      360
```

```
ggggtcactg ctccatcgag actttatcgc tgctgttgac ctataagctt cgctatccgg      420
agactttctt cctgctgcgc ggcaatcatg aatcggcgga tttgaatcgg gtatatgggt      480
ttttcgacga gtgcaagcga cgatatagca tcaagttgtg gcgctccttt gtcgattgct      540
atgactgcat gccagtggcc gccatcatag ccgatcgcat cttttgcgtc cacggcggac      600
tgagtccgga tctgaataac ctggatgaca tccggcggc                             639
```

<210> SEQ ID NO 108
<211> LENGTH: 575
<212> TYPE: DNA
<213> ORGANISM: Drosophila

<400> SEQUENCE: 108

```
cgattggagg attctccgcg agatattcgc atctacagtt ccgatcgcca aaagtgcaat      60
gtgaatccgt gcaggatcaa caacggcgga tgtgcccaga gctgtcatcc tgccccgaat     120
ggcaaggccg agtgcaagtg cgacgatagc accaaggtgg tgaacgaggg aaggatgtgt     180
gccccgcgaa acaatacttg cgaggccagc aaattctact gcaagaacgg cagatgcatt     240
tcgagaatgt ggtcctgcga tggcgacgac gactgtggcg acaactccga cgaggatccc     300
aactattgtg cctatcactc ctgctccccc aacgagttcc gctgcaacaa cggacgctgc     360
atctttaagt cgtggaagtg tgatcacgag aacgactgca aggatggttc cgatgagctg     420
ggctgcgtct atccaccatg tgtggatggt gagttcactt gcgccaatgg acggtgtatt     480
ccacaggctc aagtgtgcaa tggtgtgaat gactgcaagg ataatgccac atcggatgat     540
acgcacgaac ggtggtccat gaacaccact tgtcc                                 575
```

<210> SEQ ID NO 109
<211> LENGTH: 563
<212> TYPE: DNA
<213> ORGANISM: Drosophila

<400> SEQUENCE: 109

```
tcaaaccatt actcctacaa ttattgggtt ttcccaagcc aaacaacaca tgcttttgag      60
gattttagat cagagtctca ctattccatc gcgatggaca gggattcctg ccaaaatttc     120
tcattagact ccacgagcag ttcccatttt gctcctccgc cagtttgcgc gcccagaagg     180
aagaagccgg agaagcccgc agctgaggag gcatctcccg aatgctccaa cgtcacatcg     240
tcatcctcgt cctcgacaac caccatatcc ataggcgcct tcgattcgca atgcaacctc     300
cacaacgccc ggaatcccga ggccccgaac attggctatg agttgaacgt ggccaagtcc     360
atattgcaga agtatagcac cctcagtggg acaacttgt tcgatcatct tagtgacatc      420
ataaagaggg tgattgacga acgtcctccg aatgtgatag acttcttcga ggaatttagc     480
cgaaatgttc gcgaacagaa gttccacttg ccagaacgct ttccgcccag tggcgtgttc     540
gatgaggtgc gatctttccg ggt                                              563
```

<210> SEQ ID NO 110
<211> LENGTH: 472
<212> TYPE: DNA
<213> ORGANISM: Drosophila

<400> SEQUENCE: 110

```
cagacattgt atttcgatta aaaaaacaaa aaaaatgcca gttttgaaac ttaatgctta      60
tttcaccaaa ttcttcccat cctcgatggt gcgttccaag gagttggtgc gaagaaggta     120
```

-continued

| | |
|---|---|
| ttcgatgaag gtcgcgcagg tgcgaagatc ttacaacata aagttcaatg aagatccaga | 180 |
| attcgaatgc gatgccacag tcacgaatat gccccaatcc ttgaagacta tgattaagag | 240 |
| gaaactgctc tcaaagcgtg tgatcggtac cttcgacta agattccata gcaattcgtt | 300 |
| taagaaaagg ctcgagatca cagccacaat aaccaaccca acagttccgt cggacacaga | 360 |
| tctcgctccg gaggatgagc agctgtacga gctgtacata tgcagtagcc agggtcaatt | 420 |
| gctgggcaag attcccttcc tggagagcga ctaccggcgt gcagctcgcg ag | 472 |

<210> SEQ ID NO 111
<211> LENGTH: 529
<212> TYPE: DNA
<213> ORGANISM: Drosophila

<400> SEQUENCE: 111

| | |
|---|---|
| aatagcctgc cgaccttcag atcggtgggc ggtgcttatc gtctgcttgc tggcaaggat | 60 |
| cagaagaggg attccgcggg gcacaagacc agacagccgg aaaagccacc acaagataag | 120 |
| cagaagagta agggtgctag tggcaaacca tagagtgctg ggtcaactga ctccgacaag | 180 |
| aagaccacca aggttaccct gatcaacggc gagggcgtgg acgcgagct gatgacgcg | 240 |
| gtgcaagagg taatctgtgc tgtgaaggcc ccaatagagt gggatgtcca cgatgagttc | 300 |
| aaggccaagg acagcgatga tgtgtacccg gaggttctta agtccttgcg agccaataag | 360 |
| gctggcatca atggacccgt ggatagtcat cactggcagc gcctgatccg caagcagttc | 420 |
| gaccaggtcg tctacgtgtc attgcgctcc cacatcgacg gactggactc gccctacggt | 480 |
| gacttcgacg ttgtgatcat ccaggaccag atggagggcg actactttg | 529 |

<210> SEQ ID NO 112
<211> LENGTH: 881
<212> TYPE: DNA
<213> ORGANISM: Drosophila

<400> SEQUENCE: 112

| | |
|---|---|
| cagagaactc aaaatgaaac aattcgcggt tatattcgca ctggctctgg cttcggtttc | 60 |
| ggccatttct gtccctcagc cgggattccc cgaaggtcgc atcatcaacg gctatgaagc | 120 |
| ggcgaaggga gaggcgccct atattgtgtc cttacagacc acatccaact cgcacttctg | 180 |
| tgcaggaagc ttgctcgatg aggtgaccat tgtgaccgcc gcacactgcc tgacctacaa | 240 |
| tcagggtcag gcagttgccg gtgcacacag ccgcactgac caggagaacg ttcagattag | 300 |
| gaagttcacc aatgcccagt acgtgatcca cgagaactac ggtggcggtg tgggacccaa | 360 |
| cgacatcggc ctaattctcc tcaaggaaga ggatgccttt gacctgaatg ccgttgcccg | 420 |
| tgatggcagc aatccggttt ccgcagtaag tcttccttca aagacattcc aaggcactag | 480 |
| cgatggatat ctgtacggct ggggccgcga caactcagga ttgctgccgc tgaaccttca | 540 |
| gaaactggac gctatcattg ttgactacaa cgaatgcaag cggcgttgc catccaacaa | 600 |
| ttcgctggca gaaaccaatg tatgcaccca cacccccgga aaagccgacg gatcctgcaa | 660 |
| cggagacagt ggcggccccc tggtctcgca atccagcagt cgaggagccg agctgattgg | 720 |
| catcgtctcc tggggataca caccctgttt gtccacaacc tatccttccg tatacacatc | 780 |
| agtgtcttca ttttgcctt ggatcgatga gaaccgtaag gcgaaataga caaaaaccta | 840 |
| ttctcttata taaccactta ataaacgaac attctgtact c | 881 |

<210> SEQ ID NO 113
<211> LENGTH: 500

```
<212> TYPE: DNA
<213> ORGANISM: Drosophila

<400> SEQUENCE: 113
cttaagctct atggcttagt acattcgttt tcgttaccg atttcaaaca attgaacttg       60
taaaaataaa agtattaaag ctaactaaaa attttaagta tatacaactg ccgcagtaac      120
gcaggatacc aataacccat tgacgtaatg cattcagccg gtaggagcag tgggcaaagt      180
gcgggctcaa caccccgagg tggaggaccc aacaccatct ccggggccac agtgcgttcc      240
aagttagcgg cacctctatc gacgcagacg gcgggaacac ggcgaactgt tcacggcgga      300
gcgggcgatg ggggaaccga tgcggcttgg aagcagaccg gtcgtcgcct tggcaagcat      360
aatccacctt ctcggctggt ccagcccacg gtagcctctt cgctgagggc cagcagcaac      420
aggcagacgg ccaagcagaa gttcgagaga gcgagaggac atgagaagtc cagattagtg      480
gtgcccttgg ccaaggacac                                                 500

<210> SEQ ID NO 114
<211> LENGTH: 507
<212> TYPE: DNA
<213> ORGANISM: Drosophila

<400> SEQUENCE: 114
gttcagttgc gggtgaaaat agagtctttg acgtacgttc aagacaataa ttggacacat       60
aacccacttc ttgtttgcac aagtgaacca ttctgtgttc ccagttgaaa gggaaacccc      120
aataagtgca gaatgacgag tgcaagtcta ttgtcgcgtt ccctgctaac agaagctccg      180
cgttctaaga atcgctcggt gtttaccttg attgctggtt tggtggtcgg ctactgcctg      240
gctcaaatct tctccagcat tgcgccgcac gagagtctct atccgtatct cagcagacgg      300
ttcagcgatt cccaggtggc caccggtggt caattggctc cggagcagag cgggttgaag      360
catgatcatc gcaacgacaa cgtcagcgtg gccgagcagt tgaagaagga ggtacgcatc      420
ctctgctggg tgatgaccaa tcccacaaac cacaagaaga aggctcgcca tgtgaagcga      480
acctggggca agcgctgcaa catcttg                                         507

<210> SEQ ID NO 115
<211> LENGTH: 575
<212> TYPE: DNA
<213> ORGANISM: Drosophila

<400> SEQUENCE: 115
aagatggcca ttaagtgtct gattttgctt acttccctgc tgggaataag ccttgcagcg       60
gactattgtg ctctgcccac gtgcctggac aagcacatag cctgcaacaa caagggaaat      120
ttcagtgaaa attgtcccaa ggacgtgcgt gaggtgaaga tcgagccgca tcacaaactc      180
atcctcaatc tcttcaacga gctgcgcaac aacgtggctg gaggcaaaat agaaggacta      240
cccaaggctg ttcgcatggc caagatgtcc tggtgcgagg agctctccca tctggccttg      300
ctgaacgtaa agacctgtga gtccctgcca gataaatgtc gcagcaccga gagattcgcc      360
tacgccggcc agaacaacgc cttgttccag tacagcggag ccgagacaga gtacaccgat      420
gcggaaataa taaggagca gatcgagaac tggtttgctg agcgctcgaa tgcatctccc      480
gagatcctcg ccagcttccc ggaggagctt cccaacaagg cggtgaccaa gttcaccatc      540
gcggtggccg agaagaacac ccatgtggga tgtgc                                575

<210> SEQ ID NO 116
```

<211> LENGTH: 609
<212> TYPE: DNA
<213> ORGANISM: Drosophila

<400> SEQUENCE: 116

```
gtagccagca taaaaacttc aaaatcgaga cctattgtac ttttcaataa aatttccgaa      60
gccttggtta acttgtagaa aaataataac attcccggta cagcatgaaa atagaatctt     120
agatttcgag gacggtagta cggttgcgga ttgcaggatg gaaaccttcg ccgtcaagga     180
ctgcaatgta tcagcgggta ccaccttctg cgccagcgcc aacctgagca caacaactct     240
tctctggcat ggtcgcccat tgcaacaccc agcctggaca cttggaccca gtcaccatga     300
tcgacgaagg aatgctcgtc accaacgatg taacgataaa tatcaccgac gaaaagggaa     360
taagccataa tatcaggaac ttacctggta tcatataccg aaaaaattaa aataaatggc     420
acccattacg tcaacaatat ccgaacatca agaagaaag  cctcagtttc agctatggcc     480
caagtaaacg ttctgagaca tctagagcgt cttagtctgt catcaattca cggaatgagc     540
gttaaaaatc tgcaacacat ccaccttcaa tcccgactgc catcaggcaa cacctggatc     600
ttttgctct                                                             609
```

<210> SEQ ID NO 117
<211> LENGTH: 611
<212> TYPE: DNA
<213> ORGANISM: Drosophila

<400> SEQUENCE: 117

```
ccaacagagc aagagccgga tagacagagc cccaaacctt tgcgcagata acagcaaga      60
gtgataatcg aatcgagaca agatgtcgga tcgcaaggcg gtgatcaaga acgctgacat     120
gagcgaggag atgcagcagg acgctgttga ctgcgccacc caggccctgg agaagtacaa     180
catcgagaag gacatcgccg ccttcatcaa gaaggagttc gacaagaagt acaaccccac     240
ctggcactgc atcgtgggcc gcaacttcgg atcctatgtg acccacgaga cgcgccactt     300
catctatttc tacctgggcc aggtggccat tctgctcttc aagagcggtt aaacgcatct     360
cgacgcctga tagccgctct accatggcgc ccaccaaagt tttccggagg agtcgccaaa     420
cactattgtt ccttgaattg taaactcatg cacacttacg aatccacact cacacatacg     480
cactgcactg cattgacaca cgcacacttg acctcgcgtt gattcgtttt tcccaaatt     540
ccaaaaactt cgctgtgctg acttagccac tctgctgcca aataaatcaa atactggtcc     600
tgacttcaaa a                                                          611
```

<210> SEQ ID NO 118
<211> LENGTH: 567
<212> TYPE: DNA
<213> ORGANISM: Drosophila

<400> SEQUENCE: 118

```
cattttcctt tgccattgtg gagcggtatt tgcacaaagc cttggattga ataatgatgc      60
cggcgggatc agaggcaaac ggagaaggaa tagcttattt ccagattgaa attctcttgt     120
tggcaaaaat tttgaaacgc ttagggcctt agcaagtgat agatacaggc aactgggata     180
gtaagggcac tttgttcatt cttttaaaaa attccctctc gcaaagtttg aaatttcatt     240
tttgtaagaa aaaaattgct ggtaaagaaa gcttctaaat taaatcaaat taaatataaa     300
ttaaacccat aattcttaag catggcaaag ttttttccgtg attttttccag cacttgcctg     360
caagttgaac ccctaatcac tgcccttcgc ccaaattgca gcagcgtcat ttcagcgctg     420
```

```
ggttgccaat tgacgtggcg gtaagtcacc tctattgcat aacacctgac aaatgcaatt    480
caggcaaaat gcttcgacga tgccgatgat gatggcctca agtgaaaaac actcacgcaa    540
acacgcgacg cactttgagc tctggat                                        567

<210> SEQ ID NO 119
<211> LENGTH: 465
<212> TYPE: DNA
<213> ORGANISM: Drosophila

<400> SEQUENCE: 119
ccaagcaagg cgaatttatt tatgccacta agcgtggtat tgtccgtaaa gcgtctccaa     60
gagacaggaa tgtcgatcga atttgacaaa agcggtgtaa ccatttcgaa aaatgggtta    120
atggttgtca aaaattcaga gaatcaactg gctgacatat ttacaaaacc gttgcctgct    180
gcgagatttg tggagttacg agacaaattg gtttgctgc aagacgacca atcgaatgct     240
gaatgaaatt tttatatata tttttcaaat ttaaattcct gtaaacatat tttgttacaa    300
tgatctgatc gggttttcct gggttttccc cgtatcctcg cagcaaatgc tggatcagtt    360
aacacttccc agaatgcaca ccacccacat ttgataggta ctaatgaata ttattggtat    420
gtttttaatt atagacgtta tttttgaggg ggcgtgttgg aatat                    465

<210> SEQ ID NO 120
<211> LENGTH: 528
<212> TYPE: DNA
<213> ORGANISM: Drosophila

<400> SEQUENCE: 120
ccgacgttag ccactggcaa cgatgacaac gaccacatca cctagagaaa ccacacagac     60
cacatttacg gttcgcaaga tgacgggccg gcgaatgtca aagctatcca cagtcctgct    120
gttctgcgcc gccttgctgc tgaccaagtc ctgcggcatc ctggcgctca gcggcgacgg    180
tttgccccaa tcccaggatg tgggccaggc ggagctatgg agcgatgatg ccaccaccac    240
catcatttcg cccagcgagg agaacagcgg ttccggtggc tgggaactga ccacggaggc    300
ggacaccacc ataccgagtg aggaaactac tgcgggcaat gaggaaacca ccgtttccga    360
agaggagacc tccacggacg cctctggaga tgtagagacc accactgctg cgccggaaac    420
ttcaccagct gaccaggaga gctcttccgc tcccgaagag accacttccg ctcccgaaga    480
gaccacttcc gctcccgaag agaccacttc cgctcccgag gagagctc                 528

<210> SEQ ID NO 121
<211> LENGTH: 639
<212> TYPE: DNA
<213> ORGANISM: Drosophila

<400> SEQUENCE: 121
ttgaatcaca ctttaaagac aagggatata cccctaaaat atcacataga acactatgca     60
ttggtatgca atcctccaag gattcctcct gggaatatca tcgataatca ttttatgggt    120
acaaggagtc gttggcttgc cattggctac aaccgatctg gagtcacttc caatcgtctt    180
ggcagaggat gttccggtgg agagagctcc aaggcaagta aaaccagatc cgtcgacgtt    240
cgatattttc aaggtggatc aaagctccaa taaccaaatg cagcagaaat ccgacggctt    300
cagagtgttc gcaaagaaac tacaggatga ttatcaccgt agagctggct acaatgaaac    360
taatccgcca ccaattactg tgacccgagg aagcactact gctcctaaga aaatccataa    420
```

```
aagtggcatt cgactatttg cttctccaca agatccacct ccgcctgaag ctgcggcgcc    480
agctgatgga gctccagcgg cggcaggagc ggctgaagga ggtgccgccg aggaaaagg    540 aactgaacca cccaaagagc tgaccgtcag tattcaacaa ttcgttacaa accaatatgg   600
tgagaaggaa tacaatgctt ggggcgtcac ttttggtag                          639
```

<210> SEQ ID NO 122
<211> LENGTH: 596
<212> TYPE: DNA
<213> ORGANISM: Drosophila

<400> SEQUENCE: 122

```
atttcaaaag taaacacata atattcacaa tagtgtatca ctttaataaa attttggtt     60 accatggcga tggaaactat tttggggatc aagggaccag actttgtgat gctagcatca   120
gatacaatgc aggccaaatc gctggtcttc atgaaagatg accaatcaaa aatccaccga   180
ctatcagact tcaatatgat ggccacggtg ggtgatggtg cgataccat tcagttcacc    240 gacttcatat ccaaaaattt gcatctgtac aagatttccc acggatacca tctaagtgcg   300
aagtcagctg cccattttac caggaaaaca ctggcggatt atataaggac caacaccaga   360
taccaggtgg caatgctcct ggcaggatac gatgcggttg agggacctga cctccactac   420
atcgactcct atggcgctgc tcagtcaatc aatcatgcag gtcatggttg gggcagcatg   480
ttctgtggca gcattctgca gagatattgg aactcgaagc tcagccaaga ggatgcctac   540
tcgctgatga agaagtgcgt cctggagatc caaaggcgac tgatcatcaa ccagcg      596
```

<210> SEQ ID NO 123
<211> LENGTH: 535
<212> TYPE: DNA
<213> ORGANISM: Drosophila

<400> SEQUENCE: 123

```
gttctagttg ggagcacaca cttctgaaa ttgttaacgc ataaatcctg ctgttttacc      60 taaactttg caaacataat ggccttccgc tcggtggtta cgatggagaa gccgctccag     120
cacatttcgc tgacggactg gtatgccgt gtgaaccaga tgcggaatgt ggcggatgcc     180
cggaggtcgg acgccttcgc catccgccac tcatcccgat ccttgaggaa cgagacgcgg    240
atcgagggcg actgggccaa ctacgagaca atgaggctc tgaccgatcg catctccgag    300
ttgaatcgct ggcgggatat catttccaag tccttcgaga agatcgagcg cgagatattc    360
atgctgcagg aggagaagaa tgccacgaa cgggagctgg aggcgttggc aggtccgatt    420
tccgtgatag ccgagtgcct gaccataagg gacggtcgcc tcggatcgga gatcacctac    480
gatgaggcca caccgagat caagaacgaa ctggtcgtgc tggagaacaa ccagc         535
```

<210> SEQ ID NO 124
<211> LENGTH: 544
<212> TYPE: DNA
<213> ORGANISM: Drosophila

<400> SEQUENCE: 124

```
gatgatatga ctatgccatc atttggaaga tcttacggag gacctgctac taatgaatgt    60
cttgaggata tatcgatgcc ttcatgtggt gaaaatacag gatcgtctat aggatttagt   120
ccaatgcctc tagaaagcac aagacgcgga gcgttgatgg tgcaccgatc cagacgaggg   180
acgatgacta cgaacggct ggatgacatg acgatgccct ccttaggtag ttcagaacat    240
ggacaagcta caagtgaatg ccttgaagat atttcaatgc cttcatatgg agcgaattca    300
```

```
ggaatgtcta aaagaaagtg ccctacacca ccgaaaagaa atactccgaa tgttacaaca      360
gagtgtttga atgacatgac catgccatcg tttggtgatc caagtcatgg aaacggattt      420
ggtgaatgtc ctgagtcctt cagattgatt acagatagaa agttacaatg cccgatgacc      480
agcgaaaact tggataatat gactatgcca tcgcttggta ctttaggcca aagtcaagcc      540
taca                                                                  544

<210> SEQ ID NO 125
<211> LENGTH: 507
<212> TYPE: DNA
<213> ORGANISM: Drosophila

<400> SEQUENCE: 125
agagcgcgag tttcttacct tcagcaagac gggactgact ttccccgaag acaccacatg       60
gattctgaca atcaactacc agggacatct gcgcacagac aacggaggat tctacctatc      120
cacatatacg gatgaggagg ggaacaccaa gtatctggcc accacccagt ttgagtccac      180
tgacgcacgg cacgccttcc cctgctacga tgaaccctcg aagagggcgg agttcactat      240
caccattaag cacgatccaa gctacaatgc catcagcaat atgccagtcg attcgagcag      300
cacctctgga gtcaccgtct tccaaaagac cgtaaatatg ccatcctacc tggtcgcctt      360
tattgtgtcc gagtttgtct tctcggaggg tgagctaaat ggcttgccac agcgcgtctt      420
ctcccgcaat ggaaccgaac atgagcagga gtgggctcta accaccggaa tgctggtgga      480
gaagcgtctg tccggctact ttgatgt                                         507

<210> SEQ ID NO 126
<211> LENGTH: 615
<212> TYPE: DNA
<213> ORGANISM: Drosophila

<400> SEQUENCE: 126
ccacaacgtg cgggagttcg tgaaagttta gctagcgtta ttagtcaatg atgtcggggc       60
gttgtgcact cgaattgata gccgataatt cgcccggact gccgccgcgg cagtgaccag      120
atagatggcc atggccaact gaacggaagg agagcgcgag accagaaaaa agcgagccac      180
aagcaccaaa cagccaccaa gtgatggcct cctccacatc ctctgcgcgt gggaacaaca      240
aagcagccac caccaacacc accgcagcca ccgctcccgt ctccaccgcc tcgtcggctg      300
ccgtttccgg ttccggtgcc acctccgcgc cagctactgc ctccgctccg ccagctgtga      360
ccctaagcga gctgattggc cagcagctga agcacctgaa cgccgatgag ctgctgcaca      420
aggacgagct gcagctgctc ctgctcataa cgcctgtgca acgccagaaa ctgagccgca      480
atctggagga tggcgatctg gaggccagca cctcggcggc gccactttcg cgtcccgaaa      540
acggcgagga ggatgacgac ctgattgggg cggtgggcgg actcggtatt ttgttcccaa      600
ctacgaccaa agagc                                                     615

<210> SEQ ID NO 127
<211> LENGTH: 833
<212> TYPE: DNA
<213> ORGANISM: Drosophila

<400> SEQUENCE: 127
catcaatcaa aattttaagt aattttttt agactattta ttattttatt tttcgcgata       60
ccaactaaat tgttgaagta aaccatgctg ataagccag ccccagtggg ggcctcatgg      120
```

| | | |
|---|---|---|
| tacaccaatc tgtccgactt ccaggtgcag gccgtcgagg cactggcctt ctcgattcgg | 180 | |
| gatgacaatg cggagggtac tgtgtaccgc acccagttct gtctcagtcg cttgggagtc | 240 | |
| acgcccatgg taaagacccg gatgttgcgg aagctaattg ggatttgtcg cggcagcgac | 300 | |
| ttggcattcc tttactttct gatggaggcc tgctataagg gcacaggatc tgcgtacagt | 360 | |
| gaacggatcc tgatgtccgc catcaccttt ttggatctgg agatgaccat gagggaactg | 420 | |
| gacaaaatac tgccgccggg agtggaacgg ctgaataaga aagagtcgat agctccgcca | 480 | |
| gtggattatc gctccatgtc gttgccaaca cctttaccga ccaaacggga atcggatctc | 540 | |
| cgaaaggtcc gctcgcccta ctttaccccg ttgcccaaac caaagctacc caagggtggc | 600 | |
| gagaagttca ctgccaagag accctgcctc gtggtctcct ttccattctg gcccgctggc | 660 | |
| gagaggccca actacaaggt gaacgaggag accgctggt cgccgcctta caggttccag | 720 | |
| ccggtgaagc ggatgctctt caagatggtc ggcgacatca tgaccgacta ctggacaaag | 780 | |
| atagatggta ctcaaccggc ggagaacgaa gcgatgccca tgtgcgagtt cca | 833 | |

<210> SEQ ID NO 128
<211> LENGTH: 550
<212> TYPE: DNA
<213> ORGANISM: Drosophila

<400> SEQUENCE: 128

| | | |
|---|---|---|
| aaccgctgaa caagtacgga gtttgtaaaa tacttaatat tagctaagtc cgtgcgagcg | 60 | |
| tagccaaaca aggaaactaa ttccaacgct gccgtgacac aaacttccgt acgaaattga | 120 | |
| aagtcaaatg aattctgtac aaaactgtgt gtgtgcgtgt aattcaagcg tcaatttgtc | 180 | |
| gatgataaaa tttgcctgcg cctaatgtac acatgtctgc gtcttcgttg agcatatgag | 240 | |
| cctgtgaatg tgtgcgtatc ggtgtgagcg tcgagcataa gaaagcagca caaaacaaca | 300 | |
| acaacggcag cagcagtaac aacaacagca agaaggcaac gacgctaaga gaaagagaga | 360 | |
| aggaagggaa gagcagagca taatcggact ccattttaca aggcgaaaaa aggagtagga | 420 | |
| aagagcgcac catggccagt ttccagatcc accaagacat gagcaacaag gagaatccgg | 480 | |
| gaaagttcag gtcttccgtg acgtcagaaa tcttaatgtt gatgagaatg tggagtacgg | 540 | |
| cgccaagaaa | 550 | |

<210> SEQ ID NO 129
<211> LENGTH: 480
<212> TYPE: DNA
<213> ORGANISM: Drosophila

<400> SEQUENCE: 129

| | | |
|---|---|---|
| cgcaacaata tagcaattct gaacttggtt cgagtgtttt tgcagcacga attgataata | 60 | |
| tgccgtaggt gcggcccagc gcggatcatc agcagcagca gcgatggcct acatcaacat | 120 | |
| cgccgagtgg acgcccgacc aggtcaccga ctggataaaa ggtctggatg agtctatgaa | 180 | |
| ggggtatttg tacgagttct ccaagcagga gatcggcgga cgggcgttgc tcaacatacg | 240 | |
| gccatacgag ctggagaatc tgggcatgct gcgcattggc catcaggaga tcgtgctgga | 300 | |
| ggcggtggag aacttaagaa acttccatta tcacctgaaa aacgacaatc tgcagttcat | 360 | |
| ggccttgcat gtggccacgg cagctaagaa tctgcatcgc gaactggcca ggaatcatgc | 420 | |
| ggagagcact aagatcgata cccggatact gcacgatatt accaggacga tagctactct | 480 | |

<210> SEQ ID NO 130
<211> LENGTH: 738

```
<212> TYPE: DNA
<213> ORGANISM: Drosophila

<400> SEQUENCE: 130
taacaccttc caaacacaat tcatagcgcc tggagctaac tcaaatctat cattcgttca      60
cattttgtat acgactaaaa tggtggttgt acagggaatg tacgaagtca cggagctggt     120
ggctggcagc gtgggatgcg tgtgtctata catcgccgga tgcaatgtgc tgcccatgga     180
gcatattccc gatcttccgt cggcgctgtt cgtcctgacc gccgtgcttt ttctccatca     240
tctgagggta atgaattgcg caccgctgca gaagctttgg cttttgctgc tggaactgtt     300
ggtcttctat atgtgcaccc aggtcgtggt gcttgtgtgg ctccagttgc tcagccatat     360
gaataaactg cgggacaatg cagttaatac tcgtaccggc atgtaccttt ttgaagccta     420
tccaaaagtc tttatgtttt tgcgccaaga tgtctactat ttggggcagc ttatcatgtc     480
cgtggcgtgc acctacaagg cgataatggt cactcatgcc ctggactacg ccctaccaaa     540
tcgccggacg tacagatact atgagacaga tgagaactta tgcgatggtc cgcggcgtcc     600
tacccgaaag agcaaccagc gatcaacacc caagaagagc accgtgcgtg gtcgcaaaaa     660
atagaagctg tcgcagaaac tggatcaatc aaatcgccca atctaaacac agttttcta      720
tgctttcgat cattgaat                                                    738

<210> SEQ ID NO 131
<211> LENGTH: 528
<212> TYPE: DNA
<213> ORGANISM: Drosophila

<400> SEQUENCE: 131 cccttttgaaa ttctcaagcc cgtcgccaca gtatggcaat acaaaatttt agtaatcctc     60
ctctaggtat ttggcaaaaa tcaggagatc caagatggtg cgagtgatcg aagacatgtt    120
cggcatcgcc gtcaacccga tgacgcagaa gactgaccgt gtccggcgct tcacgctggt    180
cacagagcgc ggcatgtcgg tgtcgatcct gacgatgggt gccataatcc agtccttgaa    240
ggttcccgac ttcaacggaa agctggagga cgtgtgcctg gctacgacg acgtggcagg     300
ctactaccgt aaccagcaat acttctttgg agccaccatt ggccgggtgg ccaatcgtac    360
agcacacggg cgcttcaagc tctgcggcaa ggaggtcagt gtgagtcgaa acttgcggga    420
taggcatcac cagaacggcg ggttcgtggg cttcgacagc gtcatctggg acgtggtagg    480
ggtgcacaag gacggtgtca ccctgcagca catctcgcca gatgggca                 528

<210> SEQ ID NO 132
<211> LENGTH: 516
<212> TYPE: DNA
<213> ORGANISM: Drosophila

<400> SEQUENCE: 132
aatacgtata aaaaccaac aaaattttca acactgcaag tcgaattcca ttatgtccgg      60
tattggcatc aatggctttg ccgaatcgg tcgcatgttt gccgccagg ctctagttcg      120
caaagatgtc aagatcgtgg caatcaacga tccctcactg gatcccaagt atctggccta    180
catgctgcga tacgactcca ctcatggaca gttcaatcag aagatctctg tcgacgggaa    240
caatcttgtt gttaatggca agaagatcca gctgcttaag gagtcggacg tcaagaagat    300
taaatggtgc gacctgggcg tgcatacggt ggtggagtgc tccggtaggt ttaccaccct    360
gaaagcctgt caaggtcact tggatagtgg ggccaaaaag gtggtcatat cggcaccatc    420
```

-continued

| tgccgatgct ccgatgtttg tgtgcggagt gaatcttgag gcatacaagc cgggcacagc | 480 |
| aatcatctcg aatgcctcat gcacaaccaa ttgcct | 516 |

<210> SEQ ID NO 133
<211> LENGTH: 550
<212> TYPE: DNA
<213> ORGANISM: Drosophila

<400> SEQUENCE: 133

| ccaacaccta atattgggtt ctaaattttc aaaatagatt ttctttctaa tattgcacaa | 60 |
| aactaacaaa aatggcggtg cgacctttg gccctggacc cggcgtttac atgctgcccc | 120 |
| ccactgtggg ctatgataag catgacaacc gcaaacagcg gttgccgcag tactctttcg | 180 |
| gcatgcgcac ccgtgctcct ggtgaggatc tgggtcctgg tccaggggcc tacaaggtgg | 240 |
| acaagttgac tcgctatggc acgagcaagg gtttggagtt ctcgatggcg cccagaacca | 300 |
| atgtcatcga taagcgaagc agtcccggtc cgggagcaca cgatgttcat aataggccat | 360 |
| tcttaaggg ggttaatgct ccttcgtatt cgatgggcct acgaacggac tttaacttca | 420 |
| agaaggatgg tcccggtccc aatgcctaca agtacgaggt caatgccgtt cgtcctggag | 480 |
| tcccgagcta tagcatggga ctacaaacaa agattttgaa caagacgaat tctccgggtc | 540 |
| cggctgcata | 550 |

<210> SEQ ID NO 134
<211> LENGTH: 626
<212> TYPE: DNA
<213> ORGANISM: Drosophila

<400> SEQUENCE: 134

| aatcgaaaag ccaatcaaaa attagaaaaa aatagtttgg ctttccgaca caaacacaag | 60 |
| aaattaccac atcctggccc ataccttcta aaatttaatc cgaatcagga aattgccaac | 120 |
| ctgtctaccc aacatgtttc ctgatgactt cgacgtagaa cccttcaatc cattcaatgt | 180 |
| gggaccaccc aatagtggag cccgatctga attcaaaata cctacatgcg ttacgtatcc | 240 |
| gccaccggta ttcgtaccca agtccgaata tgtacaacca tcagaggagt tggtttcccg | 300 |
| gaagagcaac caaagtatag gcaagtcgac tatcggcgag gtggacattt ccaaggccat | 360 |
| caatgaagag atggccgtgg ccaagaagca ggccgaagtt ctcaatgaaa aagatcgcat | 420 |
| tgatgcgggt ggtgtttcaa caacgaagct gtccaaggta tctcaatcaa aggaagcggt | 480 |
| ttcaaaggac tctttgcgca ccctaatgcc aataaggtca aaccgtcagg tcagtggtga | 540 |
| tggtagagca aattccaaat tatccatatc acaattcagt gcggcatcca agacgagctg | 600 |
| cacaaataag caaagtgagg gtgacg | 626 |

<210> SEQ ID NO 135
<211> LENGTH: 542
<212> TYPE: DNA
<213> ORGANISM: Drosophila

<400> SEQUENCE: 135

| ccccattaca catttatcac taaacattca aagaattttc caaacttta ctctgtttta | 60 |
| aacacgatga cgtccatgct gaatacccg atagtctcca tcttcgattt gatggtggaa | 120 |
| cgtcacatca ggctgcgcag ggaactgaat ggaaatcttc cgccagttcg tcggcctaaa | 180 |
| gcagcacgtg gagctgccga cggaaagaaa ccttcaaat acaaccaag tccgatggag | 240 |
| tttcccttgc cagaaacact ggaattgatg tctccgccag cggcaaatgc cattactgcc | 300 |

```
gcgcatttga cccaaaaaca cactttcctt aagatccagc caccgagcga gaagaacgca    360
attaagaagc tggtggagaa gatgtcccat ggacgaggca agaccaagac cgtgtcgcca    420
aggcactccc tgtccagcaa gaagaccagt gccaattcct ccaagacggt cggcattcag    480
cctcgcaaaa agaaagtaac cgggcaggga tcattccgtg ctcagccaaa gctcggcaag    540
ac                                                                  542
```

<210> SEQ ID NO 136
<211> LENGTH: 580
<212> TYPE: DNA
<213> ORGANISM: Drosophila

<400> SEQUENCE: 136

```
cagcaaatgg taggcaccat gtctatgtat atgggcaaag ctctaatgat gttcttcgac     60
agcgagaagc ctgcactaaa gtcccagatc caggtagagt ttgacaagaa tgtgggcgaa    120
aaaccaccca agcctgttag aggagttcaa cgtagcagcg gtggaaccgc tggtaattcc    180
ccagacaatg aggacgatga tggtggggca gccggagaag aggagcccat taatatggct    240
gatcttctac cacgcgttga tattgctcca cagattacgg aggcattgct gaaggagatg    300
tccgacaagg actggaaaac tcgcaacgag ggtctgacta agctgcaggc tattatttca    360
gaggcgcggc taatcaaacc cagcattggc gacttggctc ctgctctggc ccaccgtctg    420
gtagattcca atgctaagat tgcccaaacg cacttgcca  tttgcgagca gcttgccaca    480
gccatggggg ctggttgtcg aaatcacgtg cggaacttgt tccctggctt tttacacgct    540
ctgggtgata caagagtttt tgtaagagcc gctgcccttt                          580
```

<210> SEQ ID NO 137
<211> LENGTH: 691
<212> TYPE: DNA
<213> ORGANISM: Drosophila
<220> FEATURE:
<221> NAME/KEY: misc_feature
<222> LOCATION: (1)...(691)
<223> OTHER INFORMATION: n = A,T,C or G

<400> SEQUENCE: 137

```
ctacacatac acaaacacac acgcacacca cacacgagat gaacaagccg caaaagccca     60
tcaaggtgaa gcgcgccaag cggaccggat gctccaggat tcagccgcag gaattcgtgg    120
aggctcaggt ggagaacgcg cgcagggcgg tggagcgcaa gctgatctac ctgtccgagt    180
cgaacagagc cagtgcatcc actcgggcgg ccaagcgaag cacggctggc gcaggcggag    240
gagcagggcg ggaaggatcg agcatggctg gccatgccca tggtgagcgt cgcaggcgca    300
gcaagaggag tctgctacac gctccagctc aggaagagac cgacgaggag gagagttcgc    360
cgctggagaa gacgaacaac tacgataaca gaagacgcag cagttgcaat ctattgctat    420
ctcctcgtcg caatggcctc acgccccgga actacgaggc cgaggccgag gcagcggaaa    480
tggaagccat atggccgcca cagcaagcct ccaacggaac gacgaagccc gatcatgatg    540
aaggagatgg cggngagtat cagggcggac cgtttggccg actgcagctg aagccgctgg    600
gcagctatgc cacggaccag cagctgccca gctactcgtg cggcgtgtgc ggtgccaagt    660
ttcacatccg atcgctgctg ggcgcccacc g                                   691
```

<210> SEQ ID NO 138
<211> LENGTH: 521
<212> TYPE: DNA

<213> ORGANISM: Drosophila

<400> SEQUENCE: 138

```
agctggcgaa ccggttgaaa ttcgtgctcc gccccataac tacaatggcc acgtacgaac    60
aggttaagga tgtgcccaac catccggatg tgtatcttat cgacgttcga cggaaggaag   120
agctccagca gacgggcttc attccagcca gcatcaatat acccttggat gaactggaca   180
aggctctaaa tctggatgga tctgcttta aaaacaagta cggaagatcg aagcggaga    240
agcagtcgcc aatcatattc acctgccggt cgggaaatcg agtcttggaa gcagagaaaa   300
ttgccaaaag tcaggatac agcaatgtgg tgatctacaa aggctcctgg aatgaatggg    360
ctcaaaagga gggactttga cgataaacgt cgctatattt ctgaataaat gaagattaat   420
attaattaat taattaatta ttaatagcta aaaaaaacag aaaactttaa ttatttgtta   480
atattaagct gtattttca tatatctcaa gttcttgact a                       521
```

<210> SEQ ID NO 139
<211> LENGTH: 618
<212> TYPE: DNA
<213> ORGANISM: Drosophila

<400> SEQUENCE: 139

```
tcgaagtgac agaaccacct ggaaaacagt atcagagtta aacacattcg aattcgagtt    60
cactcaaact aaaattctta tatttctttt actatatttg aacaattaaa aacgtgcaaa   120
aatgccagct catttggatt taaccctaga ggaaatgacc aggattgctt tgggtgtgcc   180
cgagttaacc cacgtaaatg tggctgtact ccaaagtctt ttgaatgtcc ttctcaagaa   240
actgaactgt cagaatgata tggtaaggat aagtggcttc gagggcaagt gtatggagcg   300
cattctcgag caatccaaaa tatctccact gcccttcgac gtggaggcta ttgttccaat   360
ttccgagcaa ttggataaag ttcaagagtt ggacaaacgc atcaagcagc tggagtgcaa   420
gttggagtgt cactttcagc agattcgcat ttgcaacaag gccaaggaca agaagtacaa   480
gatcaaccag gccgaacagt acgcctctcc ttgcgaggat ctgtgcaccg tttgcgatga   540
ggacaacaag atcgcatgca gtctgctggc caacatggac ttcatgaaaa agctaatgcg   600
acgtatagcc acacccat                                                618
```

<210> SEQ ID NO 140
<211> LENGTH: 650
<212> TYPE: DNA
<213> ORGANISM: Drosophila

<400> SEQUENCE: 140

```
taccttattc caccaggtat tcctggctat aattatccac ttggatggcc ccttcgttat    60
ccattaggtc cttattggcc taatcgacca ccatggctac caattaattc tccaccgata   120
cgtccaggtg gacttttccc tggtggacct tcccctggtg gaccttcccc tggtgaacct   180
tcacctggtg aaccttcacc tggtggacct tcccctggtg gaccttcccc tggtggacct   240
tccccctggtg ggccatcccc tggtggacct tcccctggtg gaccttcccc tggtggacct   300
ttccctggtg gatctccacc ttcaccaggc ggaccacttg gaccatggca atttccatgg   360
atactaggtg gtcctcggcc gaaccgtcca ggaagacctt tccctggtgg tatccttcct   420
ggtcatttag acggttcggt agttccaaat agtgtgctaa atgttgctgg cggaatcttt   480
ggaaacggtg gactgttcgg tacgggaatt ttcggacaac atggactttt cggaactgga   540
tttcttagtg gaccttcgtt agacccctttt ggcattttta ctccaatcgg aaatttcttt   600
```

```
ggatcactag gaaacttatt cggatttagt tcacctagtc aaattattcc              650

<210> SEQ ID NO 141
<211> LENGTH: 550
<212> TYPE: DNA
<213> ORGANISM: Drosophila

<400> SEQUENCE: 141
cgaaagtgtc gtgtacctag tcccgttttg gaaaacatag aaaaaaatca ctaaagtttt   60
catcaaaatt ttttgtcgta tttcgtgtct tgtgtttcat gtttcgtgaa aaaaaagttt  120
tttgcttgca atttaaacgg ctgaatcgca aatacgccgc ataacgaaag taaatacgaa  180
atttatagta gtaacaaaat ttggatcgcg cacacataca agttgataag aaattaagaa  240
ttcaaaatga acaaactacg taatgttctg aagtcagtag tccagcgtcg tctgcccgtt  300
tcccatttga tccaaatacg taccgcctgc ggtggtgaat ccaagtcctc caagggtctt  360
gtggtcggtg tttatcagaa ggagaacgat aatgacccaa agctaacgcc agctggcgaa  420
aaggtcaatg atcggctgca tggcaagttg caggagatga tttgccagag caaaatcact  480
ggccacttgg gcaggggcaa gatattcaac aacatagatc cagagtttcg cagtatggca  540
gtggttggtg                                                         550

<210> SEQ ID NO 142
<211> LENGTH: 600
<212> TYPE: DNA
<213> ORGANISM: Drosophila

<400> SEQUENCE: 142
agtagactag aaaccaagag aatgttcaag accatcgctg tagtagtgct cctggcagcc   60
ctggccagtg ccgagctcca tcgcgtgccg atcctcaagg agcagaactt tgtgaagacg  120
cgtcagaatg ttttggccga gaatcctat  ctgcgcacca agtaccagct gccctcgctt  180
cgcagcgtgg atgaggaaca gctgtccaac tcgatgaata tggcttacta cggagccatc  240
tccatcggaa ctcccgctca gagcttcaag gttctgttcg actcaggctc ctcgaacctg  300
tgggtgccat cgaacacctg caagagcgat gcctgcctga cccacaacca gtacgactcc  360
agcgccagct ccacctacgt ggccaacggc gaatccttct ccatccagta tggcactggc  420
agcctaactg gctacctgtc caccgatacc gtcgacgtca atggcctgag catccagagc  480
cagacctttg ctgaatccac caacgagccg ggcaccaact tcaacgatgc caacttcgat  540
ggcattctcg gtatggccta tgagtccctg gccgtggatg gtgtggctcc tccgttctac  600

<210> SEQ ID NO 143
<211> LENGTH: 626
<212> TYPE: DNA
<213> ORGANISM: Drosophila

<400> SEQUENCE: 143
ataaacccaa aatttttgaa aacggcttaa atatttgact taagttagat actcccaaaa   60
ttcttggtga atgcattgcc caaactatgc cctacagaag cagcagctaa gcaccgagct  120
ctaagaacca tcttcagcca tgctaatcaa tgatgccact agagatcgtc ccatctatca  180
ggatatccag cgtcttacag atgcccaact gagtaccatg tgcaaaagcc acggtctcat  240
tctgggtccc ataactttc  aaaatagacg catggcagag cgcaagctcc atatagcaat  300
gatcacagag cgggccaagt accgggccca tcagcagttt gccctggagt gcaacatgaa  360
```

```
aacccaagtt ccgcctgcgc agcaaaacta cggcttagtg gacgtactgc cccagaacta    420
ttaccaaccc atgccaccac aaacttactg gccatctccg ggcaccaatt tgcgcagccc    480
acctccgcct agttggaata cccaaaatcg tcgggagcga acggaccgg tgctcgagcc     540 acgtcagtac gttagttgga ggcaacagaa caggaaccaa aaaaatactg aaaattctgg    600 taataattt ctgggtttca agatgc                                          626
```

<210> SEQ ID NO 144
<211> LENGTH: 658
<212> TYPE: DNA
<213> ORGANISM: Drosophila

<400> SEQUENCE: 144

```
caaccgttaa caactattac tataagataa attcatttcg acctagccgt tttttcacct     60
ccaacagtcc aaaatgtcag aagaagaagc cccaggatct ccgggtgagg ctgttgaaga    120
agaagatacc actacatccg atgctgatac aaccacagct ggtgcccgca tgatgatgat    180
ccacccatgg ctgacggccg ccgcagtggc catgtatgcc accaaggtca tgtgggtcaa    240
gttccgtgag atcggcctgg ctaaacagga aaaacggctc aaaaatcaac tggcgaagca    300
gtctaagccc ttgcagacta ttgatgaaga tgtttccgaa tctgatgcag aatatgatgc    360
agaatctgat gcagaatctg atgcagaatc agatgcagag gacgaagacg tcgtcgggcc    420
ccaagtcgaa gatgcagcag agggaccggg attcgagcca aaccgtgtgg atatatgcca    480
tcgcccgatc gaagtctcta ctgactgctg atgttcgaat cggggatgaa ggaccgcgga    540
aggatgaaca tgcacacaca cactggacaa ctacactaat tgttgtaatg cttgcgtttt    600
ccgtagggga ggatccacgg acaatgtttg acatgtacca ccacattggg ggaccaca     658
```

<210> SEQ ID NO 145
<211> LENGTH: 350
<212> TYPE: DNA
<213> ORGANISM: Drosophila

<400> SEQUENCE: 145

```
agaatcctga ctgggaagac gccatgctgg ggcacatcgc ccagctgccc aagatgaagg     60
gtcccaccag caagggcctc ctggacaact gtgcctgcta cgagaagctg aacgaacgtc    120
acgagcagtg gtgtcccaca tcggagttgt ccaagcgact gctgcccctc ttcaatctct    180
gcaagatgca gactggcaac atagtgctga tccttagatt ggtgtgcaat ggtccgacca    240
ttgtgtccac gttccccttc agcaaggtct gctcccgcaa tcccaagtgc ccggagccct    300
gctgcggtcc ttgtggcccc tgtggtccct gcggcccctg cccaccacct              350
```

<210> SEQ ID NO 146
<211> LENGTH: 549
<212> TYPE: DNA
<213> ORGANISM: Drosophila

<400> SEQUENCE: 146

```
aggacgcatg tgcagacaac ggagcggata cgcagcgtga acgtgaacga agacatcaag     60
tacgagcatt aaggtttacc cctgttaggc atccgataat ccgtgaatca gagagaccat    120
cgtcgtcatt agggcaacca attagccaag tcagtgattg tgataatgct taaaggtgtt    180
cccacgctag ccggtcgaaa ccttcgtctc ctgacgaccc aggcacaggt gctggtccat    240
caacgcgcca aagcgtccgc cgccgagccc gtcgaggact ttgaccagga gacggatctt    300
```

-continued

| | |
|---|---|
| ttgaagcgcg ccaagttcgg acacacgggc aaacagctgc agcagaaaat aatcaatgag | 360 |
| aaaaatctgc gcgctccacc gcttatgaac ttggtgtttg ccaatcggaa gttgtccttc | 420 |
| tacgatacca gttccactcc caagaccaaa gaggataatg ccaagctcag tcagagacgc | 480 |
| cactattcga tgcggcccca tcgcgagcag gagcagcgaa atgcggagga tgtgctattc | 540 |
| gacatgttc | 549 |

<210> SEQ ID NO 147
<211> LENGTH: 528
<212> TYPE: DNA
<213> ORGANISM: Drosophila

<400> SEQUENCE: 147

| | |
|---|---|
| ctaaccaaca gaaacattcg catcctgaaa atttttacaa aatttcggta ttacgtaaaa | 60 |
| tgataggcat tcaaaaaaag cgaccagccg ccggagagta cgtagtgcca aacaattcgg | 120 |
| ctctaaatct gcagaataag cccagtatat acgatcaaac gcccaaccaa atggagaaga | 180 |
| ccaccaagtg ccgctattgt gagaacatgg ccaagaactt tctgtacctg gagagcctga | 240 |
| tccggaacaa caaggataac gacaagaaca acaagtgcag cttgtgcaac tcgtcgctaa | 300 |
| agtacttgga gtatgttaac cgcaatattc gccaggtttt cggcaacttc gattcaattg | 360 |
| tccaggcgga tcgtgctctg caatccaagc cggccatgat gcccaaatac tcggtgggcc | 420 |
| cggctccgga aaaagctgat ctgcgctcca agggtggcgc cattgtctcc cagcaaaggt | 480 |
| cggcaaaaag cctcaagtcc aagagcctaa atcccttaa atctaagt | 528 |

<210> SEQ ID NO 148
<211> LENGTH: 538
<212> TYPE: DNA
<213> ORGANISM: Drosophila

<400> SEQUENCE: 148

| | |
|---|---|
| cacaaatctt ggccagaata tgtctatctc agtgaagcgg aaaacggtga tttcaccgca | 60 |
| ggaactcctg aagacactcg agctgtccgg cgaagaggac ctcgatctgc agatcaagaa | 120 |
| ctgggtgatg tgggaccgca acgaggcgac gctccagcag gtgactgagg cagtcaggga | 180 |
| tcaggattgg aaggcgttgc gggtgagact gtgccatagg atcacctatt tgacaactgg | 240 |
| cttgagggga gtgatgcgcg caggcttcga ctctttgaac gatgtggtga tcatcgaagt | 300 |
| ggcccagggc atctgcgcct acctcgtcga tgcctatcca agcatccaga agaggcaaac | 360 |
| acagggcgtg gtcgttggct acgatggcag gtacaatagc aagcggtttg cccaactcat | 420 |
| cgccaccgtg ttcctgaaca acgacttcaa ggtgttcctc ttcactcgga tgattccgac | 480 |
| acccttata cccttcaccg tcgtcacgct ccagtgcctg gcggggatcg tggtcact | 538 |

<210> SEQ ID NO 149
<211> LENGTH: 439
<212> TYPE: DNA
<213> ORGANISM: Drosophila

<400> SEQUENCE: 149

| | |
|---|---|
| taactgatgt tttaatata tgtaggaaat ataacctaaa gttgcatccg gaaaatgtt | 60 |
| cattttcat gcatgaagtg acattcctag gtcacaaatg cacagacaaa ggagtttgc | 120 |
| cagatgacaa aaaatatgac gtcatcaaaa attatcctgt ccctcacgat gcggacagcg | 180 |
| caagacgatt tgtagcattc tgcaactatt atcgtcgatt tataaagaac ttcgccgact | 240 |
| attcacggca cataactaga ttatgtaaaa agaatgttcc ttttgaatgg tcaagcgaat | 300 |

```
gccaaaacgc attcgaatac cttaaagaaa agcttatgca ccccacatta ttacaatatc      360
ctgattttcg caaagaattt tgcatcataa cggatgctag taaacaagct tgtggagcgg      420
ttttaaccca gaaccgaga                                                   439

<210> SEQ ID NO 150
<211> LENGTH: 650
<212> TYPE: DNA
<213> ORGANISM: Drosophila

<400> SEQUENCE: 150
ttcaatacaa attaataaaa caaaaatatt aagttttgtc gatcatgcaa cctcaagagg       60
aagtgaaggc cattttcaag ctgattctaa tcggagacgg gggaactggg aaaaccacat      120
tggtcaagcg acatctgacc ggcgagttca agatgcaata caatgcgacc ttgggtgtgg      180
aggtcgagca attactgttt aacaccaaca gaggagtttt ccgcatcgat gtttgggaca      240
ctgccggtca ggagaggtac ggtggcctgc gcgatgggta cttcgtccaa tcacaatgtg      300
ccataataat gttcgatgtg gcctcgtcaa atacatataa taatgtgaaa agatggcacc      360
gcgacttggt gagagtatgc ggcaacatac cgattgtcat ttgtggcaac aaggtggata      420
tcatgcataa aaagacttgg aaaaagggtg ttgactttga tcgcaagaca aacatttacc      480
tcattgaaat gtccgcaaag tcgaactata cgtggagaa gccattcgtc tatctattgc      540
gaaaattggt gggtgatccc agcctgcagt tagtccagag ccccgctata cagcccccaa      600
aagttgtttt taccgacgag atgagccgtc aagtggaaag cttattcaat      650

<210> SEQ ID NO 151
<211> LENGTH: 656
<212> TYPE: DNA
<213> ORGANISM: Drosophila

<400> SEQUENCE: 151
aatactcaga catacatagt tagtcagtga tcatttagtt agttagtttt ttccttaaat       60
tgtctgtgat acattacata ttacggataa ttcacgatga tctgggactt ctttacccttt     120 atacgcggag ccaccgagtt cagtgccact gcgctactga ttttgctcgg ttgcatggga      180
gactcaacga accaaggtgg tgagagcaaa ttccttggtgg ccagcgttca ctatggcctg    240
acggtgatgg tggtgatgca cgtgtttggc ttcgtatccg gagcccattc gaatccatgc      300
atctcgatct catgctactt gatgggctac atcccctgg aagtgatgat gatgtacgtg       360
gtgtgtcaga tggccggtgc tttccttggt tacttcctgc taatgcaact gctgcccaag      420
gagctggtgg acaaaagcaa gccaggcatt tgcctggtac aaccgatgga cactctgtcc      480
acataccagg tcgtcatcat cgagtgcctg ctgaccgcgg tcctcgtgct cggatggtgc      540
tccttgtggg acgtgcgaaa cggaaggttc ctcgactcgg tcgccattcg catgggtctc      600
ctcgtgatcg cttgcagttt cgcagggatt caactaactg gagccagtat gaaccc         656

<210> SEQ ID NO 152
<211> LENGTH: 583
<212> TYPE: DNA
<213> ORGANISM: Drosophila

<400> SEQUENCE: 152
ccaaaagcag actgggtgaa aactgctttc gaacttctgc aataaaacgg ctcctaaccc       60
gtccttagag gcatctgtat gaagttcggt ttctgcttct cacacggttc agcatcgaac      120
```

```
acagtaaagg ggttggactt caccctcgttc ttctaatgag tcgtaatcaa aacgaaagca      180
acctccttga tatcaatgaa gatctgcctt ttgctcttgc tctgccccc gtctcaatgg       240 attcgttgca gctgaacgca gacggcaata gccccgagga caagacgctc ggtattggcc      300
gtaaaaccat tttgaatgcg cacacaaaat ctttggctcc cattgtgagt gacgaggccc      360
tgaacacgct aaatgagctc cgcgagcaaa atcttctctg cgacgcccag atttctgtgg      420
gggaggatgt gttcaacgta catcgtgcaa taatgtgttc atgtagctca tactttcgag      480
ctcaattcac agggtttaac gctgacactc ccggatgtgt agatgggtca gatgcaaaaa      540
aaaacaataa ttttattcat atccccggcg tgagttcatg tat                        583

<210> SEQ ID NO 153
<211> LENGTH: 507
<212> TYPE: DNA
<213> ORGANISM: Drosophila

<400> SEQUENCE: 153
ggcactgtgc tacaggagta cggaacgttt tggagcgaca ttgtgaacaa agtgcaggcg       60
gagcggccat aactgaaatt atgtacttac ttttaaggca gccgggcaat aaatcttaaa      120
aaccctaatt agtcaaaacg aaattgttgt ttgaggattt ttttttcgact gccattcacc    180 attccgacgt cttggacgtc ggacgccaaa ggcgccccat tgagctgtgc aatcaacatt      240
acagggcaaa attattggct ttttggctca gcgcttatga atgaccagcc cacatcccag      300
cgcccaacga ggcgaaccag ttcccgtcgc ccaccacaga cagcaccttg ccacccacat      360
ccgcccacat cctcccaccc actccactcc aagtccgaaa tggaacgcac gagccgagca      420
cgtttgggtt tccagacacg ttggccagct tctcatagga aattcgtttt gggcgccccg      480
gcaaattgga aactctaagc acctttc                                          507

<210> SEQ ID NO 154
<211> LENGTH: 558
<212> TYPE: DNA
<213> ORGANISM: Drosophila

<400> SEQUENCE: 154
gtagcagaac caccaaataa aaaccaaaa aaaaaaatac aggaacaaaa tgatgcagcc        60
gagactagtg attttgggtc tgatcggatt gacggcggtg ggcatgtgcc acgcccaggg     120
acgcatcatg ggagggagg acgcggacgc cacagccacg accttcaccg cctccttgcg      180
ggtggacaat gcccatgtgt gcggcggtag cattctctcc cagaccaaaa tcctgaccac      240
cgcccactgt gtgcatcgcg atggaaagct aatcgatgcc agtcgcctgg cgtgccgcgt      300
gggcagtacc aaccagtatg ctggtggcaa gattgtcaac gtggaatcgg ttgcagtgca      360
tccggactac tataatctga caacaacct ggccgtgatc acgctgagct ctgagctgac       420
ctacaccgat cggatcactg ccatcccgct ggtcgccagc ggagaggcac tgcccgccga     480
gggatcggag gtgatcgtgg ccggctgggg acgcaccagc gacggcacca actcctacaa      540
gatccgtcag atatcgct                                                    558

<210> SEQ ID NO 155
<211> LENGTH: 550
<212> TYPE: DNA
<213> ORGANISM: Drosophila

<400> SEQUENCE: 155
cgaaggcgac tactttatgc acagtgagaa atattcaaaa gtgaggaaac caatagtcat       60
```

| | |
|---|---|
| ataccaaagg tatcaaaaac taaaacgatt gcatgccaag acgctgaaga atatgaacta | 120 |
| atgtagtgta tctaccctca ctataactct actctacata tatataagta acgtacatac | 180 |
| attgtgacac tttgttgcaa acacaaataa acataattca catcaaagac cacatgcact | 240 |
| tacataaaca ctccagccaa tgaaatacga tctaacgctt atacataagc cgatcgcgga | 300 |
| gcgtgagaat gctgagcatg cacttagcag ctcaagtggt caagccatac ataacatatg | 360 |
| tatgccttct gcatacacat gtatatgtat atacaatatg tacaatatgt aagaacacca | 420 |
| tgtacgggta gctgtaccca aagacagcaa catagattca ttcaaataaa acgattcaaa | 480 |
| cggaacagac gctctgagct gttcaatatc tattgcactg agctattact taatacttat | 540 |
| tacatggcga | 550 |

<210> SEQ ID NO 156
<211> LENGTH: 562
<212> TYPE: DNA
<213> ORGANISM: Drosophila

<400> SEQUENCE: 156

| | |
|---|---|
| ccatttccaa tccggatgag aatccactta acgccctcaa tagtggggat tcccattcac | 60 |
| ctgatagcga gggcagtaag gagagctctc aggatagctg cacaaagaat aacccaccag | 120 |
| gcgattctga gttggaggcg gaaaccgagg cgaacaagca caagcagcgc cattcgctgg | 180 |
| actctgccat ggacgaaaac tgccgttcgt tgagcacact cactgaaagc acggatcaga | 240 |
| gtgcacccat caacttcgat atgtcaaata gggcaaagtc gccaaggggc attgaaaaca | 300 |
| ttcggccgca tttggaacag gttgacaatg tcccactgca agtatcgctt tttacggact | 360 |
| gctcagcgga agccacgcgt cagatgctgg acatcatgca atcctacggc gagattgttg | 420 |
| tctgccttgg aagttcggcc agtaatgcca atgcggacat ttttctgcag gccgactgta | 480 |
| gtatagccgt ggagccgttg tatccgcaag tgtgccagga tgtggacgcg tacacggaag | 540 |
| ccaatatcca gaacaacaaa ct | 562 |

<210> SEQ ID NO 157
<211> LENGTH: 834
<212> TYPE: DNA
<213> ORGANISM: Drosophila

<400> SEQUENCE: 157

| | |
|---|---|
| attccgagca ccagacctaa atgggatagt tttgttttcc ggcttttttg tttttcggtg | 60 |
| tgagtttgtg agcttgtaac cgttcgaaat tttgtgcttt aagtttttgt tggacaagtc | 120 |
| gctgccatgt ttcaccatga attcgaacga gatcagtgca tcatcgagga ataccaaaga | 180 |
| cgccccaaaa acgatgtcct ccaatggtag tggtgcggtg gacggcgtaa gtccttgtca | 240 |
| tctgccgca actgcggttg tttccactgc cagaggaggc gtcagagaaa cgagcagagg | 300 |
| acataaggct atccgtgtat ttttggatca ccacggtggt taggaaatcg cgttgctcta | 360 |
| aaactcgcta atcctggcca ctgcaaaaat taacttttcg atgaacacat tttgggagc | 420 |
| tattattgga ttcagattat aatagctctc atatgctggg atacccaaca ctgggatatc | 480 |
| ctacactggg taacctatac tttggtaccc tataccttgg taccctataa tttggtaccc | 540 |
| tatagttgga taccctcac ttggatgccc tacacttgga taccatacac ttggataccc | 600 |
| tacccttgga tacctaccc ttggataccc caaagcttgg ataccccaaa gcttggatac | 660 |
| cccaaatatg gataacgatt gactaggatt cgaaatatat aggataggtt tctaggatta | 720 |

| | |
|---|---:|
| acttggatac cccatatttg actgttatta ggacggctgt tcccaaactc aagaatgaat | 780 |
| agattattta aaacgtcaat ctacgttgat taattaaaga ctttaataag cgtc | 834 |

<210> SEQ ID NO 158
<211> LENGTH: 550
<212> TYPE: DNA
<213> ORGANISM: Drosophila

<400> SEQUENCE: 158

| | |
|---|---:|
| attcccagaa tttgtggcat tttgtgtggc gtcttattat cggatattta gattttaact | 60 |
| gtaataagaa cagggataac acgatgctga gccgcaagcg ccgggcgagc agcatatcca | 120 |
| gccggcagga cgaggatccg ctgcagctgg acgactcgac gccggagcag tcaccggtgc | 180 |
| agcagacgac gacacaatcg gcgcgaaaaa agcgccgtct cgatcccaca gaactgtgcc | 240 |
| agcaattgta cgattccata aggaacataa agaaggagga cggttcaatg ctgtgcgaca | 300 |
| ccttcatccg cgtgccgaag cgccggcaag agccctcgta ctatgacgtg gtggtcaatc | 360 |
| ccattgatct gctcaaggtt cagcagaagc tgaaaaccga ttcctacgac gatttggatg | 420 |
| atctgatggc cgacctggag ctgcttattg caatgccaa ggccttctac ataccgggca | 480 |
| gtagcgagca ccaggacgca gtctctctgt ggcagcacat tcattcgcag agacagcgca | 540 |
| ttatggaggc | 550 |

<210> SEQ ID NO 159
<211> LENGTH: 566
<212> TYPE: DNA
<213> ORGANISM: Drosophila

<400> SEQUENCE: 159

| | |
|---|---:|
| aaaacaaaac acacacacac attaacacca aaaatgtccc agaatcatgc ctctacggaa | 60 |
| gaagtcttgc acgtggtgga ggccatcgag gcaggtgaaa aatccgaggt agacactgtt | 120 |
| ccagtggttg tgccaccaga atcaacagct gagcccgaag tgatctccaa gccagaggag | 180 |
| ggcaaccaac cagctggcga tgagccgcgg gaggagaagc cacagatcga atctggcgca | 240 |
| attaccgccc aggtggcgac ggaggaggga caggaagcgg aaaccaccga acacgtagct | 300 |
| atcgaagcaa ctgagcttgg taatgaagtg cagcaaacgg aagcatcaga tgaactatcg | 360 |
| ccagaagaaa agaaactgaa gctgaagaag gagcgaaagg agcgtttgaa gaatttcgca | 420 |
| accactcgct ttgcaccgac agcaatcgag agcccagttc attttacacc ggaatatatg | 480 |
| gaagagatca gggataatga ggtagaggaa gaagagcagg aacaggtagt cacctttgat | 540 |
| gagcccacca ttggagacgg ggagtc | 566 |

<210> SEQ ID NO 160
<211> LENGTH: 633
<212> TYPE: DNA
<213> ORGANISM: Drosophila

<400> SEQUENCE: 160

| | |
|---|---:|
| caagaccaga ctctaaatct tatcgtaaaa aagtttacta aaattccaaa tttaacaaac | 60 |
| atatggtgca ataagatttt gcaagacaaa tcatttgtgt atatctagaa tcatgcagcg | 120 |
| ttcgtcttat cctctatgcc acactgtgcg acccagcttg actgggcttt taggcggcgg | 180 |
| atggattgac cttcgaagga ctatggcctc agattcgtgg ggacggggtg acggcaatag | 240 |
| ccagcccaat tcgccaaggg ctggcgtttc gcgtgccagt gccacatcga cggtgataag | 300 |
| tgatgccagc tcctattcgc gtggcgtcaa cactggtgct ttcgagcgac gcatcaatcg | 360 |

```
ggaggataat atgtggaggg atcagagcta tatcgataca aaatggttaa atcctcgcga    420
tcccaatgcc tatcgaccga atttccgtca aacagagccg acatcgttgc gcaagcaatt    480
catgcgcagt ccggatgaaa tatcccgtga ggtgatgggt cgtgattggg aggaaacggt    540
caggacatat aaacgcaacg cccagagcaa acacagtgtg gcgcgcacag aggagcggca    600
atcttcggat aatacacgta atcgccagca aca                                 633

<210> SEQ ID NO 161
<211> LENGTH: 600
<212> TYPE: DNA
<213> ORGANISM: Drosophila

<400> SEQUENCE: 161
aaagatttga atttgtttcg agcaataaag tcaagaaatc gataattgga attttatcaa     60
ctctggtatt tcctagtcca atgccaagta ttcaaaaaaa cacttttcgg aacatcgatc    120
aggaggtcta tggcgagcca ccggatgaga gcatcagtca tgcggccaag atatacggac    180
ttagtgtgat cctggccgcc atcgcattga cacagtggat cattataggt tacacccata    240
tgctgagcca cagcagatcg gaggagcgct acggctggtg gcttctgtgt acctttttcg    300
cagtcgccac tttatcgtgg accaagctag acgcaaggt gcccttaac tacatcatta    360 tcgcagcgat cgtggaaagc tcaactattt atatagccat ggaacagaag cacaatgaga    420
atagactcgt caacttctac gccggcattg tagtggttgc cttgatgttg gcctcgatat    480 tttgggggcgc ctactttccc atgttcattg ttcccggtga tctgctgctc agctgtttgg    540
tggcaatagc caacattatg atgatcatat tctttatcaa tgtcctattt atcaactacc    600

<210> SEQ ID NO 162
<211> LENGTH: 510
<212> TYPE: DNA
<213> ORGANISM: Drosophila

<400> SEQUENCE: 162
cgccgagcaa aatggacgaa atgccaacac agaaaccaaa aattgcacgc ctctccttgt     60
tcgttcgcca actggaggtc gatcaggaga gctgtctgaa gccggattac gtgaagcctt    120
tccgcacaaa ggatgaggcg gttaaaaggc taatcaggta tcattgcatg catgagaacg    180
acgttgagtt gccttctgac gaagacgagg aatttgagtc cactgctctg gaattccagg    240
acaaattccg ccaactgaac ggcaagttcc aggaaattct gatgcaggag tcaacgctgc    300
cacaccgaac ttctgagttg ctacaaatgc agcagctgat gatcgatgat ctcaaaggcg    360
agatcaatga gattcgaacc gctgaaaagg agttagagca gcagctaaag gaggagcaga    420
ctagcgaaaa atcgacggcg gaaagcgatg tactttcgga ggcgaaagtt aaggaggaga    480
ttaaacagga accaatagat aagtctgctc                                    510

<210> SEQ ID NO 163
<211> LENGTH: 646
<212> TYPE: DNA
<213> ORGANISM: Drosophila

<400> SEQUENCE: 163
ccactatctg tcattacaga cactcgattt taaactataa tagtgctata tttagatatg     60
tttaacacgt ttatcagctc tacacagaag ataacatata gataaataca tccctctaa    120 taaaatggaa tgtcaggaac tcaagctcgt cacggataaa gaactcattg ataagaatct    180
```

```
tgaaaaagag gagcaaacat gcaacttagt cccagcctgg agccctagga atcccttgga    240
aaacagcatc gattgccgcg agaagtcaat tgtggaaaac ataaatgcag accaggatgc    300
cattgccaaa atccaatatc ttagttcgga acatgccaag ctggataaat atttagataa    360
tcaggagcag gatgaatcac ttcgcaaata tcttgtcgtt ggagttcatt gggtttctct    420
gctcacggaa catgtgttga gccatccgtt tctagtattg cgttggcagt gtcaggttta    480
taatgcctcc aagtgttacc acttgcatcc ttttaccctg ctgccctgta ttgtccactt    540
gcacagacgc caaggactaa cgacactatg gaagggaatg ggcagctgct tgcttgttcg    600
tggaatgtcc tgcgccattg acgatgtaat atcgaaactc agcagt                    646
```

<210> SEQ ID NO 164
<211> LENGTH: 565
<212> TYPE: DNA
<213> ORGANISM: Drosophila

<400> SEQUENCE: 164

```
tcagagctgc tgaagaacgg acaagaaaat ggcagaccac agatggatgc acttcagcaa     60
cggcagcgtg ccgccgaatg ccgtggtggc tggtcacgat tcggacgggg acaccatcta    120
cgtgggccgt gccttcttct ccaacgacat gctgccggcg aaggtgattc ccaacaaggg    180
caaggcctac gtggcgtatg cgcgcgagga gcacgagctg gagaactacg aggtgctttc    240
cggctacaac tacgagtggc tgtcggcgga gaacggggag gtgccgccgg cgccgtcaa     300 agttggtcgg aatgtggacg cgagtattt gtatgcgggc aggggttatc atgccggcag    360
cttaaccatg ggcaaggtgc atccatccca cggctgcctg tatattccct acgattccga    420
tgaggttaag atctttgcct acgaggtgct gtgccagccg aacgttgga tcgacaccac     480 cgcaacaaat attccggatg gagctctggt tgctgggcac gattccaacg ggacaccat     540 ctacgtgggc agggtgttcc gcaat                                          565
```

<210> SEQ ID NO 165
<211> LENGTH: 900
<212> TYPE: DNA
<213> ORGANISM: Drosophila

<400> SEQUENCE: 165

```
gaaaccgaac actagattga cttttaaaag ctgtgccgca gtgtgccgaa cttttttcgat    60 agtctgggca tcttcggcgt cttaaactgg cacatatgca agataatcat gtaaagaaat   120
cgtcacacga atatgtgctt gtgctggttg gcagcgatgt aaataaaatt taagctgctc   180
ccgagtaaaa tcttgccgca aagtaaaaaa acttaaacgc cgaagtgcca cttgtagcaa   240
aagttcgcgg acagcgaagt ctcagcacga accgtagaga actgagcgtg gtctgcgag    300 ttctccaagt ccaaccgcca agacgctaag atgcatgcat cctccgcggc ggccactgca   360
cttgtggagt actcggacgt cagctcagag gacttctcgg atcaggaggc aggggacttg   420
gatgcggacg ccggcaaggg tgccggaaac atcaaaaaac cgaagccagc tccggataat   480
cagttctcca aggtcgtct tgatgccaag cccgataaag agggttatga taactacaga    540
agtagaaggg cggaagactc aagcgaccca gtggcggccg gatcgaggca aacgtctagc   600
agcgaggcca cgaatccgcg ggaggaacct tcgcaggcat ccaacacctc gaaggacgag   660
ctgtggggca gagagatata catgtccagc gattctatcg acaccgatga gctgcaggcg   720
gaaatgaagc ggcagaagcg caaaaagcag aaaaaggaaa aacacaaaca caagtcgaag   780
```

```
aaaaagtcca agaagcgcaa gaagaagcgg gccaagtcat actccagcat cgattcgatg    840
tcagacaatg acatcaatgc cttactggac cggcgctata ctccgccgac ggctcctagc    900
```

<210> SEQ ID NO 166
<211> LENGTH: 635
<212> TYPE: DNA
<213> ORGANISM: Drosophila

<400> SEQUENCE: 166

```
ttgatggtga ctacatacgt cactcgcgtg acaacacggc agttgcacaa ctgtgctgtt     60
ctgtgcttct agcactttcc atcgcccaa cccagcaagc tggcaatcag tattcattct    120
aatctatagc gttcgttcgt ttgtgtttcc cctatatttt cagctgagag atgggcaaag    180
acttctacaa gattctgggc ctcgagcgca aggccagcga cgatgagatc aagaaggcct    240
accgcaaact ggcactcaaa taccatcccg acaagaacaa gagcccacag gcggaggagc    300
gcttcaagga gatcgccgag gcgtacgagg tgctgtcgga caaaaagaag cgcgacatct    360
tcgacaatta cggtgaggat ggattgaagg gcggacagcc gggaccagat ggcggcggtc    420
agccgggagc gtacacttac cagttccacg gcgatccgag ggccacattt gcccagttct    480
ttggatcgtc ggatccgttt ggcgcgttct ttaccggcgg cgataacatg tttagtggcg    540
gtcagggcgg caataccaac gagatcttct ggaacattgg cggcgacgat atgtttgcct    600
taatgccca ggcacccagt cgcaagcgcc agcag                               635
```

<210> SEQ ID NO 167
<211> LENGTH: 683
<212> TYPE: DNA
<213> ORGANISM: Drosophila

<400> SEQUENCE: 167

```
tggtgtgtac gctagtactc ctagcaaaca cactcattct acaaatgtca accgttgttg     60
gtttaactca catgcctttc caattccatt ccattccttt aacctacaca tcacacaaca    120
aataaattcc tgaacataaa gatcattttt gatacctgaa atttccacac gaaatttcta    180
cacgaaattt tctgaacatg gccggagaaa cagagcagct aacgttgctt agtgaactga    240
acaatattgg aggtggcgag ttcgagtcgg gatactgcct gaatgagaaa cctattctgc    300
cgccagtgat gactgactgg aagagactgg aaatgatgcg actgcgcttg tgcgccttaa    360
ccaaggaggt ggtccagaag aggaaccaga ttacaaatcc tgaacggagg gatgcatcta    420
ccaatacaaa atcgcaacaa ggatttggtt gtccggtcat aatgggacgc ttccgccaga    480
gattacagca atcggagaca atgatctatg atcacacagc cgagatgacc atgcagattt    540
ctgctccgcc tagcatgcca attgggatga cttctcagct ggtaatggag gatgcttctc    600
tgactccgcc gcaaagagtt gttgtcacgc tgacacccgt gaagttggcc acagcagaga    660
gtgtttgggt gaccaagttg gat                                            683
```

<210> SEQ ID NO 168
<211> LENGTH: 500
<212> TYPE: DNA
<213> ORGANISM: Drosophila

<400> SEQUENCE: 168

```
gcaacacttc ctctacgaga aggaactcaa atttaagttc accagccatg ctcaactctt     60
tggccaagag aattgtgctt atgcccagcc ttatagcact ggaggatact tgtcgaacta    120
ttcacgttac cgccctaatg gcgaggatgg gaaaggattt ctgtcccgtg agtgaggttc    180
```

```
ccgactgcaa agtggtgaag aagcgaccgt gcagtcccac ggatccacct gttcgtcctt      240
gcagcgagga gggctgcacc cagccgcgat actcatgttg cgtgagtacc ggcatttcgg      300
cgaatccatg cgctgatcca agcaagaaga ccaagttcgt ttcgatgtgg aagagataca      360
aggatgatgg tagtaatcgg ccagaagcta tgtggcacta cccggaggag tgctgtccaa      420
agtgtgatga tacgcgattt gacgttttgt actatacacc gtcggacaag tgccgggagt      480
tccagcgcac ctggtgggaa                                                  500

<210> SEQ ID NO 169
<211> LENGTH: 575
<212> TYPE: DNA
<213> ORGANISM: Drosophila

<400> SEQUENCE: 169
cgctcccttg ttcgtgttat tgcagcgcaa ttaaataaga tacgttagtt gtggccagtg       60
ctgcaactta ccaccacccg gatacaccat tccctagcgc gatgtcacag gtttacttgc      120
tgccggtgct cacgttcctg atattccagg tcacctttct tggcacgtac atcttcgccg      180
tgctggaggg gcatgtggtg cccacggttc cctacatcag cgatgcggcc acctactcgc      240
cggaaagctg tgtgttcggg cagcttatca acataggcag cgttctgctt ggaattacca      300
tctacgtacg ctaccgtcag gtgctgcagc tttatgaaca ccatccggat ttggacgggt      360
cggtgctgcg ccagaaccga ctagccttgt ggttcggact ggtgtcctgc ctgggcatta      420
gcttcgtggg caacttttcag gagacgaacg tgcggattgt ccacttcatc ggagccttct      480
gctgcttcgg ctgcggcacc ttgtactttt ggatgcaggc gctcatctcg tatctgatct      540
tccccatgtc gggtacccgc attaacgctc acttg                                 575

<210> SEQ ID NO 170
<211> LENGTH: 600
<212> TYPE: DNA
<213> ORGANISM: Drosophila

<400> SEQUENCE: 170
cgacagttca gttcacaaaa tttcggtctt taattttttgg agttaaaaat ttgtagctaa       60
caaaattgaa aattcaaaaa ttcagttcgg agttttatt tcagacaaca ccctctcgtg      120
cacgcatcaa aattttttagt tctgaaaagg gagttcaatc caagacgagt caatagcaag      180
atgaatacca cttttaaaat ggctcgaacg agcctgaatc attcttggcg gtttgttagt      240
aacaaagcca aggggcaatt ttccagtttg cgacgattac cagcagttac cagccaaaat      300
cgtcgctacg cagaccgata taccttcgac gaccagactc aagcacaaat ccagggcatc      360
aagaagatga aagagatgtc cgcggtgccc cgggagtctc cttggcgtga cagcgaatgg      420
tctcccgatt ttcccgagcg tttggatgag ttgggctacg agtccactg caacgatcgc      480 ctctatatag ccaagaacaa aatccgtcac gagcaacaaa aatatgaatt ggaacgtgaa      540
gagcgtcgca agcaggccca acgaagaatc aatagtcact cgctaaaagg tcaggcagaa      600

<210> SEQ ID NO 171
<211> LENGTH: 600
<212> TYPE: DNA
<213> ORGANISM: Drosophila

<400> SEQUENCE: 171
atcttaacta aatttctatt ccttacatct ttaaaatggc aaacgaagag gttaaagaca       60
```

```
atggccaact taaggcaact atggtaaact gcaatttgaa ccccagtgtc gcggatgatt      120
ttgctgagtt cgaggcaacc cttgcgaaga tcgattgtat actgcagaac aaggcaccct      180
gtgacgatga agattcaaag gcaggtggcg atgccaagga agatcaac tttgacaact        240 tggatgtgga taaggtgcgg cttaaagtga agaaaatcg aacagtcatc aacagaaagt       300
ctctagaaga agacaatgag aagcaagtca aggatatgaa ccagaagagt ttcatggagc      360
aggtggagaa ggatgccaat gatcgtgcag aggcacgtgc caaagccgaa tacgaagcag      420
aactacagag aagtcaggga acgaagcat ttcgcagcca agtacgag aaggcaatcc        480 tacattatga caaggctatc atcaaagtta aggacagcgc tattacatat tgcaatcgcg      540
ccttgtgcta cattaagcta cagaactata agcgcgccct caagggactg cagtacgtgt      600

<210> SEQ ID NO 172
<211> LENGTH: 624
<212> TYPE: DNA
<213> ORGANISM: Drosophila

<400> SEQUENCE: 172
aaattcaacg tgagcaatcc aaaccagatt ggacggatgg atagctcggt gccatccgga      60
gccgaaagcg gtcttatcaa ggagtacaag gactttgcca aatgcctgga cgaactggag     120
ttcaagaccg atgagctgct aatcgatgct aaaatggtgg atcaggagtt ggccaactgc     180
cacaagtttc gcgaggatca gctgctgaag catctgacgg agaagaacga cgacgacgag     240
cagatgcagt tgctgcggga aaacatcgag ctcaaggcga ccggcgttga gttccaacac     300
ggcattgagc tgatcatgga aagtaccgt gagcacagcg aaggggacat gttaatcgat      360
acctaccaac tgagggagca ctacctggcc ggtttgtcga aggtggtcga agagcaggat     420
gcccgcatcg agcgtatggt tgatgtgatg aagctaactg tcgacttcga ggaccggagc     480
agtgccgaga accagcagat catttgccag ctgactgatg aaaatgagca gttgcgtcgt     540
cagttgcaga tcagtaccac cgatgagctg ttccgccagg gagcactgag ctccagcgaa     600
agtagcactc agatcggacc aaac                                             624

<210> SEQ ID NO 173
<211> LENGTH: 594
<212> TYPE: DNA
<213> ORGANISM: Drosophila

<400> SEQUENCE: 173
ttgctacacc gatcaaaacc aaagcgcttg aaaacaaaat tgtattcaac gaaataagtt      60
gtgcatttat aaatatctat atatatatat atttttttact gcacacgcac gcactataaa    120
cgttaaatct caaaatcgtg tcaaaccaac caacctacca accgaccaat ccacgaacaa     180
taaccaattg tgtctgttga atcgtatcgc gtcagtcttc cgcaatatga gcacaagacc     240
agacaccaaa gaaacatccc cacgcgtatc cttgtgtccc ccagaaccgg ctcgaaccga     300
aacgccaatt ccaccggctg acgacgccct atccattgat aactcgtgcc gagatagcga     360
agttggagac gtgccggcag ataacagcac agtcacaaag tccgatcagg tgaacgaggg     420
ctgtcaaact cggcgagact ctggaaataa tcccgaacag ccatactcgc tgaacaagat     480
ggcaggcgtg agcaatgtaa aggagcccct tgggctctgt ccaaacgaga ttaatgagga     540
gcagcaggcg tgctccaaac tcgattcacg caatccgatc acggtcctcg gcct            594

<210> SEQ ID NO 174
```

```
<211> LENGTH: 631
<212> TYPE: DNA
<213> ORGANISM: Drosophila

<400> SEQUENCE: 174
cgacttgaag cggcaacatc gtcggatcaa gcaacatata acaactttcg tgagtgccac      60
aagtgcccct tttttacgat taactgcagt aaaaggagcc agagacattt gataattgag     120
tgtgtgccaa tttttgtaaa acaagacaa ttgacaataa ttacaactcc caaccgaggc     180
tccagattaa aattgtgata ccaaacatgc tacggctgtg ggcctgcctg ctcctcctgg     240
gatcaatcca gatccaggcg gttccattct acggcgacag cggatacgac accgagttcg     300
tgccactgga gcaccagcag cagccgcagg gacgccagga gacggcggcc accgttcccg     360
ctcaaacccc cagcggtgtg gagcagaagc cgttcaatgt ggacaccatc accacggatg     420
tgaattcccc aaatccggcc atcttcttcc agcaatcgtt ccccttcttt ggcaatgagt     480
tcttcaattc gttcggaggc tttggctttg gagctgccca ggagccctgg tggaagggac     540
ccaatgtgtg caccgaaaag gaggaagacg agactgtggc cagtgaaacg gaggcagaag     600
aaaccgtgga cacctttggc caggaacgtg a                                    631

<210> SEQ ID NO 175
<211> LENGTH: 579
<212> TYPE: DNA
<213> ORGANISM: Drosophila

<400> SEQUENCE: 175
aacacatcta gttttctaac atcattttca ctttcgtaat tttatgtaat gcaaaacgta      60
aatcaacaca acatgggaa ttctgcgtcc cgtcgcagaa tccttggttg gataaacaac     120
aatcttggca ccacttacgt acgtttagag gaactgcgaa ccggcgcgga atattgtcga     180
atgcttcata agctgcaacc ttcggcgatt aggttgaaaa gggtcttcaa ggaaccaaag     240
agccattatg aatgtgtgca aaatatgaaa ttgctgcaaa agagcctctt aaaacagggc     300
gttgagaagc aaatacccat tcagcggcta gtttctcgtg gtaatagcga gagtttggag     360
tttgcccagt ggttcaaggc attctatgat cataaccacc agctgttatg cccgaaaag      420
accgaagatg caccgaagcc cctagaaaaa ttcgacgaaa agcctgacag tttcgtggat     480
accggaaaat gcaggtatgg agcaagatgt agtcatagat tagattcgac tgtaagcagt     540
cgacattcaa atcaatcagg gaagaatttt gaaaactac                            579

<210> SEQ ID NO 176
<211> LENGTH: 628
<212> TYPE: DNA
<213> ORGANISM: Drosophila

<400> SEQUENCE: 176
ataaatcgaa atgaaggacc tggacggctc cttggacact ctggagaatg cccgcttcaa      60
ctacgtgtat atgaaggaca ttgctcgcct ggcaaaggac tcgatcttct cgcataacga     120
gctgattagc attgtaatgc tctaccataa gtttgtgctg gtcaatgggc cgagagcaaa     180
gtacatgacc attcagcaac tctctgcgct gatggagctc ttgtttgaga tcgtggatcg     240
cgatctcatt gcgaccattg tgtatagaat agcccataca ccaggttcca ggcctcctga     300
cttcttttcc gacaagcata tacacttgga gtcctttgtg cggcttttca ccgtatactt     360
caccaaagat cttcagctga aaatggaatt cgcattctcg gtctacgata aaagcgattc     420
caagcagttg aatggcgagc aagttgggtt cttcgtcggc aagttctttg agagcgagga     480
```

```
tgaagacgaa tccattgagc tgcgcttgga catgaaggag atgctgttcc tcaaattcga     540
cttggacaag gataccaaca ttggggttga tgagtactac gaggtggtcc gccgacagcc     600
catgctgctg gagtgctttg gtcgcgtg                                       628
```

<210> SEQ ID NO 177
<211> LENGTH: 600
<212> TYPE: DNA
<213> ORGANISM: Drosophila

<400> SEQUENCE: 177

```
taaacaccgt tcagcggagc aaaattttgt acaacttttta tttggtcaaa aaaaaaaaaa     60
tcgaaagaaa aactgtttct ttttcaccac tttcccaaat tatttgtatt taggatttac    120
tcaaccgcaa ctcacaatat gtcgaattcg ttttcgtact ggaatggcca gccgttgaat    180
gctcccgttt atccgcagat gggtgacttc atgcagcact ctgccgctgg agcagccgct    240
ccaccaccac tatcagcaac agcagcagca ccaggattag gatcagccgg cggactagga    300
ggttggccta gccagggcgc agctcaggca cactccatgc taccatacgc cggaggagcc    360
ggtggcatgc cggctgccat gccgggtgcc atgccgggcg tcatgccggg tgccatgtcg    420
ggtgccatgc cgggtgccat gccgggtgcc atgtcgtgtg gcatgcccat tacaggagcc    480
cagcatatag tgccgccacc cgtggaccgt tcaatatatg gagacatacc cggacgaaat    540
gaaccgtgca tcgacaatgg cgaagccttc tgcgcctaca acggcatgga catgagcatg    600
```

<210> SEQ ID NO 178
<211> LENGTH: 658
<212> TYPE: DNA
<213> ORGANISM: Drosophila

<400> SEQUENCE: 178

```
ataacataaa atctaaatta ccttttttttt tgcgaattct ttcactatgc aaaaaaccaa     60
taactacaaa agcttcaaaa tcttcttcaa gaacgttcca tttcgttcat atcccgactg    120
caagaatggt aaaggttcag gcctaaaagc caagttggca agaaaaattc ctatagaacg    180
tgaaaagttt ttgggtataa agtgtctgca cggcaagaag ataattggcc agatcagtgt    240
taatagcgtg attggaggaa tgcgaggact tccacttttg ttttgcgaga catccagctt    300
ggacaaaaac aagggtattt attaccgtgg aaaactgctt aaggatgtgt gtgccaaact    360
gccacgggtg caagagggca cacaagaggg cactcccgaa ggatgtttct tcctgctgac    420
cagcggatcg atgcccacga agaaggaggc acaggaagtg accaacgagt ggctgaagcg    480
gggctcagtt ccgcgctact gcctccggat gatcgactcc atggacaagc gggtgcatcc    540
gatggcccaa ttgtgcgccg ccagtgcctg tctcaatccg cagagccagt tcgtcgaggc    600
ttacaccaaa ggggccagac gtgcagacta ctggaaatac tcctacgagg attcaatg     658
```

<210> SEQ ID NO 179
<211> LENGTH: 764
<212> TYPE: DNA
<213> ORGANISM: Drosophila

<400> SEQUENCE: 179

```
tagaggtgct cgaattcccc cagatccgga cggtggccat catcgctgaa ggtattccgg     60
aaaacatgac tcgcaagctt attattgagg cggataagaa gggagtggca atcattggac    120
ccgcaaccgt gggtggcgtt aagcccggtt gctttaagat tggcaacacc ggcggtatgc    180
```

```
tggataacat cctgcactcg aaactgtacc gtccaggcag tgttgcgtat gtttcgcgct      240
ccggaggaat gtccaatgag ctgaacaata ttatctcaaa ggccaccgac ggcgtgattg      300
agggcattgc cattggagga gataggtacc caggctccac ctttatggat cacattctgc      360
ggtatcaagc cgatccggaa accaagctga ttgtcctttt aggagaggtt ggtggaaccg      420
aggagtacga cgtttgtgcc gctctgaagg acggacgtat taccaagcct ctggtggcct      480
ggtgcattgg tacctgcgcc agcatgttta cttcggaagt ccagtttggc catgccggat      540
cctgcgcgaa ctccgaccga gagacggcta cggccaagaa caagggtctg cgagatgccg      600
gcgcctacgt tcctgattcg ttcgacacgc tgggtgaact catccaccac gtgtacggcg      660
agctggttaa gactggtcga gtagtgccga aggaggaggt gccaccacca actgtgccca      720
tggattattc gtgggcccgc gagctgggtc ttattcgcaa gccc                      764

<210> SEQ ID NO 180
<211> LENGTH: 650
<212> TYPE: DNA
<213> ORGANISM: Drosophila

<400> SEQUENCE: 180
ttaattctag agctgttaaa tttgaaacag tgttccacaa cttaaaacca tgggttcat       60 agcccacaaa aatacttta aatgatttat catcaaactt tccttgtttg tttttaatat      120
gcacataaac agttgcacca aacactctca aatgttttaa gtatggcttc ttattgtgcc      180
acatctcata tggggtcttt gaactatcaa caagtgctct actaggaatt ctgttgatta      240
aataagtagc agttaatact gcttcgcccc aaaagctttt atctagcttt gcaccactaa      300
ccatggttcg agcttttcc gtaatggtgg aggtcatcgc gagagatcaa ttgaaattaa      360
gcattaaatc acatcatgag cttcttgcgc agtgccctgc gctatgccca caccaatggc      420
tacacgggac tcctttacac tccgcgcggc gagttcatca tcacgtgcgg cacagatgga      480
gacatccggc actggacctg cattagtgac gacgatccac gctcaagttg cctgggcgag      540
ttcgtcatgt gcatagccca cacgggaacc cgtttgctgg cctcgacgga tcggaatacg      600
atccatgcct acacctttcc cgagatggac agcgatggca tcctcatgcg                650

<210> SEQ ID NO 181
<211> LENGTH: 547
<212> TYPE: DNA
<213> ORGANISM: Drosophila

<400> SEQUENCE: 181
taaagggtct tggacgtatc gagcgaatcg ttcgccagag ttgccgcaat acataattac       60
gaactgtgaa gtgaaattga cggataatat aaaaccgaaa aaatagtaga ggtaaccggc      120
gcgaaggacc aaacaatcct atcgcctatc gatagagaaa tcggaaatca gatcgtcgac      180
aaaaaagcca gcacaacgga gaccgaaacg gaaacgaaa caatgggcgg cggtgaagtg       240
aaggtcgcta ccgtcgacgt cgagggcggg gacaatatgg ccaccttgcc ggtgtcccgc      300
tcgcataccg ccggcagcac cgacagcgcc gagaagaaca cgccgccaa caaggagatg      360 gaactcaaga acgtcatgcc gcagccgctg cagaggacat cgctgttcat cgtgaccagt      420
ctggtgtacg cgatccttct gatcgtcgtg tgcattgcat acgttatcag cgatgtaacc      480
acccaccgac tgccggtttt gtactacgag acattcttca catatctata cggcgtcagc      540
atactct                                                               547
```

<210> SEQ ID NO 182
<211> LENGTH: 600
<212> TYPE: DNA
<213> ORGANISM: Drosophila

<400> SEQUENCE: 182

| | | | | | |
|---|---|---|---|---|---|
| agttttcggc | tgtgctggct | gctctacgct | gcgatctccg | ttctccgttc | tccaatcttt | 60 |
| gtaatatctg | tttagatata | catagttata | gtatatacat | acatatattt | cgtgtgctca | 120 |
| gtggagcgtc | ttccgcgttt | tgtggctgcg | tcgcttaatt | ggcccaaaag | tatctcaagt | 180 |
| gtgtgattgt | gaaagttcct | gaagcaaaat | gtacgtgaga | cgagctctgc | tcttggcctg | 240 |
| cctgctgtgc | ctccagccgc | tgggtccatc | tatggccagc | gaggatgagt | ccaatccgct | 300 |
| gctggacatg | gcctccatgt | tcttccagga | ggcgctgtcc | aaccagaacg | gtggcaacaa | 360 |
| tggaggaggc | ggtgctggtt | tggcgggtgt | ggcctcgcta | attggcacct | tcatgcaagc | 420 |
| gagtggcaaa | tctggaggcg | ccggagcagg | aggcggcggt | gctggtggcg | ccatgcagat | 480 |
| cctctcgggc | ctgggcagtc | ttctgtccaa | gagtcagggc | ggtcagagcg | gtggcttcga | 540 |
| tccctccatc | attggcaatg | tcctcgagat | gttcacccag | ggcgatgacc | aggaagccac | 600 |

<210> SEQ ID NO 183
<211> LENGTH: 600
<212> TYPE: DNA
<213> ORGANISM: Drosophila

<400> SEQUENCE: 183

| | | | | | |
|---|---|---|---|---|---|
| ttgaggtagc | cttacgaaga | gttgcgctta | taattattag | gaataatatt | aacctatcga | 60 |
| aatgtggaag | aaaataattt | tctgtgtggt | gcttgtggcc | tttgtggttg | tgccgtttgc | 120 |
| caactcactg | acctgctcca | agtgcacatc | gccgtctgga | tgcaaaagtc | cttcctccga | 180 |
| aacctgctcc | aattcgacgg | ccaatgccaa | taaggaattt | ctggaaggat | accatagtaa | 240 |
| tgtgcccacc | gttaatggca | gtctgagttt | ttcgtgtgcc | aatctcactt | actatcatgc | 300 |
| agcaaactac | actcacacct | ttgagttcct | gggctgcgtc | ttcaacgaaa | cgaatgtctg | 360 |
| caatctttcc | ctgaacaaca | ccgcgagtgg | atggagcaag | aagtgcctcc | aatgcggcac | 420 |
| cgactactgc | aatccagctg | gaacctacag | cagcagtgtc | tatacaatcg | tgggatccgc | 480 |
| cattgccgtg | attttggcca | agttctaagc | taaacttat | aatctgacga | cggagctaaa | 540 |
| cagtatttca | actacctttt | gattgtacaa | tatttatttg | aattaaaaat | aaaatcattt | 600 |

<210> SEQ ID NO 184
<211> LENGTH: 480
<212> TYPE: DNA
<213> ORGANISM: Drosophila

<400> SEQUENCE: 184

| | | | | | |
|---|---|---|---|---|---|
| gcatatattg | gtttattaca | cctcaattcc | atccctacga | ctctttccat | cggacaactg | 60 |
| gtccaaagct | atctggatgg | gcttattgag | aaagctgtgg | acatattcgg | taatacggac | 120 |
| tatttgcggg | cgaagaatct | ggacaaaata | ctccctcgta | acgccgagca | gcagatccta | 180 |
| catcaacgaa | tcccaacgga | gtcggtactt | gggtgcccta | aacgaattgg | atcattggct | 240 |
| taacaggaca | cgacaggctg | agcagatgca | cctggctgaa | aaggaacgac | tgctgtcgga | 300 |
| attggagcgg | atgcaacgag | aggacaacga | gaagatcgag | aggctggcgg | agatcttcac | 360 |
| aaggacttta | ctgcgggaca | gccaaccgtc | tgaacgcctt | cgctttgtaa | cggaaaccgg | 420 |
| tcttaaacac | atgagagcaa | aacgcgatgc | gttgtctgcg | acacgactga | ttttgatcat | 480 |

<210> SEQ ID NO 185
<211> LENGTH: 691
<212> TYPE: DNA
<213> ORGANISM: Drosophila

<400> SEQUENCE: 185

| | | | | | |
|---|---|---|---|---|---|
| ctaacccaca | aaaaatctaa | aaaatataaa | attaaaattt | caaaaaccta | caaaaaagca | 60 |
| tccaagaatg | actcagttaa | gcgagttcgc | cctggacagc | cactttgcct | ccgagctgcg | 120 |
| cagcctgcag | ttgtattcca | aggagcaccc | tgtcagccaa | gatgaccacg | acataagtca | 180 |
| gcgttggatg | cagcacttcc | aaaacgccaa | gggtttggat | aaattcgcac | gaaactgcat | 240 |
| gctgctgatg | atgtgcgaac | agttgcgaga | tcttggccac | ttgagcaaac | ccttcaccga | 300 |
| actgaagaac | ttgagtcgcc | ccatggacga | tttgctgaac | gagtaccatg | ggacgactac | 360 |
| tgtggaggag | gggcaaatgt | cgccggttga | agatattgag | gactcggaca | ccaatgtctc | 420 |
| caactatggc | agtggcagta | gttctttctc | ccctggggtg | ccctatccca | tttccacgcc | 480 |
| cgagttcgag | agcattaagc | ggtctaacca | ggatctgctt | aaggaaatcg | actcgctgca | 540 |
| ctgtcgcacg | gtggaagcgg | aaaagctata | ccttagcagg | agccaaattc | tggagaagca | 600 |
| gattgccgag | aagtcggcgt | tggccaaaac | gaaacttccc | caggagggta | tctatcaatc | 660 |
| ctgccgtgcg | gcctgccagc | ttctgaaaaa | t | | | 691 |

<210> SEQ ID NO 186
<211> LENGTH: 497
<212> TYPE: DNA
<213> ORGANISM: Drosophila

<400> SEQUENCE: 186

| | | | | | |
|---|---|---|---|---|---|
| caaacgtttc | tgtggcgctt | cttttcagat | gccgtcaatg | tgtcgttcgt | attgcatcgt | 60 |
| cgcctcacat | atcgactagt | gggtaaagta | caagtcctga | tggagctgag | gaaatctaac | 120 |
| gtggtgctgg | tgcaccttct | gctgctgatc | tgcataatgc | gcatctttta | tcagtccgga | 180 |
| ccactgtcgc | agctggaacc | gcagaagaca | ttactggata | tgggtgtacc | accagctgcc | 240 |
| gatcgcctgg | tggctttact | tatcgaatga | ctccgcacgg | acacgttatt | tcggacaac | 300 |
| tgcagtgggg | ctgtctacat | acgggatata | atcctgcgcc | aggactagt | cagcatatct | 360 |
| taaactagtg | ttccaactat | gacccgatct | gctgaagtag | ccctattcgc | tggattcaat | 420 |
| ccgatgccat | ccatattgcc | tacctctaat | ttcgatacca | ttttcaatcg | cactttggct | 480 |
| ctcgacaagg | gtgcgtt | | | | | 497 |

<210> SEQ ID NO 187
<211> LENGTH: 644
<212> TYPE: DNA
<213> ORGANISM: Drosophila

<400> SEQUENCE: 187

| | | | | | |
|---|---|---|---|---|---|
| cataactgcc | acaaaactaa | attgaaaatt | tatacatta | atgcatcact | tttaacctga | 60 |
| tccaaggtca | tgtccttgca | gtggcaaaat | gaggtggtgc | ggattacgcg | ccaagtgaag | 120 |
| cgcaatctac | cgcaccgaaa | tttccgagag | attaactttg | atcgcgagac | cataaggcaa | 180 |
| ggaatcaccc | ccctgaccta | cgatgaggcg | cgccgtctta | agggaccagt | tttcgaggct | 240 |
| ctggaggatg | agttgcgtcg | agcaggatgc | accatgctgc | cggagttttct | ccactgcctg | 300 |
| gccaccaagg | agaatgctct | tttcgagagc | ctaaatatcc | gggaacgtct | atccgatgac | 360 |
| tcggaattgc | tctacggaat | ggtggatcga | ctccgggatg | ccgaactggc | tgtttgcctg | 420 |

```
aacaagcacc ggggtctcaa aaagtgtttt ggcctattct tcgagaccat gcagctgctg      480
gagccgtatc gtcagaaata cgcatacgcc ctggtggccc tcaatgagca catcatctcg      540
ttgtgccgca acattgccgg ccaggaacat gatgccgccg agtacatatc ccgcatctac      600
tacatctatt ccatgtacct ggtgaacaca ggccagcgaa cctc                       644

<210> SEQ ID NO 188
<211> LENGTH: 614
<212> TYPE: DNA
<213> ORGANISM: Drosophila

<400> SEQUENCE: 188
tacaaaaccg agccatattt tattgtaaat aaaattcgat aaaatttcgg tggacatatt       60
ggacgaagat gtccagtctg caagatattc cgcttgccga ccccgagggc ctgtctgtgg      120
aaggtcccga ggtggccccc gctccaaagt ccaattcctt gaagcgcttc tttaagatca      180
gcaagaagcc aatgatgcgc gaccaagtgg aggatgacga cgagacatcc tcccaggaca      240
acaaggacct gggaaagtca aacactataa gtcgcttctt tacccggatg aagggagcca      300
ataaggatgt tcaagatcct tcgagctcgg tggtcgaacc cgtggagcag ataagccgt       360 tgccgaatgc aaagcccacg attaagacat ccatttcatc ctactggaag atactgttca      420
accggcagaa gagccagcgc caaaacgcag ctttagggca gaccaatgcc aataaagagg      480
ataacgagtc tgaagaagtc catgaactgc aaccagtaag ccaagatccc gataccgatc      540
ctcagccgac agtcaaggat gagcacgatg aaatggaacg tggcacagat ccggagccac      600
ccaacccgaa gccc                                                        614

<210> SEQ ID NO 189
<211> LENGTH: 493
<212> TYPE: DNA
<213> ORGANISM: Drosophila

<400> SEQUENCE: 189
aatgtagttt ggattttcat ttgaaatttc gattcgatgg gcagcaaggg caaggctggt       60
ctggacttct ccggcaaagt ggtgcttatc acgggcgcag cctccgggat cggggccgcc      120
gcggcggaga tgttctcgaa gctgggtgcc tgcctggccc tggtggatcg ggaggaggag      180
ggcctcatat gtgtgatgaa acgctgcatg aagatgggcc acgagccgta cggcatagcc      240
ggagatctgc tcaagcctcc ggagatcgaa tgcattgcgc ggaagaccac ggagcgctac      300
gagggcaagc tggatgtgct ggtaaatggg gctggcatca tgcccacggg aacgctgcag      360
agcacggaac tggcctgctt cacccacgtg atggaggcca atgtgcgttc tgggttttat      420
ctgaccaagt tgctgctgcc ccagttgctg cagtgtaagg gcagcattgt caacgtgtcc      480
agcgtctgcg gac                                                         493

<210> SEQ ID NO 190
<211> LENGTH: 550
<212> TYPE: DNA
<213> ORGANISM: Drosophila

<400> SEQUENCE: 190
ctcgtttcca accatacact ctcaattcac atctcttttt cccaaacata cttattatat       60
cttccaattg tcctgttcca catggcgctg gtttacgggg ttgaaaagaa gacggtaccc      120
acccacatga aattcgtgat gggcggaacc tccggaatgc tggccacatg cattgtccag      180
```

```
ccgttggacc ttctcaagac ccgaatgcag atatcaggaa ctttaggcac acgcgagtac      240
aagaactcat ttgaggttct atcgaaggtt ttgaagaacg aggggatatt atccttgtac      300
aatggattga gtgccggact attgagacag gccacgtaca catcagccaa gatgggtgtt      360
taccagatgg agttggattg gtatcgcaag aacttcggaa attatccatc tatggtggcc      420
agtatgacga tggcattgt ggctggcgcc tttggagcca tgtgtggaaa tccagcggag       480
gtggccctga tccggatgat gtccgataac cgcttaatcc cggaggacag gcgtaattac      540
aagaatgtgg                                                            550

<210> SEQ ID NO 191
<211> LENGTH: 570
<212> TYPE: DNA
<213> ORGANISM: Drosophila

<400> SEQUENCE: 191
aaaggaaatt aatggttaaa attaagatat gacacatgtc cggaaagggg gagatcatcc      60
agatccacat tggccaggcc ggtgtgcaga tagccaacgc ctgttgggag ctcttctgtc     120
tggagcacgg cattttggcc aatggaagac taacccagtc gcccatggac gactcgttcc     180
tcacgttctt tgagttcacc agccatcagc cgtgtgtgca acctcgactc gtcatgatcg     240
acacggagcc cacagtgata gatgaaatcc gtaccggctc ctaccgcaac ctctttcatc     300
cggatacttt gatcacgggc aaggatgaca gtggcagtaa cttcgccagg ggctacaatc     360
tgatggccag cgagctgttg gatcgctcca tgaacgccat tcgtcgcgtg gcggatcgtt     420
gcagaaatct caggggtttc ctggtctttc gagcaatcgg cggaggttct ggttccgggc     480
tagggactcg catcatggag agactggtcg aagactctgg caagaagatg actgttgtgg     540
agttccctcg ttattcttcg gcttcaatct                                     570

<210> SEQ ID NO 192
<211> LENGTH: 620
<212> TYPE: DNA
<213> ORGANISM: Drosophila

<400> SEQUENCE: 192
actcgacaag acccaaaata tattcgagct caaaagttta caatttcgaa caaagtcaag      60
gcttcacaaa attttcacat aaaattcacc gttgaaaata acttttcgtt ccgctctttt     120
ttcgttcctt ttctgtttaa atatacaata tatattagat taaacggcgt acggacccac     180
tgagttacaa tgcaacgttc cattttcaag agtagctgtt ccaggacact gatcctgctt     240
aactccctga atccatgca ccacaagagc ctgcacgtgg agcaactgtt ggaggcagct      300
ccagcgccca aaaccgctg cctggatctg ttgggtcgct tgatccatgg ccgattgagt      360
ctcttgggcg tcgtcctgt cccgcccaga ttcttaccgc tattggcggg tgatcgaagc      420
ctgtacttta atgcggacga ggacgaagag tttcgtaagc gtttggccat gcagctgaag     480
gagttgcgag agaccctgca agaaaaacag gaacttcgcg agggacaaga gcaggacttt     540
caggagctga gcaacagga cgaggaggag gatcagccgt atgtgcccag atctcgggag     600
atctccatgg aggatctcac                                                620

<210> SEQ ID NO 193
<211> LENGTH: 643
<212> TYPE: DNA
<213> ORGANISM: Drosophila

<400> SEQUENCE: 193
```

```
tcacatcaat caaattaaac agttcgatac agtaaaacag catgaacgac aaataggcgt      60
agaatccatc aggtgtagga gttctcaaga atcggcgagg gtctaatatt gggaatgtcc     120
aggcgggttt ttggcctcag tataaaatca ttccgattgt tccgaagaac tccgatccat     180
cccccagcat tccagcattt ttctggtggc gtctttcgaa cttcctttag gagtttctgc     240
gattgtcagg aacaccgaag aatggatcta ccagagggaa tacttatggg ctttggcaac     300
cccctgctgg acatcacctg caccgttgag gataatgtga tcctggagaa gtacggcctg     360
gaagcaaatg ctgcgatcat tgctgatgaa aagcacgatg ccctgtttga tgagttgatg     420
aacatggaaa atgtcatcta ttcggcgggt ggagcctgtc agaactcgat gcggatcttc     480
cagtggatcg tgcagacacc atttcgagct gtgttcatag ggtcagtggg caaggataag     540
ctaggtgatc gcatcgaaaa gagggccaaa tccgatggcc tgctaacact ttatcagctg     600
aaggaagagc tgccgacagg ctcttgtgct gtgatcatca acg                        643
```

<210> SEQ ID NO 194
<211> LENGTH: 706
<212> TYPE: DNA
<213> ORGANISM: Drosophila

<400> SEQUENCE: 194

```
cctcttcctc agtaactgcc aacgatcgga aacactcgat tgaaaattgt taaattattt      60
gtagtacaac aaaagttttt gctatttcaa aatcttcgta aaatggccaa ccgtatgaga     120
ggaggagcct gctgtccttc aagatgtcag cccgcctgtc caccatgtcc gccacctggt     180
ccgccctgcg atgcacctct ggtgcgactg gataaactgt ggccggagcc ctacaatcct     240
tgctccttca agaattgcct gatctttggc ggtcacgatg agcccatat tcgacccttt     300 gatcctaagg gttgtacacg aatgcgtcgc aatgatatcg accgatcgtt gggctatccc     360
ataggcgtag tgtctggtac gactgttata agtcgggca ttccgaatca ggagagcgtc     420
cggtttgctt caaatcttaa ggcatttgct cattcctatt acacgcggcg cgatgaatgg     480
aaaccggata cgatcgatat ggtggtgaac gagggtcagg ttttgtttaa cgattccgag     540
aacatggacc ctccgaatgc atcagactcg ccggatatct acgatgaaaa tgagcaaaag     600
gtgacgcgcc actttaagat caacgatatc gagtttgcca tggagttgga ggcgcccttt     660
gaggtctatg gctacgaaaa cgtcatacgc aatctacgca gaatct                   706
```

<210> SEQ ID NO 195
<211> LENGTH: 642
<212> TYPE: DNA
<213> ORGANISM: Drosophila

<400> SEQUENCE: 195

```
acgctcacat gtattccgtt caatttgaat attccggctt tttaaataga caaaattcaa      60
aacaaattaa actatggaat gatgtggata caccggttgc tgatggacaa gtgcacccgc     120
tatggtcatg tgctgcggca tttgattcgg gcttccaggc gaactgcgac ctcaacggga     180
catcaccaga gtgcttcggg aaaggatgtg ccaatggtgc aaataagtcc cgccgattga     240
ccaccaagtt ggctctcctc cggctgaagc tcctttggga ctgggacttc tccgagcaga     300
agttcattga gaattcgagc caggcagccg ccgttttac ggacttcgta aggcgccgcc     360
gcaatcggaa tgtggagcga tgcagtacgc ctatgggttt caagcagatc aagcacgatc     420
tgttggatga tccgcccgac tggaggctca aaatgatgcg cttcgagaag gagcacttcc     480
```

```
ggcgggccat tccgctcaag gtgcagctgc tgcggcacta cgaccatcgt ttcgccttcc    540
tggacgtggt cttcgtggcc ctgcggagat ccaatgactt tcgctcgccg gcggaactta    600
gtgagatgac ggagctgcta aaggagttca tagatcccgc tc                      642
```

<210> SEQ ID NO 196
<211> LENGTH: 537
<212> TYPE: DNA
<213> ORGANISM: Drosophila

<400> SEQUENCE: 196

```
tttcggagcg ttcggtggtg gagagcagct gcatttgtgc atttcgcatc gaacattcat     60
cgtgatccca agcgcacgaa gttgttgttt tgttttggtt tttgtcgcca aatttcgcgg    120 gatttttcg tgaacgtgtg tgtgcgcgtg catttatttc gcacactgtc gacggggcaa     180
taccaggatc tgtcgcctgt cttcgcctca gacttctcct ccggatcctg cggagcggag    240
cgtacgtatt tgtggcttca actccgtgtg tcgtatgtgc ccgtgtatgc ctctgtgtgt    300
ctgtgtgtgt ggcgtaccgg cataccgtct tgttgttgg ccaccattgt aattgcagtc     360
agtgtggcac tggcaacgcg gcgtatactt gacatcttcg ccgccaaatt gtgcgatttc    420
ttcgactcgt tcagctctcg cgctggctcc ttgaatgcgg ctccttgtga cattggcgtg    480
aagacgtgaa gagccctcaa aatccgctat tccactgtgt tcgcaatcca tttgcct       537
```

<210> SEQ ID NO 197
<211> LENGTH: 599
<212> TYPE: DNA
<213> ORGANISM: Drosophila

<400> SEQUENCE: 197

```
aaggcgaagc cagatgccac ggtgatcttt ataccacctc catccgccgc cgagggtatt     60
tgcgcgggta tcgagagtga aattggcttg attgtggcca tcaccgaggg tattccccag    120
gcggatatgg tgcggatatc gcaaatgctg aattgccagg agaagtcccg cctgctggga    180
cccaactgtc cggaatcat ctcgccggat cagtgcaaaa tcggaataat gccgggagat     240
atccacaagc gaggagtggt gggcatagtc tcgcggtcgg gaaccctgac ctacgagtcc    300
gtccatcaga ccaccaacgt gggattgggt caggctcttt gcgttggcct cggcggggat    360
ccctttaacg gaactagctt catagacgcc ctcaaagtgt ttctgtccga caaggagatc    420
aagggcattg tcatgattgg agagattggc ggatccgccg aggaagaggc tgccgatttc    480
cttaaggaga gaacactgg ctgcgaggcc aagccagtag ttggcttcat tgctggacag     540
actgctccac cgggtcgtcg aatgggtcac gccggcgcca tcatttccgg tggcaaggg    599
```

<210> SEQ ID NO 198
<211> LENGTH: 537
<212> TYPE: DNA
<213> ORGANISM: Drosophila

<400> SEQUENCE: 198

```
cccgcgagca cacgggtgac atcgctaata ccccaaaaaa aacaaaatac actacaaacg     60
acgaaaggaa cttaatggga gaaccgacga agaataagca tacaggatgt cgggggctgg    120
agaacactca gatgaagagt cctatggaga ggagtccttc gaggaggact cggagtcgga    180
ggtggaggtg gaggaagaag agattgagta tattgagcca gaggagtcaa aaccaagtga    240
cgctcttctg ttgggggaga gcgacaccca aagcgagagc gatgtgaaag aagagttcct    300
tagcggcaac ccacacgccc gtcgctattt gggcgcccga gtggtgtcct acctgagttc    360
```

```
ctcctctgac gacgaaagcc aagtggtcat caccaagacg gtagccgagg taaatcaact      420
aagtctgcga gtggacacgc ctccggagga tgagacgccc tcggtgcgca ctctgatgcc      480
aggcagtgcc cattctcggg ttaaggatga ggacgaggct gaagacgagg atgatga        537

<210> SEQ ID NO 199
<211> LENGTH: 623
<212> TYPE: DNA
<213> ORGANISM: Drosophila

<400> SEQUENCE: 199
cgcgcgagga ctttcactaa atcgagactt atcacagcag cgatataaag ttattaaata      60
ttgatttaaa ttttaggtga acattccgcg atggaaactg ataaggaaaa acaaagcgat     120
gagctcatga atcgcattcg gaacgagctt acagctatat tatctcaaga ggctgctgat     180
gattccgaca aggaggcgtc acaggaactg ctcctgagtc ccaatccgct gcccattttc     240
gggcccataa ggaaaacaag gaaagcaaaa tcgaggagtt ccaagaagaa caatagtaag     300
gcctcctcct cgtccgctgg cagtacaaag agttcgtcgt cgggtaccag atcatctgaa     360
gatcgtttaa ctggaggtgg agcccaggag aagccatcgg atccggtctc cacatcctcg     420
agctattcgc taagatcagg atatgacgct ccgcccgtgg aggccagtgc ccgtgccgac     480
ttccttgaat cgcaagcggc caaaagcatc gacgaagatg tccggaagat gcagctggag     540
ctcaagcaga gctacgaact cttccagggc attggcgaga aattggagtc ggttagcttc     600
acgggcttga aggaccgcat acg                                             623

<210> SEQ ID NO 200
<211> LENGTH: 521
<212> TYPE: DNA
<213> ORGANISM: Drosophila

<400> SEQUENCE: 200
ccccgattag tcacttttt tgtacgtttg taagctgccg ccagttttca gagtggcgcc       60
acggggatac gtggaatagc gtgttgtgct ctacgtatat tttttatatca tcattgcgga    120 accacaaagc tctcgactac tttctaactg aggaactgaa tcaaaggact ctccttcaga    180
cgcagtacaa tctccgactg gccgtcgata gcgaaacgcg gcggtcgatt tgaggcaacc    240
aagctgatta gtgtgaataa tatgtccgtg agtcgagtga ctatgatgcg aaagggccac    300
tccggggagg tagcacgcaa gcccaacact gtggtggtgt cggttccacc gctggtgaag    360
aagtccagca agagccgctc gttccacttc cgctatctgg agctgtgccg ggccaagaat    420
ctgacgccgg tgccggaaat ccgcagcaag tcgaatgcga ccaccaccttt tctggagctg    480 tgcggcgata agctggcggt cagcgattgg cagcttctaa c                        521

<210> SEQ ID NO 201
<211> LENGTH: 585
<212> TYPE: DNA
<213> ORGANISM: Drosophila

<400> SEQUENCE: 201
aagaccccgc ggctatgtgg tcatagacgc acctgtcacc gattccagtg aggatgagga     60
tgagctcgat gatgagttca aggtatccga tgtagccgga accacgagtg ccgacagcga    120
ttctgccgat tcggatgaca gtgagaagga gaaaagaag cccggaccac gtgggcgtcc    180
tcgaaaaaag ccactcaaga gaggcacgga cagcgatggg gagccttcca gcgcccaaaa    240
```

```
gaagaaatac cagccctctt cgacggcttc agtgggccca ttcgagtgtc ccaactgcga    300
cttgacgttc tcgcgcaaac aatcctatgt gctgcatcgt aagactcacg agagaataga    360
gcatgcctgt cccatctgcg gcaagaagtt caaggtggag tgggcctata aaacgcacat    420
gcaacggcac gagcaggagc gcgcccattt ccgctgcgag ctgtgcccca agatattccg    480
actgcgcgcg gaactgaagc accatatggc ccagcgacac gacgagcatg gcttcattta    540
cgagtgcaag cgctgccagc ggacgttcct cacccagcag cgact               585
```

<210> SEQ ID NO 202
<211> LENGTH: 543
<212> TYPE: DNA
<213> ORGANISM: Drosophila

<400> SEQUENCE: 202

```
ctcaacactt ccgggctgta attttatcaa aatttcagtt gaccatgtcc ggcaattggt     60
tcaaatggac tgctcttcac gggcggccaa gaactgtcgg cttaaacact aatggaagaa    120
ttctacggct tttggacgat gccgtagttc gatttcggca gccattctac gaatcttggc    180
ggcgtcgtag gcgccttgaa gacattgaaa agagagaaat cccagtgcga cagcaagttc    240
caaggatacg gcacaatcgt tgtccagggg cgaaggaaaa tccttgccgc aaaatgccca    300
gtgttcttcc tgggaagggt gaagtgcttg ttccctctcg cattcaaccg gcacggaatt    360
caatgggttt ctcagttata agattatttg gaagctccac taatgatggg ggttccggtg    420
aaccaccgga aaatcgcgaa ggaaagctca ttaagtttac agtgggttct cgcatagcca    480
aacccaaaac gggcaagatt gaaatatcaa aaaaaggacc attaggtttt gagacaacta    540
aac                                                                 543
```

<210> SEQ ID NO 203
<211> LENGTH: 600
<212> TYPE: DNA
<213> ORGANISM: Drosophila

<400> SEQUENCE: 203

```
agaaagtcaa ctagactttt aactcattct ctattcggcc ctgtatttaa aattttgttt     60
cataacaaaa cagtttgtgg aggctgtaat aggaaaatgc cgagcctggt gaacacggaa    120
attgaagccg cggtcaaggg cttcctgatc gaccaggaga gatgaccga ggtggtggag     180 cgcatgacca aggagataaa gatgggcctg gccaaggaca cgcatgcacg agcggtgatc    240
aagtgcttcg tcagccatgt gcaagatctg cccactggca aggagcgggg aaagtatttg    300
gccctggatc tgggtggctc taatttcagg gtgcttctgg tgaacctgat tagcaactcg    360
gacgtggaaa ccatgtcgaa gggctataat tttcctcaaa ctctgatgtc cggatcggga    420
aaggcgcttt tcgacttcct tgccgaatgc ctgtcggagt tttgtcactc ccatggcctg    480
gagaatgaat cactggctct gggcttcacc ttctcgtttc cgctccagca gcaggactc     540 tccaagggta tccttgtggc ctggaccaaa ggattcagct gcgaaggcgt ggtgggcaag    600
```

<210> SEQ ID NO 204
<211> LENGTH: 617
<212> TYPE: DNA
<213> ORGANISM: Drosophila

<400> SEQUENCE: 204

```
aaaaaacatc cgtgaatatt ttctacacac caaacttaaa atcaaatctt ccagacttgc     60
ttattacaga ctttgaaact gaggctccgc ccgcatcttg gttttacat ttcttttttt     120
```

```
ggacattaac tgattttagt tctactaaca atgtgcacta agacaaacga acgtgccact    180
cgacttcatg aacctggaag ggtttgcagg gagttgttgt acctcaggtc gaaggtgcca    240
gtacgtgaag ttcccgcctt cacttttcag gcactgcagc ctaatactgt ggtgaaacct    300
cctccaaaga tcgacatttt caagcggaag ccagtgaagg agaccgtatt caagatctac    360
ttcaatcgcg gcgacattcc gtgtgtgatg tccggcagga gcagcaaaca ggatccgacc    420
aaggagcgtc cggtgaagtg gcactgtgtg ccggagaatc tcgactattg ctactatctg    480
cccatcttcg tggacggact ggcggacatg gactacgaca cccggttgct agcggtcaac    540
ggagccattg acctcatcat gcggtccccc aaaaaggtgc acccgtgct gcccaagctc     600 attcttcctc tgaaacg                                                   617

<210> SEQ ID NO 205
<211> LENGTH: 670
<212> TYPE: DNA
<213> ORGANISM: Drosophila

<400> SEQUENCE: 205
cccaccgagt gcaaaccgtt tacaacgagg ttgcttttaa atcttttgta cgtgacttga     60
acaccaatct gcgggacatc ctgggcacat gtcgcgaaat ctgggtcaga tttgacccca    120
ctcagatgtc gcagggcctg ctgtttacct tcctgccgtt gttctttatc ttccttgtgg    180
taaacaactc tcggccagcg gattttccgc acatcttcaa agccaaggag gtcttctatg    240
tatacctaat caacttggcc gctggagtat ttggatatcg gtatttcaag acattctcct    300
ttaaaacaga ggagcaagga gtgatcttct ttacggcaat atccagtgct gtcatcctgg    360 cttttccatac actacgtcac tggaccagca ttgccacgaa ttggtcagca gtcaagcgat    420
ttggacacat gcccacgcgt ctgctgcttt tcggttccat ggcggtgttc ttctcgaaca    480
gcttcgtcat ccaggaggcc aagatcttat cgtacctctt ggcagcagcg atactactgc    540
tctcccacga acttcttcgg ctgagtgccc gtttggattt taggacaaaa ttcaaggcat    600
cacaatttct gcgctccaca gcgttaagat tgatcctggc cagcgttttg gcgatatgct    660
taatacgatt                                                           670

<210> SEQ ID NO 206
<211> LENGTH: 477
<212> TYPE: DNA
<213> ORGANISM: Drosophila

<400> SEQUENCE: 206
atgtgaaaat cgtcgcagct cgttccgtgt tttcgccact cgagcgggaa aatcaaaaaa     60
tatttctacg ctcaacaaaa taaattaatt gaaattgatt tttcaagcaa cagaaatagt    120
tctagaagaa ctataaatcg aggaagtcat ttttgtttta tcaaatttca agtgcaatgg    180
gttcattgtg aaatcaatct aaagtgtgtg tgtgtgtgtc attcgaataa ttactattat    240 taaaaagaa ataaatacgc agaaagagag agagagatcg aacgaggcag agtgaaagag    300
agagatagag aaaaaagcga gagatccgga gatctctcga gaatctttaa acaacagcgc    360
taaagttacg gatctaattt caaacagttt aatttacttt taattttct acaaaacaac    420 aaacttcaaa aagaaaaata cgaaccagca aaactcaaag caaaaaacga tctcata      477

<210> SEQ ID NO 207
<211> LENGTH: 714
<212> TYPE: DNA
```

<210> SEQ ID NO 207
<211> LENGTH: 714
<212> TYPE: DNA
<213> ORGANISM: Drosophila

<400> SEQUENCE: 207

| | | | | | |
|---|---|---|---|---|---|
| ttaagcacaa | ataatttagg | ctactgtaag | tttagagcga | caagatgatc | gatattttgt | 60 |
| cgctgccgcg | gcgaaataag | gtgtccggaa | acccggccct | gctaaagatg | atctcctaca | 120 |
| agactggact | acccatcaac | agtctacccg | gatgggagct | gatccctctt | aattgcaagc | 180 |
| tgccaatgct | caaatgtccc | ggcaatcagg | tcatattctc | caagaacaag | atcggacagg | 240 |
| acttcaagag | cggtaaacag | gagtttgagt | gttccgttac | cgaacacatc | ccggagtaca | 300 |
| atccgctaca | cgactccaac | ctaaagacgt | tctactccaa | tgagcgtaat | ctgaagcggt | 360 |
| tgagggaaaa | cggtgagata | acgcaggaca | acgatgtaat | atgcaatctg | aaggacttca | 420 |
| atcagcatcg | ccaggagctg | cacaaatcgc | agttgtacta | cattttgcag | gcatacaagc | 480 |
| ggcgcgagtc | ggagcaatat | gatcgaatgc | tgatcgccaa | cgcggagtcc | atcacaaaaa | 540 |
| aggatcacca | gaatctcgca | gcccgtcacc | agtgcactga | ggaggttctt | gccagaaaga | 600 |
| aactacagga | gcaggaacgc | cacgaaagaa | aggtccatct | gctgaatatc | acatatgaga | 660 |
| agtttaagcg | cttagagaac | ctggccacca | tgcagaatat | gttgctggag | cacc | 714 |

<210> SEQ ID NO 208
<211> LENGTH: 549
<212> TYPE: DNA
<213> ORGANISM: Drosophila

<400> SEQUENCE: 208

| | | | | | |
|---|---|---|---|---|---|
| ccgtacatcg | cgaatctgtg | tctcagctcc | cggatcagca | agcaagttaa | acagtatgct | 60 |
| tgtgaagtca | ttcagatcgg | ccctggttgc | ctgcctgatc | acccttgtgc | cttgcggaag | 120 |
| tgctcaagca | tacatcgcga | agccgacatc | tccgcaggga | tatcaggatg | tcaacggcgt | 180 |
| gtggcaaagc | tctttcgttt | gtcaaacagg | atatcaattg | aaagcggatg | gaaaatgtta | 240 |
| tccacagact | aacaaaacgt | gcgggcctgg | atactttctt | agcattgatg | aactatgcta | 300 |
| tcgtacgaat | cctgagcctt | gcccgcttga | atcgacgacc | actactacta | cgacaacaac | 360 |
| aacaacaaca | acagagccca | ctaccacaac | aacaacggca | gagcccacta | ccacaacaac | 420 |
| aacaacagag | cccactacca | caacaacaac | aacagagccc | actaccacaa | caacaacaac | 480 |
| agagcccact | accacaacaa | caacaacaac | aactgcgcct | cccgtcatta | cagaactgac | 540 |
| tcgctgtcc | | | | | | 549 |

<210> SEQ ID NO 209
<211> LENGTH: 368
<212> TYPE: DNA
<213> ORGANISM: Drosophila

<400> SEQUENCE: 209

| | | | | | |
|---|---|---|---|---|---|
| cacaggttgc | gcacttttcg | accgtatcac | aacactgatc | taccctagta | ttcacaggaa | 60 |
| gttgcatcct | tggcatccag | aagcctctag | aagtttctag | agacttccag | ttcgggtcgg | 120 |
| gtttttctat | aaaagcagac | gcgcggcgtt | tgccggttcg | agtcttgaaa | aaatttcgt | 180 |
| acggtgtgcg | tcgtaacaac | aaacagcgtc | tgaaaagttt | tgtgaatttc | caattctata | 240 |
| caaagcaaag | tgaaaatatc | tgtatttta | cctttattct | gtgaatagaa | cgaaaaacat | 300 |
| acatacaagg | tgagtaatgc | aattacaaga | aaagagtgaa | tagtttatca | gtggctatgg | 360 |
| ccaaaatg | | | | | | 368 |

<210> SEQ ID NO 210
<211> LENGTH: 600
<212> TYPE: DNA
<213> ORGANISM: Drosophila

<400> SEQUENCE: 210

| | | | | | |
|---|---|---|---|---|---|
| ccgtgcacgc | catccaggaa | ttcgaggtgg | gcactcacct | gaagttgtac | agcaaaaagg | 60 |
| attactatca | gggcaacaac | tcggacatcg | tggccaccga | ttcgcagaag | aacaccgtct | 120 |
| atttgctggc | gaaaaagcat | ggcatcgaaa | gtcccgagaa | gtttgccctg | ctcctggcca | 180 |
| agcactttat | taacaaatac | tcacatgtgg | aggaggcgca | cgttcatgtg | gaggcgtatc | 240 |
| cctggcagcg | agtttgccag | gaggagacca | ggaccaacgt | caatgggaag | tgcgagaacg | 300 |
| gagtccaagg | gaactgcgac | ttcagctcca | ttgacaacag | atcactgcac | aatcacgctt | 360 |
| ttatattcac | gcccaccgct | cttcactact | gcgatgtggt | tataaggaga | acaggttaag | 420 |
| tcaaacatta | cttaagcaat | aatatttaaa | actatttaat | catcaccttc | tttaatgttt | 480 |
| tagatcccaa | acaaacggtc | atcacgggca | tcaagggtct | ccgggtgctg | aagacgaccc | 540 |
| aatcctcatt | cgtgaacttc | gtgaacgatg | agttcagatc | tctgccagat | cagtatgatc | 600 |

<210> SEQ ID NO 211
<211> LENGTH: 600
<212> TYPE: DNA
<213> ORGANISM: Drosophila

<400> SEQUENCE: 211

| | | | | | |
|---|---|---|---|---|---|
| atcgctggaa | tagtttaaac | gtaaactgta | tataaaaaaa | aaaatgctcg | tcaagttgtg | 60 |
| cgctatcctt | ttggcccttg | gccttagtca | ggccattgcg | tatccgcccc | tgcaacttag | 120 |
| taatccgcac | cagaacctag | tgcagttcct | gatacaatca | cgtgatctcg | gcaacgatgg | 180 |
| tggacatacc | cttgaatgct | tggattatta | tcttcccctg | ctgaacgacg | ttgtggagac | 240 |
| ctacaaggct | gatttaaatg | cgtgtttgga | aacagctagt | caggaggtct | cacagatcaa | 300 |
| cgacaatacc | aaggaagaac | gagatgccat | cgatgcctca | gccaagagct | cctgcgatgc | 360 |
| cctcaccgca | tgtagtacaa | aggaagcggc | catagattac | ttccagtgct | acagtgaagc | 420 |
| cggctccaac | aacaccaaaa | ccatgttcac | catctccgct | aacgcttcgg | agctgctggc | 480 |
| tgctgtggag | gaggaagtgc | gtctcatcaa | ggtgaatgaa | gaggtgtgca | ccaacaagac | 540 |
| ccagagggcc | tatggagaga | gctacggtca | gctgtacgcg | gatttgggtg | attgcattgc | 600 |

<210> SEQ ID NO 212
<211> LENGTH: 550
<212> TYPE: DNA
<213> ORGANISM: Drosophila

<400> SEQUENCE: 212

| | | | | | |
|---|---|---|---|---|---|
| gaacacatcg | ggaaactttt | cgttgtctag | tgtctttgca | aaattattct | ttagtcgttt | 60 |
| cggcagtgtc | aagtctactc | aatcgtttct | cccagctccg | agcaaacaaa | attatttcca | 120 |
| ttgacaattt | tccagttttc | gtcagctcca | catcgccgtg | tcggtttgtt | tgatttcaag | 180 |
| tttctggagg | ttattgtccc | ataatcagcc | atgtccggtg | attgcaacac | gtattgccaa | 240 |
| aatgctgcg | atccctgcca | ggcgcccacg | gatttctcgc | cctgtccgcc | gaattcaacg | 300 |
| tgtccgcctt | gcgactgcgg | cgactatgca | ggatgctgct | accagcagcc | gccgcgcacc | 360 |
| atgcccatcc | tgcccaagtc | gcacttcatg | cgcttccacag | cgccgctgga | cacggacacc | 420 |
| atataccgac | gatcgttcta | tgctaactgt | ggcgacaaca | ttagggcccg | acccgtaatg | 480 |

```
ccgtgctccc aaatacgagc atccacggcg ccgctggaaa agtgcaccat acagaagtta    540
tcctacatgc                                                         550
```

<210> SEQ ID NO 213
<211> LENGTH: 181
<212> TYPE: DNA
<213> ORGANISM: Drosophila

<400> SEQUENCE: 213

```
ttgttgtttc aactattttc ctgtatttgt ttttattgtt cgctgctggt gctggtgttg     60
gttttgggta tgttagacaa caaagtttta atggtattag caagccaaat ataacacaca    120
caaaatgtta ccaacaacaa tgttgaattt gaagcgagaa gagtaacaca cacagtaata    180
t                                                                   181
```

SEQ ID NO 21
<211> LENGTH: 563
<212> TYPE: DNA
<213> ORGANISM: Drosophila

<400> SEQUENCE: 214

```
tcatcagctc cagaaactcg aggcgctgga ggatcagttt cccgagaata ccctggatgc     60
accttatcat ctgcgatacc ccttcaccga catctccatc aagccgaatg gtgtgggctc    120
ggagttggag ttcttcaagc atcgcatcca tctggagcgg gattcggtgc gtcgggccaa    180
ggaatcgcta aggacacagc gcacaaattt ccgccttaga cagcgggaga tcggccagca    240
gcggaagata accgccctat cgccgaaaca ttccattgat cagctaatcc aggaggagaa    300
ggaactgacc gagatggagg tgaatctcca tcgcactcgt tccctgctgg gcgagaaaat    360
aatacgactg cgacatttgg aacagagtct gctgaggatc tacgagaagg agaaatcgat    420
cctggacctg gcaccatgg acgatgcggc cacacttagc gatctatcgt cgcactccag    480
ttctggcttc agtagcaccg atttggccag tgccgcggat ttccacaaga agaaggacta    540
ctaccagcag gagtcgaacg agt                                           563
```

<210> SEQ ID NO 215
<211> LENGTH: 620
<212> TYPE: DNA
<213> ORGANISM: Drosophila

<400> SEQUENCE: 215

```
ttcacactgc actttacgca tagccggtcg tcccagaaat ttgaagagcc aaacagttga     60
taatggcaca ttcaatgctg aaactgggga tgatgtgtgg aatactccac ctgctgacct    120
ttggagtcat tgccgaggat cagctgaaaa acaaacacaa agtggtacat actcctctcc    180
agaactacga tcaacccaat ctccaggact acgaggaatg ccaggtgaac agggacaatt    240
gcatcaatgt ttgcgctggc aaacagtcgt gcgaggacga gtgtcctgtg tgcccggacc    300
tgtacgtcaa gcccctgatg gttcagggca ttaacgatac gaatatagtg gcaccacccc    360
aggtacctat taatacgacc aacattattc ggctgaccaa cgatatcaac aatataatcg    420
aacatcaaat ccaaaatcgc aatgaggtca atgtccaggt gaatcagaat gtctcgaagg    480
tgggaggacg ttttggactg ggctacactg acaaggatc gtgctgttat gtggtgcgtt    540
tggatcgcga gtgtaagaat gaagatggac gcgactgcag agaaagaagc cgtcagcgga    600
tctgtggcga aaagtgtcag                                               620
```

<210> SEQ ID NO 216
<211> LENGTH: 409
<212> TYPE: DNA
<213> ORGANISM: Drosophila

<400> SEQUENCE: 216

```
attatcccta atccgtaca gggcaacgat gagtcttaag ggtctcaatc tggccaaagg      60
gcaaatgatc aaactttaac agttgctggc acaagaaata gaggacgaaa gccagcagga    120
gcggaatgag ctatcaaacg atgatttcat agccaatgca ctggataaag tgcaagttta    180
tgtggaggct ggtaagccag aggcttttgt ccagctcaaa gaaccgctat tatacaaatt    240
taagattacc tcaaatggag tagctactgg atcttcggaa tcggataagt ttcaacgcgc    300
agacgccaag gaaattgctc gctggaaatc tgaccatgta ataaatttgg attgcatttc    360
agacgaggac tacgagcagt taagccaaat tcaaaccgat gaaaggact                409
```

<210> SEQ ID NO 217
<211> LENGTH: 626
<212> TYPE: DNA
<213> ORGANISM: Drosophila

<400> SEQUENCE: 217

```
atctagtact ccgttgtcat aagatccagt cacacacaag tttccaactc atatatatac     60
acattgtaaa ttaacttagg cctgttaact aaacaagatg gcagaaccag agaacaacg     120
aaaattcgta ttgggacgct gttgtatttt ccactggcgc gggaaggctt caataattat    180
acccttgatc acactgccaa ttcttattta tggctttcag accgacatgg ccgagttcaa    240
gtgcctgtgg cttattgtta ccatggccct gctgtggatc accgaaaccc taccgatata    300
tgtcacggca ttgtttcccc ttgtcttttg ccctctcctt ggtcttgtga atgcctctat    360
agtctgcaaa cagtactta ccgacaccat tgtggtattc cttggtgggc ttattgtggc    420
cttgggaatt gagtacagta atctacacac cagaattgcc ctgagggtca ttcggattgt    480
cggtggaagt cctagacgtt tattcgtagg cttgatgagc gtgagcacgt ttatgggatt    540
gtggatatcc aactcagccg gaacgggcat gatgtgcccc attgtcaaag cgctggtcaa    600
tgaattgggt accaacaaaa tatttt                                         626
```

<210> SEQ ID NO 218
<211> LENGTH: 446
<212> TYPE: DNA
<213> ORGANISM: Drosophila

<400> SEQUENCE: 218

```
ctattatggc tatagaaccg atttctgcag ttccttcttt attatccgac taccttagga     60
ctccgtcttg cccaccgaac ttacagtggg accctactgt taagatttgc ctcccaaact    120
tggattataa tcaatatgtg cctaagggac ttctgaacaa cccgagctta cctgggtcgc    180
cgtaactcgc ctgtggcaac acctggaaga aaacctggag gaagttctgg tggtggcact    240
aaggaaactc ttgaaagaaa gcctgtgcaa cgtcctgttg cgaaacctag tgttagttct    300
ggcggaggct ctgggggaag tactgaagaa aaaccaggag gaagtgctgg cggggctct    360
ggtggaagtc ctaaggataa gcctgtagaa agttctggag caagtcctgg agaaaaacca    420
gcaggtagtc cggagagcat accaga                                          446
```

<210> SEQ ID NO 219
<211> LENGTH: 636
<212> TYPE: DNA

```
<213> ORGANISM: Drosophila

<400> SEQUENCE: 219
cagaaatctt acaaaattac agtcagctac atagtatttg tttaacaatt ttgatttcaa        60
attattgcaa gtaaacgatg cagccccgaa ataaattaag caagtgtttg atctatataa       120
cgccctgtgt gcagcaattg tgtttctatg gcactaggcg acatttactg gccatgcagt       180
ccttgtccgc ccaaaggaat cggaagtctg atgtctccga aaagaaggca gtagagacaa       240
cagtcgaatg ggggcgtggc ccccaagcgg gcgaccgcct ccaacagcc gttagtctgc        300
tccgtcgaaa ttcgacagat ccgcgagga acgaggtgaa accgcattc attcgatacg         360
aaaagtctat gaacgaattg gccaaaagtg cccgaaagct atataaaaat gcccggctaa       420
ggagcttgcc tttgaggaag cccatgatgc gaggaaaaat cggtgactct gatgcaagac       480
ccctaagaac accggtgccc agtgcttggg ccataaccga gcgggaaaat aaatagctgg       540
cataagcaga agagatggtt ttaaggcaag gaaatgcgtg taaatgcgtg taatttact        600
taagtctgta gatatatatc caaatatatt tttcct                                  636

<210> SEQ ID NO 220
<211> LENGTH: 620
<212> TYPE: DNA
<213> ORGANISM: Drosophila

<400> SEQUENCE: 220
cagctttatt cgaaaagcca tttgcaccaa gatttgcaat catcgaactc cctttacaga        60
atgcaaaatt gattgcagcg tatcagcggc aaatttagca acagaaaac agcatgcgaa        120
ggaaaaagaa aagtgtaatg atagcgccaa ggaaccaaat ccgactttag tgccaattgt       180
gccgtgcgaa atgctgttag tgccgcgttg ttgttcgtgt ccatgttgtg attacataat       240
gagacgctgc tgaaagtcaa agtccaagga gaagtcccaa gtgtgtatgt aagccaggcg       300
gcagccatat ctcaacttgc cgccactaac tcagccgaag tagaaggcga agcaaaagcc       360
taaggaccag ccctccatct gcaggataac gaggagcgtg aggagccgca ggaggatgcc       420
cttcggccgc aagtccccgc tggaggcact ggcccttccc ggcgtcatgc tcgcctacaa       480
gtacagccag ttccgccagc gccgccggga ggccgccagc cgacgggtca ccgagcgcga       540
actctcggcg ctgcaccata aaatcgacaa actactgagt aaactggagg aggaaagcga       600
gccggatcct ccaacctccc                                                   620

<210> SEQ ID NO 221
<211> LENGTH: 620
<212> TYPE: DNA
<213> ORGANISM: Drosophila

<400> SEQUENCE: 221
aaaattcgac gttgctgttt tttttggttt aacattctct atatacattt ttttaaaaat        60
atggatataa cggtaccgcc gccggactcg cactggtcgt tgaggtttgt ggacatcgtg       120
aagccttttc caaacatac tttggccaat gccacttata agatcattcg cttcttttac        180
ccaccctttg ccctggaaac cgtcgatgtc acccacgtgg tcagcgatcc cgagctgaat       240
agtttaaacg tggggctgtt tgtggtagtt cccttaattc tggcctgcat cggctatggg       300
gtgtacaaat atgtgcggag tatgcataca gtggctaaac ggacaccatt aaaattgtac       360
gagcttgaac agcgtatgaa agacaagtac ggtccggaat acaagcaggg aatctggaag       420
cgaaaggaca tttctgaccc cctcctatta accactgatc catccgaacc aaaagcaaag       480
```

```
agatgtgaaa gcagcaatgc ccactggctg cgcaaaaccg atagatccga tgattaatta    540
aatcaacact cagttggatc cccactcgga tatgactggg gatcttaaaa tcgagaatcg    600
aggaaagtac cttctcgaat                                                620

<210> SEQ ID NO 222
<211> LENGTH: 607
<212> TYPE: DNA
<213> ORGANISM: Drosophila
<220> FEATURE:
<221> NAME/KEY: misc_feature
<222> LOCATION: (1)...(607)
<223> OTHER INFORMATION: n = A,T,C or G

<400> SEQUENCE: 222
tcagcgttgt ggtggcaagt ttgcgccctt cttttgcgcc aatgtcacct gtctgcagta     60
ctattgcgaa cactgttggg ccgtcatcca ttcgcgacct ggacgcgaat atcacaagcc    120
gctggtcaag gagggagccg accggccgcg tgcggtcccc tttcgctggt gttaacggcg    180
gcgctggtag gccgcgctgc acgacgagag acgccaacag agggagcaac gacaccggtt    240
gttaaacgca gcgctggcag tgcccagaat cataacagaa tcatcaggat cgggaggagt    300
cgcagaagga gcgggagtgg cagcactaga tgccgctggc ggagatgcgg atcgaaggcg    360
aagaatctag tagataacca ttagagacaa cacacgcacc accaacaccc actcacacac    420
aacagtcgga tactattctc ataagcaaaa gacaattgcc cggtggaatc acccattccg    480
aagggcaagg tgcaaataca acgggagctg acaaaggtg tcccttgaa tagccaccag    540 agtctacagt tttagaggcg agaaacgaaa gcaacatnag ttttagttct tatttattcg    600
gcaatca                                                              607

<210> SEQ ID NO 223
<211> LENGTH: 500
<212> TYPE: DNA
<213> ORGANISM: Drosophila

<400> SEQUENCE: 223
gccgagggcg ccgttctggc cgtttggcga tattgtgaca tgaactccaa gaggaagcca     60
ccacacatcc ccaaactgga gctgtacgaa tctccggact atgaaggttg gacccggggt    120
gtcttcaagg cggaggctca gaatttagct cgcaggatgt gtgatacacc tgcctgttgc    180
atgacaccaa cgcttttttgc ccaggccacg gtagatgcgc tgtgcccctg tggcattacc    240
gtcgaaatcc gcaccatgga gtggattgaa cagcagcgtc ttcattcgtt cctcatgatt    300
gccaagggca gctgtgagcc accggttctg atggagatca cctattgcgg caccaatccc    360
gaggacaaac ccatttttgtt cctgggcaag ggcattacct tcaactcggg cgccatgaat    420
ctgaggaaat gcagggggaat ggaggagtac agggcttgca tgtcgggagc tgcatcctgt    480
gtggccatga tgcgttgcgt                                                500

<210> SEQ ID NO 224
<211> LENGTH: 562
<212> TYPE: DNA
<213> ORGANISM: Drosophila

<400> SEQUENCE: 224
caacaacgat cacttcaggc tgtacgagaa aattatatgt gcgaggattt cgaaactgga     60
tcaagcaaaa aggacgaaaa ccaaacaaga gcaaaatatt ctaggctaat caaaagcaca    120
```

```
gtgaggggca aggagcattc tatcgaaaat gccttcggaa cagcatacga atataaaagt    180
ggcggttcgc gtacggccgt ataatgtccg tgaattggag caaaaacagc ggagtattat    240
caaggtcatg gatcgttcgg cactgctgtt cgatcccgac gaggaggacg atgagttctt    300
ctttcagggc gccaagcaac cgtaccgcga catcaccaag cggatgaaca aaaagttgac    360
catggaattc gacagggtat tcgatataga caattccaac caggatctgt tcgaggagtg    420
cacggcgccg ctggtcgacg cggtgttaaa tggatacaac tgctcggtat ttgtatatgg    480
agccactggc gccggaaaaa cattcacaat gctgggcagc gaggctcatc cgggtctgac    540
ctatcttacc atgcaagatc tc                                             562

<210> SEQ ID NO 225
<211> LENGTH: 900
<212> TYPE: DNA
<213> ORGANISM: Drosophila

<400> SEQUENCE: 225
gctgccggcg ctttacagta ctggattatt tgcaaccggc ttattattgc acaaaaatct     60
agtgaaatgt cctcgccagc ccccaaatcg ccagagcttt cggataaaag caagaaatac    120
gacagacaaa tcaggctgtg gggagagcat ggacagacgc tattggaggc agccacagta    180
tgtttggtga atgttacggc cgtcggctgt gaaactgcca agggactggt gctacccggt    240
atcggaggct tcactgtggc cgatggcagc accgtcaagg aggaggatct gggcaacaat    300
ttcttcctcg attccagcta tctgggcaaa tctaaagcat tggcttgcat gcaacttctc    360
caggaactca atcccgacgt aaatggcgat tatgtcgacg agagtgccga cttttttatta   420 gccaacagac cgaacttctt cgacagcttc gatttagtga ttgcctccaa tctcaatgag    480
cagactttgc ttctcctggc cgaacggtta tgggagctta acgttccatt aatctactgc    540
cgatcgcttg gcatgcttgg cacaatgctt gcaaatacgg gaacactgca tcgtggaggc    600
gcatccggat aatcgacagt ttgatctgcg tctggagcat ccattcgatg ctttgcggga    660
gcatctcgac ggcaccgagg tgaccagtaa ggtgccctgg ttgctggttc ttcacaaata    720
ccttaatgtg tggcaaaaac aacaagcgga tgggactcaa acgcctcgaa attacaaaga    780
gaagaatcag ttgaaggaga ccattagaga ggagatgaag gcggatgagg aaaactatga    840
agaggccatc aaggcggtca atacagcctt tggagcggga caggttccca aaagcctgaa    900

<210> SEQ ID NO 226
<211> LENGTH: 550
<212> TYPE: DNA
<213> ORGANISM: Drosophila

<400> SEQUENCE: 226
catagacttc aattccaaat atcacatcga tgtggacttc gaggtgccca agaagctgca     60
gtggtattac gcccctgctt tctttggctt ttggcttgtg ctctatctct cgctggtcaa    120
cacccaaatg aaccacatgc gcgcccact gacccgcagc gatgaagcca gtcatcccaa     180
ttcctttatt gcccagcgag ccgaggacac cctgattgag ctgaccagga ttggaccgcg    240
ggtggtgggc agcatggcca acgaggagag cgccgtggag ttcctgcgcg ccgaggtagc    300
caaagtggag tccgaaatga cgaccttct ggagatcgaa gtggatgtgc agcaggccag    360
tggagcctac atgcactggg agatggtcaa catgtatcag ggcattcaga atgtggtggt    420
gaaactctcc gaaagaact cgaccaacga gaattacctg ctgatcaata gtcactacga    480
ttcggtgccc ggaagtccag gagctggcga tgatggttcc atggtcgtta ccatgttgga    540
```

```
ggtgatgcgt                                                           550

<210> SEQ ID NO 227
<211> LENGTH: 977
<212> TYPE: DNA
<213> ORGANISM: Drosophila

<400> SEQUENCE: 227
agacatatac catttcaagg agttttttttt agtaaaataa aacgagaaaa ctaacaaaaa    60
aaggttcgtt tatcgcattg aatcaataaa aaacaatggt gtacaccggt tacgtaagca   120
acggattgca gaatgctgag gaaactgcat gggtgccgta tggagatccc aatgactggt   180
cacatggtct ggcagtttat gatggtttgg aactgatgag cggcaatgag gaggagttgc   240
agccctcatt gaaccgggtg atgaaaaaca tcgactacga cctggccatg aagcatccat   300
tggagcatac ctggactttg tggcacttgg agaacgatcg taccaagcgc tgggccgaaa   360
tgctcgtcga tgtgaccagc ttcaacaccg ttgaggactt cttcagtgtg tactactttg   420
tgaagccgcc atcggatctg aagatattca atgactacat ggtcttcaag aaaaatattc   480
gtcccatgtg ggaggatgac accaataaga acggtggtcg ttggatactg ctcctggaca   540
aggcctccag gacctatata gataagatgt ggcacgattt gcttttgtgc atgattggcg   600
agtgcttcca gcactcggac gagatatgtg gagtggtcat caatgtgcgc aacaaggcta   660
ataagctatc cctttggacg aaggactctc gcaatgtaga ggctatcctg tccattggca   720
ggcagataaa ggagctgctg catctgggca ttatggaaat ccagtaccag gtgcacaagg   780
atgccatggt gaaccatgga cccaatgtca atgccattta cacattgtag gccaatttcc   840
aagggcgcca tagtacattt ccaacgatag tacataagcc ttatacattt gtcaaactca   900
cattttatcc cacgcgcacc aatgcttttc gagatagata tcggttgtac catgaataaa   960
gtattgcgta gagcagt                                                   977

<210> SEQ ID NO 228
<211> LENGTH: 497
<212> TYPE: DNA
<213> ORGANISM: Drosophila

<400> SEQUENCE: 228
tacagattgt attttcgaat tcttttaagc aaaatttcag tgttcagaaa aagtaaaaaa    60
aaagtaaaac catcggcact ctcattcttc agaatcgttt ggttgttagg tcttaggatt   120
aatagcttgc gcattgattg ttggctgaag cacagatgtc tgttcgcaac tcacgccccc   180
agttatcgtg gccggagcgg gtaagtccgc aaaggactat tgacactcca acggcatccg   240
gagaaatgtt gactcgtcgt caatcggcac cagcgttggt cgtgccgccg gaggagacca   300
cgcacgttgt ggtggtcaag cggcaatccc cggacgcagc cgctgccgga gaactggtgc   360
cgtctaggcg gaaggactcg gtggctgtgc agtcgggaat tgtggccact gggccattgg   420
acacaacacg cagtggtgca agagacgatt ttctaatggc tttgctcgag tgcccggtgt   480
gctttggcta cataatg                                                   497

<210> SEQ ID NO 229
<211> LENGTH: 700
<212> TYPE: DNA
<213> ORGANISM: Drosophila

<400> SEQUENCE: 229
```

```
aagtgccatc tctagccgac gggtgggata gaatctccaa ttgggatttc catccagtga    60 ttttcctaatt aaattaattt tttccaattg cccaaaggca taggcatatt tcgcaaaacg   120
aacaaatatg tttgcttgaa gcgcatagaa tcacaaacaa aagtgcaaat ctcagagctt   180
aaaaaccaga gcaaaggaga ataacggaag aggaggcaag caaaaagaca aagaggagtg   240
caaaaaatac agcaaacatc atgcacagga catatgtaag ccatgcgata tacgccattt   300
ggctggttat attcgccact gccggcataa tggcccagct agacctggat cagatccaga   360
cccagctgcc cgaccagctg aggaagtcaa actttagcgt gaacgacgcc aaggagctat   420
ttcgcaacaa atgcatcgag gtggccggcg aggaggcggg cgtcgaggca tacggcgaga   480
tcgagtccgg attcatggtg ctaaccgagt gcctcaatgg cattgtcaac tacacggcaa   540
tgcagcagga gatacaggaa gcgtcgccca agggcgaact ggatgtggtc ttcaacaagt   600
actgcagccg gcgttcgaat gccgtcgagt gtgtggatgc gttcacggcc aaactggtgc   660
cctgtctggt gcaggaggag cgcgagggcc aggatgtcat                          700
```

<210> SEQ ID NO 230
<211> LENGTH: 594
<212> TYPE: DNA
<213> ORGANISM: Drosophila

<400> SEQUENCE: 230

```
atctattggt agaaagtaag aaaaaaaaaa ttctcaaaat ttaagttata tacaaatttg    60
gagtgaaata ttttataaac actttcggag tatctcgagc tttccacaca tcgaaaatga   120
atttttgttc agtgccttac gaagctgact acggcatgta cgccgattcc aagatgaaga   180
gcgttcctca gtacccccta agcatgggag taggtcaggg tcaaggacag tccatggcca   240
tgcagcccct gaatccaccg cagatgaatc tgcagatgca gatgcccgtg tgccagtcgg   300
gcgctttgtc gtacccaatg cagggtatgc cgctgggcat gatgcaaggg ggcaatcaga   360
tgacccccat gtccacgatg tccacccagc tgccgattgg agcggtgact cccctgagca   420
gcatgaccat gatgcccatg atgggcaatc ccatgggcgc catcgatgcc cccgggatca   480
atgcagtgct gcctgacctg cagccgatga cctcgatggg tcagatgcag ccgctgcaac   540
agtacaatcc cagtggatct accacccaaa tgcatcaagg acgtctgacg ggcg          594
```

<210> SEQ ID NO 231
<211> LENGTH: 550
<212> TYPE: DNA
<213> ORGANISM: Drosophila

<400> SEQUENCE: 231

```
ttcagataat cgtagatgtt ttttatcata agcgaataaa aaagttagca ttaattggtt    60
taaagtagtg cgtcaaaatt cggaaatcca cagaatgacc atccaaggac tgaagtgtga   120
cctcagcccg acggtgacca cttgtctgca gctgaaggac tgcgtccgtc cggactgctg   180
tcccatccgg gaccccattc cctacgatgc cgagtgcttc gttagggaca ttggccagga   240
gctggacaaa ctgacgcgcc gacacgagcg catgttcgtc aagcggcggc gtctgatgga   300
aatggccata cccaggcgac gcacctgccg ctttgtgccg aaatgcgcct gctcatttcc   360
caagtccatc gagatggtgc gaccatgtga cgcccagaat cacacacgca ccgagcaact   420
agctctgccc acggtccgtc gattgcttca caggcggcga acggccattc tggcgggcga   480
ctcaattggg gagtccatac tgaacagatg gcttcgctac agctatctat cgctgtacag   540
tcgtctcacg                                                           550
```

<210> SEQ ID NO 232
<211> LENGTH: 492
<212> TYPE: DNA
<213> ORGANISM: Drosophila

<400> SEQUENCE: 232

| | | | | | |
|---|---|---|---|---|---|
| atccagatga | aggtttttgc | tgtcttggtc | ttggcaattg | ccacagtttc | tgctgatatc | 60 |
| ctgcgccagg | acactccagt | acatcccgt | gatagctcag | ctgttccgtc | catagatggt | 120 |
| cgcattacca | atggaaacaa | ggcagctgct | aaccagtttc | cctaccaggt | gggactcagt | 180 |
| tttaaaagct | cggctggcag | ttggtggtgc | ggtggttcaa | taatagcgaa | tacatgggta | 240 |
| ctaactgctg | ctcattgcac | caaaggagcc | tcttccgtga | ccatctacta | tgggtccacc | 300 |
| gttcgcacta | gtgccaaact | gaagaaaaag | gtctccagct | ccaagtttgt | gcagcatgcc | 360 |
| ggctacaatg | cggctacttt | gcgcaacgac | atccctga | tcaagactcc | atccgtcact | 420 |
| tttacggttt | ccataaataa | gattgccctg | cccgccatcg | ccagcagcta | ctccacctac | 480 |
| gccggacaga | ct | | | | | 492 |

<210> SEQ ID NO 233
<211> LENGTH: 461
<212> TYPE: DNA
<213> ORGANISM: Drosophila

<400> SEQUENCE: 233

| | | | | | |
|---|---|---|---|---|---|
| ctacttggag | ttctcggatc | cgccagagta | cctaacttac | cccctggtct | ttccgatcaa | 60 |
| ggactggccc | gccaaacgcg | atccctcctt | catgggcatc | ttcttcagca | agtgccgtgt | 120 |
| aggacgaatt | tatccatcgg | atattgacca | gcggacgccc | ggtgtttact | tccgagtgga | 180 |
| acgtgatctg | atgggacgta | cggaccgatt | cggcgtggag | gtgcgggaac | gcaccatgtg | 240 |
| ggacatccgt | cagggagtcg | tgggcgccga | taccttcatc | cccaagcacg | tggtgatcgc | 300 |
| cacctggaag | aacgtctcct | tcgccggtgg | catcgacaac | tccctctaca | cgacaaacac | 360 |
| cttccaaatg | gtcctggcca | ctgacgaggt | ctacacctat | attattttca | actatgccgg | 420 |
| tctgaactgg | ctttctcata | ctgaggccgg | aggtgatacg | a | | 461 |

<210> SEQ ID NO 234
<211> LENGTH: 583
<212> TYPE: DNA
<213> ORGANISM: Drosophila

<400> SEQUENCE: 234

| | | | | | |
|---|---|---|---|---|---|
| ttcgaagtga | acggtcaatg | ggaaaaatgt | tcgccagcag | aggaatgctg | gtgcttggag | 60 |
| tgcttctggt | atcagcaatt | ggtggccaat | cggaatcgat | cccctgcaaa | ctcatcgatg | 120 |
| cagaacatgg | caaagtgtgc | gtctgcacgg | cggactattg | ggattatctg | gagaatcccg | 180 |
| tcctgacgga | cgaaaatgag | tggttcctta | tctccagttc | caaacaggga | cttcggttct | 240 |
| ccacaactag | tgacaaattc | ggtaaggagg | agaagtttac | cgcgcaggat | tatgtggaac | 300 |
| ccacgcagga | gactgcgaat | gcgacaatcc | tgtctcgttt | gctcgataag | gtggtggaca | 360 |
| gtgcttttac | cttggagtcc | cgggagagtt | ccataactcg | cactgtaacc | ctgcgactgg | 420 |
| acagaagtaa | gacccaccac | aagatggttg | gtttcggtgg | cagctacacc | ggagcagtgg | 480 |
| aatacctggt | tgagaacttc | aagcattcgg | aactggctga | ccatctgtac | aagtgctttt | 540 |
| acgccgagga | tggactgtgc | ttcaatctca | tgcgagtttc | cat | | 583 |

<210> SEQ ID NO 235
<211> LENGTH: 569
<212> TYPE: DNA
<213> ORGANISM: Drosophila

<400> SEQUENCE: 235

| | | | | | |
|---|---|---|---|---|---|
| caccaaacga | aagtcattcg | tatactttac | aatccatttg | atattttgat | attttcacaa | 60 |
| gttagtcggg | agttgtgcaa | taatgaattg | tttggagaag | aaatcgccgg | aggcaaatcc | 120 |
| agagtgtaag | ggcaggacga | ttgagttaaa | tccgggatct | gcttgcccgg | ctccgctaat | 180 |
| ctgtcccctg | ccgacggaac | caccctccca | ccgactgaaa | aagccaccgc | agcccgccct | 240 |
| ggtagccttg | acacctcatc | ccgatgaggc | cgcccaacag | cacctggtcc | aaaatattat | 300 |
| gggttctgcc | caagagcatc | agaagctaca | gcggatctc | caagcgggag | ttgaccaaca | 360 |
| gcagatgcaa | ttggccgata | tgcgagctga | acagtacaag | caatcgaaca | agccactcag | 420 |
| aatggaggaa | gtgcagtttg | cgcgttccat | ggaccccgaa | gcagatgact | tgcggaatcc | 480 |
| accgtgctac | ttgccccaac | agggcgatga | gttgcctcac | aaggaccagc | tgatgcccat | 540 |
| gggtccgatt | ggtccatggg | catcgggca | | | | 569 |

<210> SEQ ID NO 236
<211> LENGTH: 612
<212> TYPE: DNA
<213> ORGANISM: Drosophila

<400> SEQUENCE: 236

| | | | | | |
|---|---|---|---|---|---|
| attttctaga | agtaagcctt | acataatgga | tgtatcccag | tcagatggcc | aacagaaaa | 60 |
| tgaggctggc | ggaatgaaga | acattacaca | tcagttcgag | ttcatgtcta | ataggttgaa | 120 |
| ggagcatatg | aaatacaaca | tcctccgtaa | cgctgtgttt | tacaagaaga | ttcccctgca | 180 |
| gaagaaacta | aaacttgccc | ttgaaagaaa | tatcggtccc | catgcctata | taatagttaa | 240 |
| cgatacaatc | tacaagtgcc | aagtgttcgt | actccgcatc | tactgcaagc | tgtttaccaa | 300 |
| caacctcaag | cgggggtgaca | tagtcaagtt | tcccagggac | gcgatgagca | atgagtgctt | 360 |
| tgaattggcc | tatacctgga | tgactaataa | tgcgatacat | ttgccacgtg | acaagataat | 420 |
| aaatttgctc | gcggccgcaa | aatgtttgca | gtgcattccc | ttgatcaagc | gcatctttga | 480 |
| gtttcttaac | gactaccgaa | cccattgcga | acttttttca | tttagctgct | atttgaaggc | 540 |
| caaagatatg | ggtatgaccc | aggtagccga | catgatggtg | tccagagtga | ccaagtcctt | 600 |
| cctggtacta | gt | | | | | 612 |

<210> SEQ ID NO 237
<211> LENGTH: 505
<212> TYPE: DNA
<213> ORGANISM: Drosophila

<400> SEQUENCE: 237

| | | | | | |
|---|---|---|---|---|---|
| ctcctctttt | gaacccctca | cctcatctaa | caaacattgc | caagtgctc | gtagctaata | 60 |
| gaaaccctg | tcgaaattcg | attcccaact | aacctatcca | cttttggac | gcatccacag | 120 |
| caacaagcag | caccacggat | cccgagacag | aagactccag | gcggggcgcg | gaggatgatt | 180 |
| tgcctgcccc | gccgccactg | acctccggat | cttctattcc | ggtgccggag | tacgtgcccg | 240 |
| agcagtccac | acagctgaca | ccctgtccct | gctgcagtcg | caccttcgcc | gtggacacgc | 300 |
| tgcgcaagca | cgtcgtcatc | tgcgagaagg | cctccaagaa | gcgcaagatc | ttcgactcgt | 360 |
| cgcgccaacg | ccgcgatgga | accgctctct | ccacgtacgt | gctgcccaag | aactttggcc | 420 |

```
ttcccaatgc ggaacgcacg gcgggattac catctcctcc gatcaacagt cgcgagacca    480
cgtcagtaaa tgctgctccc gagac                                          505
```

<210> SEQ ID NO 238
<211> LENGTH: 649
<212> TYPE: DNA
<213> ORGANISM: Drosophila

<400> SEQUENCE: 238

```
tagcctgaaa tatagttgcc aagcttgggt tgtcgatttt cttcattcgg tcgagcttag     60
cctagcagtg ctcaacctgt ctaaaagcta agctacaaa tatatttata acttgtgaaa    120
aagtgtgaga tccagtgata gtccgtccat aaagtgcctt caagccacat agtgaaaatg    180
tcgatctttg accatcccga acagctgaaa atgctgcagg gccttctgaa tcccaatcag    240
agaagaggcg gcattgacta cagcagtagc gaggatgagg aggagtcaat ggttgtcaat    300
aagatgaacc ctggaacaat tggacgtcct aatggggagg atggaaccgc taagggtaag    360
aagaaaaaga agcccaaccc tttgtgcact cccttggtgg aggaagagaa aaaacagccc    420
gagagtctgg aagaatggca agatcagcag agaaggaag acatggatat acttgaatcg    480
cggaagactc ccgagtatac gatgacctat cgccaagcag tgggcactga ggatgtcttc    540
ttgcagatgg gcaatcgcac tggatcctcg gccagctgtg aggacctcat tttggaggtt    600
tccctgccgg acgaggaaat gactgctgac aaaatgtcgc tcagcttgc                649
```

<210> SEQ ID NO 239
<211> LENGTH: 599
<212> TYPE: DNA
<213> ORGANISM: Drosophila

<400> SEQUENCE: 239

```
aaacatttaa cgataataag cataagaatg agctctcttg ttgataccag tcactcggat     60
atcgatgaca atgactcctt ccactcgttc gaccaaagcg aagatatcat ggacaacctt    120
agcctctcgc tctcggagag cgactgcgac agcgccgcgg actttgattc cggctcggcg    180
gatgagattt ccatggaaaa aaaatgggt ggtgcacccg cccagctggg ccagggcgca    240
ggaaatactt tgaagcccac gccttccgac gtcttcgtaa agccaaagtc gcccgttttg    300
gaggtccatt ccagcgactc atacacctgc gatgcgtct ccgctggcaa gcccacacag    360
gttgcgggct gtttcaagtc tcccaagaag tttaccgttt cgccgatcag tgagcaaaag    420
cagagaccac tgcccttgtg tcccagagat gttccgggac tttcctcgag ccagatacca    480
tgcataaaac actttgacct tgaccactca gtaacagtcc gaaaagagca cctgatctcc    540
aatcccgaaa cggaggcctt acaataacac cgccttcacc gaaatttgga tcgattcgc    599
```

<210> SEQ ID NO 240
<211> LENGTH: 525
<212> TYPE: DNA
<213> ORGANISM: Drosophila

<400> SEQUENCE: 240

```
agtagtcggt attttgttgg tgatctcctt agttggacac gagacaaacg caaaaagtgt     60
ggccaacacc ttggccaacc aaatcggtca ggatgcttcc gatttcggta atgaattagg    120
ccaagaggtc atccaatatg gccaagaagc tgccaacagc ggcttgaagt acggagaagc    180
agcggaaaat gcctcctccg gttgggaact tggaatggat ggcagcattt ttggtcacga    240
```

| | |
|---|---|
| attgggagat gagggcaatt tgttgggaca ggaggtttcc aatagcgcta ttaactttgg | 300 |
| acatcaagtg tcccaggaag cggaagaggc agccagtgca gaactcaaag ccatggcaag | 360 |
| ccaatctgcc aatcaatcca gtaagaaatc tgtcagtaag cgtgatttaa caagtagcaa | 420 |
| cgagaatcct tcggttacct gtgcttgcac ctgttccacc gatggcgctg cttccaaagt | 480 |
| gggaaataag gtagcagagt cggccggaaa ggcagctcat gatgt | 525 |

<210> SEQ ID NO 241
<211> LENGTH: 372
<212> TYPE: DNA
<213> ORGANISM: Drosophila

<400> SEQUENCE: 241

| | |
|---|---|
| acatccggag cggactcctc tgggaacaaa ccgccaatag aagggtactc gaagcgattg | 60 |
| tgaaagagct tgtgaccaat tcgtgaggtg tgcgtttcga cggactcgga ggtcactgca | 120 |
| tacacgacat agtcgttgat atggacctgg ataacaggtg ccgtgaagct gtagctggcc | 180 |
| actggctttt cgttctcact gtaccacttt ccttgcgcag agaactggta cagaaagccg | 240 |
| tccacactgc tggccacgag gagggcgtgt cctatgcacc tctggtgctg agaagactta | 300 |
| agcgtccggc ggtttacgtg cttaaacgtg gtcacagcac tgggcacctg gtggttgccc | 360 |
| atgtcatact ca | 372 |

<210> SEQ ID NO 242
<211> LENGTH: 550
<212> TYPE: DNA
<213> ORGANISM: Drosophila

<400> SEQUENCE: 242

| | |
|---|---|
| gtatagcgga acgcaacaaa gcccggacaa cccgaccact gtcttttttac cgcattcgcc | 60 |
| aaataatcag tcagccagcg gagagaaacc tggcggtgcc acatcaaaat caccaaacgc | 120 |
| agccaaaact tcgccaacaa tgacggacta cctgtcgctg cactcgcgac tcgcccaggt | 180 |
| gggccaggag cacctgctca gttctggcc ggaactaacg aatgacgaac gcatcgacct | 240 |
| ggtgcgggac atcgaggagc tgaatctgga cgagatcaag ctgtatttcg accgcgccac | 300 |
| ggtctcaatg aacgagaatg gcatcaagct ggacgatcgc ctgcagccgc tgcccgaggg | 360 |
| caagctaatc tccattgcca gggcgccgct ggagaaattg gacgcctacc gagacgaggg | 420 |
| tctcctccag atcagcaacg gacatgtcgc tgtgctgctt atggcaggcg gacaaggcac | 480 |
| acgacttggc ttcgatcatc ccaagggaat gtacgatgtg ggactgcagt ctcgaaagac | 540 |
| cctgttccgc | 550 |

<210> SEQ ID NO 243
<211> LENGTH: 720
<212> TYPE: DNA
<213> ORGANISM: Drosophila

<400> SEQUENCE: 243

| | |
|---|---|
| agaaaaaata aattatttat ttgaaattta aagtcaactt gtcatttaat gtcttgtaga | 60 |
| cttttgaaag tcttacgata cattagtatc tatatacatg gttcattcta cattctatat | 120 |
| tagtgatgat ttctttagct agtaatacat tttaattata ttcggctttg atgattttct | 180 |
| gatttttttcc gaacggattt tcgtagaccc tttcgatctc ataatggctc attttattgc | 240 |
| gatgacggt caggagagct cattttgaat ttctgttcgc agacaccgca tttgtagcac | 300 |
| atagccggga catccggttt ggggagattt tcagtctctg ttgcaattgg ttttcgggaa | 360 |

```
tgcgttgcag gcgcatacgc tctatatcct ccgaacggcg ctggttgacc ctagcattta    420
cataaggatc agcagcaaaa tttgcctcta cttcattgcc cggaatcaca gcaatcagat    480 gtcccttcg gttacgatgg atattcaggt gcgaaccgca caacaaagct ctcgccgcac    540
actccacact gatatggtcg ctcgcccgtg tggcgccgca tatggatctt aaggtcgttg    600
gactgcacaa agctcttgct gcacattttg caggagtacg gcctttgacc cgtgtgcaat    660
cgcacttgtg tccacttgtg tcgcgccagc ttgttctgcg aaataaactt cttggagcag    720

<210> SEQ ID NO 244
<211> LENGTH: 478
<212> TYPE: DNA
<213> ORGANISM: Drosophila

<400> SEQUENCE: 244
gatttatgag ttggccaccc tgaagaagcg acgtcacttg gagctgccga gcaaccatcg     60
caatgcggag atacagcaga tgatctttac caatgactcc agatcggtgg ccctgatcac    120
ccgcccgccg gaggaaaccc ttattatgtt ggtgctggac aagaccagta cagtgatcga    180
gggcagggcc acaatcccgg gatctcatgg aggcgccgag tgcatcgctg caatccaaa     240 cgattgcaat tttatggcgg tcggaggcga gcgcacgttg ttgctgatga gtaaatcgga    300
gcgaggattt agtatcagca ataatctgaa ggtgaaatat agggtcaccct cgatggcttt    360 tctatcgctg gacctgctga tgattggtac gtcggatgat cagttgatcc tggtggagaa    420
cggcgagcag aagttggctc aaaaggcgag cgatgcggac actgtggact tgatgatc      478

<210> SEQ ID NO 245
<211> LENGTH: 600
<212> TYPE: DNA
<213> ORGANISM: Drosophila

<400> SEQUENCE: 245
tcggcagaaa aatatttctg gaataacaaa aacagacaaa attacccgta tccgaaccga     60
gtcgttattc caacaccaaa catgaactgg cacaagggca acattgcgga ggccgtggcg    120
gcatcaaagg ccaagggcgc cgtgtttgtc gtcttcatcg agggccagga cgaaatgacc    180
cgaaaactag agcggttcgt ggatgacagt caggtgcgct cccgcctgga aacctccgat    240
tttgtcgcca tcaaagtcca gggaaatagc tccgcctacg acagttcat gtcgttatac     300 aaaatcgtgc caattccctc gctcttcttt attggcaaaa cgggtacacc tctggagata    360
gccactgggg ttacggccag cgtagatgaa ctgacggaaa agatcgataa ggttctgatc    420
ctggcgggaa aacgaaccga gcctgtggca gccagcagct cttcatgtgc gaagacactt    480
gaccccaatg aagtcaggag cttcgccgga gcagatggct caagcagcac tggggaatct    540
caagtagttc aaacagcatc agaaaacttt agagatcctg aaaccacctc agtttcaaac    600

<210> SEQ ID NO 246
<211> LENGTH: 546
<212> TYPE: DNA
<213> ORGANISM: Drosophila

<400> SEQUENCE: 246
tcaaggcggt agagctgcag tccaccagtc ccacgccacc taaaggatac aggccagcgg     60
aagctcaaca caagaagcg aaatggaggc gtcagcaagt ataaatttgc agccggtggt    120
gaacgttcct acgatttata aggatccctg gtacatgatc acagtgctgg tcctctatct    180
```

```
gtacttcgtc accaaagcgg gtccgcattt catggaatgg cgcaaacctt acgagctcaa    240
gcgacttatc ttgctacata atttcatcca ggtggtttcc tgcatatatg ctatcaaaga    300
ggtcctgtac attacggaca acaccatata catcttttgg aagtgccgcg acatcgggag    360
cagcccagag ctcgtgaggc ggtactacaa cttggcctac tttctcttct ggctgaagat    420
ctctgagctg attgaaaccg tgatctttgt gcttcgcaag aaacaaaacc aggtgtccaa    480
gctgcacatc tttcatcact tctccacggt aacgctggtc tacgcactga tcaacttcaa    540
cgaaaa                                                               546

<210> SEQ ID NO 247
<211> LENGTH: 608
<212> TYPE: DNA
<213> ORGANISM: Drosophila

<400> SEQUENCE: 247
gcaccacata gtgtttaaga tctattggca aatttcaaac gtattttcct tacctttcgc     60
gagttttttc ggtctagatt tgtagttttg taaatacgat aaccgtttac tttaatcgaa    120
gttgttcgtt tttggcgaga taaactgaat tcaattggat tgatcgccac ccacgcccaa    180
ccacatccac tgacgcctcc tggcgacatt tactggcctg cctctgctgc tgttgctgct    240
gccgacgacg atttgtttgt tttgtgccaa ctttgatgac tcaccggaga gactcagact    300
ggaactgaat ctgagactga gtctgagccg ggtctgcggc agctaaacaa gctcagtcgc    360
gtcatcacct tgaccaaagc ccacacacga gctctgcagc aatcgcatcg aattcaaacg    420
actgccatcg catcgaacag actccatttg gcaatggcgt cacaaggttc cggagatatg    480
aagacctcaa ggctggcgca aatgcagatg cgtttccagc agcgcacgca acaggagcag    540
gaggtgcgta tgcgggagct gatgagcacg aagtcaagtg ccgagaacct ggccactgga    600
gcacccag                                                             608

<210> SEQ ID NO 248
<211> LENGTH: 641
<212> TYPE: DNA
<213> ORGANISM: Drosophila

<400> SEQUENCE: 248
cataaatata caggtactgg tctgaaacat ttattacaaa aaattcaaaa aacaaaaata     60
tagcgaagaa ggataaagac catgtacaac aatattaagg gcctacacat aaatgaatac    120
cagagggaga atggagataa taccagaaag ctggcgtgtg aaggtacagt gaagctaaac    180
gccaatgccc aagaatttgt gccacgttac aagagggaac aaccagcaaa agatgatgct    240
atagttggta acagtaacat gagcaacacc aataacgacg accaaaaacc aaaatctaac    300
cttatgttgc cgtggaaagg atttccgaat aaatctcaaa aaccttctcg caatgtggac    360
tacatagttc taccgagcac caaaagattt aaaaagccca ttggccaaca actcgtggaa    420
aatgtttcca ctacgccctc aaaagtccat ttaaatgatc ctgttccagc tggaaatcgc    480
attgatcacg aggaaaggcg ccgcgaacac gatagaaaaa tcgctgtgga agccttaaag    540
ttggccgaac agcgtagaat gagggatcct gtcattgccc ccacggaggg caatgaaaac    600
tcaaagaacg tgccgccaat tataaatatc tcacgatctc c                        641

<210> SEQ ID NO 249
<211> LENGTH: 590
<212> TYPE: DNA
<213> ORGANISM: Drosophila
```

-continued

<400> SEQUENCE: 249

```
attgacaagc aaaatcactc acaacgcttt tgttagcagt tgaaatcaac tgtgtgaaat      60
atttttttg aaaataaatt tttttttaga aattttaaga ccaaagacaa aattgaaaaa     120
tgtgttcacg cgatacggcg tcaaatcaat tgattgacta taagaacaat gactccgagg    180
tgcaaaggga gatcacgaca tccagtggaa ctccagttgg cgtcaaggat gccatacaga    240
cggtgggacc aagggtcct gccctgctgc aggatttcca gttcctcgac gaggtgatgc     300
acttcgactc ggagcggatt cccgaacggg tggcctacgc caagggagcc ggcgcctttg    360
gttacttcga gtgcacccat gacatttcaa aattctgtgc agcctccata ttcgataagg    420
ttagaaaacg aactgccgtc gcgatgagat tctcggtggc ctgcggtgaa cagggatctg    480
cggatacggt acgtgaacag cgcggatttg ccgtcaaatt ctacaccgac gacggcatct    540
gggacattgt gggttgcaac atgcccgtgc attatgtccg ggatcccatg              590
```

<210> SEQ ID NO 250
<211> LENGTH: 644
<212> TYPE: DNA
<213> ORGANISM: Drosophila

<400> SEQUENCE: 250

```
ctcacaagac tgccgagcac caaattgggg atcctcccca aaaagaggcg gcagctgatt     60
tcgaggcagc catcgatgcc gctggctttg gaatgttcaa catcctcctg ctggtggccg    120
ccgtgccagc ggccatgggc accgtctacg agacctccac gatgtcctac atcctgccca    180
gcgccgagtg tgatcttaag ctgagcctcc tggacaaggg catcctgaat gccattacct    240
atgcgggcat gatcagttcg gcggtgcttt ggggctactt ggccgacatc aagggcagaa    300
gaaacctcct gattgtgggc tatgccgccg atacgatatg cgttttgggc ggagcactca    360
gtcaaagtag gatccaactg atggttttta aataccttgg aggcttttgt atgagtggcc    420
cctttgccgt tcttatgacc tatttgacgg aactccatgg acggaagcat cgacagcgta    480
tcatgatgat ggtgggcatc atgttctcaa ttgcaacgct aacgctaccg ggactggcca    540
tgctgatatt gcccgagacg tggaacattc agatctggac tttgtcgttg acatcctggc    600
agttttctgt cgccgtcacc gcacttccca gtcttctgag cttt                    644
```

<210> SEQ ID NO 251
<211> LENGTH: 375
<212> TYPE: DNA
<213> ORGANISM: Drosophila

<400> SEQUENCE: 251

```
ctcacacaga attataatca caaaaaaaaa aaaaccgaca ttttcttaaa aattcctaaa     60
tggagaacaa caattgcgag ggcgagcaac catcgacatc cggtgcattc tgtaggtgct    120
ccgagtctgg cattggtata tctgccgtcc tggatctcgc tcagtcggag tactccctgg    180
acaccacgcc ggaagctgtg atggcgagtg catgtcgtct ggagaacgag aacgatggta    240
atgataccga tgaggatgtg gagatctgct tcaccagctt gatgcccgat caccgtaagc    300
gcttgtatat ggactgcaag ctgtctcttc cggcgggcgg aagagtgccc atgcgcggcg    360
gcgcagaagc cattt                                                    375
```

<210> SEQ ID NO 252
<211> LENGTH: 524
<212> TYPE: DNA

<213> ORGANISM: Drosophila

<400> SEQUENCE: 252

```
cagccactat agtgaaagct tcgatctgtg ttgaatgggt ctgcgatctg gtgtctgggg    60
tttgggggat ctgcccactt tgctgctcac ttcggtcgct ccggctgctt tcactcgacc   120
caattccagg ggcaatcttc taaccagttt agaagtgtcc actttggagc gagtcacgat   180
ttcctggact ggaaaaacac gcgcccctcg agaaaaacgg ggcagtgatc tcagcgatgt   240
gtccatcatc aagcgaatgc gtggagtgga agttctggct cttagtgtca acaagatcag   300
cacgctgtcg accttcgagg attgcaccaa actgcaggca ctatatttgc gcaagaacag   360
catctctgac atcaacgaga tcgcctacct acaaaatctt ccgagtctca ggaatctctg   420
gctggaggaa aatccctgct gcgaacgagc gggtcccaac tatcgttcga tcgtattacg   480
cgccctgccg aacctcaaga aactcgacaa tgttgaggtc acac                    524
```

<210> SEQ ID NO 253
<211> LENGTH: 598
<212> TYPE: DNA
<213> ORGANISM: Drosophila

<400> SEQUENCE: 253

```
ttcgacccat cccctccaaa tccaatcagt caaacatttc ttaccacaca cgtacaaccc    60
gaacccccgct tagtcatttc aaattcaagt atatagacta cattgatttt ggaagagtta   120
gccacaatgt tcatccgcgg agatgcgcca caagcttccc ggggcaaaat tccccagatc   180
cccagctcca tgacgcccta tgtggcggca gtgaagcgcg gaccctacac aatgaccaat   240
ccggtgtaca acacccacaa tcccaacctg gtgggcttgg atggccaggt ggaggattcc   300
cggcccaagc acacctttaa tgtgaagagg caagagctgg agaataacta ccggcaccac   360
cagcggctga tccccgtgcc cacttccgg aggacgatgc ccaagatccg atcccacata   420
gtgatgaacg agcagcggga gctgtatcgc cagcaccgcg atcgaatgtc caacatcaag   480
ggcaaggtca acacctatct gccgcccccg aaggtgcaga tcgagggaaa tggcatggag   540
ctctcctaca tggagatgct gaccgcactc tacaagaaga gcaacaacac gctgcgga    598
```

<210> SEQ ID NO 254
<211> LENGTH: 600
<212> TYPE: DNA
<213> ORGANISM: Drosophila

<400> SEQUENCE: 254

```
cttttcgagt atgataggtg tatttcgttt tgtgcctcca aaatttcaga tattattcag    60
ctacacacag acaggcctcc caaatttgta agctctgtaa attcaaaacc agaactgctg   120
caggccagtg gcgaagttaa tttgtcagag gaaaactcaa gccatctcca tggataaaaa   180
ccacaagtcg gaagaggggt ttggacgttc aatgtctagt agcagtcgcc gcgtcatgtg   240
gaagctcaac gaggaggagg agacattcga ctccttggtc aattatcggc ggcttccttc   300
gcgcagccta aaccgaagtc aggtgaccga tgtgcccacc aagggacaca ctacctccga   360
aaattgccag ctgccagcgc aagagttgga aacaaagagc gccaccaacg aacaaggtgc   420
attgggcata atgtcggtta gcctaccgca aacaaccagg aattcccatc aatcgtcggc   480
cacgtcactg ccggaggcca agggatgcac tgccaccgaa aactgccagt tgctagcgca   540
agaggcggaa acaagaacg ccagcaacga acaaggtgga ttgggcaaaa tgtcggttag   600
```

<210> SEQ ID NO 255
<211> LENGTH: 613
<212> TYPE: DNA
<213> ORGANISM: Drosophila

<400> SEQUENCE: 255

| | | | | | | |
|---|---|---|---|---|---|---|
| cataaacaaa | taaaacgatt | tgaagatgaa | tccgctaaca | aatatgaaaa | atgtgctcaa | 60 |
| actgagcgaa | cacgaactgc | aacatggcgg | aaagaagagc | tggcacgaca | tgtacaagga | 120 |
| ctcagcctgg | attttcgtcg | caggatttcc | gtatacccta | actgagggcg | acttggtttg | 180 |
| cgtattctcg | cagtacggcg | aagtggtcaa | catcaatcta | attcgagatt | caaaaacggg | 240 |
| aaagtccaag | ggcttctgct | tcctgtgcta | cgaggaccag | agatccacag | tgctggccgt | 300 |
| ggacaacctg | aatggcatca | agatcctcga | taggacacta | agggtcgatc | acgtggccga | 360 |
| ctacaagcct | cccaaggaaa | acgagaagat | ggacgaggaa | acccttcgcc | tttacatgga | 420 |
| gggctgtgcg | ccgaaacctc | aacttcagca | catcaagact | gagaagaaag | acagcaaaaa | 480 |
| ttatagatga | taagataagg | ttagcttaaa | catagcaaag | catgcaaaca | gaattttat | 540 |
| attaacttaa | attttttagt | tattaaacgc | taaattatac | tactaaaaaa | aaaaaatcaa | 600 |
| aactgaaatt | cta | | | | | 613 |

<210> SEQ ID NO 256
<211> LENGTH: 664
<212> TYPE: DNA
<213> ORGANISM: Drosophila

<400> SEQUENCE: 256

| | | | | | | |
|---|---|---|---|---|---|---|
| cggaacgtcg | agcgcacgaa | ttcggaatta | tcgttgaaac | aaacgtcgcc | gcgtgtgatc | 60 |
| gaaaatccaa | gttaggctca | ttcgttggga | agctgcgagt | tcactctctc | tcacacacac | 120 |
| acgcacgaat | attaccccg | gcgcgttta | cttccatctc | gctcccacaa | aggcggaaga | 180 |
| gttaaacaca | aaaaaaaaag | aaaaatagaa | agaaattat | aaacgaaaaa | ctgccaccgc | 240 |
| cgctgctcaa | taatttgtgc | atttttaag | tttcatcaca | atgtcctcaa | atctaattta | 300 |
| aataagtaag | aagtgtaaca | agcgacacgc | agcgaaacaa | atagcgctga | atagaggagc | 360 |
| acgccaaggc | aaacagcaac | aaatggccaa | caattgaatg | gcggccatca | gttggcccca | 420 |
| gcggcatcca | ttgagcaatc | aacaccattt | ctcccacatc | aaatcaagca | ccacttccag | 480 |
| caacaccatc | acctcaacca | cctcagtcac | caccgccgtc | acagctttgg | gaatcagaac | 540 |
| cacagtccaa | gacccagtcg | aaaccaccac | caccaccagt | aaaagccaca | gcctagcagg | 600 |
| accacaacca | ctgagctcca | tcgccaacaa | ataccagaac | cgggtgcagc | tgctcgaatt | 660 |
| attt | | | | | | 664 |

<210> SEQ ID NO 257
<211> LENGTH: 628
<212> TYPE: DNA
<213> ORGANISM: Drosophila

<400> SEQUENCE: 257

| | | | | | | |
|---|---|---|---|---|---|---|
| aagtataaag | ccttgcggat | ccaaagttaa | ctgctgattt | tccaagaaca | acagttaaga | 60 |
| tcaaaatttt | cttaaaatgc | ccgaacaagt | cacagatcag | gagaaccagg | ctccacagca | 120 |
| gcagactact | gctgtgcatg | cctacaatcc | cgaagtcctg | caggatatgt | tgcccgtgta | 180 |
| ttacaggcgc | ctctttcccc | acctgcccctt | ctaccgttgg | ctatcgtatg | gatcatccga | 240 |
| ggatgctatc | ttttccaatc | gtgaaatttc | ctttacactg | caggacgata | tctacatacg | 300 |

| | |
|---|---|
| ttacctctgc tttgataccc aagctgaatt ggaaaaggag atctgctcga ggaatcctat | 360 |
| taagattgac ataggaccag taatgcattc caaacccaaa aaccatcgtt caattcctgg | 420 |
| cggcttaacg cccgtacaac gtgaactcgt ttttgatata gatatgacgg attacgacga | 480 |
| ggtgcgtacc tgttgctctg gagcaggggt atgcctgaaa tgctggaagt ttatggtgct | 540 |
| ggctgccagg gttttggatg tcgctttgcg cgaggatttc ggtttcgagc acataatctg | 600 |
| gattttctca ggtagacgag gtatccat | 628 |

<210> SEQ ID NO 258
<211> LENGTH: 600
<212> TYPE: DNA
<213> ORGANISM: Drosophila

<400> SEQUENCE: 258

| | |
|---|---|
| ctggcacaga tcaacagact gacgttgtaa ttgcatctgg aggtttacca aggctgggac | 60 |
| tccttctaca gcacaacaaa agcaacattg tgaaggaggc tgcctggacg gtcagcaaca | 120 |
| tcacagcagg taaccagaag cagatccagg ctgtgattca ggccggcatc ttccagcagc | 180 |
| tgcgcaccgt gctggagaag ggtgatttca aggctcaaaa agaggctgcc tgggcggtga | 240 |
| caaacaccac gacatctggc actcccgaac agatcgtcga tctaattgag aagtacaaaa | 300 |
| tattgaagcc ttttatcgat ttgctggaca caaaggatcc gcgtaccatc aaggtggtgc | 360 |
| agacgggcct atccaatctg tttgccctgg cggagaaact tggtggcacc gagaacctat | 420 |
| gcttgatggt cgaggagatg ggcggtctag acaagctgga aactctgcag cagcacgaga | 480 |
| acgaggaggt ctacaagaag gcctacgcca tcattgacac atacttcagc aacggcgacg | 540 |
| acgaggccga gcaagagctc gcacctcagg aggtcaacgg agccctcgag ttcaatgcca | 600 |

<210> SEQ ID NO 259
<211> LENGTH: 3312
<212> TYPE: DNA
<213> ORGANISM: Drosophila

<400> SEQUENCE: 259

| | |
|---|---|
| ttttttttt actatttccc accagcggtc agacggttga cgttcccaat tcggcatttc | 60 |
| aatttggcat acgtccccga aaatggagc tagcctagcc agagtccaac aggattaggc | 120 |
| caaactcatt gcgaaacgaa acgcctgaag atacatctac aagccgtgat tgcgtgcgac | 180 |
| aattgcacag tatttacgtc agcatcggtt aagtgaggcg attgcaccat ggacttcaag | 240 |
| gaataccgcc aaaggggcaa ggagatggtc gactatattg cagactatct ggagaacatc | 300 |
| cgggaacgcc gagttttttcc ggatgtcagt ccgggctata tgcgccagtt actgccggag | 360 |
| tccgctccga tcgaaggtga accgtggccg aaaatattct cggatgtgga gcgtatcgtg | 420 |
| atgccgggca taacccactg gcaatcgccc cacatgcacg cctactttcc ggccctcaac | 480 |
| tccatgcctt ccctactggg cgacatgctg gcggatgcga ttaactgcct gggattcacc | 540 |
| tgggcgagct cgccagcctg caccgaactg gagatcatag tgatgaactg gctgggcaag | 600 |
| atgatcggtc tgccggatgc ctttctccac ctgagctccc aaagtcaggg cggtggagtg | 660 |
| ctgcagacca ctgccagtga agctactcta gtttgtctgc tggcgggacg gactcgggct | 720 |
| attcagcgat tccatgagcg acatcctggc tatcaggatg cggagatcaa cgcccggctg | 780 |
| gtggcctact gctccgatca ggcgcactcc agtgtggaga aggcggcgct cattggactc | 840 |
| gtgaggatgc gttacatcga ggcggatgag gacctggcga tgcgcggcaa actgttgcgc | 900 |
| gaggccatcg aggatgacat taagcagggc ctggtcccct tctgggtctg cgccacactc | 960 |

```
gggaccaccg gcagctgcag cttcgataac ctggaggaga ttggcatcgt ttgtgcggag    1020
caccacctgt ggctccacgt tgacgccgcg tacgccggca gcgccttcat ctgcccggag    1080
tttcgcacct ggctgcgtgg cattgagcgg gcggattcga tagccttcaa tccgtccaag    1140
tggctgatgg tgcacttcga tgcgaccgca ttgtgggttc gggatagcac cgctgtccac    1200
aggaccttca atgtggagcc gctgtatctg cagcacgaga attccggagt ggcagtggac    1260
tttatgcact ggcagatacc gctgagtcgc cgattccgtg ccctgaaggt gtggttcgtc    1320
ctgcgatcct acgggatcaa aggcctacag cgccacattc gcgaaggcgt tcgattggct    1380
cagaaattcg aggccctcgt cctggccgat catcgtttcg agctgcccgc taaaaggcat    1440
cttggcctgg tggtattccg gatacgcggc gataatgaga taaccgagaa gttgctgaag    1500
aggctgaatc accgaggcaa ccttcattgc atcccatcgt cgctgaaggg acagtatgtc    1560
atccgcttta ccatcacatc gacgcacacg accttggacg atattgtcaa ggattggatg    1620
gagatccgtc aggtggcctc cactgtgctg gaggagatga acatcacaat ttcgaatcgc    1680
gtctatctca aggaaaccaa ggagaaaaac gaagccttcg gctcgagtct tctgctctct    1740
aattctccgc tctcgcctaa ggtggtaaat ggctcctttg cggctatatt cgatgcggat    1800
gagttcctgg ccaaaaccta tgccggcgtt cggatagcgc accaggaatc gccatcgatg    1860
agacgacgtg tgcgtggcat cctcatgtcg ggcaagcagt tctcgctgga ctcccacatg    1920
gacgtggtgg ttcagacgac cctggacgcc ggcaatggag ccactcgtac cagcaccacc    1980
aactcctatg gccacaccac ttctgcggcc caggcaaact cggagaggca ggccagcatc    2040
caagaggaca acgaggagtc gccggaagaa actgaattgc tgtcactgtg caggaccagc    2100
aatgtaccca gccccgagca cgcccactcc ctatccactc ctagtcgcag ctgtagctcc    2160
agctcccact cactgaccca ctctctcact caatcctcag cgcgatcctc accagtcaac    2220
caatttcgac acattacttt gtgcgcagtg cccagtcaaa gccatctttc aatgcccctt    2280
gccatgcccc tgcccaatcg caatgtcacc gtgtccgtgg atagcctcct gaacccggtc    2340
accacctgca acgtctacca tggcaagcgg tttctggagc ccctcgagaa tctcgcccag    2400
accagtgcct ccttcagcag cagcatctt cgcctgccga cacccatggc cacgcccacc    2460
cgggaatcgc cggaggatcc ggactggccg gcaaagacct tcagccagct gctgttggag    2520
cgctactcct cgcagtccca gtccctgggc aataactcct cgacggagag cagcagtctc    2580
agcggcgggg ccactcccac gcccactccc atgagcagcc tggatgaatt ggtgacacca    2640
ctgctgctct cattcgcatc cccctcgcag ccgatgctct ccgcccatgg cattggcgag    2700
ggtcagcggg agcggggcag cgactcggat gccaccgttt gttcgacaac ctcatcgatg    2760
gagtcgcttt agtgatagcc ttaaaaattc catattaagt tttactatac tatgaatcta    2820
aggacagaag aagtacctaa ttatatgatc tttttctctt tgtttaaacc aagaagtagt    2880
tggtaatgat ccaactatac atcttatttg tttagcttac tcaatctgaa gttacacatt    2940
ttatttggat cccatgactt acgttattat tcaatataat ttgacatctc agttcattgt    3000
atataagtgt gattgggaaa gagggtaaa tcatcgaacg ctgctgtgca atcaatcaat    3060
aatgcaatca atcgtaattc caatcaatgt tgtgccgtac cgttaatcta caaaatatgc    3120
atgcccatac cataatacta taaatttcct attttaagct aacaatcggt caagactcaa    3180
aactcaaaaa cttaccggct tacatatgta tctccatgtc taatcaattt cagtgtgatt    3240
aaagtttcaa agttctagtt acaacacaaa aaaaaaaaaa aaaaaaaaaa aaaaaaaaaa    3300
```
aaaaaaaaaa aa                                                            3312

<210> SEQ ID NO 260
<211> LENGTH: 2873
<212> TYPE: DNA
<213> ORGANISM: Drosophila

<400> SEQUENCE: 260

| | |
|---|---|
| atgcagagtc tgcggatctc gggatgcacg cccagcggta cgggtggctc ggccacgccc | 60 |
| tcgccggtgg gcctggtgga tccgaatttc atagtcagca actatgtggc cgcctcgccg | 120 |
| caggaggagc gcttcattca gatcattcag gccaaggagc tcaagataca ggaaatgcaa | 180 |
| agggccctcc agttcaagga caacgaaata gccgagctaa agtcgcactt ggacaaattc | 240 |
| cagagtgtct ttcccttcag ccgtggcagt gcggctggtt gtgcgggcac gggcggagcg | 300 |
| tcgggatctg gagccggcgg aagtggcggc agtggtcccg gcaccgccac aggtgccaca | 360 |
| cgcaagtcgg gtcagaattt ccagaggcag agggcattgg gtatctccgc cgagccacag | 420 |
| agcgagtcct cgctgctcct cgagcacgtc agctttccca aatacgacaa ggatgagcgc | 480 |
| tcccgtgaac ttatcaaggc tgccatattg gataatgatt tcatgaagaa tctggatctg | 540 |
| acgcagatcc gcgagatcgt tgactgcatg tatccggtta agtatccagc caagaatctg | 600 |
| atcatcaagg agggagatgt cggaagcatc gtttatgtca tggaagatgg acgcgtcgag | 660 |
| gtttcccgcg agggcaagta cctctccaca ttgtcgggag cgaaggtcct tggcgaattg | 720 |
| gcgatcctgt acaactgcca gcggacggcg accatcaccg cgatcaccga gtgcaacctg | 780 |
| tgggccatcg agcgccagtg cttccagacc atcatgatgc gaacgggcct gatccggcag | 840 |
| gcggagtaca cgcgatttcct caagagtgtg cccatcttca aagacctggc ggaagacacg | 900 |
| ctcatcaaaa tctccgatgt cttggaggag acgcactacc agcgtggcga ccacatagtg | 960 |
| cgccagggcg cccgaggcga taccttcttc atcatctcca agggaaaagt gcgagtgacg | 1020 |
| atcaagcagc aggacaggca ggaggagaag ttcattcgca tgctgggcaa aggggatttc | 1080 |
| tttggagaga aggctctcca gggcgatgat ctgcgcacgg cgaatattat ttgcgagtcc | 1140 |
| gccgatggcg tcagttgtct ggtcatcgat cgcgagacct tcaatcagct aatttccaat | 1200 |
| ctagacgaga tcaagcatcg ctacgacgac gagggcgcca tggaacgcag aaagatcaac | 1260 |
| gaggaattcc gggacattaa cctcacagat ctgcgcgtca tcgcaaccct tggagttgga | 1320 |
| ggcttcggtc gcgtagagct ggtccaaact aatggagata gctccaggtc cttcgcgctc | 1380 |
| aagcagatga aaaagtcaca gattgtggag acgcgtcagc agcaacacat catgtccgag | 1440 |
| aaggagatca tgggcgaggc caattgccag ttcatcgtga agctgttcaa gaccttcaag | 1500 |
| gacaagaagt acctgtacat gctgatggag agttgcctgg cgagagagct ctggacgatt | 1560 |
| ctacgggaca agggcaactt cgacgacagc accacccgct tctacacggc atgtgtggtg | 1620 |
| gaggccttttg attacttgca ctcgcgtaac atcatctacc gcgatcttaa gccggagaac | 1680 |
| ctgctgctca tgaacgagg atatgggaag ctggtggact ttggctttgc caagaagctg | 1740 |
| cagacgggca ggaagacctg gactttctgc ggcactccag agtacgtggc tcccgaggtg | 1800 |
| attctcaacc ggggccacga catcagtgcg gattactggt cgctgggagt gctcatgttc | 1860 |
| gagttactta ctggtacccc tccattcacg ggctcggatc ccatgcgcac ctacaacatt | 1920 |
| atacttaagg gcatcgacgc catcgaattc ccaaggaata tcacccgcaa tgccagcaac | 1980 |
| ctgatcaaga agctctgtcg cgacaatcca gccgagcgtt gggctacca gcgtgggga | 2040 |
| atcagcgaga tccaaaagca caaatggttc gatggcttct attggtgggg cctgcagaac | 2100 |

```
tgcacactgg aaccgcccat taagcccgcc gtgaaaagcg ttgtggatac aacaaacttt    2160
gatgactatc ctcccgatcc tgagggtccg ccgccagatg atgtcactgg atgggacaag    2220
gacttctgag gagaatcaga acccgtttcc tagacgatgc tctctaaacg cttctgctgc    2280
agaaaaccag gaggatatga aagccaggga agaaaaattg atcttaagtg cgccatatgt    2340
acgccaaagc caacagcaac agtcagcagc tcgcatcgaa aagctgccat aaaaaaaaac    2400
aaagaaacgt agcagtcgca aggtcaaggg ccgacacaaa agcacaatca tccatcgtcg    2460
tagctccatt tgagatttat agatacgtct ccgtgatgtt ataaccatga gtgcaacgc     2520 aatgaatcta ttaacgagtt tataactatt attttataat gaggatatat gtgtctagtt    2580
cgcttggaat tgatgtaaat tgtaagtagg tctgtgactc tgtttcagag ctctgttagc    2640
catgtgcatt gtataaattc agctatttgt atctattaaa tattttttaac ataattatta   2700 cacatcattg ttaaagcata caaatcgggt tgccttatag tctgtaagag aacatttgaa    2760
agcaacattt gaccaagatc ttccgtcaca catttcttaa aattctatgt ggcctctcta    2820
ctgtctttca ttagtcttag cgatcatgtc tattatatgt acgataacat gcc            2873
```

<210> SEQ ID NO 261
<211> LENGTH: 1080
<212> TYPE: DNA
<213> ORGANISM: Drosophila

<400> SEQUENCE: 261

```
actgcataac caaatatttg cgtggctcca actcgactcc gtatttgcct gggctgaagg    60
accgccgctg cctgcggatg acatgtattg gtcctgcgga tgacaccgat actgacgctc    120 ttggggttgcg tggtcgggcg gtctcccgca gtgggttatc cagtccaggt tgctatataa   180
gtcgaggatg cgccaaccga cgttcattcg caagtctcct gctgcaggtg ttccgtgctc    240
agttcctgct cctggccacc ctttcagctc ctcggactaa tggctcgctt cacgtacctt    300
gtcgcccttg tgcttctggc catttgctgc cagtggggat aatgcggcgc catggccatg    360
ccggatgagg agcgctatgt gcgcaaggag tacaatcggg atctcctcga ctggttcaac    420
aacgtgggcg tgggacagtt cagtcccggc caagtggcca ctctctgtcg ctatccgctg    480
atcctcgaga actccttggg cccatccgtg cccatcagga agcgcaactc ggagctaatc    540
aactccttgt tgagtctgcc caagaacatg aacgatgcgg gcaagtaaga acggaaaatg    600
ctgaaggatt aggacgaccc accactgaaa gttggaacct ggacaagaac ttattatttg    660
atgttatcgt atgatttttt ggtgcgtcga aggaaaatga aaatccgcag ataaaagccg    720
gtgtagtcat ctaatagaga gaaaagaccg tataacttttt gttgctttaa acctaaatag    780
aaaaatatac aagtagccta ttgtagaaat gttgtatatt attaggctta ctgctgaaat    840
aaacgttttc tggattgttt cgacttgaaa tctggtacaa caactagtca ggattttttat   900 tcttaatcac agatactaaa gctagttaaa gatattggtt atccccgtaa agggcgaacc    960
aatgaaagcc aaaggtgttc tcaaagtaga ttttgttcaa tgctacgatt ggaataaata    1020 gatgttttcta gcttagaata gcagccccat ttcgtttatt gacttcattt attatgctat   1080
```

METHODS FOR IDENTIFYING COMPOUNDS FOR MOTION SICKNESS, VERTIGO AND OTHER DISORDERS RELATED TO BALANCE AND THE PERCEPTION OF GRAVITY

This application is a continuation of application Ser. No. 09/669,751, filed Sep. 26, 2000, now U.S. Pat. No. 6,551,575, which claims the benefit of U.S. Provisional Application No. 60/168,579, filed Dec. 2, 1999, the entire contents of which is incorporated herein by reference.

BACKGROUND OF THE INVENTION

Motion sickness is a condition produced by road, sea, air, or space travel, or by interacting with virtual environments. It is caused by the effect of any pronounced movement on the organ of balance in the inner ear or by sensory conflict about body motion as perceived by different receptors (visual, vestibular, and body proprioceptors). Symptoms may include headache, excessive sweating and salivation, loss of appetite, malaise, nausea, vomiting, gastrointestinal disturbances and fatigue. Vertigo is the illusion that one's surroundings or self are spinning, either horizontally or vertically, resulting from a disturbance of the semicircular canals in the inner ear or nerve tracts leading from them. It can be induced by motion, zero gravity or disease, and may be accompanied by vomiting, ringing in the ears and unsteadiness.

Travel related motion sickness is experienced by approximately 1% of air travelers and can be as high as 100% of ocean travelers on heavy seas. Children between the ages of 3 and 12 are the most susceptible. 50% of astronauts experience "space motion sickness" during space travel. While a source of discomfort, motion sickness and vertigo can also result in impaired performance by crew members on ships, planes or spacecraft, by drivers suffering from circulatory ailments, or by users of computer-based virtual environments.

Currently available drugs to treat motion sickness and vertigo produce a variety of undesirable side effects, some producing drowsiness, blurred vision, impaired reaction time and pattern recognition, others negatively affecting mood and sleep.

The genes that play important roles in the proper functioning of the vestibular system remain largely uncharacterized. Identification of such genes can provide methods for screening individuals with genetic susceptibility to motion sickness or vertigo and can also provide targets for developing new therapeutic agents that specifically modulate the expression or activity of genes associated with motion sickness or vertigo. Unfortunately, identification of such genes in mammals can be difficult and time consuming.

Therefore, there is a need to identify drugs that alleviate motion sickness and vertigo without undesirable side effects. There also exists a need to identify genes whose expression or activity is associated with conditions such as motion sickness or vertigo. The present invention satisfies these needs and provides related advantages as well.

SUMMARY OF THE INVENTION

The present invention provides a method of identifying a compound that modulates a mammalian vestibular system. The method consists of administering a test compound to an invertebrate, andmeasuring a geotactic behavior of the invertebrate, where a compound that modulates the geotactic behavior of said invertebrate is characterized as a compound that modulates a mammalian vestibular system. The invention also provides a method of identifying a gene that modulates a mammalian vestibular system consisting of obtaining a first and a second strain of an invertebrate; subjecting the first and second invertebrate strains to conditions in which the first strain exhibits a geotactic behavior different than a geotactic behavior exhibited by the second strain; measuring gene expression levels in the first and second strains, and identifying one or more genes that are differentially expressed in the first strain relative to the second strain, whereby a mammalian gene having substantially the same nucleic acid sequence as the one or more differentially expressed genes modulates the mammalian vestibular system.

DETAILED DESCRIPTION OF THE INVENTION

Figure 1:
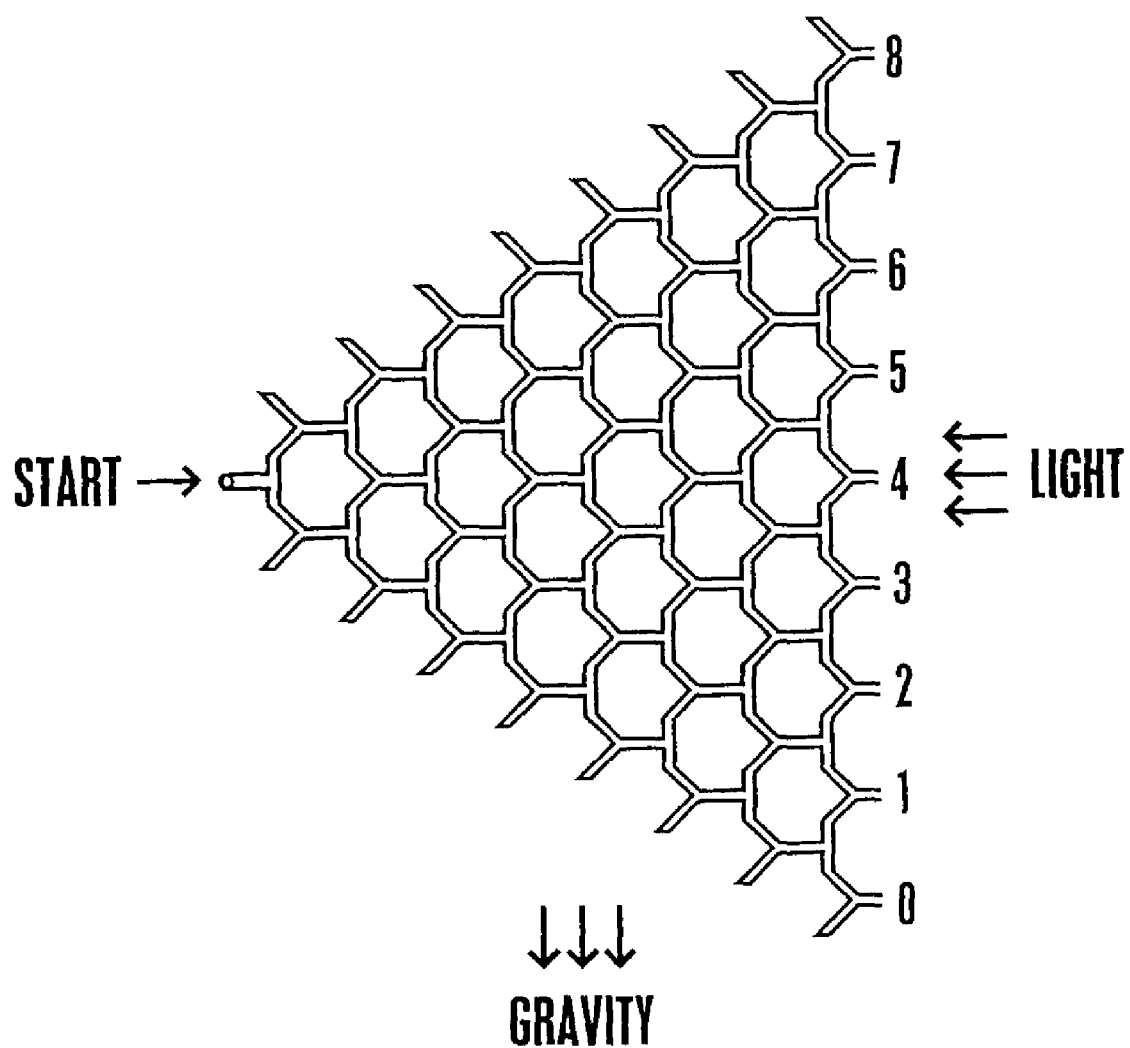
FIG. 1 shows a schematic of the geotaxis maze used in measuring geotactic scores of *Drosophila*.

The present invention provides methods of rapidly and efficiently identifying compounds that modulate a mammalian vestibular system, including compounds that decrease dizziness or nausea, or increase balance. The compounds identified by the methods of the invention can be used to treat individuals suffering from motion sickness, vertigo, or other graviperceptive disorders. The present invention also provides mammalian genes that modulate a mammalian vestibular system. A compound identified by the method of the invention can act to modulate the activity or expression of a mammalian gene of the invention.

Genetic and molecular studies of perception and response to gravity have not been extensively pursued in multi-cell organisms. As a result, little knowledge exists regarding the molecules that play important roles in perception of gravity and motion. There has been no indication that the manner in which mammals perceive gravity resembles the manner in which invertebrates perceive gravity or that the relative genetic simplicity of invertebrates compared to mammals provides networks of genes controlling graviperceptive behavior in invertebrates that are similar to those operating in mammals. In fact, invertebrates have been shown to have dissimilar pharmaclolgical responses compared to mammals within the same class of receptors. Thus, the use of invertebrates to test compounds affecting mammalian behaviors including, for example, graviperception also has not been pursued.

The methods and compounds disclosed herein are based on the discovery that administration of a compound used for treating motion sickness in humans can be effective in changing geotactic behavior of invertebrates and that the network of genes controlling the mammalian vestibular system is similar to the network of genes controlling geotactic behavior of invertebrates. The invention provides a method of identifying a compound that modulates a mammalian vestibular system. The method consists of administering a test compound to an invertebrate and measuring a geotactic behavior of the invertebrate. A candidate compound that modulates the geotactic behavior of the invertebrate is characterized as a compound that modulates a mammalian vestibular system.

The methods of the invention provide a means to identify a compound that modulates a mammalian vestibular system because the methods are based on screening geotactic behavior of invertebrates which is a natural system that performs a similar function. Thus, the methods provide for screening compounds in a context similar to the context of the mammalian vestibular system. Additionally, compounds that modulate a mammalian system to various degrees can be identified by the methods of the invention because strains of invertebrates that have naturally evolved different geotactic behaviors and degrees of response can be used with the methods of the invention.

According to the methods of the invention, changes in expression of one or more representative genes in a network of genes can be associated with changes in geotactic behavior of an invertebrate to identify compounds that modulate the mammalian vestibular system. Representative genes can include one gene, a set of all genes whose expression changes upon modulation of the mammalian vestibular system, or any subset of genes thereof. The methods of the invention can be used to identify compounds that modulate a mammalian vestibular system by identifying the effects of a compound on a subset of genes involved in the geotactic behavior of invertebrates because the change detected in the subset of genes occurs in the context of a natural network of genes controlling geotactic behavior.

As used herein, the term "modulate" refers to an increase, decrease or alteration. The term can be used to indicate an increase, decrease or alteration of a level, activity or function characteristic of a behavior, organ, protein, or other detectable phenomenon. For example, a mammalian vestibular system can be modulated by a compound that increases or decreases graviperception, increases or decreases neuronal response to a graviperceptive signal, and the like.

As used herein, the term "compound" as used in regard to modulating invertebrate geotaxis, a mammalian vestibular system, or protein expression or activity, refers to an inorganic or organic molecule such as a drug; a peptide, or a variant or modified peptide or a peptide-like molecule such as a peptidomimetic or peptoid; or a protein such as an antibody, a growth factor, or cytokine, or a fragment thereof such as an Fv, Fd or Fab fragment of an antibody, which contains a binding domain; or a nucleic acid or chemically modified nucleic acid such as an antisense nucleic acid; or a carbohydrate or lipid. Methods of determining compounds useful for modulating invertebrate geotaxis, a mammalian vestibular system, or protein expression or activity are provided herein, and include administering a compound to an invertebrate and identifying whether the compound modulates invertebrate geotaxis, administering a compound to an invertebrate or invertebrate cell culture and identifying whether the compound modulates expression of one or more genes associated with invertebrate geotaxis, and administering a compound to a mammal or mammalian cell culture and identifying compounds that modulate the expression or activity of a protein that modulates the mammalian vestibular system. If desired, a candidate compound can be combined with, or dissolved in, an agent that facilitates uptake of the compound by the invertebrate, such as an organic solvent, for example, DMSO or ethanol; or an aqueous solvent, for example, water or a buffered aqueous solution; or food.

A compound identified in the method of the invention modulates a mammalian vestibular system and also modulates geotactic behavior of an invertebrate. A compound that modulates invertebrate geotactic behavior can, for example, increase or decrease a geotactic behavior. Additionally, a compound can increase or decrease a first geotactic behavior while decreasing or increasing, respectively, a second geotactic behavior. For example, a compound can increase geotactic behavior in response to light, while decreasing geotactic behavior in response to heat or humidity.

A compound that modulates the activity or expression of a protein can, for example, increase or decrease the expression level or activity of a protein, or influence both expression and activity. For example, a compound can increase the activity but decreases the expression of a protein, as in the case of increased activity of a transcription factor that auto-regulates by feedback inhibition.

As described in the present invention, a compound that modulates invertebrate geotaxis can also modulate a mammalian vestibular system. Accordingly, a compound that modulates invertebrate geotaxis can increase or decrease the sensitivity of a mammalian vestibular system. For example, a compound that increases negative geotaxis in an invertebrate can decrease the sensitivity of a mammalian vestibular system.

As used herein, the term "mammalian vestibular system" refers to the organ of the inner ear of a mammal containing semicircular ducts and the nerve fibers extending therefrom. The nerve fibers can extend from the inner ear to the central parts of the brain and include, for example, the vestibular nuclei, trochlear nucleus, oculomotor nucleus, abducens nucleus, and vestibulospinal tracts. Typically, a mammalian vestibular system is used to maintain balance, perceive motion and perceive orientation relative to a force vector such as gravity or a physical force such as change in velocity or direction. A mammalian vestibular system can provide signals to the brain that result in graviperceptive disorders.

As used herein, a "graviperceptive disorder" refers to any condition that disturbs normal perception of gravity, motion or orientation. A graviperceptive disorder can have genetic or familial basis or can be induced by sickness or other physical conditions such as high blood pressure, or can be brought about by motion, changes in amplitude or direction of a gravitational or physical force, or changes in orientation. Exemplary graviperceptive disorders include, but are not limited to, labyrinthitis, Meniere's disease, motion sickness, vertigo, acoustic neuroma, multiple sclerosis, syphilis, trauma, infection of the middle ear, exposure to ototoxic agents, epilepsy and the like. A graviperceptive disorder is characterized by one or more symptoms such as dizziness, nausea, headache, excessive sweating and salivation, loss of appetite, malaise, gastrointestinal disturbances and fatigue. A variety of graviperceptive disorders in humans are known in the art and are described in, for example, Brandt, *Vertigo: Its Multisensory Syndromes*, $2^{nd}$ Ed., Springer Verlag (1999).

Mammals are understood to refer to members of the class mammalia, and particularly include placental mammals such as sheep, goats, cows, horses, pigs, dogs, cats, rats, mice, primates, humans and the like.

Modulation of a mammalian vestibular system can decrease or increase the sensitivity of a mammalian vestibular system, influencing the ability of an individual to maintain balance, perceive motion or perceive orientation, and can also result in, for example, a decrease in the symptoms associated with a graviperceptive disorder such as motion sickness, vertigo, labyrinthitis, Meniere's disease, acoustic neuroma, multiple sclerosis, syphilis, trauma, infection of the middle ear, exposure to ototoxic agents, epilepsy and the like. The term "sensitivity" when used in terms of a mammalian vestibular system refers to the responsiveness of semicircular ducts in sensing motion or orientation or the responsiveness in signaling of semicircular ducts or neurons connected thereto. Such sensitivity can influence symptoms of a graviperceptive disorder such as motion sickness, vertigo, labyrinthitis, Meniere's disease, acoustic neuroma, multiple sclerosis, syphilis, trauma, infection of the middle ear, exposure to ototoxic agents and epilepsy. Typically, decreased sensitivity of a mammalian vestibular system will result in a decrease in symptoms associated with a graviperceptive disorder.

A mammalian vestibular system can be modulated by a gene whose expression increases or decreases graviperception, increases or decreases nueronal response to a graviperceptive signal, and the like. In accordance with the present invention, such a gene comprises a nucleic acid sequence substantially the same as an invertebrate gene which modulates invertebrate geotactic behavior.

Examples of such genes are PROX1, comprising substantially the same sequence as SEQ ID NO:15, mammalian tectorin-α, comprising substantially the same sequence as SEQ ID NO:233; mammalian glycoprotein 330, comprising substantially the same sequence as SEQ ID NO:108; mammalian protein inhibitor of nNOS, comprising substantially the same sequence as SEQ ID NO:117; mammalian synaptic vesicle transporter, comprising substantially the same sequence as SEQ ID NO:250; mammalian actin-binding double-zinc-finger protein, comprising substantially the same sequence as SEQ ID NO:21; mammalian spinocerebellar ataxia type 2 protein, comprising substantially the same sequence as SEQ ID NO:1; mammalian APP-binding protein, comprising substantially the same sequence as SEQ ID NO:225; and the like. Further examples are mammalian genes substantially the same as genes containing the nucleic acid sequences of SEQ ID NOS:1-261.

The term "geotactic behavior" or "geotaxis" of an invertebrate refer to the behavioral response of an invertebrate to perception of a force vector such as gravity, a visual stimulus or a combination of the two. Geotactic behavior can be manifested by crawling, walking or flying in a specific direction and/or orientation in response to a force vector such as gravity. For example, an invertebrate having a walking pattern characterized as negative geotactic behavior walks in opposition to the force vector, or "upward." Conversely positive geotactic behavior is displayed by an invertebrate which walks in the same direction as the force vector, or "downward." As another example, the orientation of an invertebrate in flight with respect to a force vector, such as, upright, upside-down and the like, is a geotactic behavior. Wild type geotactic behavior refers to a geotactic behavior in an invertebrate which has not been selected for positive or negative geotactic behavior, abnormal flight behavior or other geotactic variant behavior. Exemplary wild type geotactic behavior can be manifest by an equal likelihood of a specific invertebrate to walk against a force vector "upward" as the likelihood of walking with the force vector "downward." Therefore, wild type geotactic behavior can result an invertebrate exhibiting, on average, neither positive nor negative geotactic behavior. Methods for determining geotactic behavior are disclosed herein and are well known in the art, as exemplified in the publications by Horn, "Gravity" in *Comprehensive Insect Physiology biochemistry and Pharmacology* Vol 6, Pergamon Press (1985) and Schwartzkopff, "Mechanoreception" in *The Physiology of Insecta* Academic Press (1974), which are incorporated herein by reference. These methods include monitoring the crawling direction of an invertebrate with respect to gravity, monitoring the static orientation of an invertebrate with respect to gravity and monitoring the orientation of flight with respect to gravity. An exemplary apparatus for measuring the crawling direction of an insect is provided in Example I.

The modulation of invertebrate geotactic behavior results in increased geotactic behavior, decreased geotactic behavior, or otherwise altering a behavioral response in reaction to a force vector, such as altering flying behavior by, for example, attempting to fly upside-down. As used herein, "increased geotactic behavior" refers to a change from negative to positive geotactic behavior, a lessened extent of negative geotactic behavior, or an increased extent of positive geotactic behavior. Correspondingly, "decreased geotactic behavior" refers to an change from positive to negative geotactic behavior, a lessened extent of positive geotactic behavior, or an increased extent of negative geotactic behavior.

Invertebrates are understood to refer to members of the division invertebrata. As disclosed herein, *Drosophila melanogaster* is an example of an invertebrate that exhibits geotactic behavior that can be measured. Those skilled in the art understand that other *Drosophila* species are also likely to exhibit similar geotactic behavior and express genes associated with geotactic behavior, including *D. simulans, D. virilis, D. pseudoobscura D. funebris, D. immigrans, D. repleta, D. affinis, D. saltans, D. sulphurigaster albostrigata* and *D. nasuta albomicans*. Likewise, other flies, including, sand flies, mayflies, blowflies, flesh flies, face flies, houseflies, screw worm-flies, stable flies, mosquitos, northern cattle grub, and the like will also exhibit geotactic behavior and express genes associated with geotactic behavior.

Furthermore, insects other than flies can also exhibit geotactic behavior and express genes associated with geotactic behavior. For example, the invention can also be practiced with insects such as cockroaches, honeybees, wasps, termites, grasshoppers, moths, butterflies, fleas, lice, boll weevils, beetles, *Apis mellifera, A. florea, A. cerana, Tenebrio molitor, Bombus terrestris, B. lapidarius*, and members of Hydrocorisae.

Arthropods other than insects also can exhibit geotactic behavior and express genes associated with geotactic behavior. For example, the invention can also be practiced using arthropods such as scorpions, spiders, mites, crustaceans, centipedes and millipedes.

Due to the high degree of genetic similarity across invertebrate species, invertebrates other than arthropods, such as flatworms, nematodes (e.g. *C. elegans*), mollusks (e.g. Aplysia or Hermissenda), echinoderms and annelids will exhibit geotactic behavior and express genes associated with geotactic behavior, and can be used in the methods of the invention.

Those skilled in the art can determine, using the assays described herein, whether a particular invertebrate exhibits geotactic behavior and expresses genes associated with geotactic behavior and, therefore, would be applicable for use in the methods of the invention. The choice of invertebrate will also depend on additional factors, for example, the availability of the invertebrates, the normal activity levels of the invertebrates, the availability of molecular probes for genes associated with geotactic behavior, the number of invertebrates and compounds one intends to use, the ease and cost of maintaining the invertebrates in a laboratory setting, the method of administering and type of compounds being tested, and the particular property being evaluated. Those skilled in the art can evaluate these factors in determining an appropriate invertebrate to use in the screening methods.

For example, if it is desired to evaluate gene expression in the methods of the invention, an invertebrate that is genetically well-characterized, such that homologs of genes associated with geotactic behavior are known or can be readily determined, can be used. Thus, appropriate invertebrates in which to evaluate gene expression can include, for example, *Drosophila* and *C. elegans*. If it desired to evaluate behavioral properties in the methods of the invention, an invertebrate that exhibits one or more geotactic behaviors, such as fruit flies, cockroaches, honeybees, wasps, moths, mosquitos, scorpions, and the like, can be used.

As used herein, a "strain" refers to a population of organisms of a species having at least one similar phenotype, typically a geotactic phenotype. This population of organisms can have either identical or a somewhat heterogeneous genetic makeup, although heterogeneous populations typically contain individuals that are homozygous for one or more chromosomes. For example, a population of organisms having a similar phenotype can be a population of organisms of a species sharing a similar genetic origin as the result of either being isolated from a particular geographic area, sharing particular chromosomes or alleles, or having been bred for multiple generations for a particular phenotype.

The term "substantially the same" as used herein in reference to the relationship between a mammalian gene and an invertebrate gene refers to a mammalian nucleic acid or corresponding amino acid sequence that has a high degree of homology to an invertebrate nucleic acid or corresponding amino acid sequence and retains at least one function specific to the invertebrate nucleic acid or corresponding amino acid sequence. In the case of a nucleotide sequence, a first nucleic acid that is substantially the same as a second nucleic acid can selectively hybridize to a sequence complementary to the second nucleic acid under moderately stringent conditions or under highly stringent conditions. Therefore, a first nucleic acid molecule having substantially the same sequence compared to a second nucleic acid sequence can include, for example, one or more additions, deletions or substitutions with respect to the second sequence so long as it can selectively hybridize to a complement of that sequence. In the case of an amino acid sequence, a first amino acid sequence that is substantially the same as a second amino acid sequence can contain minor modifications with respect to the second amino acid sequence, so long as the polypeptide containing the first amino acid sequence retains one or more functional activities exhibited by the whole polypeptide containing the second amino acid sequence. Typically, a substantial similarity is represented by at least about 20% identity between mammalian and invertebrate sequences; mammalian and invertebrate sequences that are substantially the same can also share at least about 30% identity, at least about 40% identity, at least about 50% identity, at least about 60% identity, at least about 70% identity, at least about 80% identity, at least about 90% identity, at least about 95% identity, at least about 97% identity, or at least about 99% identity over the length of the two sequences being compared. Those skilled in the art know that two or more polypeptides having low overall sequence similarity can be substantially similar if the polypeptides have similar domains with substantial sequence similarity. For example, polypeptides having 20% overall identity can be substantially similar if the polypeptides contain one or more domains of substantial similarity. A larger number of similar domains between two or more polypeptides correlates with increased similarity. Therefore, substantial similarity can be identified according to sequence identity within similar domains of two or more polypeptides. Examples of methods for determining substantial similarity using sequence identity or a combination of sequence identity and similarity in domain structure are described below.

The appropriate function to be retained will depend on the desired use of the nucleic acid molecule. For example, a mammalian gene substantially the same as an invertebrate gene associated with geotactic behavior can be a polypeptide having substantially the same immunogenicity, antigenicity, enzymatic activity, binding activity, or other biological property, including invertebrate geotactic behavior modulating activity which will correspond to mammalian vestibular system modulating activity, as the polypeptide encoded by the invertebrate nucleic acid molecule.

Methods for determining that two sequences are substantially the same are well known in the art. For example, one method for determining if two sequences are substantially the same is BLAST, Basic Local Alignment Search Tool, which can be used according to default parameters as described by Tatiana et al., *FEMS Microbiol Lett.* 174:247-250 (1999) or on the National Center for Biotechnology Information web page at ncbi.nlm.gov/BLAST/. BLAST is a set of similarity search programs designed to examine all available sequence databases and can function to search for similarities in protein or nucleotide sequences. A BLAST search provides search scores that have a well-defined statistical interpretation. Furthermore, BLAST uses a heuristic algorithm that seeks local alignments and is therefore able to detect relationships among sequences which share only isolated regions of similarity including, for example, protein domains (Altschul et al., *J. Mol. Biol.* 215:403-410 (1990)).

In addition to the originally described BLAST (Altschul et al., supra, 1990), modifications to the algorithm have been made (Altschul et al., *Nucleic Acids Res.* 25:3389-3402 (1997)). One modification is Gapped BLAST, which allows gaps, either insertions or deletions, to be introduced into alignments. Allowing gaps in alignments tends to reflect biologic relationships more closely. For example, gapped BLAST can be used to identify sequence identity within similar domains of two or more proteins. A second modification is PSI-BLAST, which is a sensitive way to search for sequence homologs. PSI-BLAST performs an initial Gapped BLAST search and uses information from any significant alignments to construct a position-specific score matrix, which replaces the query sequence for the next round of database searching. A PSI-BLAST search is often more sensitive to weak but biologically relevant sequence similarities.

A second resource that can be used to determine if two sequences are substantially the same is PROSITE, available on the world wide web at ExPASy. PROSITE is a method of determining the function of uncharacterized proteins translated from genomic or cDNA sequences (Bairoch et al., *Nucleic Acids Res.* 25:217-221 (1997)). PROSITE consists of a database of biologically significant sites and patterns that can be used to identify which known family of proteins, if any, the new sequence belongs. In some cases, the sequence of an unknown protein is too distantly related to any protein of known structure to detect similarity by overall sequence alignment. However, a protein that is substantially the same as another protein can be identified by the occurrence in its sequence of a particular cluster of amino acid residues, which can be called a pattern, motif, signature or fingerprint, that is substantially the same as a particular cluster of amino acid residues in the other protein including, for example, those found in similar domains. PROSITE uses a computer algorithm to search for motifs that identify proteins as family members. PROSITE also maintains a compilation of previously identified motifs, which can be used to determine if a newly identified protein is a member of a known protein family.

The term "moderately stringent conditions," as used here is intended to refer to hybridization conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 500. In contrast, "highly stringent conditions" are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 65°. Other suitable moderately stringent and highly stringent hybridization buffers and conditions are well known to those of skill in the art and are described, for example, in Sambrook et al., *Molecular Cloning: A Laboratory Manual*, Cold Spring Harbor Laboratory, New York (1992) and in Ausubel et al., *Current Protocols in Molecular Biology*, John Wiley and Sons, Baltimore, Md. (1998).

The sequences of corresponding genes associated with geotactic behavior of desired species can be determined by methods well known in the art, which include methods such as PCR or screening genomic, cDNA or expression libraries derived from that species.

A modification of a nucleic acid molecule can also include substitutions that do not change the encoded amino acid sequence due to the degeneracy of the genetic code. Such modifications can correspond to variations that are made deliberately, or which occur as mutations during nucleic acid replication. Additionally, a modification of a nucleic acid molecule can correspond to a splice variant form of the recited sequence.

Additionally, a fragment of a mammalian gene can be substantially the same as an invertebrate gene or a fragment of an invertebrate gene. As used herein, a "fragment" of a gene refers to a portion of a gene that retains at least one biological function of the wild type gene. A mammalian gene can be substantially the same as an invertebrate gene, for example, when one of several domains encoded by a mammalian gene corresponds to a domain encoded by an invertebrate protein. Such a fragment typically is encoded by at least 30 nucleotides, and the mammalian and invertebrate genes encoding that fragment share at least about 50% identity, at least about 60% identity, at least about 70% identity, at least about 80% identity, at least about 90% identity, at least about 95% identity or at least about 98% identity. Methods for determining that a fragment of a mammalian gene is substantially the same as an invertebrate gene or a fragment of an invertebrate gene include those described above for comparing mammalian and invertebrate genes. Such a fragment can be encoded by 30 or more nucleotides, for example, 45 or more nucleotides, 60 or more nucleotides, 90 or more nucleotides, 150 or more nucleotides, 210 or more nucleotides, or 300 or more nucleotides.

Biological functions retained by a fragment can include the ability to modulate a mammalian vestibular system, the ability to modulate invertebrate geotaxis, the ability to bind an antibody that binds to a full-length protein which comprises the fragment, or an enzymatic or binding activity characteristic of the full length protein. For example, a 30 amino acid fragment of prospero interacts with miranda for subcellular localization as described in Hirata et al. *Nature* 377:627-630 (1995) and peptides corresponding to 30 amino acid domains of CaMKII and PKC inhibit the respective full length enzymes as described in Kane et al., *Neuron* 18:307-314 (1997), Broughton et al., *J. Cell. Biochem.* 62:484-494 (1996), Broughton et al., *J. Cell. Biochem.* 60:584-600 (1996) and Griffith et al., *Neuron* 10:501-509 (1993).

The term "administering" a compound refers to any method of delivering a compound to an invertebrate or mammalian subject in such a way that invertebrate geotaxis or a mammalian vestibular system can be modulated. Administration of a compound can be carried out using one of a variety of methods known to those of skill in the art. For example, a compound can be administered intravenously, intramuscularly, by ingestion, inhalation, absorption such as absorption through the skin or tear duct, or any other method of administration known in the art. A compound can be administered, for example, to a fruit fly by ingestion.

An appropriate method of administering a compound to an invertebrate can be determined by those skilled in the art and will depend, for example, on the type and developmental stage of the invertebrate, whether the invertebrate is active or inactive at the time of administering, whether the invertebrate is exhibiting a geotactic behavior at the time of administering, the number of animals being assayed, and the chemical and biological properties of the compound (e.g. solubility, digestibility, bioavailability, stability and toxicity). For example, as shown in Example I below, antihistamine can be administered to *Drosophila melanogaster* by dissolving the drugs in fly food and providing the food to the flies.

A compound that can modulate a mammalian vestibular system, invertebrate geotaxis, or protein expression or activity can be administered to a subject in an effective amount. The term "effective amount" of a compound, as used herein, refers to an amount that causes a change in a mammalian vestibular system, invertebrate geotaxis, or protein expression or activity. Measurement of such a change can be made by one of a variety of assay methods known to one of skill in the art and include monitoring invertebrate geotactic behavior, measurement of gene expression level, or measurement of activity levels of one or more proteins; measurements can also include clinical indices such as assessment of improvement of a graviperceptive disorder such as vertigo or motion sickness in a subject by decreased symptoms related to the graviperceptive disorder, for example, nausea, dizziness, fatigue and the like.

A candidate compound can be administered to an invertebrate in a single dose, or in multiple doses. The modulation of invertebrate geotactic behavior will be dose dependent. An effective amount of a compound used in the methods of the invention can be determined by those skilled in the art, and can depend on the chemical and biological properties of the compound and the method of contacting. Exemplary concentration ranges to test include from about 10 μg/ml to about 500 mg/ml, such as from about 100 μg/ml to 250 mg/ml, including from about 1 mg/ml to 200 mg/ml.

A candidate compound can also be administered to a mammal. Administration to a mammal can be in a single dose, or in multiple doses. The modulation of a mammalian vestibular system will be dose dependent. An effective amount of a compound used in the methods of the invention can be determined by those skilled in the art, and can depend on the chemical and biological properties of the compound and the method of contacting. Exemplary concentration ranges to test include from about 10 μg/ml to about 500 mg/ml, such as from about 100 μg/ml to 250 mg/ml, including from about 1 mg/ml to 200 mg/ml. Exemplary mammals to which a candidate compound can be administered include mice, rats, rabbits, pigs, dogs, cats, non-human primates, an other animals known to be useful for laboratory testing.

A subject with a graviperceptive disorder such as motion sickness, vertigo, labyrinthitis, Meniere's disease, acoustic neuroma, multiple sclerosis, syphilis, trauma, infection of the middle ear, exposure to ototoxic agents or epilepsy sickness can be treated for such a disorder by administering to the subject an effective amount of a compound that modulates a mammalian vestibular system. In treatment of the disorder, administration of an effective amount of the compound can be carried out upon a single occasion or multiple occasions. Administration can be regular, periodic administration such as one administration per day, symptomatic administration such as upon experiencing increasing nausea or dizziness, or prophylactic administration, such as prior to road, sea, air or space travel.

It will be understood that the efficacy and safety of a compound in laboratory mammals can be evaluated before administering the compound to humans or veterinary animals. For example, the compound can be tested for its maximal efficacy and any potential side-effects using several different invertebrates or laboratory mammals, across a range of doses, in a range of formulations, and at various times of day, such as before or after sleeping, before or after eating, and the like. Generally, a compound identified using the methods of the invention will cause few or no deleterious or unwanted side effects.

The term "conditions" when used in the context of invertebrate geotactic behavior refers to environmental and biological factors that can increase, decrease or otherwise modify invertebrate geotactic behavior. Environmental factors encompass the physical environment such as temperature, pressure, light intensity, light position, and the like; components of the gaseous environment such as humidity, % oxygen, presence of a compound such as a drug or hormone, and the like; and the structural makeup of the chamber in which the invertebrate is housed, including volume, particularly as it influences density of invertebrates, shape, composition of the chamber, and the like. Typical environmental conditions are about 20° C., 1 atmosphere, in the presence of a horizontal 15 W fluorescent light source, at ambient air conditions. An exemplary chamber is provided in the Examples below. Biological factors that can influence invertebrate geotaxis can include genetic factors including presence of particular alleles of genes or chromosomes, either naturally occurring or induced in the laboratory, biorhythmic factors such as time of day, relative activity level of an invertebrate, length of time an invertebrate has been active, and the like, also include biochemical factors such as developmental and hormonal state of an invertebrate, fasting state of the invertebrate, presence in the invertebrate of a compound administered by, for example, ingestion, and the like, and further include factors such as gender and age of the invertebrate. Typically, geotactic behavior experiments are carried out on adult invertebrates during the daytime, at least about two hours after sunrise and at least about two hours before sunset, and at least two hours after invertebrates have been at a relatively increased level of activity. An "increased level of activity" as used herein refers to the "alert" state of an invertebrate that often occurs in the daytime in contrast to the "resting" state of an invertebrate that often occurs during the nighttime. Change of some of these conditions can result in a change in geotactic behavior of an invertebrate. For example, addition of a compound such as a drug to the gaseous environment can result in modulated invertebrate geotaxis.

Conditions in which a first invertebrate strain can exhibit a geotactic behavior different than a geotactic behavior in a second invertebrate strain refers to environmental or biorhythmic factors that, when imposed on two different invertebrate strains, results in the two strains exhibiting dissimilar geotactic behavior. For example, conditions can cause a first invertebrate strain to exhibit negative geotaxis while cause a second strain to exhibit positive geotaxis. The first and second strain can be any combination of strains, including a mutant strain and a wild type strain, two different mutant strains, and also can be two different or even identical strains, where the two strains differ in, for example, age, gender, presence of a drug in one strain or different drugs in the two strains, and the like. These conditions also include the structure of the chamber in which the invertebrates are housed. For example, two strains can be placed in a chamber that is so shaped as to have pathways that lead upwards, against the force of gravity, as well as pathways that lead downwards, with the force of gravity. In such a chamber, a first strain can demonstrate strongly negative geotaxictic behavior, thereby rising along the upward pathways, while a second strand can demonstrate normal or "wild-type" geotaxictic behavior, in which no particular preference is manifest for either rising or descending along the various pathways. In a chamber of such a shape, further environmental or biorhythmic factors can be changed, for example, by administering a compound to the invertebrates, which can change the geotactic behavior of one or both invertebrate strains.

Determination of a geotactic behavior of a first invertebrate that is termed "different" than a geotactic behavior of a second invertebrate can be accomplished by analysis of a geotactic behavior of the two invertebrates. For example, in order for a geotactic behavior of a first invertebrate to be different than a geotactic behavior of a second invertebrate, the mean geotatic measurement, typically termed the geotaxis score, of the first invertebrate will differ from the geotaxis score of the second invertebrate strain if a pairwise t-test of two scores is significantly different at the 0.05 level, or if multiple pairwise comparisons between strains are significantly different after applying a correction for experiment wise-error. A significantly different score refers to a score that is different by a statistically meaningful amount. Alternatively, two geotactic scores are considered different if a first mean geotactic score is not within as desired region of the probability distribution of the second geotactic score. For example, a first mean geotactic score can be different if it is not within the 80% probable region of a probability distribution of the second geotactic score, or within the 85%, 90%, 95% or 98% probable region of the distribution of the second geotactic score. Correspondingly, geotactic scores considered to be substantially the same are geotactic scores that do not differ by a more than a desired standard deviation or are within a desired probable region of a probability distribution. Methods for the determination of mean, standard deviation and characteristics of normal distributions are known in the art as demonstrated by texts such as *Biostatistical Analysis*, 4th ed., Zar, Prentice-Hall Inc. (1999).

Measuring gene expression levels can be carried out by determining the amount of RNA transcribed or protein translated from each of one or more genes. This amount can be relative to another amount, for example, the RNA transcribed from a constitutively expressed gene, relative to total RNA or protein, or can be an absolute measure of the amount of RNA transcribed or protein translated.

A variety of assays well known in the art can be used to evaluate expression of particular genes, including the invertebrate genes comprising SEQ ID NOS: 1-261, and mammalian genes substantially the same as invertebrate genes comprising SEQ ID NOS: 1-261. Assays that detect mRNA expression generally involve hybridization of a detectable agent, such as a complementary primer or probe, to the nucleic acid molecule. Such assays include, for example, RNA or dot blot analysis, primer extension, RNase protection assays, reverse-transcription PCR, competitive PCR, real-time quantitative PCR (TaqMan PCR), nucleic acid array analysis, and the like.

Additionally, constructs containing the promoter of a gene and a reporter gene (e.g. β-galactosidase, green fluorescent protein, luciferase) can be made by known methods, and used to generate transgenic non-human mammals and invertebrates. In transgenic non-human mammals, expression of the reporter gene is a marker for expression of a gene that modulates a mammalian vestibular system. Likewise, expression of a reporter gene in transgenic invertebrates is a marker for expression of a gene that modulate a geotactic behavior.

Assays that detect protein expression can also be used to evaluate expression of particular genes. Such assays generally involve binding of a detectable agent, such as an antibody or selective binding agent, to the polypeptide in a sample of cells or tissue from the animal. Protein assays include, for example, immunohistochemistry, immunofluorescence, ELISA assays, immunoprecipitation, immunoblot or other protein-blot analysis, and the like.

Those skilled in the art will appreciate that the methods of the invention can be practiced in the absence of knowledge of the sequence or function of the genes associated with a geotactic behavior or genes that modulate the mammalian vestibular system whose expression is evaluated. Expression of such genes can thus be evaluated using assays that examine overall patterns of gene expression characteristic of a geotactic behavior. It will be understood that as these genes are identified or sequenced, specific probes, primers, antibodies and other binding agents can be used to evaluate their expression more specifically using any of the above detection methods.

One assay to examine patterns of expression of genes associated with a geotactic behavior or genes that modulate the mammalian vestibular system, that does not require prior knowledge of their sequence, is mRNA differential display, which is described, for example, in Cirelli et al., *Mol. Brain Res.* 56:293 (1998) and Liang and Pardee, *Mol. Biotech.* 10:261-7 (1998). In such a method, RNA from the animal is reverse-transcribed and amplified by PCR using a particular combination of arbitrary primers. A detectable label, such as an enzyme, biotin, fluorescent dye or a radiolabel, is incorporated into the amplification products. The labeled products are then separated by size, such as on acrylamide gels, and detected by any method appropriate for detecting the label, including autoradiography, phosphoimaging or the like.

Such a method allows concurrent examination of expression of thousands of RNA species. Methods for determining which RNA species correspond to a gene associated with a geotactic behavior or a gene that modulates the mammalian vestibular system, are disclosed herein, for example, comparing gene expression levels in invertebrates that exhibit different geotactic behavior. It can be readily determined whether a particular compound alters this pattern of gene expression, such as by increasing or decreasing the intensity of bands corresponding to genes associated with a geotactic behavior or genes that modulate the mammalian vestibular system.

A further assay to examine patterns of expression of genes is array analysis, in which nucleic acids representative of all or a portion of the genome of an invertebrate or mammal, or representative of all or a portion of expressed genes of an invertebrate or mammal, are attached to a solid support, such as a filter, glass slide, chip or culture plate. Detectably labeled probes, such as cDNA probes, are then prepared from mRNA of an animal, and hybridized to the array to generate a characteristic, reproducible pattern of spots associated with, for example, a geotactic behavior. It can be readily determined whether a particular candidate compound alters this pattern of gene expression, such as by increasing or decreasing the intensity of one or more spots.

Following identification of patterns of gene expression, those skilled in the art can clone the genes, if desired, using standard molecular biology approaches. For example, a band identified by differential display can be eluted from a gel and sequenced, or used to probe a library to identify the corresponding cDNA or genomic DNA. Likewise, a gene from an array can be identified based on its known position on the array, or cloned by PCR or by probing a library.

If desired, any of the expression and activity assays described above can be used in combination, either sequentially or simultaneously. Such assays can also be partially or completely automated, using methods known in the art.

Samples of the invertebrate collected for measuring gene expression levels can include any organ known or suspected of influencing geotaxis. Exemplary organs can be found in the head, neck, legs and antennae, and include, for example, a brain. Samples can be collected from an invertebrate at various occasions, including before and/or after feeding, before and/or after administration of a compound, before, during and/or after a period of high activity level, or before and/or after participating in a measurement of the geotactic behavior of the invertebrate. Typically, samples are collected under the same conditions as the conditions that geotactic measurements are carried out, for example at about the same time of day, about the same amount of time after feeding, about the same environmental conditions, and the like. Samples can also be collected immediately following measurement of geotactic behavior. For example, samples from a first and a second invertebrate can be collected immediately after subjecting the first and second invertebrates to conditions in which the first invertebrate exhibits a geotactic behavior different than a geotactic behavior exhibited by the second invertebrate. In the context of sample collection, "immediately after" refers to a short time period following measurement of geotactic behavior in which little or no manipulation of the invertebrate occurs after geotactic measurement but prior to sample collection. Typically, this time period is less than 5 minutes after measuring geotactic behavior, but the time period can also be less than 10 minutes, less than 20 minutes or less than 30 minutes after measuring geotactic behavior.

Assays to evaluate expression of genes can involve sacrificing the animal at a selected time, homogenizing the entire animal, or a portion containing the brain or sensory organs, and extracting either mRNA or proteins therefrom. Alternatively, such assays can be performed in biopsied tissue from the invertebrate.

Gene expression levels can be measured on two or more occasions or in two or more groups of invertebrates, and compared to each other. For example, gene expression can be measured in a strain that exhibits negative geotaxis and gene expression can be measured in a strain showing "normal" (wild type) geotaxis. Gene expression levels of the two strains can then be compared, and genes expressed at significantly different levels identified. Genes that are expressed at significantly different levels can be termed "differentially expressed" genes. Significantly different levels are levels that vary from each other by an amount greater than a reference amount. A reference amount can be, for example, based on the variability of expression levels between invertebrates that ideally would have identical expression levels (i.e., having identical genetic makeup, age, gender, raised under identical conditions, and the like). In such a situation, a significantly different level can be a difference that is greater than the mean difference observed between expression levels, or greater than the largest expression level difference observed between most or all genes in the ideally identical organisms. Alternatively, significantly different levels can be based on the composite variability of gene expression levels between two or more strains. For example, the mean or median difference between gene expression levels can be determined between a large number of different strains. Any difference in expression that is greater than the mean or median difference can be considered differentially expressed. Other reference levels defining a significant difference can be determined by one of skill in the art according to the desired comparison between two or more invertebrates.

Differential expression can also be determined for invertebrates of the same strain that have been subjected to conditions in which a first group of members of a strain exhibit a geotactic behavior different from the geotactic behavior of a second group of members of the strain. This can be carried out, for example, by administration of a compound, presence of light, time of day, and the like. Differential expression is then determined by measuring expression levels in the two groups and identifying genes expressed at significantly different levels.

A gene that is differentially expressed in two invertebrate groups that exhibit different levels of geotactic behavior can be considered a gene associated with invertebrate geotactic behavior. As used in regard to invertebrate geotactic behavior, "associated" refers to the correlation of a gene with a modulation in invertebrate geotactic behavior. For example, a gene associated with geotactic behavior can be a gene identified as more highly expressed in invertebrates that exhibit negative geotactic behavior than in invertebrates that exhibit positive geotactic behavior, or alternatively, wild type geotactic behavior. The sequence and function of such an associated gene can be previously known or unknown. Exemplary genes associated with invertebrate geotactic behavior are protein tyrosine phosphatase, non-muscle myosin heavy-chain, cysteine proteinase-1, serine/threonine protein kinase, macrophage receptor protein, cryptochrome, prospero, pigment-dispersing-factor, cyclin A and pendulin. Additional exemplary genes associated with invertebrate geotactic behavior are genes that contain a nucleic acid sequence selected from SEQ ID NOS:1-261. Such a gene associated with invertebrate geotactic behavior can be substantially the same as at least one mammalian gene that modulates a mammalian vestibular system. Therefore, genes such as protein tyrosine phosphatase, non-muscle myosin heavy-chain, cysteine proteinase-1, serine/threonine protein kinase, macrophage receptor protein, cryptochrome, prospero, Pigment-dispersing factor, cyclin A and pendulin, and genes that contain a nucleic acid sequence selected from SEQ ID NOS:1-261 can be substantially the same as genes that modulate a mammalian vestibular system.

As used herein, the term "expression profile" refers to any read-out that provides a qualitative or quantitative indication of the expression or activity of a single gene, or of multiple genes. An expression profile can, for example, indicate the expression or activity of one, or of least 2, 5, 10, 20, 50, 100, 265, or more genes. An expression profile can, for example, indicate the expression or activity in a mammal of mammalian homologs of one or more genes associated with invertebrate geotactic behavior. An expression profile can also, for example, indicate the expression or activity in an invertebrate of one more genes associated with invertebrate geotactic behavior. An expression profile can indicate expression or activity of one, a few, many, or all of these genes. An expression profile can also indicate expression or activity of other genes not previously associated with geotactic behavior.

The methods of the invention can be used to identify expression levels of any subset of genes desired to characterize a particular graviperceptive disorder. A subset of genes can be chosen based on functional linkage of the genes including, for example, genes expressing proteins that interact in a signal transduction system or a metabolic system; physical linkage of the genes including, for example, proximity on a chromosome or any other criteria.

An expression profile can be, for example, a quantitative or qualitative measure of expression of mRNA expressed by one or more genes. A variety of methods of detecting or quantitating mRNA expression have been described above in connection with invertebrate screening assays and include, but are not limited to, Northern or dot blot analysis, primer extension, RNase protection assays, differential display, reverse-transcription PCR, competitive PCR, real-time quantitative PCR (TaqMan PCR), and nucleic acid array analysis.

An expression profile can also be a quantitative or qualitative measure of expression of polypeptides encoded by one or more genes. Methods of detecting or quantitating protein expression have been described above in connection with invertebrate screening assays, and include, but are not limited to, immunohistochemistry, immunofluorescence, immunoprecipitation, immunoblot analysis, and various types of ELISA analysis, including ELISA analysis using arrays of polypeptide-specific antibodies bound to solid supports. Additional methods include two-dimensional gel electrophoresis, MALDI-TOF mass spectrometry, and ProteinChip™/SELDI mass spectrometry technology.

An expression profile can also be a direct or indirect measure of the biological activity of polypeptides encoded by one or more genes. A direct measure of the biological activity of a polypeptide can be, for example, a measure of its enzymatic activity, using an assay indicative of such enzymatic activity. An indirect measure of the biological activity of a polypeptide can be its state of modification (e.g. phosphorylation, glycosylation, or proteolytic modification) or localization (e.g. nuclear or cytoplasmic), where the particular modification or localization is indicative of biological activity. A further indirect measure of the biological activity of a polypeptide can be the abundance of a substrate or metabolite of the polypeptide, such as a neurotransmitter, where the abundance of the substrate or metabolite is indicative of the biological activity of the polypeptide. Appropriate assays for measuring enzyme activity, polypeptide modifications, and substrates and metabolites or polypeptides, will depend on the biological activity of the particular polypeptide.

The appropriate method to use in determining an expression profile can be determined by those skilled in the art, and will depend, for example, on the number of genes being profiled; whether the method is performed in vivo or in a sample; the type of sample obtained; whether the assay is performed manually or is automated; the biological activity of the encoded polypeptide; the abundance of the transcript, protein, substrate or metabolite being detected; and the desired sensitivity, reproducibility and speed of the method.

An expression profile can be established in vivo, such as by diagnostic imaging procedures using detectably labeled antibodies or other binding molecules, or from a sample obtained from an individual. As changes in gene expression in the brain are likely to be most relevant to modulation of geotactic behavior or of a mammalian vestibular system, appropriate samples can contain neural tissue, cells derived from neural tissues, or extracellular medium surrounding neural tissues, in which polypeptides to be detected or their metabolites are present. Thus, an appropriate sample for establishing a expression profile in humans can be, for example, cerebrospinal fluid, whereas in laboratory animals an appropriate sample can be, for example, a biopsy of the brain.

However, expression of genes can also be modulated in tissues other than neural tissue, and polypeptides or their metabolites can be secreted into bodily fluids. In particular, in the case of genetic disorders, including familial vestibulopathy, periodic vestibulocerebellar ataxia, Meniere's disease, von Hippel-Lindau syndrome, osteogenesis imperfecta, myokymia with periodic ataxia, Friedreichs ataxia, autosomal dominant nonsyndromic sensorineal deafness 9 or enlarged vestibular aqueduct syndrome, any alteration in gene expression or function can be manifest in every cell in the body that expresses the gene. Alternatively, a genetic disorder can be determined using any cell that contains geomic DNA, by detecting a mutation such as an insertion, deletion or modification of a gene associated with invertebrate geotaxis or a gene that modulates a mammalian vestibular system. An expression profile or presence of a genetic mutation can be determined from any convenient cell or fluid sample from the body, including blood, lymph, urine, breast milk, skin, hair follicles, cervix or cheek. Additionally, cells can readily be obtained using slightly more invasive procedures, such as punch biopsies of the breast or muscle, from the bone marrow or, during surgery, from essentially any organ or tissue of the body.

An expression profile can also be determined from cells in culture. These cells can be immortalized cells from a selected individual invertebrate or mammal, or can be cells from any known established invertebrate or mammalian cell line, such as those available from ATCC (Mannassas, Va.). The expression profile of these cells can be measured, for example, in the absence and presence of a compound. A compound that modulates the expression of an invertebrate gene associated with geotactic behavior or of a mammalian gene substantially the same as an invertebrate gene associated with geotactic behavior can be a compound that modulates the mammalian vestibular system.

The number of different compounds to screen in the methods of the invention can be determined by those skilled in the art depending on the application of the method. For example, a smaller number of candidate compounds would generally be used if the type of compound that is likely to modulate geotactic behavior is known or can be predicted, such as when derivatives of a lead compound are being tested. However, when the type of compound that is likely to modulate geotactic behavior is unknown, it is generally understood that the larger the number of candidate compounds screened, the greater the likelihood of identifying a compound that modulates geotactic behavior. Therefore, the methods of the invention can employ screening individual compounds separately or populations of compounds including small populations and large or diverse populations, to identify a compound that modulates geotactic behavior, and thereby also modulates a mammalian vestibular system.

Methods for producing libraries of candidate compounds to use in the methods of the invention, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art. Libraries containing large numbers of natural and synthetic compounds also can be obtained from a variety of commercial sources.

Genetic methods of identifying new genes associated with invertebrate geotactic behavior that are applicable to a variety of invertebrates are known in the art. For example, the invertebrate can be mutagenized using chemicals, radiation or insertions (e.g. transposons, such as P element mutagenesis), appropriate crosses performed, and the progeny screened for phenotypic differences in geotatic behavior compared with normal controls. The gene can then be identified by a variety of methods including, for example, linkage analysis or rescue of the gene targeted by the inserted element. Genetic methods of identifying genes are described for *Drosophila*, for example, in Greenspan, *Fly Pushing: The Theory and Practice of Drosophila Genetics*, Cold Spring Harbor Laboratory Press (1997).

In accordance with another embodiment of the invention, a method is provided for identifying a gene that modulates a mammalian vestibular system. The invention is carried out by obtaining a first and a second strain of an invertebrate, subjecting the first and second invertebrate strains to conditions in which said first strain exhibits a geotactic behavior different than a geotactic behavior exhibited by the second strain, measuring gene expression levels in the first and second strains, and identifying one or more genes that are differentially expressed in the first strain relative to the second strain, where a mammalian gene containing substantially the same nucleic acid sequence as the one or more differentially expressed genes modulates the mammalian vestibular system.

There are numerous important diagnostic, therapeutic, and screening applications that arise from identification of novel genes that modulate a mammalian vestibular system, together with knowledge that modulation of expression or activity of such genes that modulate a mammalian vestibular system is an effective method of modulating a mammalian vestibular system. For example, an expression or activity profile of one or many genes that modulate a mammalian vestibular system can be established that is a molecular fingerprint of the sensitivity of a mammalian vestibular system or disorder thereof. Thus, in diagnostic applications, it can readily be determined, by comparing the expression profile of an individual to one or more reference profiles, whether that individual suffers from, or is susceptible to, a particular graviperceptive disorder. Likewise, the sensitivity of a mammalian vestibular system and the effect of medications or medical procedures on the sensitivity of a mammalian vestibular system, can be determined at the molecular level. Such determinations allow for more appropriate determination and use of therapeutics for treating graviperceptive disorders.

In screening applications, identification of genes that modulate a mammalian vestibular system and their role in the sensitivity of a mammalian vestibular system allows novel compounds that modulate a mammalian vestibular system to be identified, lead compounds to be validated, and the molecular effects of these compounds and other known compounds that modulate a mammalian vestibular system to be characterized, by determining the effect of these compounds on an expression profile. For example, the ability of a compound to alter an expression profile of an individual to correspond more closely to a desired sensitivity of a mammalian vestibular system can be determined. Likewise, the ability of a compound, administered to an individual with a particular graviperceptive disorder, to alter the expression profile to correspond more closely to the profile of an unaffected or normal individual can be determined. The compounds so identified, validated or characterized from such assays can be administered to unaffected or normal individuals to enhance or reduce sensitivity of a mammalian vestibular system, as desired, or to individuals having a graviperceptive disorder to treat the disorder or induce more normal mammalian vestibular system sensitivity.

The invention thus provides an isolated nucleic acid having mammalian vestibular system-modulating activity, or fragment thereof, comprising substantially the same nucleic acid sequence as a nucleic acid selected from the group consisting of SEQ ID NOS:1-261.

The isolated nucleic acid molecules of the invention having mammalian vestibular system modulating activity contain sequences substantially the same as sequences from genes associated with invertebrate geotactic behavior identified from mRNA differential display analysis performed in *Drosophila melanogaster* (SEQ ID NOS:1-258). SEQ ID NOS: 1-23 correspond to genes that are downregulated in invertebrates that exhibit negative geotactic behavior relative to invertebrates that exhibit positive geotactic behavior. SEQ ID NOS: 24-258 correspond to genes that are upregulated in invertebrates that exhibit negative geotactic behavior relative to invertebrates that exhibit positive geotactic behavior.

In accordance with the present invention, various nucleic acids selected from SEQ ID NOS:1-261 are homologous to known genes. For example, SEQ ID NO:233 is similar to mouse α-tectorin, which is one of the major noncollagenous components of the tectorial membrane of the inner ear (Legan et al., *J. Biol. Chem.* 272:8791-8801 (1997)). Mutations in human α-tectorin cause a variety of hereditary forms of deafness and inner ear disorders (Verhoeven et al., *Nature Genet.* 19:60-62 (1998); Mustapha et al., *Hum. Molec. Genet.* 8:409-412 (1999)).

The nucleic acid of SEQ ID NO:108 is similar to the protein gp330/megalin/SGP2, which encodes an endocytic receptor for apolipoprotein J/clusterin (Kirszbaum et al., *EMBO J.* 8:711-718 (1989)) and is widely expressed in the brain (Danik et al., *J. Comp. Neurol.* 334:209-227 (1993)). Knockout mice die perinatally with altered development of the brain (Wilnow et al., *Proc. Natl. Acad. Sci. USA* 93:8460-8464 (1996)).

SEQ ID NOS:117 and 250 are similar to two human genes involved in regulating synaptic function which are respectively termed PIN, protein inhibitor of neuronal nitric oxide synthase (Jaffrey and Snyder, *Science* 274:774-777 (1996)), and SV2, synaptic vesicle transporter-2 (Schivell et al., *J. Biol. Chem.* 271:7770-7775 (1996)).

SEQ ID NO:225 is similar to a human gene, APP-binding protein, which can be associated with synaptic mechanisms (Russo et al., *FEBS Lett.* 434:1-7 (1998)).

The SCA2/ataxin-2 gene, which is similar to SEQ ID NO:1, is responsible for a hereditary spinocerebellar ataxia in humans and mice (Imbert et al., *Nature Genet.* 14:285-291 (1997)). It is expressed throughout brain especially in the trochlear nuclei which receive projections from the ear (Pulst et al., *Nature Genet.* 14:269-276 (1996)). The protein contains a consensus cleavage site for an obligatory processing step by apopain, a cysteine protease (Sanpei et al., *Nature Genet.* 14:277-284 (1996)). Thus this gene not only plays a role in a hereditary ataxia, but also requires cleavage by a cysteine-protease. SEQ ID NO:113 corresponds to Cp1, the fly's cysteine-protease (Blake et al., *Dev. Biol.* 203:177-188 (1998)). In this context, it may be significant that SEQ ID NO:1 and 113 are reciprocally regulated in the two different geotactic strains.

SEQ ID NO:98 corresponds to protein tyrosine phosphorylase Ptp61F. Protein tyrosine phosphatases regulate the cytoskeleton (Helmke et al, *J. Cell. Sci.* 111:2465-2475 (1998); Guvakova and Surmacz, *Exp. Cell. Res.* 251:244-255 (1999); Boonstra, *FASEB J.* 13:S35-S42 (1999)), which is key in the mechanotransduction events associated with gravity perception (Ingber, *FASEB J.* 13:S3-S15 (1999)). Non-muscle myosin heavy chain zip, corresponding to SEQ ID NO:37, is another regulator of the cytoskeleton (Young et al., *Genes Dev.* 7:29-41 (1993)). Non-muscle myosins have also been identified in hereditary ataxias and inner ear disorders such as Usher Syndrome in humans (Weil et al., *Proc Natl.Acad. Sci. USA* 93:3232-3237 (1995)) and Snell's walzer in mice (Avraham et al., *Hum. Molec. Genet.* 6:1225-1231 (1997)). SEQ ID NO:191 is similar to α-tubulin, which also fits into this cytoskeletal group, as does the actin-binding double-zinc-finger protein, similar to SEQ ID NO:21 (Roof et al., *J. Cell. Biol.* 138:575-588 (1997)).

Also relevant as a source of phenotypic differences between the selected strains is axon guidance, which is influenced by proteins such as protein tyrosine phosphatases (Desai et al., *Cell* 84:599-609 (1996)), actin-binding double zinc-finger proteins (Lundquist et al., *Neuron* 21:385-392 (1998)) and serine/threonine kinases, such as the serine/threonine kinase nemo, similar to SEQ ID NO:256 (Broughton et al., *J. Cell. Biochem.* 60:584-600 (1996); Broughton et al., *J. Cell. Biochem.* 62:484-494 (1996)). SEQ ID NO:174 corresponds to the mfas (midline fasciclin) gene, which is also involved in axon guidance (Hu et al., *J. Neurobiol.* 35:77-93 (1998)).

The croquemort gene in *Drosophila*, corresponding to SEQ ID NO:8, encodes a macrophage receptor for apoptotic cells (Franc et al., *Immunity* 4:431-443 (1996)) and is involved both in apoptosis and in tissue modeling. of possible relevance to graviperception and response is the onset of apoptosis in vestibular nuclei after prolonged stimulation (Mitchell et al., *Neurosci. Lett.* 198:153-156 (1995)) and in lymphocytes after space-flight (Lewis et al., *FASEB J.* 12:1007-1018 (1998)).

SEQ ID NO:166 is similar to DnaJ, a highly conserved protein that mediates gravity responsiveness in plants (Sedbrook et al., *Proc. Natl. Acad. Sci. USA* 96:1140-1145 (1999)). DNAJ is also associated with spinocerebellar ataxia in humans (Cummings et al., *Nat. Genet.* 19:148-54 (1998)). Cryptochrome (cry), which corresponds to SEQ ID NO:17, is a flavo-protein highly conserved from flies to plants to humans that is involved in responses to environmental stimuli (Cashmore et al., *Science* 284:760-765 (1999)).

Several sequences corresponding to *Drosophila* genes with roles in neuronal development or signaling also showed differential expression. These include SEQ ID NO:15, corresponding to the prospero gene, a homeobox gene important for sensory neuron specification (Vaessin et al., *Cell* 67:941-953 (1991), Reddy and Rodrigues, *Development* 126:2083-2092 (1999)) SEQ ID NO:3, and homologous to PROX1 (human homolog NP_002754) corresponding to pigment dispersing factor which is involved in mediating circadian rhythms and interacting with circadian clock components, such as cryptochrome (Park and Hall, *J. Biol.*

Rhythms 13:219-228 (1998), Ceriani et al., *Science* 285:553-556 (1999)); SEQ ID NO:128, corresponding to the cell cycle gene cyclin A; and SEQ ID NO:258, corresponding to the Pendulin gene homolog of a nuclear import protein (Torok et al., *J. Cell Biol.* 129:1473-1489 (1995)).

The isolated nucleic acid molecules comprising SEQ ID NO: 1-261 hybridize to mammalian genes, and thus can be used in the diagnostic and screening methods described below. Additionally, the isolated nucleic acid molecules containing sequences substantially the same as one of SEQ ID NOS: 1-261 can be administered in gene therapy methods, including antisense and ribozyme methods, to increase or decrease expression of polypeptides that modulate a mammalian vestibular system. The isolated nucleic acid molecules of the invention can also be used as probes or primers to identify larger cDNAs or genomic DNA, or to identify homologs of the nucleic acid molecules in other species. The isolated nucleic acid molecules can further be expressed to produce polypeptides for use in producing antibodies or for rationally designing inhibitory or stimulatory compounds. Other uses for the isolated nucleic acid molecules of the invention can be determined by those skilled in the art.

As used herein, the term "nucleic acid molecule" refers to both deoxyribonucleic acid (DNA) and ribonucleic acid (RNA) molecules, and can optionally include one or more non-native nucleotides, having, for example, modifications to the base, the sugar, or the phosphate portion, or having a modified phosphodiester linkage. The term nucleic acid molecule includes both single-stranded and double-stranded nucleic acids, representing the sense strand, the anti-sense strand, or both, and includes linear, circular or branched molecules. Exemplary nucleic acid molecules include genomic DNA, cDNA, mRNA and oligonucleotides, corresponding to either the coding or non-coding portion of the molecule, and optionally containing sequences required for expression. A nucleic acid molecule of the invention, if desired, can additionally contain a detectable moiety, such as a radiolabel, a fluorochrome, a ferromagnetic substance, a luminescent tag or a bindably detectable agent such as biotin.

The term "isolated" in reference to a nucleic acid molecule is intended to mean that the molecule is substantially removed or separated from components with which it is naturally associated, or otherwise modified by a human hand, thereby excluding nucleic acid molecules as they exist in nature. An isolated nucleic acid molecule of the invention can be in solution or suspension, or immobilized on a filter, glass slide, chip, culture plate or other solid support. The degree of purification of the nucleic acid molecule, and its physical form, can be determined by those skilled in the art depending on the intended use of the molecule.

The term "comprising" or "containing" in reference to a nucleic acid molecule of the invention, is intended to mean that the nucleic acid molecule can contain additional nucleotide sequences at either the 5' or 3' end of the recited sequence, or branching from an internal position within the recited sequence. The additional nucleotide sequences can, if desired, correspond to sequences that naturally occur within the gene, including intron or exon sequences, promoter sequences, coding sequence, or untranslated regions. Alternatively, the additional nucleotide sequence can correspond to linkers or restriction sites useful in cloning applications; to other regulatory elements such as promoters and polyadenylation sequences that can be useful in gene expression; to epitope tags or fusion proteins useful in protein purification; or the like. Those skilled in the art can determine appropriate sequences flanking the recited nucleotide sequences for a particular application of the method.

The invention also provides isolated oligonucleotides containing at least 15 contiguous nucleotides of a nucleotide sequence referenced as SEQ ID NOS: 1-261, or the anti-sense strand thereof. The isolated oligonucleotides of the invention are able to specifically hybridize to nucleic acid molecules associated with invertebrate geotaxis or with modulation of a mammalian vestibular system under moderately or highly stringent hybridization conditions and thus can be advantageously used, for example, as probes to detect DNA or RNA of a gene associated with invertebrate geotaxis or with modulation of a mammalian vestibular system in a sample; as sequencing or PCR primers; as antisense reagents to administer to an individual to block translation of RNA in cells; or in other applications known to those skilled in the art in which hybridization to a nucleic acid molecule associated with invertebrate geotaxis or with modulation of a mammalian vestibular system is desirable.

As used herein, the term "oligonucleotide" refers to a nucleic acid molecule that includes at least 15 contiguous nucleotides from the reference nucleotide sequence, can include at least 16, 17, 18, 19, 20 or at least 25 contiguous nucleotides, and often includes at least 30, 40, 50, 60, 70, 80, 90, 100, 125, 150, 175, 200 or more contiguous nucleotides from the reference nucleotide sequence.

As used herein, the term "specifically hybridize" refers to the ability of a nucleic acid molecule to hybridize, under moderately or highly stringent conditions as described above, to a desired nucleic acid molecule, without substantial hybridization under the same conditions with nucleic acid molecules that are not the desired nucleic acid molecule. Those skilled in the art can readily determine whether an oligonucleotide of the invention hybridizes to the recited nucleic acid sequence under moderately or highly stringent conditions by performing a hybridization assay in the presence of other nucleic acid molecules, such as total cellular nucleic acid molecules, and detecting the presence or absence of hybridization to the other nucleic acid molecules.

Depending on the intended use of the oligonucleotides of the invention, those skilled in the art can determine whether it is necessary to use an oligonucleotide that specifically hybridizes to the recited nucleic acid molecules. For example, when there are a large number of potential contaminating nucleic acid molecules in the sample, it may be desirable to use an oligonucleotide that specifically hybridizes to the recited nucleic acid molecules. However, when background hybridization is not considered detrimental, when there are few contaminating molecules, or when the oligonucleotide is being used in conjunction with a second molecule, such as a second primer, an oligonucleotide of the invention can be used that does not specifically hybridize to the recited nucleic acid molecules.

If desired, the oligonucleotide containing at least 15 contiguous nucleotides of a nucleotide sequence referenced as SEQ ID NOS: 1-261 can further be capable of specifically hybridizing with a reference nucleic acid molecule. Such a reference nucleic acid sequence can be any pre-determined sequence such as a ployA sequence, a sequence containing a restriction site sequence or a sequence that uniquely identifies the invention oligonucleotice (e.g. a "zip code" sequence).

In one embodiment, the invention provides a primer pair for detecting nucleic acid molecules associated with invertebrate geotaxis or with modulation of a mammalian vestibular system. The primer pair contains two isolated oligonucleotides, each containing at least 15 contiguous nucleotides of one of the nucleotide sequences referenced as SEQ ID NOS: 1-261, with one sequence representing the sense strand, and one sequence representing the anti-sense strand. The primer pair can be used, for example, to amplify nucleic acid molecules associated with invertebrate geotaxis or with modulation of a mammalian vestibular system by RT-PCR or PCR.

The isolated nucleic acid molecules and oligonucleotides of the invention can be produced or isolated by methods known in the art. The method chosen will depend, for example, on the type of nucleic acid molecule one intends to isolate. Those skilled in the art, based on knowledge of the nucleotide sequences disclosed herein, can readily isolate the nucleic acid molecules of the invention as genomic DNA, or desired introns, exons or regulatory sequences therefrom; as full-length cDNA or desired fragments therefrom; or as full-length mRNA or desired fragments therefrom, by methods known in the art.

One useful method for producing an isolated nucleic acid molecule of the invention involves amplification of the nucleic acid molecule using the polymerase chain reaction (PCR) and oligonucleotide primers specific for the desired nucleic acid molecule and, optionally, purification of the resulting product by gel electrophoresis. Either PCR or reverse-transcription PCR (RT-PCR) can be used to produce a nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

A further method of producing an isolated nucleic acid molecule of the invention is by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled nucleic acid molecule having a nucleotide sequence disclosed herein. Additionally, an expression library can be screened with an antibody raised against a polypeptide encoded by a nucleic acid disclosed herein. The library clones containing nucleic acid molecules of the invention can be isolated from other clones by methods known in the art and, if desired, fragments therefrom can be isolated by restriction enzyme digestion and gel electrophoresis.

Furthermore, isolated nucleic acid molecules and oligonucleotides of the invention can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and nucleic acid molecules containing modified nucleotides or linkages.

In one embodiment, the isolated nucleic acid molecules or oligonucleotides of the invention are attached to a solid support, such as a chip, filter, glass slide or culture plate, by either covalent or non-covalent methods. Methods of attaching nucleic acid molecules to a solid support, and the uses of nucleic acids in this format in a variety of assays, including manual and automated hybridization assays, are well known in the art. A solid support format is particularly appropriate for automated diagnostic or screening methods, where simultaneous hybridization to a large number of genes associated with invertebrate geotaxis or with modulation of a mammalian vestibular system is desired, or when a large number of samples are being handled.

In another embodiment, the invention provides kits containing two or more isolated nucleic acid molecules or oligonucleotides. At least one nucleic acid molecule of the kit contains a nucleotide sequence selected from the group consisting of SEQ ID NOS: 1-261, or modification thereof or at least 15 contiguous nucleotides of a nucleic acid sequence referenced as SEQ ID NO: 1-261. An exemplary kit is a solid support containing an array of isolated nucleic acid molecules or oligonucleotides of the invention, including, for example, at least 3, 5, 10, 20, 30, 40, 50, 75, 100, 265 or more isolated nucleic acid molecules or oligonucleotides.

A further exemplary kit contains one or more PCR primer pairs, or two or more hybridization probes, which optionally can be labeled with a detectable moiety for detection of nucleic acid molecules. The kits of the invention can additionally contain instructions for use of the molecules for diagnostic purposes in a clinical setting, or for drug screening purposes in a laboratory setting.

If desired, the kits containing two or more isolated nucleic acid molecules or oligonucleotides can contain nucleic acid molecules corresponding to genes that are upregulated in invertebrates exhibiting negative geotactic behavior, or are downregulated in invertebrates exhibiting negative geotactic behavior. Additionally, the kits containing two or more isolated nucleic acid molecules or oligonucleotides can contain nucleic acid molecules corresponding to sequences identified from *Drosophila* screens or other invertebrate screens, from rat screens, from screens in other mammals, or any combination thereof.

The invention also provides a vector containing an isolated nucleic acid molecule associated with invertebrate geotaxis or with modulation of a mammalian vestibular system. The vectors of the invention are useful for subcloning and amplifying an isolated nucleic acid molecule, for recombinantly expressing a polypeptide, and in gene therapy applications, described further below. A vector of the invention can include a variety of elements useful for cloning and/or expression of nucleic acid molecules associated with invertebrate geotaxis or with modulation of a mammalian vestibular system, such as enhancer sequences and promoter sequences from a viral, bacterial, invertebrate or mammalian gene, which provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillan resistance gene, useful for selecting transformants in prokaryotic cells; and versatile multiple cloning sites for inserting nucleic acid molecules of interest.

A variety of cloning and expression vectors are commercially available, and include, for example, viral vectors such as a bacteriophage, baculovirus, adenovirus, adeno-associated virus, herpes simplex virus and retrovirus; cosmids or plasmids; bacterial artificial chromosome vectors (BACs) and yeast artificial chromosome vectors (YACs). Such vectors and their uses are well known in the art.

The invention also provides host cells that contain a vector containing a nucleic acid molecule of the invention.

Exemplary host cells include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (e.g. *Drosophila*), yeast cells (e.g. *S. cerevisiae, S. pombe*, or *Pichia pastoris*) and prokaryotic cells (e.g. *E. coli*). Further exemplary host cells are cells publicly available through sources such as ATCC (Manassas, Va.). Methods of introducing a vector of the invention into such host cells are well known in the art.

The methods of isolating, cloning and expressing nucleic acid molecules of the invention referred to herein are routine in the art and are described in detail, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (2000), which are incorporated herein by reference.

The invention further provides transgenic non-human animals that are capable of expressing wild-type nucleic acids, dominant-negative nucleic acids, antisense nucleic acids, or ribozymes that target nucleic acids, where the nucleic acids are associated with invertebrate geotaxis or with modulation of a mammalian vestibular system. Such animals have correspondingly altered expression of polypeptides associated with invertebrate geotaxis or with modulation of a mammalian vestibular system, and can thus be used to elucidate or confirm the function of such polypeptides, or in whole-animal assays to determine or validate the physiological effect of compounds that potentially modulate a mammalian vestibular system. The transgene may additionally comprise an inducible promoter and/or a tissue specific regulatory element, so that expression can be induced or restricted to specific cell types. Exemplary transgenic non-human animals expressing nucleic acids and nucleic acids that alter gene expression include mouse and *Drosophila*. Methods of producing transgenic animals are well known in the art.

The invention also provides an isolated polypeptide having mammalian vestibular system-modulating activity, or fragment thereof, containing substantially the same amino acid sequence as an amino acid sequence encoded by a nucleic acid sequence selected from the group consisting of SEQ ID NOS:1-261. Isolated polypeptides of the invention can be used in a variety of applications. For example, isolated polypeptides can be used to generate specific antibodies, or in screening or validation methods where it is desired to identify or characterize compounds that alter the activity of polypeptides that with modulate a mammalian vestibular system.

The isolated polypeptides of the invention can be prepared by methods known in the art, including biochemical, recombinant and synthetic methods. For example, invention polypeptides can be purified by routine biochemical methods from neural cells or other cells that express abundant amounts of the polypeptide. An invention polypeptide having any desired boundaries can also be produced by recombinant methods. Recombinant methods involve expressing a nucleic acid molecule encoding the desired polypeptide in a host cell or cell extract, and isolating the recombinant polypeptide, such as by routine biochemical purification methods described above. To facilitate identification and purification of the recombinant polypeptide, it is often desirable to insert or add, in-frame with the coding sequence, nucleic acid sequences that encode epitope tags or other binding sequences, or sequences that direct secretion of the polypeptide. Methods for producing and expressing recombinant polypeptides in vitro and in prokaryotic and eukaryotic host cells are well known in the art. Furthermore, invention polypeptides can be produced by chemical synthesis. If desired, such as to optimize their functional activity, stability or bioavailability, such molecules can be modified to include D-stereoisomers, non-naturally occurring amino acids, and amino acid analogs and mimetics.

Also provided are antibodies that specifically bind polypeptides encoded by the nucleic acid molecules of the invention. Such antibodies can be used, for example, in diagnostic assays such as ELISA assays to detect or quantitate the expression of polypeptides of the invention; to purify polypeptides of the invention; or as therapeutic compounds to selectively target polypeptide of the invention. Such antibodies, if desired, can be bound to a solid support, such as a chip, filter, glass slide or culture plate.

As used herein, the term "antibody" is used in its broadest sense to include polyclonal and monoclonal antibodies, as well as antigen binding fragments of such antibodies. An antibody of the invention is characterized by having specific binding activity for a polypeptide associated with invertebrate geotaxis or with modulation of a mammalian vestibular system or fragment thereof of at least about $1 \times 10^5$ M$^{-1}$. Thus, Fab, F(ab')$_2$, Fd and Fv fragments of a polypeptide-specific antibody of the invention, which retain specific binding activity for the polypeptide associated with invertebrate geotaxis or with modulation of a mammalian vestibular system, are included within the definition of an antibody. Methods of preparing polyclonal or monoclonal antibodies against polypeptides are well known in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be produced or obtained by methods known in the art, including constructing the antibodies using solid phase peptide synthesis, recombinant production, or screening combinatorial libraries consisting of variable heavy chains and variable light chains.

The invention provides diagnostic methods based on the newly identified and characterized genes described herein. In one embodiment, the invention provides a method of diagnosing a graviperceptive disorder in an individual. The method consists of determining an expression profile of the individual, and comparing that profile to a reference profile indicative of the graviperceptive disorder. Correspondence between the profile of the individual and the reference profile indicates that the individual has the graviperceptive disorder. In one embodiment, at least one of the genes profiled is a gene containing a nucleic acid sequence substantially the same as one of SEQ ID NOS: 1-261. Typically, at least one of the genes profiled is selected from the group consisting of α-tectorin, gp 390, PIN, SV2, PROX1, actin-binding double-zinc-finger protein, SCA2 and APP-binding protein.

The methods of diagnosing graviperceptive disorders have numerous applications. For example, a variety of different types of graviperceptive disorders are known, many of which are extremely common in a given population, some of which are more rare. Appropriate diagnosis of a graviperceptive disorder will allow more effective treatments: using currently available mammalian vestibular system modulating compounds or methods; using compounds identified from the screens described herein; using the therapeutic methods described herein; or any combination of these treatments. Likewise, the methods of diagnosing graviperceptive disorders are applicable to monitoring the course of therapy for the disorder, such that appropriate modifications can be made if needed.

Furthermore, the methods of diagnosing graviperceptive disorders are applicable to screening for graviperceptive disorders among the general population, or among populations in whom graviperception influences the safety of the individual or the general population (e.g. transportation workers, individual operating heavy machinery, and the like). Additional useful applications of the diagnostic methods of the invention can be determined by those skilled in the art.

Appropriate laboratory animal models of human graviperceptive disorders of interest are known in the art or can readily be developed by transgenic and knockout methods that alter expression or activity of genes associated with invertebrate geotaxis or with modulation of a mammalian vestibular system, or by pharmacological, surgical or environmental manipulation.

The diagnostic methods of the invention can also advantageously be used to characterize previously unrecognized graviperceptive disorders, or to newly categorize graviperceptive disorders, based on characteristic patterns of expression or activity of genes associated with invertebrate geotaxis or modulation of a mammalian vestibular system. Such newly characterized or categorized disorders are also encompassed by the term "graviperceptive disorder." The diagnostic methods of the invention can also be advantageously used to identify the specific genes most closely associated with, and thus likely to play a causative role, in particular graviperceptive disorders. Such genes are targets for modulation by gene therapy methods or by selective targeting of the encoded product with therapeutic compounds.

In a further embodiment of the diagnostic methods of the invention, there is also provided a method of determining sensitivity of the vestibular system in an individual. The method consists of determining an expression profile of the individual, and comparing that profile to a reference profile indicative of a predetermined sensitivity of a vestibular system. Correspondence between the profile of the individual and the reference profile indicates that the individual exhibits the predetermined sensitivity of a vestibular system. At least one of the vigilance genes profiled is a gene containing a nucleic acid sequence substantially the same as one of SEQ ID NOS: 1-261.

Those skilled in the art understand that the methods described above for diagnosing graviperceptive disorders and determining sensitivity of a vestibular system can readily be applied to methods of screening for novel mammalian vestibular system-modulating compounds; to methods of validating the efficacy of mammalian vestibular system-modulating compounds identified by other methods, such as by the invertebrate screening methods described above; to methods of determining effective dose, time and route of administration of known mammalian vestibular system-modulating compounds; to methods of determining the effects of mammalian vestibular system-modulating compounds on homeostatic regulation of graviperception; to methods of determining the molecular mechanisms of action of known mammalian vestibular system-modulating compounds; and the like. Such methods can be performed in laboratory animals, such as mice, rats, rabbits, dogs, cats, pigs or primates, in veterinary animals, or in humans.

Thus, in one embodiment, the invention provides a method of determining the efficacy of a compound in treating a graviperceptive disorder. The method consists of administering a compound to an individual having a graviperceptive disorder, and determining an effect of the compound on the expression profile of the individual. A compound that modulates the expression profile of the individual to correspond to an unaffected or normal profile indicates that the compound is effective in treating the graviperceptive disorder. At least one of the vigilance genes profiled is a gene containing a nucleic acid sequence substantially the same as one of SEQ ID NOS: 1-261.

As used herein, the term "treating" is intended to include preventing, ameliorating, curing, and reducing the severity of the graviperceptive disorder or symptoms associated with a graviperceptive disorder. Those skilled in the art understand that any degree of reduction in severity of a graviperceptive disorder can improve the health or quality of life of the individual. The effect of the therapy can be determined by those skilled in the art, by comparison to baseline values for symptoms or clinical or diagnostic markers associated with the disorder.

In another embodiment, the invention provides a method of determining the efficacy of a compound in modulating a mammalian vestibular system. The method consists of administering the compound to an individual, and determining an effect of the compound on the expression profile of the individual. A compound that modulates the expression profile indicates that the compound modulates a mammalian vestibular system. At least one of the genes profiled is a gene containing a nucleic acid sequence substantially the same as one of SEQ ID NOS: 1-261.

The genes to profile can be determined by those skilled in the art, depending on the type of mammalian vestibular system-modulating compound it is desired to identify or characterize. For example, it may be advantageous to examine the effect of a compound primarily on single genes such as α-tectorin, gp330, PIN, SV2, PROX1, actin-binding double-zinc-finger protein, SCA2 and APP-binding protein; or only primarily on a gene substantially the same as an invertebrate gene whose upregulated expression or activity corresponds to negative invertebrate geotaxis; or only primarily on a gene substantially the same as an invertebrate gene whose downregulated expression or activity corresponds to negative invertebrate geotaxis.

The compounds so identified that alter an expression profile can, for example, increase or, decrease graviperception as described above in relation to invertebrate screening methods. The effect of these compounds on graviperception can be corroborated, or further evaluated, in either invertebrates or mammals. Compounds that beneficially modulate the sensitivity of a mammalian vestibular system can be administered as therapeutics to humans and veterinary animals.

Once genes associated with graviperceptive disorders are identified, the expression or activity of such genes in humans or veterinary animals can be selectively targeted in order to prevent or treat the graviperceptive disorder. The diagnostic, screening and validation methods of the invention are useful in determining appropriate genes to target and appropriate therapeutic compounds to use for a particular indication. Additional genes associated with invertebrate geotaxis or with modulation of a mammalian vestibular system can be identified by the methods described herein or by other methods, including differential display, arrays, and other forms of expression or activity analysis in invertebrates and mammals; genetic methods, such as by randomly or specifically targeting genes in model organisms such as *Drosophila* or mouse, or by mapping genes associated with graviperceptive disorders or from screens for genes associated with other behaviors or molecular pathways that are subsequently determined to be associated with graviperception.

Thus, in one embodiment, the invention provides a method of treating a graviperceptive disorder in an individual. The method consists of administering to an individual having a graviperceptive disorder a compound that modulates the expression profile of the individual to correspond to a normal expression profile. At least one of the genes profiled is a gene containing a nucleic acid sequence substantially the same as one of SEQ ID NOS: 1-261. In one embodiment, the modulated gene is a gene containing a nucleic acid sequence substantially the same as one of SEQ ID NOS: 1-261.

In a further embodiment, the invention provides a method of modulating the vestibular system in a mammal. The method consists of administering to an individual a compound that modulates the activity or expression of a gene that modulates a mammalian vestibular system. In one embodiment, the modulated gene is a gene containing a nucleic acid sequence substantially the same as one of SEQ ID NOS: 1-261.

The therapeutic methods of the invention involve determining the effect of the compound on an expression profile. Thus, the therapeutic methods of the invention are not intended to encompass administration of mammaliam vestibular system-modulating drugs which inherently may modulate expression or activity of one or more genes associated with invertebrate geotaxis or with modulation of a mammalian vestibular system, in the absence of a determination that such drugs predictably modulate invertebrate geotaxis or predictably modulate expression profile of one or more genes associated with invertebrate geotaxis or with modulation of a mammalian vestibular system. The effect of the compound on the expression profile of a particular individual to whom the compound is administered need not be determined, however, if the effect of the compound on expression profile in other individuals has previously been established, and such effect on expression profile can be shown to be reproducible across individuals. Of course, it is understood that the expression profile of the individual can, if desired, be determined prior to administration of the compound, and/or monitored during the course of therapy, using modifications of the diagnostic methods described herein.

A variety of compounds can be used to modulate the expression profile in individuals having a graviperceptive disorder or in whom modulation of sensitivity of the vestibular system is desired. Compounds can be determined or designed to alter gene expression or activity by a variety of mechanisms, such as by directly or indirectly increasing or decreasing the expression of a gene. For example, a compound can directly interact with a gene promoter; can interact with transcription factors that regulate gene expression; can bind to or cleave a gene transcript (e.g. antisense oligonucleotides or ribozymes); can alter half-life of the transcript; or can itself be an expressible gene associated with invertebrate geotaxis or with modulation of a mammalian vestibular system. A compound can also act by increasing or decreasing activity of one or more encoded polypeptides. For example, the compound can specifically bind to a polypeptide and alter its activity or half-life; can bind to a substrate or modulator of a polypeptide; or can be a polypeptide associated with invertebrate geotaxis or with modulation of a mammalian vestibular system or active portion thereof.

The type of compound to be used can be determined by those skilled in the art, and will depend, for example, on factors such as the severity of the disorder; the time period over which treatment of the disorder is desired; the cellular location of the molecule to be targeted; whether the compound is administered in a clinical setting or by the individual; or whether an individual is presently experiencing symptoms of a graviperceptive disorder or anticipates experiencing symptoms of a graviperceptive disorder.

Compounds can be formulated in pharmaceutical compositions in such a manner to ensure proper distribution in vivo. For example, the blood-brain barrier (BBB) excludes many highly hydrophilic compounds. To ensure that the compounds of the invention cross the BBB, they can be formulated, for example, in liposomes, or chemically derivatized. Methods of introduction of a compound of the invention include, but are not limited to, intradermal, intramuscular, intraperitoneal, intravenous, subcutaneous, oral, intranasal, intraspinal and intracerebral routes. A compound can also appropriately be introduced by rechargable or biodegradable polymeric devices, which provide for the slow release or controlled delivery of drugs. Appropriate formulations, routes of administration and dose of a compound can be determined by those skilled in the art.

If desired, the compounds of the invention can include gene therapy molecules that modulate expression or activity of a gene associated with invertebrate geotaxis or with modulation of a mammalian vestibular system, including genes encoding polypeptides or active or inhibitory portions thereof; genes expressing antisense molecules that block expression of genes associated with invertebrate geotaxis or with modulation of a mammalian vestibular system; and genes expressing ribozymes that target genes associated with invertebrate geotaxis or with modulation of a mammalian vestibular system. Such methods are advantageous in treating graviperceptive disorders or for providing long-lasting prophylactic effects to an individual. Methods of introducing and expressing genes in animals, including humans, are well known in the art.

Gene therapy methods can be performed ex vivo, wherein cells (e.g. hematopoietic cells, including stem cells) are removed from the body, engineered to express a polypeptide associated with invertebrate geotaxis or with modulation of a mammalian vestibular system, and returned to the body. Gene therapy methods can also be performed in situ, in which an expressible nucleic acid molecule is placed directly into an appropriate tissue, such as the brain or CNS, by a direct route such as injection or implantation during surgery. Gene therapy methods can also be performed in vivo, wherein the expressible nucleic acid molecule is administered systemically, such as intravenously. Appropriate vectors for gene therapy can be determined by those skilled in the art for a particular application of the method, and include, but are not limited to, retroviral vectors (e.g. replication-defective MuLV, HTLV, and HIV vectors); adenoviral vectors; adeno-associated viral vectors; herpes simplex viral vectors; and non-viral vectors. Appropriate formulations for delivery of nucleic acids can also be determined by those skilled in the art, and include, for example, liposomes; polycationic agents; naked DNA; and DNA associated with or conjugated to targeting molecules (e.g. antibodies, ligands, lectins, fusogenic peptides, or HIV tat peptide). Gene therapy methods, including considerations for choice of appropriate vectors, promoters, formulations and routes of delivery, are reviewed, for example, in Anderson, *Nature* 392:25-30 (1998).

It is understood that modifications which do not substantially affect the activity of the various embodiments of this invention are also included within the definition of the invention provided herein. Accordingly, the following examples are intended to illustrate but not limit the present invention.

EXAMPLE I

This example shows the measurement of geotaxis scores for strains of *Drosophila* that have varying geotactic behaviors. This example also describes preparation of sub-lines of a *Drosophila* strain that have homozygous sets of chromosomes.

Established *Drosophila* lines that had been subjected to divergent behavioral selection for positive or negative geotaxis, called 'hi' for the negatively geotactic line, 'lo' for the positively geotactic line, and 'hi5' for the most recently re-selected 'hi' line were obtained from Dr. Jerry Hirsch, Department of Psychology, University of Illinois at Champagne-Urbana and are described in Erlenmeyer-Kimling et al., *J. Comp. Physiol. Psychol.* 55: 722-731, (1962); Ricker and Hirsch, *Behav. Genet.* 18: 13-25, (1988), and Stoltenberg and Hirsch, *J. Comp. Psychol.* 110:252-259 (1996).

These strains and a standard laboratory wild-type strain (Canton-S, obtained from the Bloomington *Drosophila* Stock Center, Indiana University at Bloomington) were then tested in a geotaxis maze constructed according to the design of Hirsch (*J. Comp. Physiol. Psychol.* 52:304-308 (1959)) as modified by McMillan and McGuire (*Behav. Genet.* 22:557-573 (1992)), shown in FIG. 1.

The geotaxis maze was fashioned from plexiglass and the maze chambers were hollowed out as semi-circular depressions in the slab, such that when the two slabs were bolted together a circular tube was formed in maze. This design thus made it possible to observe the entire time course of the assay. Additionally, this maze is easy to clean and standardize.

For each strain, a geotaxis score was determined. In separate measurements, twenty to thirty flies of each strain were loaded into a starting tube on the left (see FIG. 1). The maze was set upright in front of a light source on the right, and, after turning on the light, each strain was scored according to the distribution of the flies in the nine collecting tubes on the right. A perfect score for positive geotaxis would be 1, for negative geotaxis, 9, and for an even distribution, 5. The geotaxis measurments were repeated 3-5 times for each strain (see Table 1).

TABLE 1

| Strain | N (20-30 flies in each) | Geotaxis score | SEM |
| --- | --- | --- | --- |
| Canton-S | 3 | 5.53 | 0.61 |
| lo | 5 | 4.19 | 0.26 |
| hi | 5 | 7.25 | 0.59 |
| hi5 | 5 | 8.37 | 0.17 |

A control assay was carried out in which the maze was placed flat on the table so that all nine collecting tubes were chosen by the flies at the same level with respect to gravity. The control assay yielded a random distribution through the maze. Thus, the flies have retained their selected phenotype, even to the extent of showing a lower variance for the recently re-selected 'hi5' strain than for the older 'hi' strain (Stoltenberg and Hirsch, supra, (1996)).

In order to decrease the genetic heterogeneity of the 'hi5' line, sub-lines were derived that were homozygous for a set of chromosomes from the 'hi5' strain. This was carried out by mating flies of the 'hi5' strain to flies carrying multiple balancer chromosomes according to the method of Greenspan, *Fly Pushing: The Theory and Practice of Drosophila Genetics*, Cold Spring Harbor Laboratory Press, Cold Spring Harbor, N.Y., 1997.

TABLE 2

| Strain | N (15-25 flies in each) | Geotaxis score |
| --- | --- | --- |
| hi5-3a1 | 2 | 8.45 |
| hi5-3d | 2 | 8.19 |
| hi5-1a | 2 | 7.03 |

These results show that the essential phenotype of the selected lines can be captured in homozygous sets of chromosomes and thus can be characterized as a combination of homozygous alleles. The sub-line 'hi5-1a' falls short of the score for the original strain, demonstrating that it contains a subset of the relevant alleles.

EXAMPLE II

This example demonstrates the dramatic change in geotaxis score that occurs in mutant *Drosophila* that do not synthesize histamine or wild type *Drosophila* treated with a histamine receptor antagonist.

Several mutants were tested for alterations in geotactic behavior as judged by being consistently more positive or negative than the unselected wild-type strain Canton-S. A mutant with abnormally positive geotactic behavior was the $Hdc^{P211}$ allele of Histidine decarboxylase, an enzyme in the histamine biosynthetic pathway (Burg et al., *EMBO J.* 12:911-919 (1993)), as shown in Table 3. Those whose geotactic behavior was similar to Canton-S included $for^s$, a hypomorphic allele of the dg2 locus encoding cGMP-dependent protein kinase (Osborne et al., *Science* 277:834-836 (1997)), and Appl, a null allele of the gene encoding the *Drosophila* homolog of the amyloid precursor protein (Luo et al., *Neuron* 9:595-605 (1992)).

TABLE 3

| Strain | N (15-25 flies in each) | Geotaxis score |
| --- | --- | --- |
| $Hdc^{P211}/Hdc^{P211}$ | 2 | 7.51 |
| Canton-S | 3 | 5.53 |
| Canton-S fed for 2 hr on 20 mg/ml hydroxyzine | 1 | 8.50 |
| $for^s/for^s$ | 2 | 5.35 |
| Appl/Appl | 2 | 5.20 |

Extreme negative geotaxis is induced after interference with histamine, in both the histidine decarboxylase mutant $Hdc^{P211}$, which fails to make histamine, and in Canton-S flies fed with the histamine receptor antagonist, hydroxyzine. The geotactic behavior of the $Hdc^{P211}$ mutant and hydroxyzine-treated wild type is particularly significant given the long established role of anti-histamines in the treatment of motion sickness and vertigo (Brand and Perry, Pharmac. Rev., 18:895-924, 1966) and the ability of histamine to modulate activity in the vestibular system (Yabe et al., Exp. Brain Res., 93: 249-58, 1993).

These results show that an anti-histamine compound that modulates vestibular system activity can also change fly geotaxis, and that a genetic mutation effecting histamine synthesis can result in geotaxis similar to that caused by the anti-histamine compound.

EXAMPLE III

This example demonstrates the identification of nucleic acids that are differently expressed in *Drosophila* that exhibit negative geotaxis in comparison to *Drosophila* that exhibit positive geotaxis.

To examine the molecular basis for the behavioral difference in response to gravity between fly strains, differences in mRNA levels between the 'hi5' and 'lo' strains were measured. The assays were carried out using microarrays containing 8,800 unique cDNA EST (expressed sequence tag) clones from the Berkeley *Drosophila* Genome Project and made available through Research Genetics (Huntsville, Ala.). This number of cDNA clones represents approximately 65% of the *Drosophila* genome (Rubin et al., *Science* 287:2204-2215 (2000)). The microarrays consist of DNA samples printed in a high-density array onto treated glass slides which can then be hybridized with reverse-transcribed, single-stranded cDNA that has incorporated a fluorescently labeled nucleotide, Cy3- or Cy5-conjugated dTTP (Schena et al., *Science* 270:467-470 (1995); Shalon et al., *Genome Res.* 6:639-645 (1996)).

A previous control experiment has determined biological variability by taking animals from different vials and preparing polyA+ RNA independently from each (White et al., *Science*, 286:2179-2184, 1999). In this previous control experiment, no gene was differentially expressed more than 2.5-fold; so 2.5-3-fold was set as the cut-off criterion for a significant difference in expression in the present experiment. Threshold was arbitrarily set at signal intensity of 1000. The value of 1000 is typically between 2 and 3 standard deviations above the mean background value in microarray experiments.

In reciprocal experiments, PolyA+ RNA from ~500 isolated heads (mostly brain) from 3-5 day old flies of the 'hi5' strain and the 'lo' strain was fluorescently labeled with Cy3 and Cy5, respectively or Cy5 and Cy3, respectively, according to the method of Schena et al. supra and Shalon et al. supra. In each of the reciprocal experiments, microarrays were simultaneously hybridized with 5 µg fluorescently labeled RNA from both strains. Averaged results from the reciprocal experiments indicated that 25 genes exhibited a 2.5-fold or greater differential in 'lo' relative to 'hi5' (SEQ ID NOS:1-23), and 240 genes exhibited a three-fold or greater differential in the 'hi5' strain relative to the 'lo' strain (SEQ ID NOS:24-258).

The majority of differentially expressed sequences were unidentified ESTs. Some correspond to previously cloned *Drosophila* genes and others were homologous to genes cloned in other species. Examples of genes with particular significance for human gravity response are shown in Table 4 below, and a complete list of all differentially expressed genes is included in the sequence listing.

These results demonstrate that at least 265 genes can be differently expressed in flies that demonstrate-negative geotaxis relative to flies that demonstrate positive geotaxis.

TABLE 4

| Expression difference | Drosophila genes | Mammalian genes | Other organisms |
|---|---|---|---|
| up in 'hi5' vs. 'lo' | protein tyrosine phosphatase (Ptp61F) | tectorin-α (mouse) | DnaJ |
| up in 'hi5' vs. 'lo' | non-muscle myosin heavy chain (zip) | glycoprotein 330/megalin (human) | α-tubulin |
| up in 'hi5' vs. 'lo' | cysteine-proteinase-1 (Cp1) | protein inhibitor of nNOS/PIN (rat) | |
| up in 'hi5' vs. 'lo' | serine/threonine protein kinase (nemo) | synaptic vesicle transporter/SV2 (rat) | |
| down in 'hi5' vs. 'lo' | croquemort (macrophage receptor protein) | actin-binding double-zinc-finger protein (human) | hemocyte protease-2 |
| down in 'hi5' vs. 'lo' | cryptochrome (cry) | spinocerebellar ataxia type 2, SCA2 (human) | |

EXAMPLE IV

This example demonstrates determination of the effects of gene expression levels on geotaxis behavior in flies by artificially manipulating expression levels of genes previously identified to differ in expression level between 'hi5' and 'lo' strains.

Expression of prospero (SEQ ID NO:15) and Pigment-dispersing-factor (SEQ ID NO:3), were both found to be reduced in the negatively geotactic 'hi5' strain compared to the 'lo' strain. Flies containing pros[17] which is a mutant allele of prospero (SEQ ID NO:15), which has been described in Doe et al., Cell 65:451-464 (1991), were obtained from the *Drosophila* Stock center at Indiana University at Bloomington. Flies containing Pdf[01] (SEQ ID NO:261) which is a mutant allele of Pigment-dispersing-factor (SEQ ID NO:3) and flies containing a transgenic chromosome bearing a copy of the Pigment-dispersing-factor (SEQ ID NO:3) locus were obtained from Dr. Paul Taghert at Washington University, St. Louis and are described in Renn et al., Cell 99:791-802 (1999). Flies containing pros[17] and Pdf[01] (SEQ ID NO:261) were tested for alterations in geotactic behavior as described in Example I. Results of geotaxis assays are shown in Table 5.

TABLE 5

| Strain | N (20-30 Flies in each) | Geotaxis score | SEM |
|---|---|---|---|
| Canton-S | 4 | 6.023 | 0.240152 |
| Canton-S/Pdf[01] | 10 | 6.471 | 0.066273 |
| Canton-S/pros[17] | 12 | 5.901 | 0.064508 |
| Pdf[01]/Pdf[01] | 6 | 7.908 | 0.197879 |
| Pdf[01]/Pdf[01]/Dp | 6 | 7.413 | 0.138604 |
| Pdf[01]/Pdf[01]/Dp/Dp | 4 | 6.793 | 0.27834 |
| Pdf[01]/pros[17] | 8 | 8.178 | 0.108689 |

As shown in Table 5, geotaxis score increases as the copy number of the mutant Pdf[01] (SEQ ID NO:261) allele increases. Geotaxis score decreases as the copy number of the normal Pigment-dispersing-factor (SEQ ID NO:3) increases. Further, as shown in Table 5, flies bearing both the Pdf[01] (SEQ ID NO:261) and pros[17] alleles have an increased geotaxis score compared to flies bearing a single Pdf[01] (SEQ ID NO:261) allele or single pros[17] allele.

These results demonstrate that artificially manipulating the expression levels of Pdf, can convert a normal, geotactically neutral, lab strain (Canton-S) into a negatively geotactic strain. This example also demonstrates that titration of the gene dosage of Pdf titrates the geotactic phenotype such that lower amounts of gene product produce increasingly negative geotactic behavior. These results further demonstrate that prospero and Pigment-dispersing-factor operate in a network influencing geotactic behavior in invertebrates.

Throughout this application various publications have been referenced. The disclosure of these publications in their entireties are hereby incorporated by reference in this application in order to more fully describe the state of the art to which this invention pertains.

I claim:
1. A method of identifying a compound that modulates a mammalian vestibular system comprising:
   (a) administering a test compound to an invertebrate, and
   (b) measuring a geotactic behavior of said invertebrate, a compound that modulates the geotactic behavior of said invertebrate is characterized as a compound that modulates a mammalian vestibular system, wherein said compound modulates the expression or activity of one or more mammalian proteins.

2. The method of claim 1, wherein said one or more mammalian proteins are expressed in a mammalian vestibular system.

* * * * *